US008785473B2

(12) United States Patent
Miyata et al.

(10) Patent No.: US 8,785,473 B2
(45) Date of Patent: Jul. 22, 2014

(54) PLASMINOGEN ACTIVATOR INHIBITOR-1 INHIBITOR

(75) Inventors: Toshio Miyata, Sendai (JP); Kenji Murano, Osaka (JP); Nagahisa Yamaoka, Osaka (JP); Akihisa Maeda, Osaka (JP)

(73) Assignee: Renascience Co., Ltd., Tokyo (JP)

( * ) Notice: Subject to any disclaimer, the term of this patent is extended or adjusted under 35 U.S.C. 154(b) by 129 days.

(21) Appl. No.: 13/262,259

(22) PCT Filed: Mar. 31, 2010

(86) PCT No.: PCT/IB2010/000731
§ 371 (c)(1),
(2), (4) Date: Sep. 30, 2011

(87) PCT Pub. No.: WO2010/113022
PCT Pub. Date: Oct. 7, 2010

(65) Prior Publication Data
US 2012/0022080 A1  Jan. 26, 2012

(30) Foreign Application Priority Data
Mar. 31, 2009  (JP) .................... 2009-088400

(51) Int. Cl.
*A61K 31/4709* (2006.01)
*C07D 217/26* (2006.01)
*C07D 217/16* (2006.01)

(52) U.S. Cl.
CPC ................. *C07D 217/16* (2013.01)
USPC .......................... 514/307; 546/144

(58) Field of Classification Search
CPC .................................................. C07D 217/16
USPC ................. 514/357, 307; 546/333, 144
See application file for complete search history.

(56) References Cited

U.S. PATENT DOCUMENTS

| 5,532,276 | A  | 7/1996 | Mederski et al. |
| 6,291,478 | B1 | 9/2001 | Galey et al. |
| 2005/0124667 | A1 | 6/2005 | Sartori et al. |
| 2005/0143384 | A1 | 6/2005 | Sartori et al. |
| 2008/0119402 | A1 | 5/2008 | Zheng et al. |
| 2009/0124620 | A1 | 5/2009 | Miyata et al. |
| 2009/0240052 | A1 | 9/2009 | Yokotani et al. |

FOREIGN PATENT DOCUMENTS

| EP | 0120352 | 10/1984 |
| EP | 0376166 | 7/1990 |
| EP | 1666469 | 6/2006 |
| JP | 56-7716 | 1/1981 |
| JP | 02-256667 | 10/1990 |
| JP | 07-196656 | 8/1995 |
| JP | 2000-503308 | 3/2000 |
| JP | 2000-290252 | 10/2000 |
| JP | 2005-275352 | 10/2005 |
| JP | 2007-22943 | 2/2007 |
| JP | 2007-502264 | 2/2007 |
| JP | 2008-502699 | 1/2008 |
| WO | 93/11764 | 6/1993 |
| WO | 97/26244 | 7/1997 |
| WO | 02098839 | 12/2002 |
| WO | 03099276 | 12/2003 |
| WO | 2004018414 | 3/2004 |
| WO | 2005/016870 | 2/2005 |
| WO | 2005/123072 | 12/2005 |
| WO | 2006057845 | 6/2006 |
| WO | 2006062093 | 6/2006 |
| WO | 2006/107719 | 10/2006 |
| WO | 2007002559 | 1/2007 |
| WO | 2007/083689 | 7/2007 |
| WO | 2008/070831 | 6/2008 |
| WO | 2008111299 | 9/2008 |
| WO | 2008111300 | 9/2008 |
| WO | 2008124610 | 10/2008 |
| WO | 2009/013915 | 1/2009 |
| WO | 2009/038842 | 3/2009 |
| WO | 2009/123241 | 10/2009 |

OTHER PUBLICATIONS

Partial European Search Report dated May 27, 2013 from the European Patent Office in corresponding European Patent Application No. 13001154.7.
Jones, A. et al., Parallel synthesis and spectroscopic analysis of a collection of heterocycles based on the diazabenz[e]aceanthrylene core structure, Tetrahedron 65 (2009) 563-578.
Vaughan, D. et al., PAI-1 antagonists: Predictable indications and unconventional applications, Current Drug Targets, 2007, vol. 8, pp. 962-970.
International Search Report for PCT/IB2010/00731, dated Jul. 13, 2010.
Database CA [Online], Chemical Abstracts Service, Sheradsky, T. et al., Reaction of carbanions with N-(tosyloxy) phthalimide, Formation of 3,3-disubstituted quinoline-2,4-diones, XP002680341, retrieved from STN, Database accession No. 1987:4834.
Database CA [Online], Chemical Abstracts Service, Ito, K. et al., Preparation of amides as serotonin antagonists, XP002680342, retrieved from STN, Database accession No. 1999:804348.
Supplementary European Search Report dated Aug. 22, 2012, from the European Patent Office in corresponding European Application No. 10758123.3.
Aya, N. et al., Tissue-type plasminogen activator and its inhibitor in human glomerulonephritis, Journal of Pathology, 1992, vol. 166, pp. 289-295.
Lassila, M. et al., Plasminogen activator inhibitor-1 production is pathogenetic in experimental murine diabetic renal disease, Diabetologia, 2007, vol. 50, pp. 1315-1326.

(Continued)

*Primary Examiner* — Taofiq A Solola
(74) *Attorney, Agent, or Firm* — Roylance, Abrams, Berdo & Goodman, L.L.P.

(57) ABSTRACT

The present invention provides a novel compound having plasminogen activator inhibitor-1 inhibitory activity, and an inhibitor of PAI-1 comprising the compound as an active ingredient. The present invention also provides a pharmaceutical composition having an inhibitory action on PAI-1 activity and being efficacious in the prevention and treatment of various diseases whose onset is associated with PAI-1 activity.

14 Claims, 3 Drawing Sheets

(56) References Cited

OTHER PUBLICATIONS

Yoshida, Y. et al., Enhanced expression of plasminogen activator inhibitor 1 in patients with nephrotic syndrome, Nephron, 2001, vol. 88, pp. 24-29.

Oda, T. et al., PAI-1 deficiency attenuates the fibrogenic response to ureteral obstruction, Kidney International, 2001, vol. 30, pp. 587-596.

Matsuo, S. et al., Multifunctionality of PAI-1 in fibrogenesis: Evidence from obstructive nephropathy in PAI-1-overexpressing mice, Kidney International, 2005, vol. 67, pp. 2221-2238.

Huang, Y. et al., Noninhibitory PAI-1 enhances plasmin-mediated matrix degradation both in vitro and in experimental nephritis, Kidney International, 2006, vol. 70, pp. 515-522.

Eddy, A. et al., Plasminogen activator inhibitor-1 in chronic kidney disease: Evidence and mechanisms of action, Journal of American Society Nephrology, 2006, vol. 17, pp. 2999-3012.

Roelofs, J. et al., Plasminogen activator inhibitor-1 regulates neutrophil influx during acute pyelonephritis, Kidney International, 2009, vol. 75, pp. 52-59.

Huang, Y. et al., A mutant, noninhibitory plasminogen activator inhibitor type 1 decreases matrix accumulation in experimental glomerulonephritis, The Journal of Clinical Investigation, 2003, vol. 112, pp. 379-388.

Haraguchi, M. et al., t-PA promotes glomerular plasmin generation and matrix degradation in experimental glomerulonephritis, Kidney International, 2001, vol. 59, pp. 2146-2155.

Ha, H. et al., The role of plasminogen activator inhibitor 1 in renal and cardiovascular diseases, Nephrology, 2009, vol. 5, pp. 203-211.

Durand, M. et al., Plasminogen activator inhibitor-I and tumour growth, invasion, and metastasis, Thromb Haemost, 2004, vol. 91, pp. 438-449.

Dan, J. et al., Plasminogen activator inhibitor-I in the aqueous humor of patients with and without glaucoma, Arch Ophthalmol, 2005, vol. 123, pp. 220-224.

Basu, A. et al., Plasminogen activator inhibitor-1 (PAI-1) facilitates retinal angiogenesis in a model of oxygen-induced retinopathy, Investigative Ophthalmology & Visual Science, 2009, vol. 50, No. 10, pp. 4974-4981.

Milliat, F. et al., Essential role of plasminogen activator inhibitor type-1 in radiation enteropathy, The American Journal of Pathology, 2008, vol. 172, No. 3, pp. 691-701.

Eren, M. et al., Reactive site-dependent phenotypic alterations in plasminogen activator inhibitor-1 transgenic mice, Journal of Thrombosis and Haemostasis, 2007, vol. 5, pp. 1500-1508.

Devin, J. et al., Transgenic overexpression of plasminogen activator inhibitor-1 promotes the development of polycystic ovarian changes in female mice, Journal of Molecular Endocrinology, 2007, vol. 39, pp. 9-16.

Suzuki, Y. et al., Unique secretory dynamics of tissue plasminogen activator and its modulation by plasminogen activator inhibitor-1 in vascular endothelial cells, Blood, 2009, vol. 113, No. 2, pp. 470-478.

Maemura, K. et al., Circadian rhythms in the CNS and peripheral clock disorders: Role of the biological clock in cardiovascular diseases, Journal of Pharmacological Sciences, 2007, vol. 103, pp. 134-138.

Schoenhard, J. et al., Plasminogen activator inhibitor-1 has a circadian rhythm in blind Individuals, Thromb Haemost, 2007, vol. 98, pp. 479-481.

Egelund, R. et al., A regulatory hydrophobic area in the flexible joint region of plasminogen activator inhibitor-1, defined with fluorescent activity-neutralizing ligands, The Journal of Biological Chemistry, 2001, vol. 276, pp. 13077-13086.

Crandall, D. et al., Modulation of adipose tissue development by pharmacological inhibition of PAI-1, Arteriosclerosis, Thrombosis, and Vascular Biology, 2006, vol. 26, pp. 2209-2215.

Eitzman, D. et al., Bleomycin-induced pulmonary fibrosis in transgenic mice that either lack or overexpress the murine plasminogen activator inhibitor-1 gene, The Journal of Clinical Investigation, 1996, vol. 97, pp. 232-237.

Hattori, N. et al., Bleomycin-induced pulmonary fibrosis in fibrinogen-null mice, The Journal of Clinical Investigation, 2000, vol. 106, No. 11, pp. 1341-1350.

Kosaka, H. et al., Interferon-gamma is a therapeutic target molecule for prevention of postoperative adhesion formation, Nature Medicine, 2008, vol. 14, No. 4, pp. 437-441.

Jacobsen, J. et al., Enhanced clearance of Aβ in brain by sustaining the plasmin proteolysis cascade, Proceeding of the National Academy of Science, USA, 2008, vol. 105, No. 25, pp. 8754-8759.

Matsuo, O. et al., Plasminogen activator in bronchoalveolar fluid, Haemostasis, 1986, vol. 16, pp. 43-50.

Kivirikko, K. et al., Modifications of a specific assay for hydroxyproline in urine, Analytical Biochemistry, 1967, vol. 19, pp. 249-255.

Ashcroft, T. et al., Simple method of estimating severity of pulmonary fibrosis on a numerical scale, Journal of Clinical Pathology, 1988, vol. 41, pp. 467-470.

Milton, J. et al, Biaryl acids: Novel non-nucleoside inhibitors of HIV reverse transcriptase types 1 and 2, Bioorganic & Medicinal Chemistry Letters, 1998, vol. 8, pp. 2623-2628.

International Search Report for PCT/JP2009/056755, dated Jun. 16, 2009.

International Search Report for PCT/JP2008/054543, dated Jun. 17, 2008.

Examination Report dated Dec. 11, 2012, from the European Patent Office in corresponding European Patent Application No. 09729173.6.

PLASMINOGEN ACTIVATOR INHIBITOR-1 INHIBITOR

TECHNICAL FIELD

The present invention relates to a novel compound having plasminogen activator inhibitor-1 (hereinafter referred to as "PAI-1") inhibitory activity, and a PAI-1 inhibitor comprising the compound as an active ingredient. The present invention further relates to a pharmaceutical composition having an inhibitory action on PAI-1 activity and being efficacious in the prevention and treatment of various diseases whose development is influenced by PAI-1 activity.

BACKGROUND ART

Atrial thrombus caused by atrial fibrillation and thrombi formed by the disruption of atheroma (atherosclerotic vessels) in the aorta or carotid artery may cause ischemic cerebrovascular diseases such as cerebral embolism, cerebral infarction, transient ischemic attack, etc., and ischemic heart diseases such as angina pectoris, myocardial infarction, atrial thrombus caused by atrial fibrillation, cardiac insufficiency, etc. While blood circulation must have good fluidity to deliver oxygen and nutrients to body tissues and remove waste (from the circulatory system), it is required to be coagulative to stop bleeding for the prevention of blood loss due to injury. When the balance between such opposed functions of fluidity and coagulation is lost and shifts to coagulation, an intravascular thrombus is formed, which is thought to cause ischemic cerebrovascular disorders and heart diseases.

The fibrinolytic system plays important roles in thrombolysis, tissue destruction and repair, cell migration, etc. The fibrinolytic system is activated when plasminogen activator (hereinafter referred to as "PA") converts plasminogen to plasmin, whereas plasminogen activator inhibitor-1 (PAI-1) inhibits PA.

Tissue plasminogen activator (hereinafter referred to as "t-PA") converts plasminogen, i.e., the precursor of plasmin, to plasmin. Plasmin converts fibrin to a fibrin degradation product by breaking it down.

PAI-1 is a serine protease inhibitor that specifically inhibits t-PA and urokinase plasminogen activator (hereinafter referred to as "u-PA"), suppresses plasmin generation, and as a result inhibits fibrin degradation.

Based on tertiary structural differences, PAI-1 is present in an active form that shows PA inhibitory activity and in a latent form that shows no PA inhibitory activity.

In plasma, PAI-1 is known to be typically present in a concentration of 20 ng/mL, and produced in hepatocytes, megakaryocytes and lipocytes in addition to the vascular endothelial cells, which are the primary PAI-1 producing cells.

PAI-1 is an acute phase protein, and is thought to be one of the factors that cause ischemic organ dysfunctions in sepsis and disseminated intravascular coagulation syndrome (DIC) through accelerated production due to various cytokines and growth factors. Further, genetic polymorphism due to single base substitutions in the PAI-1 gene promoter is known, and it has been revealed that plasma PAI-1 concentration increases as a result of such genetic polymorphism.

Furthermore, in diabetes mellitus, accelerating arteriosclerosis and microvascular complications are presumed to be factors in ischemic heart disease, diabetic retinopathy, and renal damage, i.e., all are critical complications of diabetes mellitus. For example, in diabetic nephropathy, increased extracellular matrix in the glomerulus and fibrous stroma are observed characteristics, and PAI-1 expression is increased in the glomerulus and renal tubules. In proximal renal tubule incubation, increased PAI-1 production is evident under hyperglycemic conditions. Further, a correlation between PAI-1 expression in renal tissues and macrophage infiltration is confirmed in experiments using a model mouse with renal interstitial fibrosis (see Non-Patent Documents 1 and 2).

Furthermore, PAI-1 concentrations in urine are documented as being high in nephrotic syndrome patients based on the measurement results of PAI-1 levels in urine collected over a 24-hour period from nephrotic syndrome patients (see Non-Patent Document 3).

As described above, deep involvement of PAI-1 in kidney diseases such as diabetic nephropathy, chronic kidney disease (CKD), nephrotic syndrome, post-renal kidney injury, and pyelonephritis has been extensively studied and reported (see Non-Patent Documents 4 to 8). In contrast thereto, as a result of administrating an inactive PAI-1 mutant or t-PA as a PAI-1 antagonist to a Thy-1 nephritis model, it is reported that the alleviation of inflammation (cellular infiltration), TGF-β suppression, and a decrease in mesangial matrix are observed, whereby Thy-1 nephritis is alleviated (Non-Patent Documents 9 and 10).

Reduced fibrinolytic activity due to an increased PAI-1 concentration in plasma is associated with ischemic heart diseases such as angina pectoris, myocardial infarction, cardiac insufficiency; deep-vein thrombosis and pulmonary embolism originated therefrom; and diabetic angiopathy (for example, see Non-Patent Document 11). In addition to reduced fibrinolytic activity, some other thrombogenic abnormalities including hypercoagulation and platelet hyper-aggregation are also seen in diabetic patients. They are caused by microthrombus formation, and play important roles in the progression of diabetic microangiopathy and diabetic macroangiopathy.

As described above, PAI-1 is presumably involved in the formation and progression of various pathological conditions of various diseases, specifically, various kinds of thrombosis, cancer, diabetes mellitus, ocular diseases such as glaucoma and retinopathy, polycystic ovary syndrome, radiation damage, alopecia (calvities), splenohepatomegaly, arteriosclerosis, etc. (see Non-Patent Documents 12 to 17). In addition, PAI-1 is also presumably involved in control of the circadian rhythm, which is presumed to be involved in the formation of vascular endothelial cells and the occurrence of events such as cerebral infarction and myocardial infarction (Non-Patent Documents 18 to 20). For this reason, a compound that inhibits PAI-1 activity is useful as a preventive and treatment agent for various diseases such as thrombosis, cancer, diabetes mellitus, diabetic complications, various kidney diseases, ocular diseases such as glaucoma and retinopathy, polycystic ovary syndrome, alopecia, bone-marrow regeneration, splenomegaly due to extramedullary hematopoiesis, amyloidosis, and arteriosclerosis (see Non-Patent Documents 21 and 22). In particular, Non-Patent Document 14 reports that PAI-1 promotes angiogenesis in the retina, and a PAI-1 inhibitor is therefore considered to be useful as an agent for preventing and treating retinopathy and various other diseases that occur in association with angiogenesis. Further, Non-Patent Document 23 states that a low-molecular-weight PAI-1 inhibitor inhibits differentiation of adipose cells, thereby inhibiting the development of diet-induced obesity. Therefore, a PAI-1 inhibitor is presumably effective for preventing and treating obesity.

Tissue fibril formation occurs in many tissues and organs such as the lungs, heart, blood vessels, liver, kidneys, etc. A report has disclosed that the progression of pulmonary fibrosis can be suppressed by the administration of a PA or PAI-1 inhibitor to activate the fibrinolysis system (Non-Patent Document 24). Therefore, a PAI-1 inhibitor is known to be effective for treating tissue fibrosis, in particular pulmonary fibrosis (Non-Patent Documents 22, 25, and 26). However, there is no drug available to treat them radically. In reality, adrenocorticotropic hormones such as predonisolone, corticosteroid, etc., and cytotoxic drugs such as cyclophosphamide (alkylating agent) and azathioprine (antimetabolites, immunosuppressants) have been used as palliative therapy based on experience.

Further, it is believed that the onset of Alzheimer's disease is triggered by the accumulation of amyloid β peptide (Aβ) in the brain. Therefore, current research and development of drugs for preventing or treating Alzheimer's disease has been conducted with a focus on suppressing the production of Aβ or promoting decomposition of Aβ. It was recently discovered that the decomposition of Aβ can be promoted by inhibiting PAI-1; this finding suggests that a PAI-1 inhibitor may be usable as a drug for treating Alzheimer's disease (Non-Patent Document 27).

CITATION LIST

Non-Patent Document

Non-Patent Document 1: Aya N. et al., J. Pathol., 166, 289-295, 1992

Non-Patent Document 2: M. Lassila et al., Plasminogen activator inhibitor-1 production is pathogenetic in experimental murine diabetic renal disease. *Diabetologia* (2007) 50:1315-1326

Non-Patent Document 3: Yoshida Y et al., Nephron, 88, 24-29, 2001

Non-Patent Document 4: Takashi Oda et al., PAI-1 deficiency attenuates the fibrogenic response to ureteral obstruction. *Kidney International*, Vol. 30 (2001), pp. 587-596

Non-Patent Document 5: Shunya Matsuo et al., Multifunctionality of PAI-1 in fibrogenesis: Evidence from obstructive nephropathy in PAI-1-overexpressing mice. *Kidney International*, Vol. 67 (2005), pp. 2221-2238

Non-Patent Document 6: Y Huang et al., Noninhibitory PAI-1 enhances plasmin-mediated matrix degradation both in vitro and in experimental nephritis. *Kidney International* (2006) 70, 515-522

Non-Patent Document 7: Allison A. et al., Plasminogen Activator Inhibitor-1 in Chronic Kidney Disease: Evidence and Mechanisms of Action. *J Am Soc Nephrol* 17: 2999-3012, 2006

Non-Patent Document 8: Joris J T H Roelofs et al., Plasminogen activator inhibitor-1 regulates neutrophil influx during acute pyelonephritis. *Kidney International*, Vol. 75 (2009), pp. 52-59

Non-Patent Document 9: W. A. Border et al., J. Clin. Invest., 112, 379, 2003

Non-Patent Document 10: W. A. Border et al., Kidney Int., 59, 246, 2001

Non-Patent Document 11: Hunjoo Ha et al., The role of plasminogen activator inhibitor 1 in renal and cardiovascular diseases. *Nephrology*, Volume 5, APRIL 2009, 203

Non-Patent Document 12: Michelle K. et al., Plasminogen activator inhibitor-1 and tumour growth, invasion, and metastasis. *Thromb Haemost* 2004; 91: 438-49

Non-Patent Document 13: Dan J, Belyea D, et al., Plasminogen activator inhibitor-1 in the aqueous humor of patients with and without glaucoma. *Arch Ophthalmol.* 2005 February; 123 (2): 220-4

Non-Patent Document 14: Anupam Basu et al., Plasminogen Activator Inhibitor-1 (PAI-1) Facilitates Retinal Angiogenesis in a Model of Oxygen-Induced Retinopathy *IOVS*, October 2009, Vol. 50, No. 10, 4971-4981

Non-Patent Document 15: Fabien Milliat et al., Essential Role of Plasminogen Activator Inhibitor Type-1 in Radiation Enteropathy. *The American Journal of Pathology*, Vol. 172, No. 3, March 2008, 691-701

Non-Patent Document 16: M. EREN et al., Reactive site-dependent phenotypic alterations in plasminogen activator inhibitor-1 transgenic mice. *Journal of Thrombosis and Haemostasis*, 2007, 5: 1500-1508

Non-Patent Document 17: Jessica K Devin et al., Transgenic overexpression of plasminogen activator inhibitor-1 promotes the development of polycystic ovarian changes in female mice. *Journal of Molecular Endocrinology* (2007) 39, 9-16

Non-Patent Document 18: Yuko Suzuki et al., Unique secretory dynamics of tissue plasminogen activator and its modulation by plasminogen activator inhibitor-1 in vascular endothelial cells. *Blood*, January 2009, Volume 113, Number 2, 470-478

Non-Patent Document 19: Koji Maemura et al., Circadian Rhythms in the CNS and Peripheral Clock Disorders: Role of the Biological Clock in Cardiovascular Diseases. *J Pharmacol Sci* 103, 134-138 (2007)

Non-Patent Document 20: John A. Schoenhard et al., Plasminogen activator inhibitor-1 has a circadian rhythm in blind individuals. *Thromb Haemost* 2007; 98: 479-481

Non-Patent Document 21: Egelund R et al., J. Biol. Chem., 276, 13077-13086, 2001

Non-Patent Document 22: Douglas E. Vaughan et al., PAI-1 Antagonists: Predictable Indications and Unconventional Applications. *Current Drug Targets*, 2007, 8, 962-970

Non-Patent Document 23: David L. Crandall et al., Modulation of Adipose Tissue Development by Pharmacological Inhibition of PAI-1. *Arterioscler. Thromb. Vasc. Biol.* 2006; 26; 2209-2215

Non-Patent Document 24: D T Eitzman et al., J. Clin. Invest. 97, 232-237, 1996

Non-Patent Document 25: Noboru Hattori et al., Bleomycin-induced pulmonary fibrosis in fibrinogen-null mice. *J. Clin. Invest.* 106: 1341-1350 (2000).

Non-Patent Document 26: Hisashi Kosaka et al., Interferon-γ is a therapeutic target molecule for prevention of postoperative adhesion formation. *Nature Medicine*, Volume 14, No. 4, APRIL 2008, 437-441

Non-Patent Document 27: Jacobsen J S et al., Proc Natl Acad Sci USA, 105(25), 8754-9, 2008 Jun. 16

[Patent Document]

Patent Document 1: WO 2009/013915 A1

SUMMARY OF INVENTION

Technical Problem

Urokinase, i.e., u-PA, is known as a fibrinolysis promoter. This drug is obtained by the purification of human urine, and is not considered to be highly productive or safe. Moreover, urokinase is a high-molecular-weight compound having a molecular weight of about 54,000. Other known fibrinolysis promoters include tisokinase, alteplase (gene recombinant), nasaruplase (cell culture), nateplase (gene recombinant), monteplase (gene recombinant), pamiteplase (gene recombinant), and batroxobin; however, they are all high-molecular-weight compounds. Considering this fact, a highly safe low-molecular-weight compound drug that can be synthesized in large amounts is in demand as a fibrinolysis promoter. Also expected is the development of drugs efficacious in radically treating fibrous tissue and the alleviation thereof.

In order to solve the foregoing problems, focus was placed on PAI-1 that is involved in the inhibition of activation of the fibrinolytic system as well as the formation and progression of various pathological conditions such as various types of thrombosis; cancer; diabetes mellitus; diabetic complications such as macroangiopathy and microangiopathy; tissue fibrosis such pulmonary fibrosis, hepatic fibrosis, and renal fibrosis; various kidney diseases such as diabetic nephropathy, chronic kidney disease (CKD), nephrotic syndrome, post-renal kidney injury, and pyelonephritis; ocular diseases such as glaucoma, diabetic retinopathy, and oxygen-induced retinopathy; polycystic ovary syndrome; radiation damage; alopecia (calvities); splenohepatomegaly; bone-marrow regeneration; obesity; amyloidosis; Alzheimer's disease; and arteriosclerosis. With that focus, the present invention aims to provide a highly safe pharmaceutical composition that has an inhibitory action on the PAI-1 and contains, as an active component, a low-molecular-weight that can be synthesized in large amounts. More specifically, the present invention aims to provide a pharmaceutical composition that is useful as fibrinolysis promoter as an anti-thrombogenic agent or a thrombolytic agent; cancer progression inhibitor; anti-tissue fibrosis agent such as anti-pulmonary fibrosis agent, anti-hepatic fibrosis agent, or anti-renal fibrosis agent; antidiabetic drug; drug for treating diabetic complications such as macroangiopathy or microangiopathy; drug for treating various kidney diseases such as diabetic nephropathy, chronic kidney disease (CKD), nephrotic syndrome, post-renal kidney injury, or pyelonephritis; drug for treating ocular diseases such as diabetic retinopathy, oxygen-induced retinopathy, or glaucoma; drug for treating polycystic ovary syndrome; anti-radiation damage drug; drug for treating alopecia (calvities); drug for treating splenohepatomegaly; agent for promoting bone-marrow regeneration; anti-obesity drug; anti-amyloid drug; anti-arteriosclerosis agent, or anti-Alzheimer's drug.

Another object of the present invention is to provide a novel compound effective as an active component for a pharmaceutical composition that is effective for prevention and treatment of the above-described various pathological conditions and diseases.

Solution to Problem

The present inventors have conducted studies to solve the above problems, and found that a compound represented by the following formula (I) or a salt thereof, or a solvate thereof (hereinafter collectively referred to as "compound (I) of the present invention" or simply referred to as "compound (I)"), as well as the compound described in an international publication (patent document 1), has high inhibitory activity on plasminogen activator inhibitor-1 (PAI-1). As described above, it is known that PAI-1 inhibitor has effects as a fibrinolysis promoter as well as an anti-fibrosis agent for inhibiting tissue fibrosis such as pulmonary fibrosis. In addition to these effects, PAI-1 inhibitor is know to have effects of preventing or treating diseases and pathological conditions such as cancer; diabetes mellitus; diabetic complications such as macroangiopathy and microangiopathy; ocular diseases such as diabetic retinopathy, oxygen-induced retinopathy, and glaucoma; various kidney diseases (diabetic nephropathy, chronic kidney disease (CKD), nephrotic syndrome, post-renal kidney injury, and pyelonephritis); polycystic ovary syndrome; radiation damage; alopecia (calvities); splenohepatomegaly; bone-marrow regeneration; obesity; amyloidosis; and arte-riosclerosis. Further, current studies suggest that PAI-1 inhibitor is useful as a therapeutic medicine for Alzheimer's disease, which is considered to be caused by Aβ deposition in the brain.

Accordingly, in addition to the fact that the compound (I) of the present invention is effective as a fibrinolysis promoter, based on its inhibitory action on the PAI-1 activity, the compound (I) is considered to be capable of significantly ameliorating tissue fibrosis as an anti-fibrosis agent and is also capable of preventing or ameliorating various diseases and pathological conditions described above, as well as Alzheimer's disease as an anti-Alzheimer's drug.

The present invention has been accomplished based on these findings.

More specifically, the present invention encompasses the following embodiments.

(1) Compound (I) and a Salt Thereof (1-1) A compound represented by Formula (I) or a salt thereof:

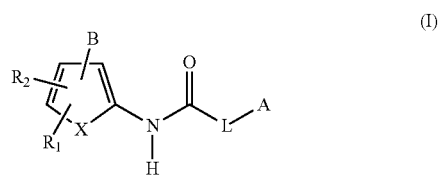

wherein —$R_1$ and $R_2$ are the same or different, and each represents hydrogen, halogen, $C_{1-6}$-alkyl, $C_{3-6}$-cycloalkyl, $C_{3-8}$-cycloalkyl-$C_{1-6}$-alkyl, $C_{3-8}$-cycloalkenyl, $C_{2-6}$-alkynyl, $C_{3-8}$-cycloalkyl-$C_{2-6}$-alkynyl, substituted or unsubstituted aryl, or substituted or unsubstituted heteroaryl;

—X represents sulfur or —CH=CH—;

-A represents fluorenyl, substituted or unsubstituted quinolyl, or a group shown in any of the following (a) to (e):

(a) A Group Represented by Formula (II)

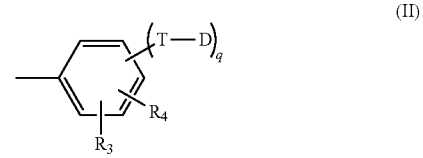

wherein $R_3$ and $R_4$ are the same or different, and each represents hydrogen, substituted or unsubstituted $C_{1-6}$-alkyl, or $CF_3$;

T represents a single bond, substituted or unsubstituted $C_{1-3}$-alkylene, oxygen, —CO—, —O—$C_{1-3}$-alkylene, or $C_{2-6}$-alkynylene;

D represents substituted or unsubstituted aryl, heteroaryl, or benzo-condensed heteroaryl; substituted or unsubstituted $C_{3-8}$-cycloalkyl or heterocycloalkyl; substituted or unsubstituted $C_{3-8}$-cycloalkenyl or heterocycloalkenyl; or adamantyl;

q represents an integer 0 or 1 (when both $R_3$ and $R_4$ are hydrogen, q is 1);

provided that when, in Formula (I), L is substituted or unsubstituted $C_{1-6}$-alkylene-NHCO— and T is a single bond, D is not unsubstituted phenyl;

(b) A Group Represented by any of Formulae (III) to (V)

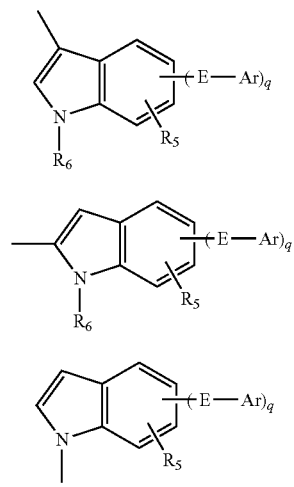

wherein, in Formulae (III) to (V) above, $R_5$ represents hydrogen or halogen; $R_6$ represents hydrogen, $C_{1-6}$-alkyl, or $C_{1-6}$-hydroxyalkyl; E represents a single bond or —O—$C_{1-6}$-alkylene; Ar represents substituted or unsubstituted aryl or heteroaryl; and q is as defined above (when $R_5$ is hydrogen, q is 1);

(c) A Group Represented by Formula (VI)

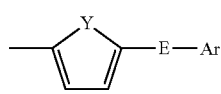

wherein Y represents sulfur or oxygen, and E and Ar are as defined above;

(d) A Group Represented by Formula (VII)

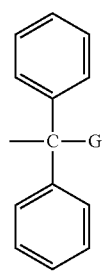

wherein G represents hydrogen or $C_{1-6}$-alkyl;

(e) A Group Represented by Formula (VIII)

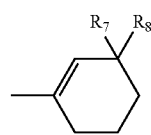

wherein $R_7$ and $R_8$ represent a group wherein these substituents are simultaneously hydrogen, or alkylene which binds to each other to form 3- to 8-membered ring cycloalkane;

-L represents a single bond, substituted or unsubstituted $C_{1-6}$-alkylene (some carbon atoms in the alkylene optionally form a cycloalkyl ring), substituted or unsubstituted $C_{1-6}$-alkylene-O-(some carbon atoms in the alkylene optionally form a cycloalkyl ring), substituted or unsubstituted $C_{1-6}$-alkylene-NHCO— (in alkylene-NHCO—, some carbon atoms in the alkylene optionally form a cycloalkyl ring), substituted or unsubstituted $C_{1-6}$-alkylene-NH— (in alkylene-NH—, some carbon atoms in the alkylene optionally form a cycloalkyl ring), substituted or unsubstituted $C_{1-6}$-alkenylene, substituted or unsubstituted $C_{1-6}$-alkynylene, —CO—, —NH—, —CONH— (in this case, A is a group represented by Formula (II), q is 1, T is a single bond, and D is adamantyl), 1,4-piperazidinyl (in this case, A is a group represented by Formula (VII)), $C_{1-6}$-alkylene-1,4-piperazidinyl (in this case, A is a group represented by Formula (VII)), adamantylene, or a group represented by the following Formula (IX):

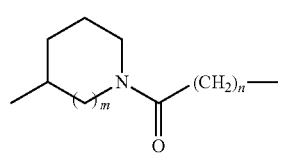

wherein, in $(CH_2)_n$, one or more carbons are optionally substituted and may form cycloalkyl with a substituent of the carbon, provided that m is an integer 0 or 1, and n is an integer 0 to 2);

—B is $COOR_9$ wherein $R_9$ represents hydrogen;

a group converted to hydrogen in vivo which is selected from the group consisting of $C_{1-6}$-alkyl, aryl, aralkyl; a group represented by —$CH(R_{10})$—O—CO—$R_{11}$ or —$CH(R_{10})$—O—CO—$OR_{11}$ ($R_{10}$ is hydrogen or $C_{1-6}$-alkyl, and $R_{11}$ is $C_{1-6}$-alkyl or $C_{3-8}$-cycloalkyl]; and (5-alkyl-2-oxo-1,3-dioxolen-4-yl)methyl represented by the following formula:

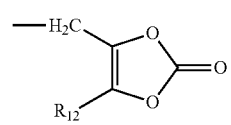

wherein $R_{12}$ represents $C_{1-6}$ alkyl; or a heterocyclic group represented by any of the following Formulae (XI)-(XIII):

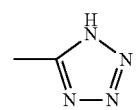

-continued

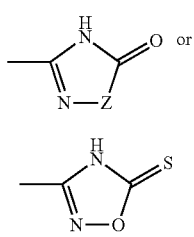
(XII) or (XIII)

wherein Z represents oxygen or sulfur,
provided that the following compounds and salts thereof are excluded:
2-{[(4-tert-butylphenyl)carbonyl]amino}-5-chlorobenzoic acid,
2-[(biphenyl-4-ylcarbonyl)amino]-5-chlorobenzoic acid,
5-chloro-2-{[(4-cyclohexylphenoxy)acetyl]amino}benzoic acid,
5-chloro-2-({[4-(phenylcarbonyl)phenyl]carbonyl}amino) benzoic acid,
5-chloro-2-[(5,6,7,8-tetrahydronaphthalen-2-ylcarbonyl) amino]benzoic acid,
5-chloro-2-[(diphenylacetyl)amino]benzoic acid, and
5-chloro-2-({[4-(1H-pyrrol-1-yl)phenyl]carbonyl}amino) benzoic acid.

(1-2) The compound according to (1-1) or a salt thereof, wherein the compound represented by Formula (I) above is a compound represented by Formula (Ia):

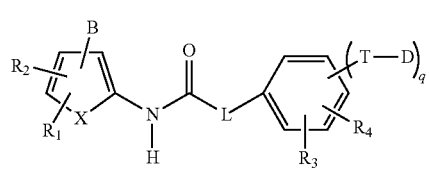
(Ia)

wherein $R_1$ to $R_4$, B, X, L, T, D, and q are as defined above.

(1-3) The compound according to (1-2) or a salt thereof, wherein the compound represented by Formula (Ia) above is a compound represented by any of the following Formulae (Ia-1) to (Ia-4):

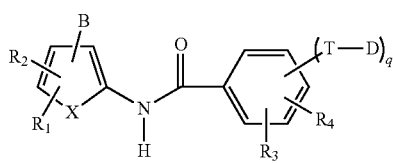
(Ia-1)

wherein $R_1$ to $R_4$, B, X, T, D, and q are as defined above;

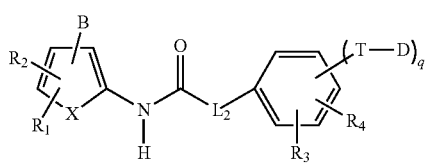
(Ia-2)

wherein $R_1$ to $R_4$, B, X, T, D, and q are as defined above; and $L_2$ represents substituted or unsubstituted $C_{1-6}$-alkylene-O—;

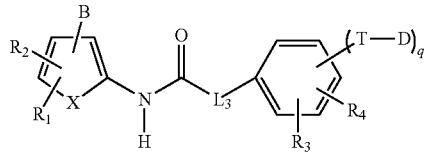
(Ia-3)

wherein $R_1$ to $R_4$, B, X, T, D, and q are as defined above; and $L_3$ represents substituted or unsubstituted $C_{1-6}$-alkylene, $C_{2-6}$-alkenylene, or $C_{2-6}$-alkynylene;

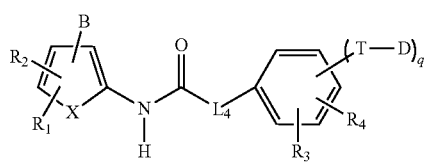
(Ia-4)

wherein $R_1$ to $R_4$, B, X, T, D, and q are as defined above; and $L_4$ represents —NH—, substituted or unsubstituted $C_{1-6}$-alkylene-NH—, —CO—, —CONH—, substituted or unsubstituted $C_{1-6}$-alkylene-NHCO—, or a group represented by the following formula (IX):

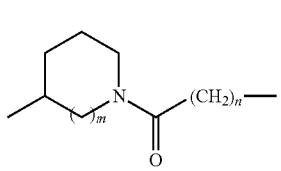
(IX)

wherein, in $(CH_2)_n$, one or more carbons are optionally substituted and may form cycloalkyl with a substituent of the carbon, provided that m is an integer 0 or 1, and n is an integer 0 to 2).

(1-4) The compound according to (1-1) or a salt thereof, wherein the compound represented by Formula (I) above is a compound represented by any of Formulae (Ib-III) to (Ib-V):

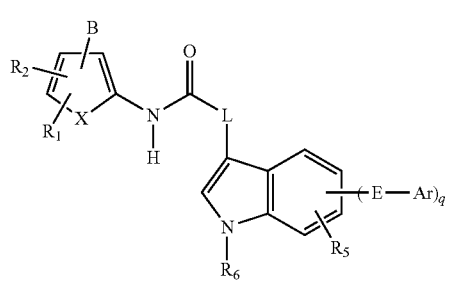
(Ib-III)

-continued

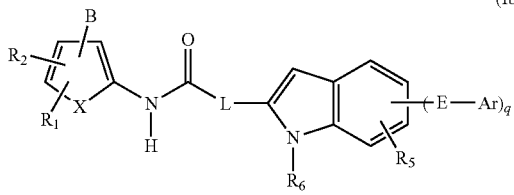
(Ib-IV)

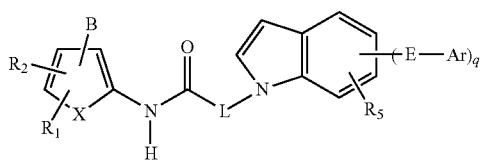
(Ib-V)

wherein $R_1$, $R_2$, $R_5$, $R_6$, B, X, L, E, Ar, and q are as defined above.

(1-5) The compound according to (1-1) or a salt thereof, wherein the compound represented by Formula (I) above is a compound represented by Formula (Ic):

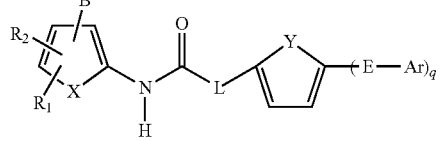
(Ic)

wherein $R_1$, $R_2$, B, X, L, Y, E, Ar, and q are as defined above.

(1-6) The compound according to (1-1) or a salt thereof, wherein the compound represented by Formula (I) above is a compound represented by Formula (Id):

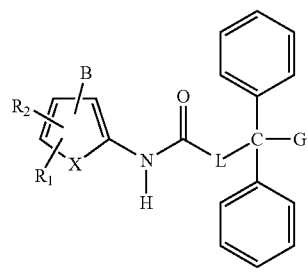
(Id)

wherein $R_1$, $R_2$, B, X, L, and G are as defined above.

(1-7) The compound according to (1-1) or a salt thereof, wherein the compound represented by Formula (I) above is a compound represented by Formula (Ie):

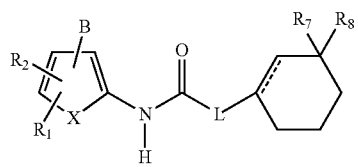
(Ie)

wherein $R_1$, $R_2$, $R_7$, $R_8$, B, X, and L are as defined above.

(1-8) The compound according to (1-1) or a salt thereof, wherein the compound represented by Formula (I) above is a compound wherein A is fluorenyl.

(1-9) The compound according to (1-1) or a salt thereof, wherein the compound represented by Formula (I) above is a compound wherein A is substituted or unsubstituted quinolyl.

(1-10) The compound according to any of (1-1) to (1-9) or a salt thereof, wherein the compound (I) above is at least one compound selected from the group consisting of compounds of Examples 1 to 107 described in Tables 1 and 2.

(2) Method for Producing Compound (I)

(2-1) A method for producing a compound represented by Formula (I-2), comprising the following steps (a) and (b):
(a) a step of condensing a compound (1) and a compound (2), which are represented by the following formulae, to form an ester compound (I-1); and
(b) a step of removing $R_{9a}$ in the compound (I-1) formed in step (a) above to form a carboxylic acid (I-2):

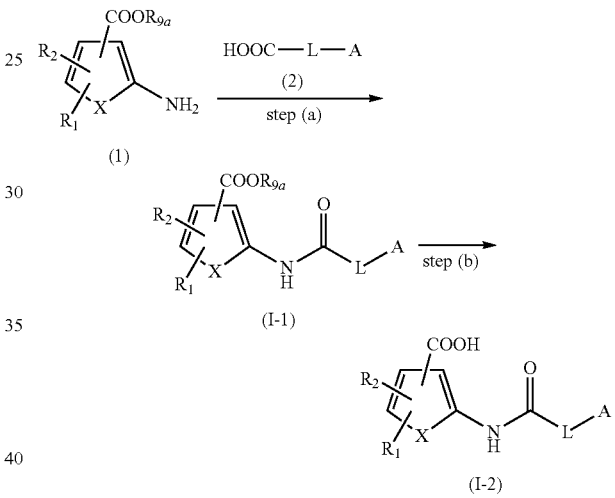

wherein $R_1$, $R_2$, X, L, and A are as defined above; and $R_{9a}$ represents alkyl, aryl, or aralkyl.

(2-2) A method for producing a compound represented by Formula (I-2), comprising the following steps (a') and (c):
(a') a step of condensing a compound (1') and a compound (2), which are represented by the following formulae, to form an ester compound (3); and
(c) a step of replacing Hal in the compound (3) formed in step (a') above by COOH to form a carboxylic acid (I-2):

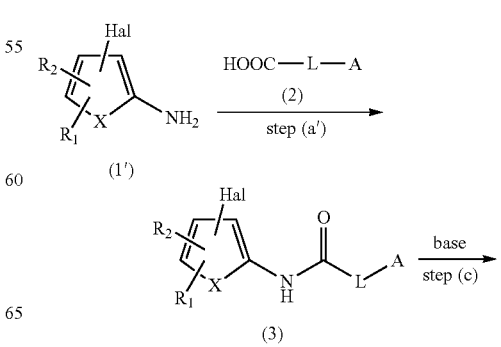

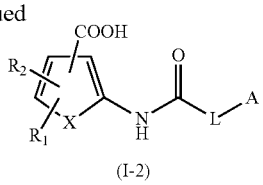

(I-2)

wherein $R_1$, $R_2$, X, A, and L are as defined above; and Hal represents iodine or bromine.

(2-3) A method for producing a compound represented by Formula (I-3), comprising the following steps (a″) and (d):

(a″) a step of condensing a compound (1″) and a compound (2), which are represented by the following formulae, to form a nitrile compound (4); and (d) a step of reacting the nitrile compound (4) formed in step (a″) above with an azide (5) to form a tetrazole compound (I-3):

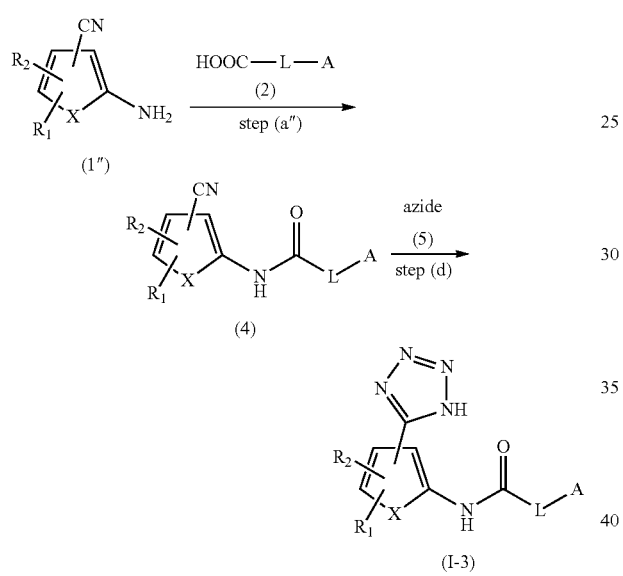

wherein $R_1$, $R_2$, X, A, and L are as defined above.

(2-4) A method for producing a compound represented by Formula (I-1'), comprising step (e) of esterifying a carboxylic acid (I-2):

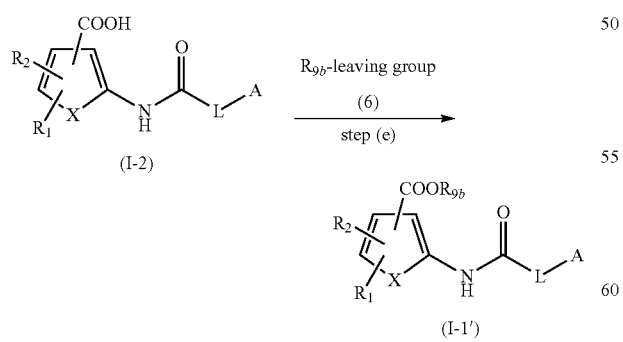

wherein $R_1$, $R_2$, X, L, and A are as defined above; $R_{9b}$ represents a group converted to hydrogen in vivo, which is selected from the group consisting of $C_{1-6}$-alkyl, —CH($R_{10}$)—O—CO—$R_{11}$, —CH($R_{10}$)—O—CO—O$R_{11}$ ($R_{10}$ is hydrogen or $C_{1-6}$-alkyl, and $R_{11}$ is $C_{1-6}$-alkyl or $C_{3-6}$-cycloalkyl) and (5-alkyl-2-oxo-1,3-dioxolen-4-yl)methyl represented by Formula (X).

(2-5) A method for producing a compound represented by Formula (I-4), comprising the following steps (f) and (g):

(f) a step of reacting a nitrile compound (4) with hydroxylamine hydrochloride (7), which are represented by the following formulae, to form an amide oxime compound (8); and (g) a step of reacting the amide oxime compound (8) formed in step (f) above with an active carbonyl compound (9) to form a compound (I-4) having a 4,5-dihydro-5-oxo-4H-1,2,4-oxadiazol-3-yl group:

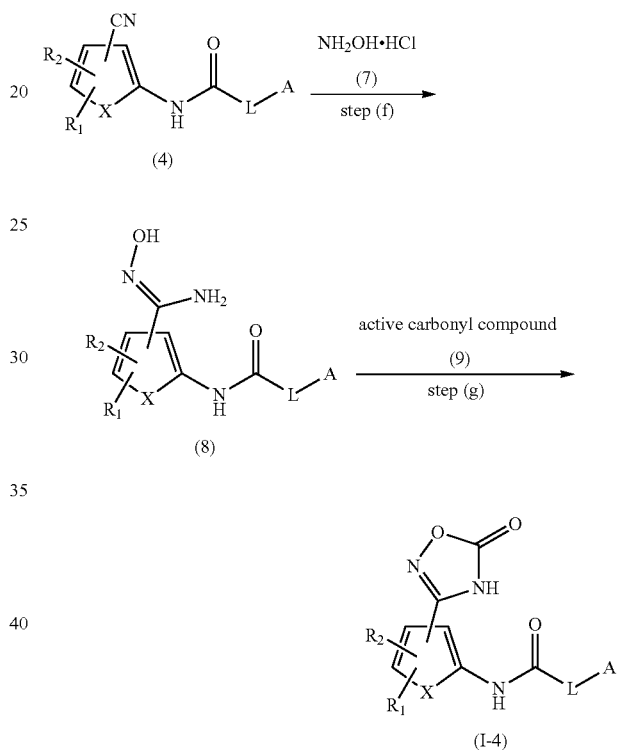

wherein $R_1$, $R_2$, A, L, and X are as defined above.

(2-6) A method for producing a compound represented by Formula (I-5), comprising the following step (h):

(h) a step of reacting an amide oxime compound (8) with a 1,1'-thiocarbonyldiimidazole (10), which are represented by the following formulae, to form a compound (I-5) having a 4,5-dihydro-5-thioxo-4H-1,2,4-oxadiazol-3-yl group:

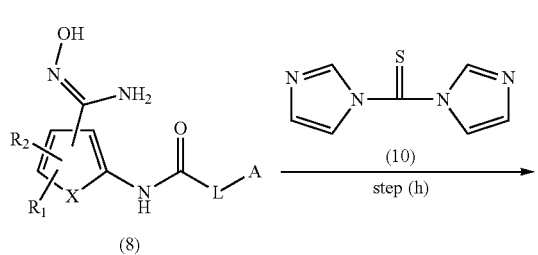

-continued

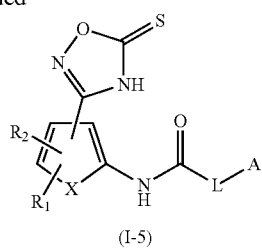

(I-5)

wherein $R_1$, $R_2$, A, L, and X are as defined above.

(2-7) A method for producing a compound represented by Formula (I-6), comprising the following step (i):

(i) a step of reacting an amide oxime compound (8) with 1,1'-thiocarbonyldiimidazole (10), which are represented by the following formulae, in the absence of a base, followed by a reaction with an acid to form a compound (I-6) having a 4,5-dihydro-5-oxo-4H-1,2,4-thiadiazol-3-yl group:

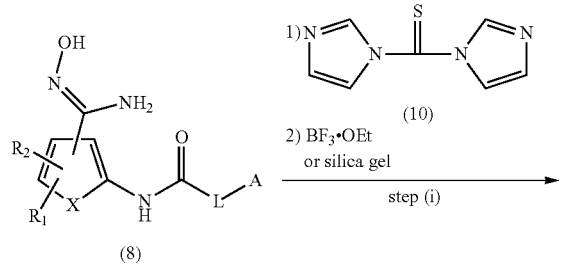

wherein $R_1$, $R_2$, A, L, and X are as defined above.

(2-8) A method for producing a compound represented by Formula (I-1) or a compound (5), comprising the following steps (j) and (k):

(j) a step of condensing a compound (1) or (1″) and a compound (12), which are represent by the following formulae, to form a compound (13); and (k) a step of reacting the compound (13) formed in step (j) above with a compound (14) or (15) to form a compound (I-1) or a compound (5):

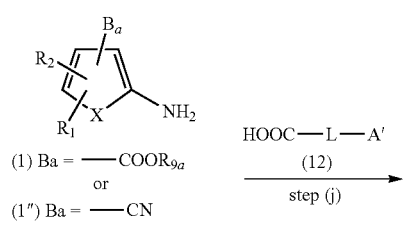

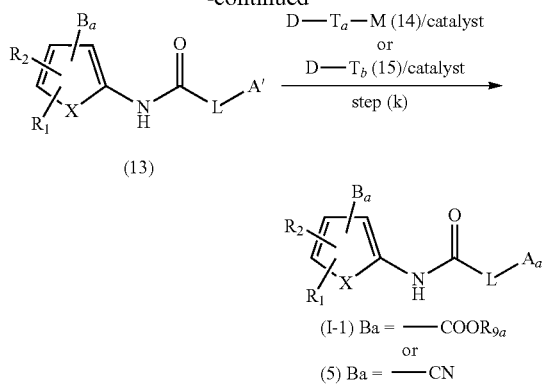

wherein $R_1$, $R_2$, D, L, $R_{9a}$, and X are as defined above, provided that Aa represents a group in which W in a group represented by the following Formula (XIV) is replaced by D-Ta— or D-Tb—, or a group in which W in a group represented by the following Formula (XV), (XVI), or (XVII) is replaced by D-Ta—; Ba represents ester (—COOR$_{9a}$) or cyano; A' represents a group represented by the following Formula (XIV), (XV), (XVI), or (XVII) having halogen or trifluoromethanesulfonyloxy represented by W; Ta represents a single bond or $C_{1-3}$ alkylene; Tb represents alkynylene having a triple bond at its end; M represents —B(OR$_{13}$)OR$_{13}$ (R$_{13}$ represents hydrogen or alkyl: in the case of alkyl, R$_{13}$ substituents may bind to each other to form a ring); or —ZnV (Zn represents zinc, and V represents halogen):

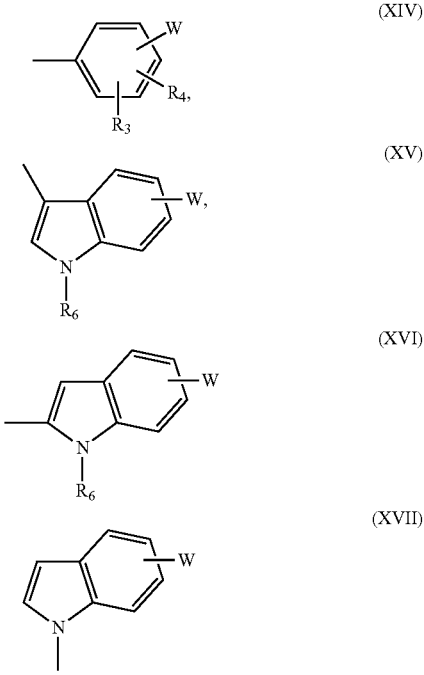

wherein $R_3$, $R_4$, and $R_6$ are as defined above; and W represents halogen or trifluoromethanesulfonyloxy.

(2-9) A method for producing a compound represented by Formula (I-1), a halogen compound (4), or a nitrile compound (5), wherein L is substituted or unsubstituted $C_{1-6}$ alkylene-O—, the method comprising the following steps (l) and (m):

(l) a step of condensing a compound (1), (1'), or (1") and a compound (16), which are represented by the following formulae, to produce a compound (17);

(m) a step of reacting the compound (17) formed in step (l) above with a compound (18) to form an ester compound (I-1), a halogen compound (4), or a nitrile compound (5):

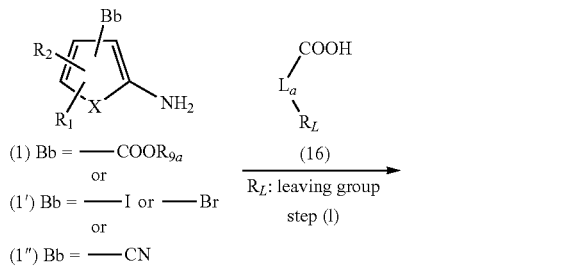

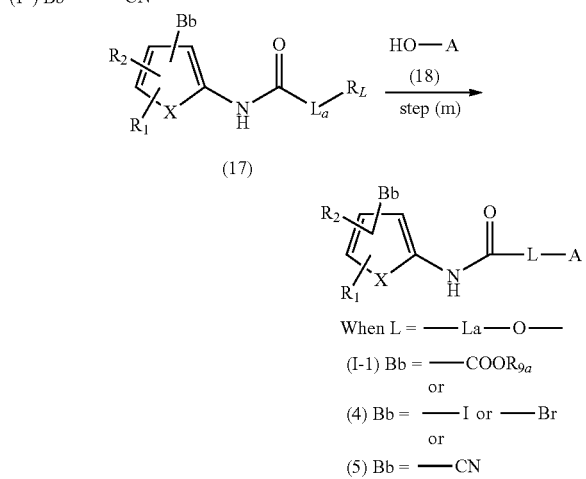

wherein $R_1$, $R_2$, X, $R_{9a}$, and A are as defined above; Bb represents ester (—COOR$_{9a}$), halogen (iodine or bromine), or cyano; $R_L$ represents a leaving group; La represents substituted or unsubstituted $C_{1-6}$ alkylene (some carbon atoms in the alkylene optionally form a cycloalkyl ring).

(2-10) A method for producing an ester compound represented by Formula (I-1), a halogen compound (4), or nitrile compound (5), wherein L is Formula (IX), the method comprising the following steps (n) to (p):

(n) a step of condensing a compound (1), (1'), or (1") and a compound (19), which are represented by the following formulae, to form a compound (20);

(o) a step of removing a protecting group P in the compound (20) formed in step (n) above to form a compound (21); and (p) a step of condensing the compound (21) formed in step (o) above and a compound (22) to form a ester compound (I-1), a halogen compound (4), or a nitrile compound (5):

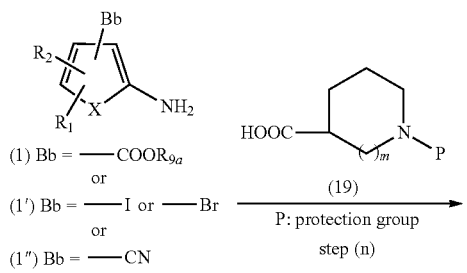

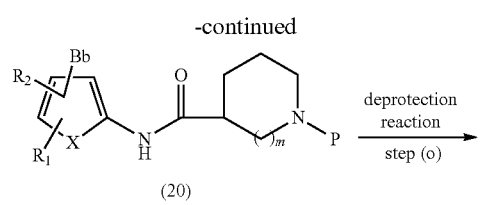

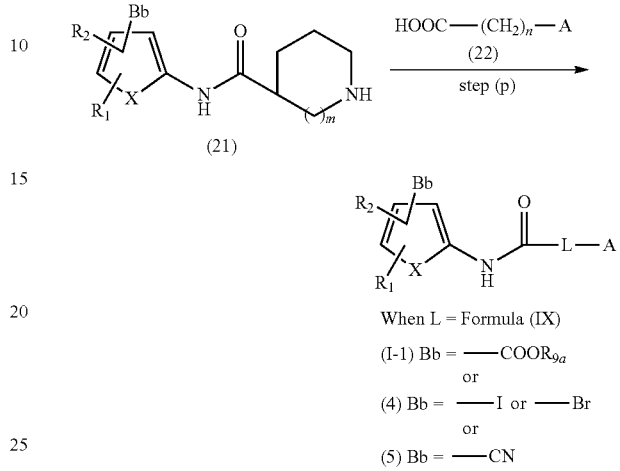

wherein $R_1$, $R_2$, $R_{9a}$, X, m, n, Bb, and A are as defined above; and P represents a protecting group of an amino group.

(2-11) A method for producing a compound represented by Formula (I-1), a halogen compound (4), or a nitrile compound (5), wherein L is substituted or unsubstituted $C_{1-6}$ alkylene-NHCO—, the method comprising the following steps (q) to (s):

(q) a step of condensing a compound (1), (1'), or (1") and a compound (23), which are represented by the following formulae, to form a compound (24);

(r) a step of removing a protecting group P in the compound (24) formed in step (q) above to form an amine compound (25); and (s) a step of condensing the amine compound (25) formed in step (r) above and a compound (22) to form an ester compound (I-1), a halogen compound (4), or a nitrile compound (5):

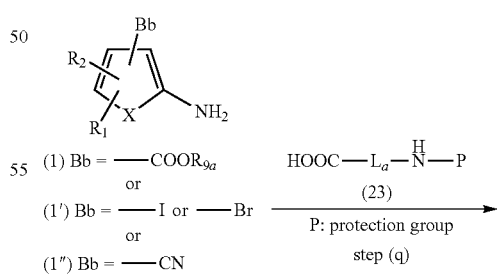

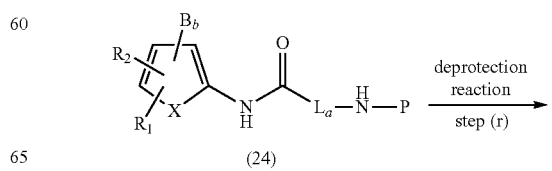

-continued

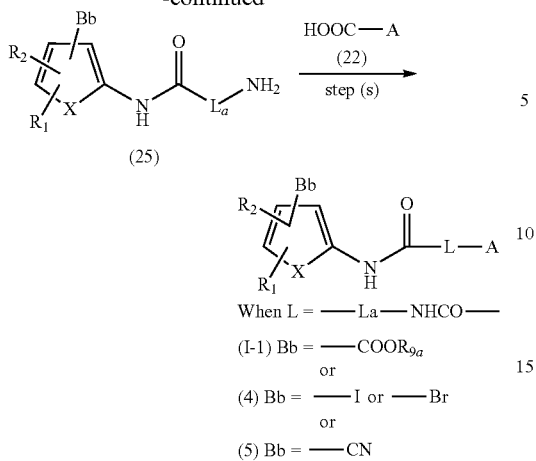

When L = —La—NHCO—
(I-1) Bb = —COOR$_{9a}$
or
(4) Bb = —I or —Br
or
(5) Bb = —CN wherein $R_1$, $R_2$, $R_{9a}$, X, La, Bb, P, and A are as defined above.

(2-12) A method for producing a compound represented by Formula (I-1), a halogen compound (4), or a nitrile compound (5), the method comprising the following step (t):

(t) a step of reacting a compound (26) with a compound (27), which are represented by the following formulae, further followed by condensation with a compound (1), (1'), or (1") to form a compound represented by Formula (I-1), a halogen compound (4), or a nitrile compound (5):

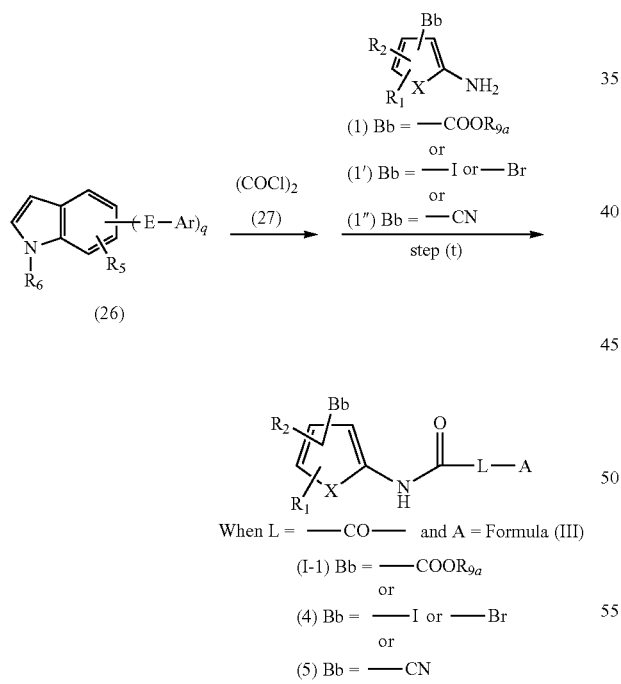

When L = —CO— and A = Formula (III)
(I-1) Bb = —COOR$_{9a}$
or
(4) Bb = —I or —Br
or
(5) Bb = —CN wherein $R_1$, $R_2$, $R_5$, $R_6$, E, Bb, Ar, $R_{9a}$, and X are as defined above.

(2-13) A method for producing a compound represented by Formula (I-2), comprising the following step (u):

(u) a step of reacting a compound (1a) and a compound (28), which are represented by the following formulae, to produce a compound (I-2):

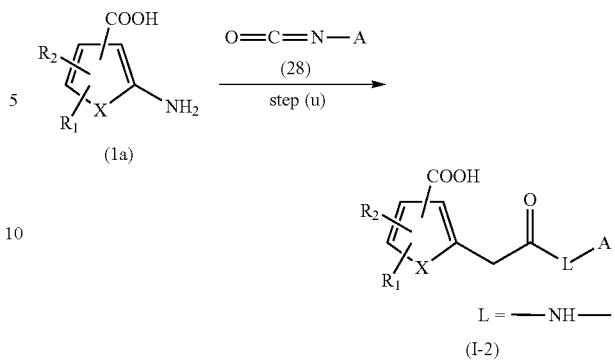

L = —NH—
(I-2)

wherein $R_1$, $R_2$, X, and A are as defined above.

(2-14) A method for producing a compound represented by Formula (I-1), a halogen compound (4), or a nitrile compound (5), wherein L represents 1,4-piperazidinyl or —NH—, the method comprising the following step (v):

(v) a step of condensing a compound (1), (1'), or (1") and a compound (29), which are represented by the following formulae, further followed by condensation with a compound (30) or a compound (31) to form a compound represented by Formula (I-1), a halogen compound (4), or a nitrile compound (5):

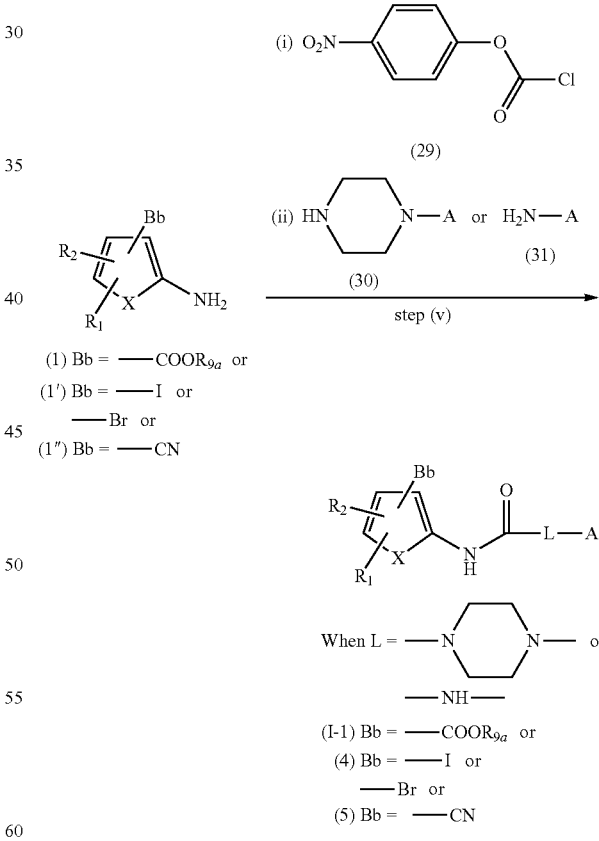

When L = —N⟨piperazine⟩N— or
—NH—
(I-1) Bb = —COOR$_{9a}$ or
(4) Bb = —I or
—Br or
(5) Bb = —CN wherein $R_1$, $R_2$, $R_{9a}$, Bb, A, and X are as defined above.

(2-15) A method for producing a compound represented by Formula (I-2), comprising the following step (w):

(w) a step of reacting a compound (32) with a compound (31), which are represented by the following formulae, to produce a compound represented by Formula (I-2):

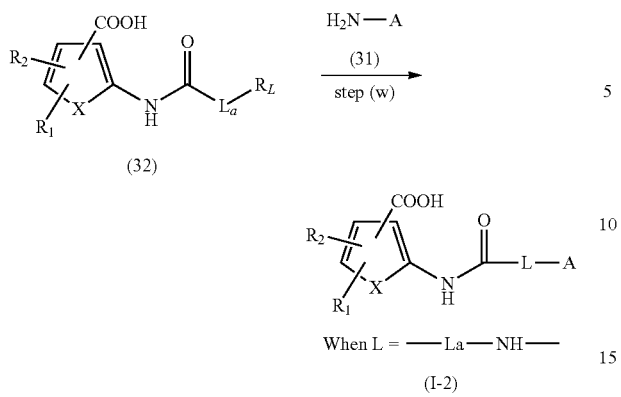

When L = —La—NH—

(I-2)

wherein $R_1$, $R_2$, X, La, $R_L$, and A are as defined above.

(2-16) A method for producing a compound represented by Formula (I-1) or a nitrile compound (5), comprising the following steps (x) and (y):

(x) a step of reacting a compound (33) with a compound (2), which are represented by the following formulae, to produce a compound (34); and (y) a step of reacting the compound (34) produced in step (x) above with a compound (14) or a compound (15) to form a compound represented by Formula (I-1) or a nitrile compound (5):

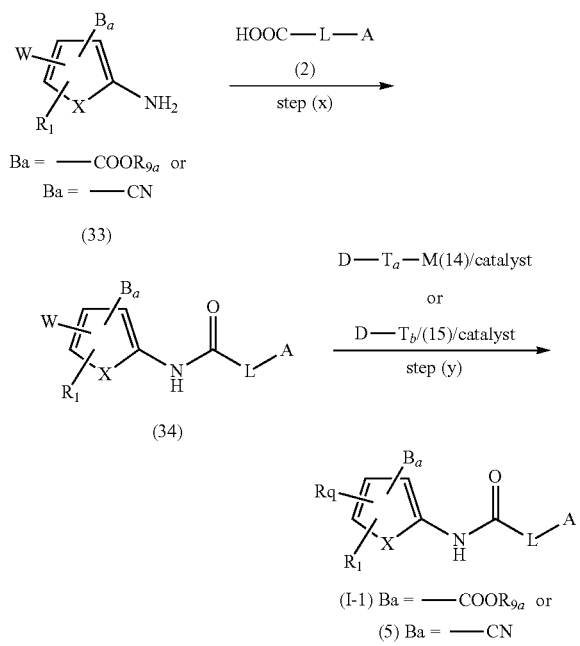

wherein $R_1$, Ba, W, X, L, A, D, Ta, Tb, M, and $R_{9a}$ are as defined above; and Rq represents D-Ta— or D-Tb—.

(2-17) A method for producing the production intermediate (1) or the compound (1'), comprising the following step (z):

(z) a step of reacting a compound (33) with a compound (14) or a compound (15), which are represented by the following formulae, to produce the compound (1) or the compound (1"):

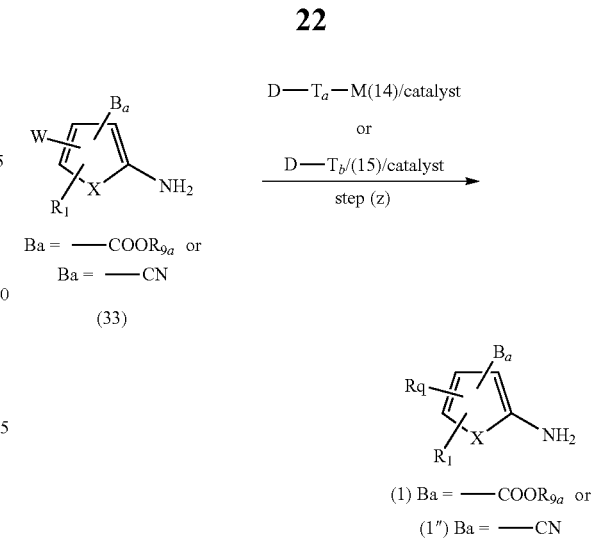

wherein $R_1$, Ba, W, X, D, Ta, Tb, M, Rq, and $R_{9a}$ are as defined above.

(2-18) A method for producing the production intermediate (2), wherein A is as defined in (2-8), comprising the following steps (aa) and (ab):

(aa) a step of reacting a compound (35) with a compound (14) or a compound (15), which are represented by the following formulae, to form a compound (36); and (ab) a step of removing $R_{14}$ in the compound (36) formed in step (aa) above to form the compound (2):

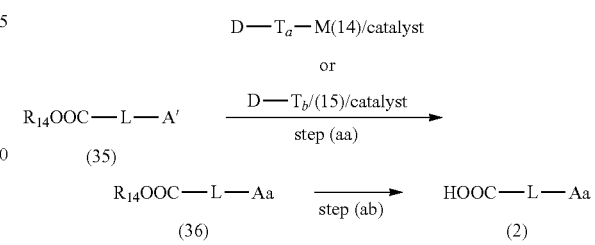

wherein A', Aa, L, D, Ta, Tb, and M are as defined above; $R_{14}$ represents alkyl, aryl, aralkyl, or hydrogen; and A is as defined in (2-8)).

(2-19) A method for producing the production intermediate (13), comprising the following step (ac); steps (ad) to (af); or step (ag):

(ac) a step of reacting a compound (37) with a compound (38), which are represented by the following formulae, to produce a compound (13):

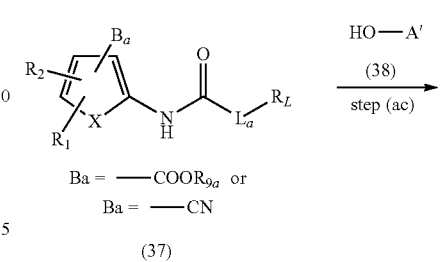

-continued

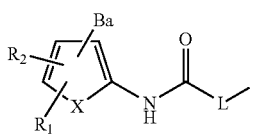

When L = —L$_a$—O—
Ba = —COOR$_{9a}$ or
Ba = —CN (13)

wherein R$_1$, R$_2$, A', Ba, L$_a$, X, R$_L$ and R$_{9a}$ are as defined above;

(ad) a step of reacting a compound (38) with a compound (39), which are represented by the following formulae, to form a compound (40); and (ae) a step of removing R$_{15}$ in the compound (40) formed in step (ad) above to form a carboxylic acid compound (41); and (af) a step of condensing the compound (41) formed in step (ae) above with a compound (1) or a compound (1') to form a compound (13):

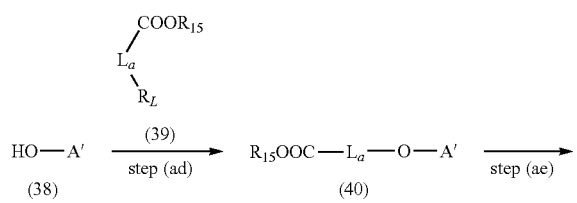

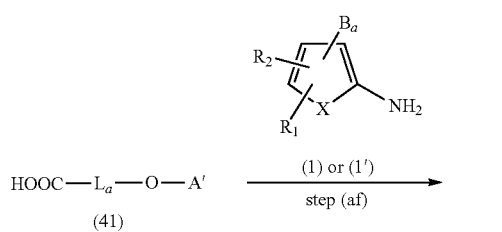

When L = —L$_a$—O—
Ba = —COOR$_{9a}$ or
Ba = —CN (13)

wherein R$_1$, R$_2$, A', Ba, L$_a$, X, R$_L$, and R$_{9a}$ are as defined above; R$_{15}$ represents alkyl, aryl, or aralkyl; and L represents substituted or unsubstituted C$_{1-6}$ alkylene-O— (some carbon atoms in the alkylene optionally form a cycloalkyl ring);

(ag) a step of reacting a compound (42) with a compound (43), which are represented by the following formulae, to form a compound (13):

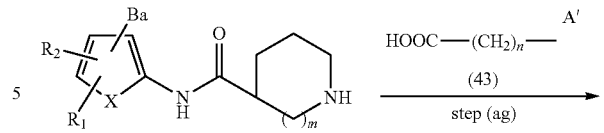

Ba = —COOR$_{9a}$ or
Ba = —CN (42)

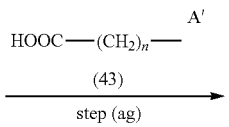

When L = Formula (II)
Ba = —COOR$_{9a}$ or
Ba = —CN (13)

wherein R$_1$, R$_2$, Ba, X, m, n, A' and R$_{9a}$ are as defined above.

(3) PAI-1 Inhibitor (3-1) A PAI-1 inhibitor comprising, as an active ingredient, a compound according to any of (1-1) to (1-10) (including the compounds described in the provision in (1-1)) or a salt thereof, or a solvate thereof.

(3-2) A compound according to any of (1-1) to (1-10) or a salt thereof, or a solvate thereof, which is used as a PAI-1 inhibitor.

(4) Pharmaceutical Composition (4-1) A pharmaceutical composition comprising an effective amount of the compound having an inhibitory action on the PAI-1 activity according to any of (1-1) to (1-10) (including the compounds described in the provision in (1-1)) or a salt thereof, or a solvate thereof; and a pharmacologically acceptable carrier or additive.

(4-2) The pharmaceutical composition according to (4-1), the composition being a prophylactic or therapeutic agent for a disease whose development is contributed by PAI-1 activity.

(4-3) The pharmaceutical composition according to (4-2), wherein the disease whose development is attributed to PAI-1 activity is thrombosis in arteries; thrombosis in veins; deep-vein thrombosis (DVT) during surgical operations; disseminated intravascular coagulation syndrome (DIC); diabetic complications such as angiopathy (macroangiopathy or microangiopathy), neuropathy, retinopathy (diabetic retinopathy), or nephropathia (diabetic nephropathy); restenosis after percutaneous transluminal coronary angioplasty (PTCA); cancer; diabetes mellitus; ocular diseases such as glaucoma or oxygen-induced retinopathy; kidney disease (chronic kidney disease (CKD), nephrotic syndrome, post-renal kidney injury, or pyelonephritis); polycystic ovary syndrome; radiation damage; alopecia (calvities); splenohepatomegaly; bone-marrow regeneration; obesity; amyloidosis; arteriosclerosis; or Alzheimer's disease.

(4-4) The pharmaceutical composition according to (4-3), wherein the thrombosis in arteries is thrombosis in the brain, specifically, cerebral infarction (cerebral thrombosis, cerebral embolism or transient ischemic attack), thrombosis in the heart (angina pectoris or cardiac infarction), thrombosis in the lower extremities (acute lower extremity arterial thrombosis), or thrombosis in the upper intestinal tract (upper intestinal tract arterial thrombosis);

and the thrombosis in veins is thrombosis occurring in the limbs (deep-vein thrombosis) or thrombosis occurring when a blood clot travels to the lung (pulmonary embolism).

(4-5) The pharmaceutical composition according to (4-2), wherein the disease whose development is attributed to PAI-1 activity is a disease accompanied by tissue fibrosis.

(4-6) The pharmaceutical composition according to (4-5), wherein the disease accompanied by tissue fibrosis is pulmonary fibrosis.

(4-7) The pharmaceutical composition according to (4-1) as a fibrinolysis promoter; cancer progression inhibitor; anti-tissue fibrosis agent (anti-pulmonary fibrosis agent, anti-hepatic fibrosis agent, or anti-renal fibrosis agent); antidiabetic drug; drug for treating diabetic complications such as macroangiopathy or microangiopathy; drug for treating kidney disease (diabetic nephropathydrug, chronic kidney disease (CKD) drug, drug for nephrotic syndrome, drug for post-renal kidney injury, or drug for pyelonephritis); anti-glaucoma agent; anti-diabetic retinopathy agent; drug for preventing oxygen-induced retinopathy; drug for treating polycystic ovary syndrome; anti-radiation damage drug; anti-alopecia agent; drug for treating splenohepatomegaly; agent for promoting bone-marrow regeneration; anti-obesity drug; anti-amyloid drug; anti-arteriosclerosis agent, or anti-Alzheimer's drug.

(4-8) The pharmaceutical composition according to any one of (4-1) to (4-7), the composition being orally administered.

(5) Method for Preventing or Treating a Disease Whose Development is Contributed by PAI-1 Activity (5-1) A method for treating or preventing a disease whose development is attributed to PAI-1 activity, the method comprising administering a subject being affected or potentially affected with the disease an effective amount of the compound having an inhibitory action on the PAI-1 according to any one of (1-1) to (1-10) (including the compounds described in the provision in (1-1)) or a salt thereof, or a solvate thereof in a combination with a pharmacologically acceptable carrier or additive.

(5-2) The method according to (5-1), wherein the disease whose development is attributed to PAI-1 activity is thrombosis in arteries; thrombosis in veins; deep-vein thrombosis (DVT) during surgical operations; disseminated intravascular coagulation syndrome (DIC); diabetic complications such as angiopathy (macroangiopathy or microangiopathy), neuropathy, retinopathy (diabetic retinopathy), or nephropathia (diabetic nephropathy); restenosis after percutaneous transluminal coronary angioplasty (PTCA); cancer; diabetes mellitus; ocular diseases such as glaucoma or oxygen-induced retinopathy; kidney disease (chronic kidney disease (CKD), nephrotic syndrome, post-renal kidney injury, or pyelonephritis); polycystic ovary syndrome; radiation damage; alopecia (calvities); splenohepatomegaly; bone-marrow regeneration; obesity, amyloidosis; arteriosclerosis; or Alzheimer's disease.

(5-3) The method according to (5-2), wherein the thrombosis in arteries is thrombosis in the brain (cerebral thrombosis, cerebral embolism, or transient ischemic attack), thrombosis in the heart (angina pectoris or myocardial infarction), thrombosis in the lower extremities (lower extremity acute arterial thrombosis), or thrombosis in the upper intestinal tract (upper intestinal tract arterial thrombosis); and the thrombosis in veins is thrombosis in the extremities (deep-vein thrombosis) or thrombosis occurring when a blood clot travels to the lung (pulmonary embolism).

(5-4) The method according to (5-1), wherein the disease whose development is attributed to PAI-1 activity is a disease accompanied by tissue fibrosis.

(5-5) The method according to (5-4), wherein the disease accompanied by tissue fibrosis is pulmonary fibrosis.

(6) A Compound Used for Preventing or Treating the Disease Whose Development is Attributed to PAI-1 Activity (6-1) A compound having an inhibitory action on the PAI-1 according to any of (1-1) to (1-10) (including the compounds described in the provision in (1-1)) or a salt thereof, or a solvate thereof, used for preventing or treating a disease whose development is attributed to PAI-1 activity.

(6-2) The compound according to (6-1) or a salt thereof, or a solvate thereof, wherein the disease whose development is attributed to PAI-1 activity is thrombosis in arteries; thrombosis in veins; deep-vein thrombosis (DVT) during surgical operations; disseminated intravascular coagulation syndrome (DIC); diabetic complications such as angiopathy (macroangiopathy or microangiopathy), neuropathy, retinopathy (diabetic retinopathy), or nephropathia (diabetic nephropathy); restenosis after percutaneous transluminal coronary angioplasty (PTCA); cancer; diabetes mellitus; ocular diseases such as glaucoma or oxygen-induced retinopathy; kidney disease (chronic kidney disease (CKD), nephrotic syndrome, post-renal kidney injury, or pyelonephritis); polycystic ovary syndrome; radiation damage; alopecia (calvities); splenohepatomegaly; bone-marrow regeneration; obesity; amyloidosis; arteriosclerosis; or Alzheimer's disease.

(6-3) The compound according to (6-2) or a salt thereof, or a solvate thereof, wherein the thrombosis in arteries is thrombosis in the brain (cerebral thrombosis, cerebral embolism, or transient ischemic attack); thrombosis in the heart (angina pectoris or myocardial infarction); thrombosis in the lower extremities (lower extremity acute arterial thrombosis); or thrombosis in the upper intestinal tract (upper intestinal tract arterial thrombosis); and the thrombosis in veins is thrombosis in the extremities (deep-vein thrombosis) or thrombosis occurring when a blood clot travels to the lung (pulmonary embolism).

(6-4) The compound according to (6-1) or a salt thereof, or a solvate thereof, wherein the disease whose development is attributed to PAI-1 activity is a disease accompanied by tissue fibrosis.

(6-5) The compound according to (6-4) or a salt thereof, or a solvate thereof, wherein the disease accompanied by tissue fibrosis is pulmonary fibrosis.

Effects of Invention

The present invention provides a novel low-molecular-weight compound having a highly inhibitory effect on PAI-1. Such a compound is useful as an active ingredient of a pharmaceutical composition such as a prophylactic or therapeutic agent for various kinds of diseases and pathological conditions whose development is attributed to PAI-1 activity.

The present invention provides a pharmaceutical composition that comprises, as an active ingredient, a low-molecular-weight compound that can be synthesized in large amounts. As described above, the pharmaceutical composition comprises, as an active ingredient, a compound (PAI-1 inhibitor) that has a highly inhibitory effect on PAI-1, and that can thus be effectively used as a prophylactic or therapeutic agent for various diseases whose development is attributed to PAI-1 activity. Specifically, the pharmaceutical composition of the present invention is effective as a fibrinolysis promoter for preventing or treating thrombosis in arteries; thrombosis in veins; deep-vein thrombosis (DVT) during surgical operations; disseminated intravascular coagulation syndrome (DIC); diabetic complications such as angiopathy (macroangiopathy or microangiopathy), neuropathy, retinopathy (diabetic retinopathy), or nephropathia (diabetic nephropathy); or restenosis after percutaneous transluminal coronary angioplasty (PTCA). The pharmaceutical composition of the present invention is also effective as an anti-fibrosis agent for preventing or treating various kinds of diseases associated with tissue fibrosis, particularly pulmonary fibrosis. Further, the pharmaceutical composition of the present invention is effective in preventing or treating various diseases and pathological conditions such as cancer; diabetes mellitus; ocular diseases such as glaucoma, diabetic retinopathy, and oxygen-induced retinopathy; kidney diseases (diabetic nephropathia, chronic kidney disease (CKD), nephrotic syndrome, post-renal kidney injury, pyelonephritis, and the like); polycystic ovary syndrome; radiation damage; alopecia (calvities); splenohepatomegaly; bone-marrow regeneration; obesity; amyloidosis; and arteriosclerosis. Further, the pharmaceutical composition of the present invention is effective, based on the Aβ decomposition-promoting effect achieved by the PAI-1 inhibition, for preventing and treating Alzheimer's disease, which is considered to be caused by Aβ deposition in the brain.

BRIEF DESCRIPTION OF DRAWINGS

FIG. 3 shows the anti-fibrotic effects of N,N'-bis[3,3'-carboxy-4,4'-(2,2'-thienyl)-2,2'-thienyl]hexanedicarboxyamide (compound b) on bleomycin-induced pulmonary fibrosis, wherein FIG. 3a shows fibrosis scores, and FIG. 3b shows images of histological stains (see Reference Test Example (3)).

Figure 1:
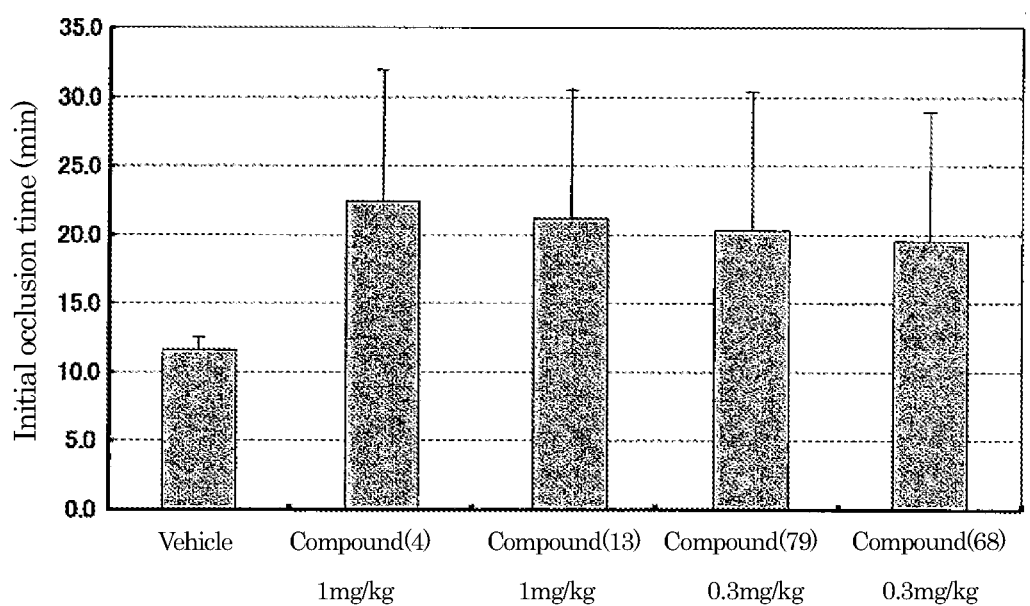
FIG. 1 shows results of Test Example 3 showing that the compounds of the present invention (compounds (4), (13), (68), and (79)) have an excellent antithrombotic effect.

DESCRIPTION OF EMBODIMENTS (1) Compound (I) of the Present Invention

The compounds of the present invention are represented by Formula (I) below.

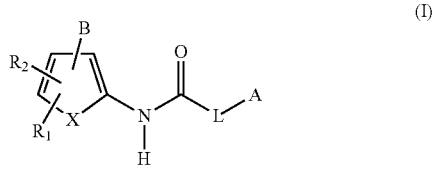

(I)

wherein $R_1$ and $R_2$ are the same or different, and each represents hydrogen, halogen, $C_{1-6}$ alkyl, $C_{3-8}$ cycloalkyl, $C_{3-8}$-cycloalkyl-$C_{1-6}$-alkyl, $C_{3-8}$-cycloalkenyl, $C_{2-6}$-alkynyl, $C_{3-8}$-cycloalkyl-$C_{2-6}$-alkynyl, substituted or unsubstituted aryl; or substituted or unsubstituted 5- to 6-membered ring heteroaryl. Preferable examples include hydrogen, halogen, $C_{1-6}$ alkyl, aryl optionally having one or two substituents, and 5- to 6-membered ring heteroaryl optionally having one or two substituents. $R_1$ and $R_2$ are not hydrogen at the same time. In more preferable examples, either $R_1$ or $R_2$ is hydrogen and the other is halogen, aryl optionally having one substituent, or 5-membered ring heteroaryl.

X represents sulfur or vinylene (—CH═CH—). Preferably, X is vinylene.

A represents fluorenyl, substituted or unsubstituted quinolyl, or the groups of (a)-(e) described below.

(a) Group Represented by Formula (II) Below

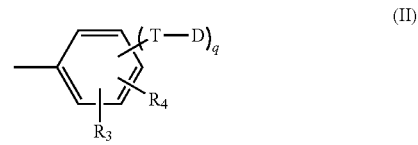

(II)

In Formula (II), q is an integer 0 or 1.

$R_3$ and $R_4$ are the same or different, and represent hydrogen, substituted or unsubstituted $C_{1-6}$ alkyl, or $CF_3$. When q is 0, $R_3$ and $R_4$ are not hydrogen at the same time. When q is 1, preferably $R_3$ and $R_4$ are hydrogen at the same time or either $R_3$ or $R_4$ is hydrogen. When both $R_3$ and $R_4$ are groups other than hydrogen, preferably q is 0.

T is a single bond, substituted or unsubstituted $C_{1-3}$ alkylene, oxygen, —CO—, —O—$C_{1-3}$-alkylene, or $C_{2-6}$ alkynylene. T is preferably a single bond.

D is substituted or unsubstituted aryl, heteroaryl, or benzo-fused heteroaryl; substituted or unsubstituted $C_{3-8}$ cycloalkyl or $C_{3-8}$ heterocycloalkyl; substituted or unsubstituted $C_{3-8}$ cycloalkenyl or $C_{3-8}$ heterocycloalkenyl; or adamanthyl. D is preferably aryl, heteroaryl, or benzo-fused heteroaryl, which is optionally having one or two substituents.

When L in Formula (I) is substituted or unsubstituted $C_{1-6}$ alkylene-NHCO—, and T in Formula (II) is a single bond, D is not an "unsubstituted phenyl".

(b) Group Represented by any of Formulae (III)-(V)

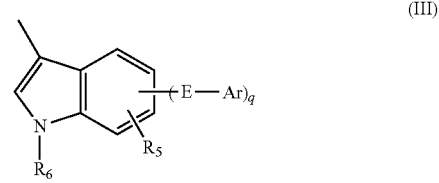

(III)

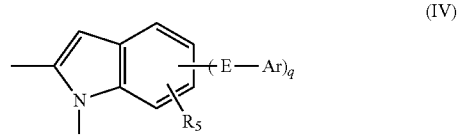

(IV)

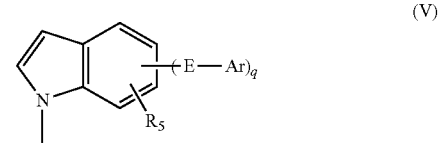

(V)

In Formulae (III)-(V), q is an integer 0 or 1; however, when $R_5$ described later is hydrogen, q is 1.

$R_5$ is hydrogen or halogen. Preferably, when q is 0, $R_5$ is halogen, and when q is 1, $R_5$ is hydrogen.

$R_6$ is hydrogen, $C_{1-6}$ alkyl, or $C_{1-6}$ hydroxyalkyl. Preferably, $R_6$ is hydrogen or $C_{1-6}$ alkyl.

E is a single bond or —O-alkylene. Preferably, E is a single bond.

Ar is substituted or unsubstituted aryl, or substituted or unsubstituted heteroaryl. Preferably, Ar is unsubstituted aryl.

(c) Group Represented by Formula (VI)

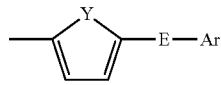

(VI)

In Formula (VI), Y is sulfur or oxygen.

E is a single bond or —O-alkylene. Preferably, E is a single bond.

Ar is substituted or unsubstituted aryl, or substituted or unsubstituted heteroaryl. Preferably, Ar is substituted or unsubstituted aryl.

(d) Group Represented by Formula (VII)

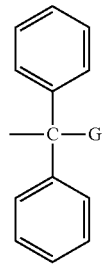

(VII)

In Formula (VII), G is hydrogen or $C_{1-6}$ alkyl. Preferably, G is hydrogen.

(e) Group Represented by Formula (VIII)

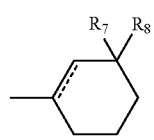

(VIII)

In Formula (VIII), $R_2$ and $R_8$ are hydrogen or alkylene at the same time and bind to each other to form 3- to 8-membered ring cycloalkane. When $R_2$ and $R_8$ are hydrogen at the same time, L described later is substituted or unsubstituted $C_{1-6}$ alkenylene. Preferably, $R_2$ and $R_8$ are hydrogen or alkylene that bind to each other to form cyclohexane.

In Formula (VIII), ----- a single or double bond.

Among the groups represented by Formulae (II) to (VIII), the groups represented by Formulae (II), (III), (IV), (V) and (VIII) are preferable, and the groups represented by Formula (II), (III) and (IV) are more preferable.

L is a single bond, substituted or unsubstituted $C_{1-6}$ alkylene (some carbon atoms in the alkylene optionally form cycloalkyl), substituted or unsubstituted $C_{1-6}$ alkylene-O— (some carbon atoms in the alkylene optionally form cycloalkyl), substituted or unsubstituted $C_{1-6}$ alkylene-NHCO— (in alkylene-NHCO—, some carbon atoms in the alkylene optionally form cycloalkyl), substituted or unsubstituted $C_{1-6}$ alkylene-NH— (in alkylene-NH—, some carbon atoms in the alkylene optionally form cycloalkyl), substituted or unsubstituted $C_{2-6}$ alkenylene, substituted or unsubstituted $C_{2-6}$ alkynylene, —CO—, —NH—, —CONH—, 1,4-piperazidinyl, $C_{1-6}$ alkylene-1,4-piperazidinyl, adamantylene, or a group represented by the following Formula (IX):

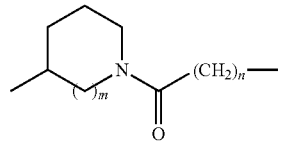

(IX)

wherein, in $(CH_2)_n$, one or more carbons are optionally substituted and may form cycloalkyl with a substituent of the carbon, provided that m is an integer 0 or 1, and n is an integer 0 to 2);

L is preferably a single bond, $C_{1-6}$ alkylene optionally having one or two substituents, $C_{1-6}$ alkylene-O— optionally having one or two substituents, $C_{2-6}$ alkenylene optionally having one or two substituents, $C_{2-6}$ alkynylene optionally having one or two substituents, or a group represented by Formula (IX) below. L is more preferably a single bond, $C_{1-6}$ alkylene, $C_{1-6}$ alkylene-O—, or a group represented by Formula (IX) above.

When L is —CONH—, however, A is a group represented by Formula (II), q is 1, T is a single bond, and D is adamanthyl. More preferably, A is a group represented by Formula (II), wherein q is 1, T is a single bond, D is adamanthyl, and both $R_3$ and $R_4$ are hydrogen. Here, the compound (I) is aromatic carboxylic acid whose X is vinylene or a biological equivalent thereof.

When L is 1,4-piperazidinyl or $C_{1-6}$ alkylene-1,4-piperazidinyl, A is a group represented by Formula (VII). Here, the compound (I) is aromatic carboxylic acid whose X is vinylene or a biological equivalent thereof.

B is $COOR_9$ or a heterocyclic group represented by any of Formulae (XI) to (XIII).

In the formulae, $R_9$ in $COOR_9$ is, for example, hydrogen; or a group converted to hydrogen in vivo, which is selected from the group consisting of $C_{1-6}$ alkyl, aryl, aralkyl, —CH($R_{10}$)—O—COR$_{11}$, —CH($R_{10}$)—O—CO—OR$_{11}$, and (5-alkyl-2-oxo-1,3-dioxolen-4-yl)methyl represented by the following Formula (X):

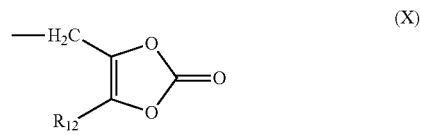

(X)

wherein $R_9$ is hydrogen or $C_{1-6}$ alkyl, and $R_{10}$ is $C_{1-6}$ alkyl or $C_{3-8}$ cycloalkyl. $R_{11}$ and $R_{12}$ each represent $C_{1-6}$ alkyl. $R_9$ in $COOR_9$ preferably is hydrogen.

The heterocyclic group is represented by any of Formulae (XI) to (XIII) shown below.

(XI)

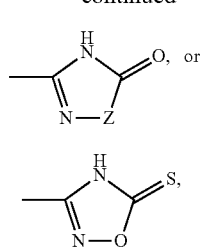

(XII)

(XIII)

wherein Z is sulfur or oxygen in the heterocyclic group represented by Formula (XII).

B is preferably carboxy (when the $R_9$ in $COOR_9$ is hydrogen), or a heterocyclic group represented by Formula (XI).

The designation of each group represented by these characters and specific examples thereof are described below.

Examples of the "alkyl" represented by $R_1$ to $R_4$, $R_6$, $R_9$ to $R_{12}$, or G in the compound of the present invention, unless otherwise specified, generally include $C_{1-6}$ linear or branched alkyl groups. Examples of such alkyl groups include methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, etc. Preferable groups are $C_{1-4}$ lower alkyl groups such as methyl, ethyl, propyl, isopropyl, butyl and isobutyl; more preferable are methyl and ethyl; and particularly preferable is methyl.

Among these, the "alkyl" represented by $R_3$ to $R_4$ optionally has one or two substituents. Examples of such substituents include halogen, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, and alkoxycarbonyl. Examples of the "alkoxy" or "alkoxy" in "alkoxycarbonyl" include hydroxyl substituted with preferably $C_{1-6}$ and particularly preferably $C_{1-4}$ alkyl. Examples of such alkoxy include methoxy, ethoxy, 1-propoxy, 2-propoxy, 1-buthoxy, 2-buthoxy, 2-methyl-1-propoxy, 2-methyl-2-propoxy, 1-pentyloxy, 2-pentyloxy, 3-pentyloxy, 2-methyl-2-butoxy, 3-methyl-2-butoxy, 1-hexyloxy, 2-hexyloxy, 3-hexyloxy, 2-methyl-1-pentyloxy, 3-methyl-1-pentyloxy, 2-ethyl-1-butoxy, 2,2-dimethyl-1-butoxy, 2,3-dimethyl-1-butoxy, etc. Preferable among these are methoxy, ethoxy, 1-propoxy, and 2-propoxy, with methoxy being more preferable.

The "alkyl" represented by $R_3$ or $R_4$ include $C_{3-6}$ branched alkyl among the "alkyl" explained above. A preferable example of such branched alkyl is t-butyl.

Examples of "cycloalkyl" represented by $R_1$, $R_2$, or D in the compound of the present invention or "cycloalkyl ring" of L formed by some carbon atoms in the alkylene include typically $C_{3-8}$, preferably $C_{3-6}$, and more preferably $C_5$ or $C_6$ cyclic alkyl. Examples of such cycloalkyl groups include cyclopropyl, cyclobutyl, cyclopentyl, cyclohexyl, cycloheptyl, cyclooctyl, etc. Among these, the "cycloalkyl" represented by D and "cycloalkyl ring" formed by some carbon atoms of L in the alkylene optionally have one or two substituents at any position. Examples of such substituents include halogen, $C_{1-4}$ alkyl, $C_{1-4}$ halogen-substituted alkyl, $C_{1-4}$ alkoxy, $C_{1-4}$ halogen-substituted alkoxy, hydroxyl, $CF_3$, $CF_3O$, $CHF_2O$, $CF_3CH_2O$, cyano, carboxy, alkoxycarbonyl, etc. Here, the meanings of "alkoxy" and "alkoxy" in "alkoxycarbonyl" are as described above.

Examples of "heterocycloalkyl" represented by D in the compound of the present invention include 3- to 8-membered ring cycloalkyls having one or more same or different heteroatoms selected from the group consisting of nitrogen, oxygen, and sulfur. Specific examples thereof include oxiranyl (e.g., 2-oxiranyl), azetidinyl (e.g., 2-azetidinyl), oxetanyl (e.g., 2-oxetanyl and 3-oxetanyl), thietanyl (e.g., 2-thietanyl and 3-thietanyl), pyrrolidinyl (e.g., 1-pyrrolidinyl and 2-pyrrolidinyl), tetrahydrofuryl (e.g., tetrahydrofuran-2-yl and tetrahydrofuran-3-yl), thiolanyl (e.g., 2-thiolanyl and 3-thiolanyl), piperidyl (e.g., piperidino, 2-piperidyl, 3-piperidyl, and 4-piperidyl), tetrahydropyranyl (e.g., 2-tetrahydropyranyl, 3-tetrahydropyranyl, and 4-tetrahydropyranyl), thianyl (e.g., 2-thianyl and 3-thianyl), morpholinyl (e.g., morpholino), thiomorpholinyl (e.g., thiomorpholino), 1,1-dioxido-thiomorpholinyl (e.g., 1,1-dioxido-thiomorpholino), piperazinyl (e.g., 1-piperazinyl and 2-piperazinyl), oxazolidinyl (e.g., oxazolidin-2-yl), thiazolidinyl (e.g., thiazolidin-2-yl), imidazolidinyl (e.g., imidazolidin-1-yl and imidazolidin-2-yl), azepanyl (e.g., 1-azepanyl, 2-azepanyl, 3-azepanyl, and 4-azepanyl), oxepanyl (e.g., 2-oxepanyl, 3-oxepanyl, and 4-oxepanyl), thiepanyl (e.g., 2-thiepanyl, 3-thiepanyl, and 4-thiepanyl), oxazepanyl (e.g., 2-oxazepanyl, 3-oxazepanyl, and 4-oxazepanyl), thiazepanyl (e.g., 2-thiazepanyl, 3-thiazepanyl, and 4-thiazepanyl), azocanyl (e.g., 1-azocanyl, 2-azocanyl, 3-azocanyl, and 4-azocanyl), oxocanyl (e.g., 2-oxocanyl, 3-oxocanyl, and 4-oxocanyl), thiocanyl (e.g., 2-thiocanyl, 3-thiocanyl, and 4-thiocanyl), oxazocanyl (e.g., 2-oxazocanyl, 3-oxazocanyl, and 4-oxazocanyl), thiazocanyl (e.g., 2-thiazocanyl, 3-thiazocanyl, and 4-thiazocanyl), and the like.

5- to 6-Membered ring cycloalkyl having nitrogen is preferable, and pyrrolidinyl is more preferable.

As is the case with the cycloalkyl described above, the cycloheteroalkyl may have one or two substituents at any position. Examples of such substituents are the same as those for the cycloalkyl.

In the compound of the present invention, the "$C_{3-8}$-cycloalkyl-$C_{1-6}$-alkyl groups" represented by $R_1$ or $R_2$ are $C_{1-6}$ alkyls having a typically $C_{3-8}$, preferably $C_{3-6}$, and more preferably $C_5$ or $C_6$ cycloalkyl as a substituent. The number of carbon atoms of the alkyl is preferably 1 to 4, and more preferably 1 or 2. Examples of such cycloalkylalkyl groups include cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl, cycloheptylethyl, cyclooctylmethyl, cyclooctylethyl, etc.

Examples of the "cycloalkenyl" represented by $R_1$, $R_2$, or D in the compound of the present invention include cycloalkyl having one or more double bonds. Specific examples thereof are $C_{3-8}$ cyclic alkenyl having 1 or 2 double bonds. The cyclic alkenyls preferably have 3 to 6 carbon atoms, and more preferably 5 or 6 carbon atoms (5- or 6-membered ring). Such cycloalkenyl groups include cyclopropenyl groups (cycloprop-1-en-1-yl, cycloprop-2-en-1-yl, cycloprop-3-en-1-yl, etc.), cyclobutenyl groups (cyclobut-1-en-1-yl, cyclobut-2-en-1-yl, cyclobut-3-en-1-yl, and cyclobut-4-en-1-yl), cyclobutadienyl groups (cyclobuta-1,3-dien-1-yl and cyclobuta-2,4-dien-1-yl), cyclopentenyl groups (cyclopen-1-en-1-yl, cyclopen-2-en-1-yl, cyclopen-3-en-1-yl, cyclopen-4-en-1-yl, and cyclopen-5-en-1-yl), cyclopentadienyl groups (cyclopenta-2,4-dien-1-yl), cyclohexenyl groups (cyclohex-1-en-1-yl, cyclohex-2-en-1-yl, cyclohex-3-en-1-yl, cyclohex-4-en-1-yl, cyclohex-5-en-1-yl, etc.), and cyclohexadienyl groups (cyclohexa-1,3-dien-1-yl, cyclohexa-2,4-dien-1-yl, cyclohexa-3,5-dien-1-yl, etc.), cycloheptenyl groups, cycloheptdienyl groups, cyclooctenyl groups, cyclooctdienyl groups, and the like.

Preferable examples thereof are $C_5$ or $C_6$ cyclic alkenyl groups having one double bond, and more preferably cyclohexenyl groups.

Examples of "heterocycloalkyl" represented by D in the compound of the present invention include the groups having one or two carbon atoms of the aforementioned cycloalkenyl substituted with same or different heteroatoms selected from the group consisting of nitrogen, oxygen, and sulfur. A preferable example is a $C_5$ or $C_6$ cyclic alkenyl group having one double bond and a more preferable example is a group in which one of the carbon atoms in a cyclohexenyl group is replaced with an oxygen atom.

The "cycloalkenyl" and "heterocycloalkenyl" represented by D may have one or two substituents at any position. Examples of such substituents include halogen, $C_{1-4}$ alkyl, $C_{1-4}$ halogen-substituted alkyl, $C_{1-4}$ alkoxy, $C_{1-4}$ halogen-substituted alkoxy, hydroxyl, $CF_3$, $CF_3O$, $CHF_2O$, $CF_3CH_2O$, cyano, carboxy, and alkoxycarbonyl. Here, the meanings of "alkoxy" and the "alkoxy" in "alkoxycarbonyl" are as defined above.

Examples of the "alkynyl" represented by $R_1$ or $R_2$ in the compound of the present invention include $C_{2-6}$ linear or branched alkynyl groups having a triple bond. Specific examples of such alkynyl groups include ethynyl, 2-propynyl, 2-butynyl, 3-butynyl, 1-methyl-2-propynyl, 2-pentynyl, 2-hexynyl, etc. Among these, ethynyl is preferable.

Examples of "$C_{3-8}$-cycloalkyl-$C_{2-6}$-alkynyl" represented by $R_1$ or $R_2$ in the compound of the present invention include $C_{2-6}$ alkynyl groups having a $C_{3-8}$, preferably $C_{3-6}$, and more preferably $C_5$ or $C_6$ cycloalkyl substituent. The number of carbon atoms in the alkynyl is preferably 2 to 3, and more preferably 2. Such cycloalkylalkynyl groups include cyclopropylethynyl, cyclobutylethynyl, cyclopentylethynyl, cyclohexylethynyl, cycloheptylethynyl, cyclooctylethynyl, and the like.

Preferable examples of the "aryl" represented by $R_1$, $R_2$, D, or Ar in the compound of the present invention include $C_{6-14}$ aromatic hydrocarbon groups. Examples of such aryl groups include phenyl, naphthyl, anthryl, phenanthryl, acenaphthylenyl, etc. Preferable among these are phenyl and naphthyl, and more preferable is phenyl. These groups may have one or two substituents at any position. However, in the compound (I), when L is a substituted or unsubstituted alkylene-NHCO—, and, at the same time, A is a group represented by Formula (II) (provided that T is a single bond), the aryl represented by D is an aryl other than "unsubstituted phenyl". An example of such an aryl is a phenyl having one or more substituents.

Examples of the substituents in the aryl represented by $R_1$, $R_2$, D, or Ar include halogen, $C_{1-6}$ alkyl (preferably $C_{1-4}$ alkyl), $C_{1-6}$ cycloalkyl, $C_{1-6}$ alkoxy (preferably $C_{1-4}$ alkoxy), $C_{1-6}$ cycloalkoxy, $C_{1-6}$ halogen-substituted alkoxy, hydroxyl, $CF_3$, $CF_3O$, $CHF_2O$, $CF_3CH_2O$, cyano, carboxy, alkoxycarbonyl, benzoyl, and phenyl.

Here, the meanings of "alkyl" and "cycloalkyl", and "alkoxy" in "alkoxy", "halogen-substituted alkoxy", and "alkoxycarbonyl" are as defined above. Examples of "cycloalkoxy" include $C_{3-8}$, preferably $C_{3-6}$, and more preferably $C_{4-5}$ cyclic alkoxy groups. Such cycloalkoxy groups include cyclopropyloxy, cyclobutyloxy, cyclopentyloxy, cyclohexyloxy, cycloheptyloxy, cyclooctyloxy, etc.

Examples of "heteroaryl" represented by $R_1$, $R_2$, D, or Ar in the compound of the present invention include 3- to 6-membered ring aryl groups and preferably 5- to 6-membered ring aryl groups having one or more same or different heteroatoms selected from the group consisting of nitrogen, oxygen, and sulfur. Specific examples thereof include pyrrolyl, furyl, thienyl, pyrazolyl, imidazolyl, oxazolyl, isoxazolyl, thiazolyl, isothiazolyl, oxadiazolyl, thiadiazolyl, triazolyl, tetrazolyl, pyridyl, pyridazinyl, pyrimidinyl, pyrazinyl, and like unsaturated monoheterocyclic groups.

These groups may have one or two substituents at any position. Examples of substituents of the heteroaryl include halogen, $C_{1-6}$ alkyl (preferably $C_{1-4}$ alkyl), $C_{3-8}$ cycloalkyl, $C_{1-6}$ alkoxy (preferably $C_{1-4}$ alkoxy), $C_{3-8}$ cycloalkoxy, $C_{1-6}$ halogen-substituted alkoxy, hydroxyl, $CF_3$, $CF_3O$, $CHF_2O$, $CF_3CH_2O$, cyano, carboxy, alkoxycarbonyl, benzoyl, phenyl, and phosphonooxymethyl. Here, the meanings of "alkyl" and "cycloalkyl", and "alkoxy" in "alkoxy", "cycloalkoxy", "halogen-substituted alkoxy", and "alkoxycarbonyl" are as defined above. Further, the phosphonooxymethyl group is a substituent of "heteroaryl" at the 1-position when the heteroaryl is pyrazolyl or pyrrolyl that is removed in vivo and converts to a pyrazolyl or pyrrolyl group unsubstituted at the 1-position, allowing the pyrazolyl or pyrrolyl group to show PAI-1 inhibition activity. In other words, phosphonooxymethyl is a substituent that serves as a so-called prodrug.

When a substituent of D or Ar is cycloalkyl or cycloalkoxy, the substituent may also have a substituent. Examples of such substituents include halogen, $C_{1-6}$ alkyl, $C_{1-6}$ alkoxy, $C_{1-6}$ halogen-substituted alkoxy, hydroxyl, $CF_3$, $CF_3O$, $CHF_2O$, $CF_3CH_2O$, cyano, carboxy, alkoxycarbonyl, benzoyl, and phenyl.

Examples of the "benzo-fused heteroaryl" represented by D in the compound of the present invention include groups in which the benzene ring is fused with the above-mentioned heteroaryl. Specific examples thereof include indolyl, isoindolyl, benzofuranyl, benzothienyl, benzimidazolyl, benzisoxazolyl, benzothiazolyl, benzisothiazolyl, quinolyl, isoquinolyl, quinazolinyl, quinoxalinyl, benzoxadiazolyl, benzothiadiazolyl, etc.

The above benzo-fused heteroaryl may have one to three substituents at any position. Examples of such substituents include halogen, $C_{1-4}$ alkyl, $C_{1-4}$ halogenated alkyl, $C_{1-4}$ alkoxy, $C_{1-4}$ halogenated alkoxy, hydroxyl, $CF_3$, $CF_3O$, $CHF_2O$, $CF_3CH_2O$, aryl (preferably phenyl), halogenated aryl, cyano, carboxy, alkoxycarbonyl having $C_{1-4}$ alkoxy, etc. Here, the meanings of "alkyl", "alkoxy", and "aryl" are as defined above.

Examples of the "alkylene group" and the "alkylene" in "alkylene-O—", "alkylene-NH—", "alkylene-NHCO—", and "alkylene-piperazidinyl" represented by L in the compound of the present invention include typically $C_{1-6}$, and preferably $C_{1-4}$ linear or branched alkylene. Examples of such alkylene groups include methylene, ethylene, propylene, trimethylene, 1-ethyl-1,2-ethylene, 1-propyl-1,2-ethylene, 1-isopropyl-1,2-ethylene, 1-butyl-1,2-ethylene, 1,2-dimethyl-1,2-ethylene, tetramethylene, pentamethylene, and hexamethylene. Among these, methylene and ethylene are preferable.

The "alkylene group" and the "alkylene" in "alkylene-O—", "alkylene-NH—", and "alkylene-NHCO—" may be those in which some of the carbon atoms in the alkylene bind to form a $C_{3-8}$ cycloalkyl ring (cycloalkane). Examples of such cycloalkyl rings include cyclopropane, cyclobutane, cyclopentane, cyclohexane, cycloheptane, and cyclooctane.

Examples of "alkenylene" represented by L in the compound of the present invention include $C_{2-6}$ linear or branched alkenylene having 1 to 3 double bonds. Examples of such alkenylene groups include vinylene, 1-methylvinylene, propenylene, 1-butenylene, 2-butenylene, 1-pentenylene, 2-pentenylene, etc. Preferably, the alkenylene is vinylene.

Examples of the "alkynylene" represented by L and T in the compound of the present invention include $C_{2-6}$ linear or branched alkynylene groups having one triple bond. Examples of such alkynylene groups include ethynylene, propynylene, 1-methylpropynylene, 1-butynylene, 2-butynylene, 1-methylbutynylene, 2-methylbutynylene, 1-pentynylene, and 2-pentynylene.

The "alkylene", "alkylene-O—", "alkylene-NH—", "alkylene-NHCO—", "alkenylene", and "alkynylene" each may have one or two substituents. Examples of such substituents include halogen, $C_{1-4}$ alkoxy, $C_{1-4}$ halogen-substituted alkoxy, hydroxyl, $CF_3$, $CF_3O$, $CHF_3O$, $CF_3CH_2O$, cyano, carboxy, alkoxycarbonyl, amino, acylamino, benzyloxycarbonylamino (Cbz-NH—), alkoxycarbonylamino (e.g., t-butoxycarbonylamino (tBoc-NH—), methoxycarbonylamino, ethoxycarbonylamino, propoxycarbonylamino, isopropoxycarbonylamino, and butoxypropoxycarbonylamino), acyl, etc. The meaning of the "alkoxy" is as defined above.

Examples of "alkylene" represented by T and E in the compound (I) of the present invention and "alkylene" represented by T in "—O-alkylene" include typically $C_{1-3}$ linear or branched alkylenes. Such alkylenes include methylene, ethylene, propylene, and trimethylene. Preferably, the alkylene is methylene, ethylene, or trimethylene.

Examples of the "halogen atom" in the compound of the present invention include fluorine, chlorine, bromine, and iodine. Preferable are chlorine, bromine, and fluorine; chlorine is more preferable.

The quinolyl represented by A in Formula (I) may have one or two substituents at any position. Examples of such substituents include halogen, $C_{1-4}$ alkyl, $C_{1-4}$ halogenated alkyl, $C_{1-4}$ alkoxy, $C_{1-4}$ halogenated alkoxy, hydroxyl, $CF_3$, $CF_3O$, $CHF_2O$, $CF_3CH_2O$, aryl (preferably phenyl), halogenated aryl, cyano, carboxy, alkoxycarbonyl having $C_{1-4}$ alkoxy, etc. The meanings of "alkyl", "alkoxy", and "aryl" are as defined above. Among these, phenyl is preferable.

Examples of the groups represented by B in Formula (I) include, in addition to carboxyl (COOH), (1) alkoxycarbonyl, aryloxycarbonyl, and aralkyloxycarbonyl, which can be converted to carboxyl when absorbed in vivo; (2) groups that can be easily converted to carboxyl when absorbed in vivo; and (3) groups that have been designated as a group that is biologically equivalent to a carboxyl group. Here, examples of the alkoxycarbonyl, aryloxycarbonyl, and aralkyloxycarbonyl in (1) above include groups that are each represented by $COOR_9$, wherein $R_9$ is $C_{1-6}$ alkyl, aryl (preferably phenyl), or aralkyl (preferably benzyl).

Specific examples of the groups in (2) above include groups represented by $COOR_9$, wherein $R_9$ is a (5-alkyl-2-oxo-1,3-dioxolen-4-yl)methyl group represented by the following formula:

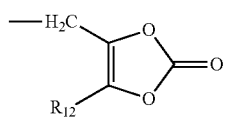

wherein $R_{12}$ is $C_{1-6}$ alkyl,
and a group represented by —CH($R_{10}$)—O—CO$R_{11}$ or —CH($R_{10}$)—O—CO—O$R_{11}$, wherein $R_{10}$ is hydrogen or $C_{1-6}$ alkyl, and $R_{11}$ is $C_{1-6}$ alkyl or $C_{3-8}$ cycloalkyl.

Examples of the groups in (3) above include heterocyclic groups such as 1H-tetrazol-5-yl, 4,5-dihydro-5-oxo-4H-1,2,4-oxadiazol-3-yl, 4,5-dihydro-5-oxo-1,2,4-thiadiazol-3-yl, and 4,5-dihydro-5-thioxo-4H-1,2,4-oxadiazol-3-yl represented by the following formulae in order from the left (see, for example, Kohara et al. J. Med. Chem., 1996, 39, 5228-5235).

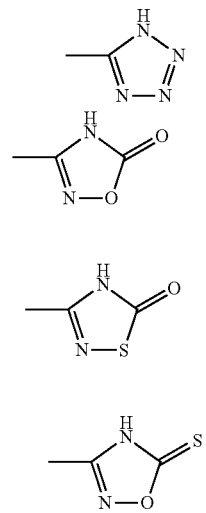

In the present invention, the groups of (1) to (3) mentioned above may each be called a group that is biologically equivalent to a carboxyl group. In this specification, salts of the compound (I) and the compound (I) having the above groups (groups that are biologically equivalent to a carboxyl group) may be collectively called a bioisostere of the carboxylic acid.

Specific examples of the "alkoxycarbonyl" represented by B (when B represents —$COOR_9$, wherein $R_9$ is alkyl) in Formula (I) include t-butoxycarbonyl, methoxycarbonyl, ethoxycarbonyl, propoxycarbonyl, isopropoxycarbonyl, butoxycarbonyl, etc.

The compound (I) targeted by the present invention preferably includes aromatic or heterocyclic carboxylic acids represented by the formula below, and bioisosteres thereof.

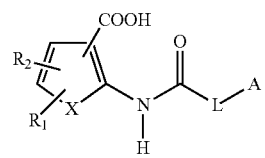

wherein $R_1$, $R_2$, X, L, and A are as defined above.

The compounds (I) of the present invention can be classified into the following categories (a) to (g) depending on the types of substituent A.

(a) Compounds Wherein A is a Group Represented by Formula (II) Below

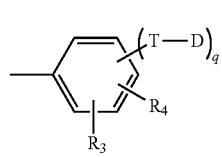

(II)

wherein $R_3$, $R_4$, T, D, and q are as defined above.

(b) Compounds Wherein A is a Group Represented by any of Formulae (III) to (V)

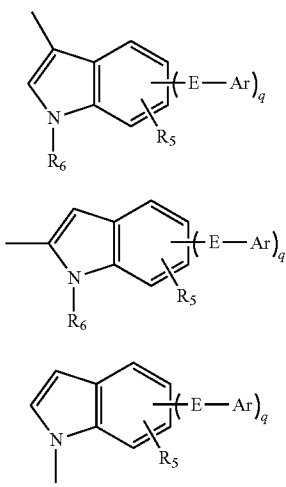

wherein $R_5$, $R_6$, E, Ar, and q are as defined above.
(c) Compounds Wherein A is a Group Represented by Formula (VI)

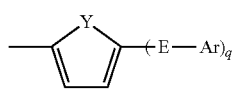

wherein Y, E, Ar, and q are as defined above.
(d) Compounds Wherein A is a Group Represented by Formula (VII)

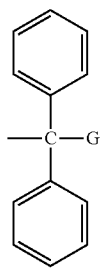

wherein G is as defined above.
(e) Compounds Wherein A is a Group Represented by Formula (VIII)

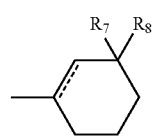

wherein $R_7$ and $R_8$ are as defined above.
(f) Compounds Wherein A is Fluorenyl
(g) Compounds Wherein A is a Substituted or Unsubstituted Quinolyl The compounds (I) of the present invention are explained in detail below for each category of the compounds described above.
(a) Compounds Wherein A is a Group Represented by Formula (II)

Examples of compounds (Ia) belonging to this category include aromatic or heterocyclic carboxylic acids represented by the formula below, and bioisosteres thereof.

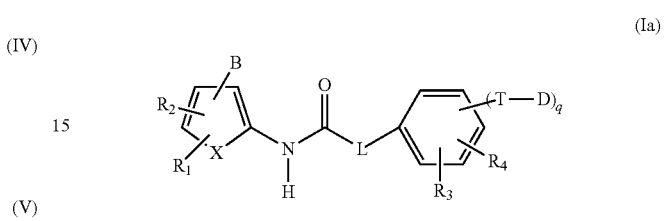

wherein $R_1$ to $R_4$, B, X, L, T, D, and q are as defined above.
The compounds (1a) can be further classified into (Ia-1) to (Ia-5) described below depending on the types of L.
(Ia-1) Compounds wherein L is a single bond;
(Ia-2) Compounds wherein L is substituted or unsubstituted $C_{1-6}$-alkylene-O—;
(Ia-3) Compounds wherein L is substituted or unsubstituted $C_{1-6}$-alkylene, $C_{1-6}$-alkenylene, or $C_{1-6}$-alkynylene;
(Ia-4) Compounds wherein L is —NH—, —CO—, —CONH—, substituted or unsubstituted $C_{1-6}$-alkylene-NH—, substituted or unsubstituted $C_{1-6}$-alkylene-NHCO—, or a compound represented by Formula (IX); and
(Ia-5) Compounds wherein L is adamantylene.
(Ia-1) Compounds Wherein L is Single Bond

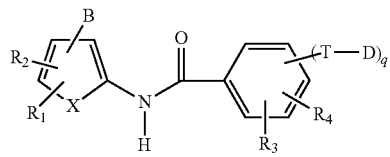

wherein $R_1$ to $R_4$, B, X, T, D, and q are as defined above.
Examples of compound (Ia-1) include aromatic carboxylic acids and bioisosteres thereof wherein X in Formula (Ia-1) is vinylene (—CH=CH—), and heterocyclic carboxylic acids and bioisosteres thereof wherein X in Formula (Ia-1) is sulfur. Aromatic carboxylic acids and bioisosteres thereof wherein X is vinylene are preferable.

In Formula (Ia-1), B, $R_1$, and $R_2$ may be located at any of the ortho, meta, or para positions on the benzene ring to which imino is bound, or the 3-position to 5-position on the thiophene ring. When X is vinylene, preferably B is located at the ortho position, and $R_2$ and $R_1$ are located at the meta and para position, respectively, on the benzene ring. Preferably, B is located at the ortho position, and $R_2$ and $R_1$ are located at the meta and para position, respectively, on the benzene ring. When X is sulfur, preferably, B is located at the 3-position on the thiophene ring, and $R_2$ and $R_1$ are located at the 4-position and 5-position, respectively.

When X is vinylene, more specifically, when the compound represented by Formula (Ia-1) is benzene carboxylic acid or a bioisostere thereof, $R_1$ and $R_2$ are as defined above. Preferably, $R_1$ and $R_2$ are the same or different, and each represents hydrogen, halogen, $C_{3-8}$-cycloalkyl, $C_{3-8}$-cycloalkyl-$C_{1-6}$-alkyl, $C_{3-8}$-cycloalkyl-$C_{2-6}$-alkynyl, $C_{3-8}$-cycloalkenyl, or $C_{2-6}$-alkynyl. More preferably, $R_2$ located at the meta position is hydrogen, and $R_1$ located at the para position is halogen, $C_{3-8}$-cycloalkyl, $C_{3-8}$-cycloalkyl-$C_{1-6}$-alkyl, $C_{3-8}$-cycloalkyl-$C_{2-6}$-alkynyl, $C_{3-8}$-cycloalkenyl, or $C_{2-6}$-alkynyl. Preferably, $R_1$ at the para position is halogen.

Here, halogen is preferably chlorine or bromine, and more preferably chlorine. The $C_{3-8}$ cycloalkyl is preferably cyclohexyl. The $C_{3-8}$-cycloalkyl-$C_{1-6}$-alkyl is preferably $C_{3-6}$ alkyl having cyclohexyl as a substituent, and more preferably $C_{1-4}$ alkyl having cyclohexyl as a substituent. The $C_{3-8}$-cycloalkyl-$C_{2-6}$-alkynyl is preferably $C_{2-6}$ alkynyl having cyclohexyl as a substituent, and more preferably $C_{2-3}$ alkynyl having cyclohexyl as a substituent. The $C_{3-8}$-cycloalkenyl is preferably a cyclohexenyl, and more preferably cyclohex-1-en-1-yl or cyclohex-6-en-1-yl. The $C_{2-6}$-alkynyl is preferably $C_{2-4}$ alkynyl, and more preferably $C_{2-3}$ alkynyl.

In the formula, q, $R_3$, and $R_4$ are as defined above; however, preferably, when q is 1, $R_3$ and $R_4$ are both hydrogen, and when q is 0, at least one of $R_3$ and $R_4$ is $CF_3$, and more preferably both are $CF_3$.

T is as defined above, and is preferably a single bond, oxygen, —O—$C_{1-3}$-alkylene, —CO—, $C_{2-3}$-alkynylene, or substituted or unsubstituted alkylene, and more preferably a single bond.

D is as defined above, and preferable examples thereof include aryl optionally having one or two substituents, heteroaryl optionally having one or two substituents, benzofused heteroaryl optionally having one or two substituents, substituted or unsubstituted $C_{3-8}$ cycloalkyl, $C_{3-8}$ heterocycloalkyl optionally having one or two substituents, $C_{3-8}$ cycloalkenyl optionally having one or two substituents, $C_{3-8}$ heterocycloalkenyl optionally having one or two substituents, and adamanthyl.

Preferable examples of aryl include phenyl optionally having one substituent and naphthyl, and more preferably phenyl. Examples of the substituents are as described above, and preferable are alkyl and alkoxy.

Preferable examples of the heteroaryl include pyridyl, thienyl, and furyl optionally having one substituent. Examples of the substituents are as described above, and preferable are unsubstituted pyridyl, thienyl, and furyl. Specific examples of pyridyl include pyridin-2-yl, pyridin-3-yl, and pyridin-4-yl; pyridin-4-yl is preferable. Specific examples of thienyl include thiophen-2-yl and thiophen-3-yl; thiophen-2-yl is preferable. Specific examples of furyl include furan-2-yl and furan-3-yl; furan-3-yl is preferable.

Preferable examples of benzo-fused heteroaryl include quinolyl and isoquinolyl optionally having one substituent. Examples of the substituents are as described above, and preferable are unsubstituted quinolyl and isoquinolyl. There is no limitation to the binding site of quinolyl and isoquinolyl, and when the substituent is quinolyl, preferable positions are, for example, the 2-position (quinolin-2-yl), 3-position (quinolin-3-yl), 6-position (quinolin-6-yl), and 8-position (quinolin-8-yl); when the substituent is isoquinolyl, for example, the 4-position (isoquinolin-4-yl) and 5-position (isoquinolin-5-yl) are preferable.

Examples of $C_{3-8}$ cycloalkyl include preferably cyclohexyl optionally having one substituent; examples of $C_{3-8}$ heterocycloalkyl include a 5-membered ring having nitrogen as a heteroatom, and preferably pyrrolidinyl optionally having one substituent. Specific examples of pyrrolidinyl include pyrrolidin-1-yl, pyrrolidin-2-yl, pyrrolidin-3-yl, pyrrolidin-4-yl, pyrrolidin-5-yl, and pyrrolidin-6-yl; pyrrolidin-1-yl is preferable. Examples of the substituents are as described above, and preferable are unsubstituted cycloalkyl and heterocycloalkyl.

Preferable examples of $C_{3-8}$ cycloalkenyl include cyclohexenyl optionally having one substituent. Specific examples of cyclohexenyl include cyclohex-1-en-1-yl, cyclohex-2-en-1-yl, cyclohex-3-en-1-yl, cyclohex-4-en-1-yl, cyclohex-5-en-1-yl, and cyclohex-6-en-1-yl; cyclohex-1-en-1-yl is preferable.

Examples of $C_{3-8}$ heterocycloalkenyl include a 6-membered ring heterocyclohexenyl with oxygen as a heteroatom optionally having one substituent. Examples of such a group include dihydro-2H-pyranyl, and preferably 3,6-dihydro-2H-pyran-4-yl. Examples of the substituents are as described above, and preferable are unsubstituted cycloalkenyl and heterocycloalkenyl.

Preferable examples of adamanthyl include adamanthyl optionally having one substituent, and the adamanthyl is preferably adamantan-1-yl.

In Formula (Ia-1), (T-D)q, $R_3$, and $R_4$ may be located at any of the ortho, meta or para positions on the benzene ring to which carbonyl is bound. When q is 1, (T-D)q is located preferably at the meta position or para position, and more preferably at the meta position on the benzene ring, and $R_3$ and $R_4$ are located at other positions. When q is 0, $R_3$ and $R_4$ may be located at any position on the benzene ring, and preferably $R_3$ and R4 are each located at the meta position.

Specific examples of the aromatic carboxylic acids (benzene carboxylic acid) of the present invention represented by the above formula, or bioisosteres (Ia-1) of the carboxylic acid, include the following compounds:

5-chloro-2-({[3-(furan-3-yl)phenyl]carbonyl}amino)benzoic acid (Example 2)

2-[(biphenyl-3-ylcarbonyl)amino]-5-chlorobenzoic acid (Example 4)

2-[(biphenyl-2-ylcarbonyl)amino]-5-chlorobenzoic acid (Example 6)

5-chloro-2-({[4-(thiophen-2-yl)phenyl]carbonyl}amino) benzoic acid (Example 7)

5-chloro-2-({[3-(pyridin-4-yl)phenyl]carbonyl}amino)benzoic acid (desalted product of Example 8).

5-chloro-2-{[(4'-methylbiphenyl-3-yl)carbonyl] amino}benzoic acid (Example 32)

5-chloro-2-{[(2'-methoxybiphenyl-3-yl)carbonyl] amino}benzoic acid (Example 33)

5-chloro-2-({[4-(3,6-dihydro-2H-pyran-4-yl)phenyl] carbonyl}amino)benzoic acid (Example 34)

2-({[4-(adamantan-1-yl)phenyl]carbonyl}amino)-5-chlorobenzoic acid (Example 40)

5-chloro-2-{[(4-phenoxyphenyl)carbonyl]amino}benzoic acid (Example 42)

2-({[3,5-bis(trifluoro-methyl)phenyl]carbonyl}amino)-5-chlorobenzoic acid (Example 43)

2-({[4-(adamantan-1-ylmethoxy)phenyl]carbonyl}amino)-5-chlorobenzoic acid (Example 52)

2-({[4-(adamantan-1-ylcarbonyl)phenyl]carbonyl}amino)-5-chlorobenzoic acid (Example 56)

5-chloro-2-({[3-(naphthalen-1-yl)phenyl]carbonyl}amino) benzoic acid (Example 58)

2-({[3-(adamantan-1-yl)phenyl]carbonyl}amino)-5-chlorobenzoic acid (Example 62)

5-chloro-2-({[3-(quinolin-3-yl)phenyl]carbonyl}amino) benzoic acid (desalted product of Example 63)

5-chloro-2-({[3-(isoquinolin-4-yl)phenyl]carbonyl}amino) benzoic acid (desalted product of Example 64)

5-chloro-2-({[3-(quinolin-6-yl)phenyl]carbonyl}amino) benzoic acid (desalted product of Example 65)

5-chloro-2-({[3-(isoquinolin-5-yl)phenyl]carbonyl}amino) benzoic acid (desalted product of Example 66)

5-chloro-2-({[4-(quinolin-8-yl)phenyl]carbonyl}amino) benzoic acid (desalted product of Example 67)

5-chloro-2-({[3-(quinolin-8-yl)phenyl]carbonyl}amino) benzoic acid (desalted product of Example 68)

5-chloro-2-{[(4-cyclohexylphenyl)carbonyl]amino}benzoic acid (Example 69)

5-chloro-2-({[3-(cyclohex-1-en-1-yl)phenyl]carbonyl}amino)benzoic acid (Example 79)

5-chloro-2-{[(3-cyclohexylphenyl)carbonyl]amino}benzoic acid (Example 80)

5-(cyclohex-1-en-1-yl)-2-{[(4-cyclohexylphenyl)carbonyl]amino}benzoic acid (Example 81)

5-cyclohexyl-2-{[(4-cyclohexylphenyl)carbonyl]amino}benzoic acid (Example 82)

5-chloro-2-({[4-(pyrrolidin-1-yl)phenyl]carbonyl}amino) benzoic acid hydrochloride (Example 83)

5-chloro-2-({[3-(cyclohexylethynyl)phenyl]carbonyl}amino)benzoic acid (Example 87)

5-chloro-2-({[4-(cyclohexylethynyl)phenyl]carbonyl}amino) acid (Example 88)

5-(cyclohexylethynyl)-2-{[(4-cyclohexylphenyl)carbonyl]amino}benzoic acid (Example 92)

5-(2-cyclohexylethyl)-2-{[(4-cyclohexylphenyl)carbonyl]amino}benzoic acid (Example 93)

2-{[(4-cyclohexylphenyl)carbonyl]amino}-5-ethynylbenzoic acid (Example 95)

2-({[4-(adamantan-1-ylmethyl)phenyl]carbonyl}amino)-5-chlorobenzoic acid (Example 96)

2-[({4-[adamantan-1-yl(hydroxy)methyl]phenyl}carbonyl) amino]-5-chlorobenzoic acid (Example 97)

5-chloro-2-({[4-(1-methylcyclohexyl)phenyl]carbonyl}amino)benzoic acid (Example 98)

5-chloro-2-({[3-(quinolin-2-ylmethoxy)phenyl]carbonyl}amino)benzoic acid (desalted product of Example 99)

5-chloro-2-({[4-(quinolin-2-ylmethoxy)phenyl]carbonyl}amino)benzoic acid (desalted product of Example 100)

N-[4-chloro-2-(1H-tetrazol-5-yl)phenyl]-3-(quinolin-8-yl) benzamide (Example 102)

When X is sulfur, i.e., the compound represented by Formula (Ia-1) is heterocyclic carboxylic acid (thiophenecarboxylic acid) or bioisosteres thereof, $R_1$ and $R_2$ are as defined above, preferably are the same or different, and each represents $C_{1-6}$ alkyl and aryl optionally having one or two substituents. The alkyl is preferably $C_{1-4}$ alkyl, and more preferably methyl. A preferable example of aryl is phenyl. Examples of the substituents of aryl are as described above, and unsubstituted phenyl is preferable. Either $R_1$ or $R_2$ (e.g., $R_2$ at the 4-position on the thiophene ring) is preferably aryl, and the other (e.g., $R_1$ at the 5-position on the thiophene ring) is alkyl.

q, $R_3$, and $R_4$ are as defined above, preferably q is 1, and both $R_3$ and $R_4$ are hydrogen.

T is as defined above, and preferably is a single bond.

D is as defined above, and preferably is $C_{3-6}$ cycloalkyl optionally having one or two substituents, and heteroaryl optionally having one or two substituents. A preferable example of cycloalkyl is cyclohexyl. Examples of the heteroaryl include pyridyl, thienyl, and furyl. Among these, furyl is preferable. Specific examples of furyl include furan-2-yl and furan-3-yl, and furan-3-yl is preferable. Examples of substituents are as described above, and cycloalkyl and heteroaryl are preferably groups that do not have a substituent.

In Formula (Ia-1), (T-D)q, $R_3$, and $R_4$ may be located at any of the ortho, meta, or para positions on the benzene ring to which carbonyl is bound. When q is 1, (T-D)q is preferably located at the meta position or para position on the benzene ring, and $R_3$ and $R_4$ are located at other positions. When q is 0, $R_3$ and $R_4$ may be located at any position on the benzene ring.

Specific examples of the thiophenecarboxylic acids of the present invention and bioisosteres thereof (Ia-1) include the following compounds:

2-({[3-(furan-3-yl)phenyl]carbonyl}amino)-5-methyl-4-thienylthiophene-3-carboxylic acid (Example 5)

2-{[(4-cyclohexylphenyl)carbonyl]amino}-5-methyl-4-phenylthiophene-3-carboxylic acid (Example 74)

(Ia-2) Compounds Wherein L is Substituted or Unsubstituted $C_{1-6}$-alkylene-O—

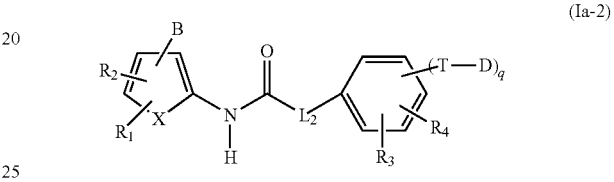

wherein $R_1$ to $R_4$, B, X, T, D, and q are as defined above, and $L_2$ is substituted or unsubstituted $C_{1-6}$-alkylene -O—.

In the compound (Ia-2), L (in the formula above, represented as "$L_2$") is $C_{1-6}$ alkylene-O—, preferably $C_{1-4}$ alkylene-O—, and more preferably $C_{1-3}$ alkylene-O—. The alkylene may be linear or branched. The alkylene may have 1 or 2 substituents, and is preferably unsubstituted alkylene.

Preferable examples of the compound (Ia-2) include those represented by Formula (Ia-2) wherein X is vinylene (—CH═CH—).

In the formula, B, $R_1$, and $R_2$ may be located at any of the ortho, meta, or para positions on the benzene ring to which imino is bound. Preferably, B is located at the ortho position, and $R_2$ and $R_1$ are located at the meta and para position, respectively, on the benzene ring.

In the compound (Ia-2), $R_1$ and $R_2$ are as defined above, preferably $R_1$ and $R_2$ are the same or different, and each represents hydrogen, halogen, aryl optionally having one or two substituents, or 5- to 6-membered ring heteroaryl optionally having one or two substituents. More preferably, $R_2$ located at the meta position is hydrogen, and $R_1$ located at the para position is halogen, aryl optionally having one substituent, or 5- to 6-membered ring heteroaryl optionally having one substituent. $R_1$ is preferably halogen.

Here, halogen is preferably chlorine, bromine, or fluorine, and more preferably chlorine.

A preferable example of aryl is phenyl, and a preferable example of 5- to 6-membered ring heteroaryl is aryl having one or two atoms selected from oxygen, sulfur, and nitrogen; the atoms may be the same or different. Preferably, the aryl is 5- to 6-membered ring aryl having one oxygen as a heteroatom. A preferable example thereof is furyl, and specific examples thereof include furan-1-yl, furan-2-yl, furan-3-yl, furan-4-yl, and furan-5-yl. Particularly preferable is furan-3-yl. Examples of the substituents of aryl and heteroaryl are as described above, and preferable are halogen, $C_{1-6}$ (preferably $C_{1-4}$) alkyl, and $C_{1-6}$ (preferably $C_{1-4}$) alkoxy. Among these, $C_{1-4}$ alkyl is preferable, and more preferable are methyl and ethyl.

$R_3$ and $R_4$ are as defined above, and preferably when q is 1, both are hydrogen, and when q is 0, either $R_3$ or $R_4$ is hydrogen and the other is substituted or unsubstituted $C_{1-6}$, or preferably branched alkyl. A preferable example of branched alkyl is tert-butyl.

T is as defined above, and is preferably a single bond.

D is as defined above, and preferable examples thereof include aryl optionally having one or two substituents, heteroaryl optionally having one or two substituents, $C_{3-8}$ cycloalkyl optionally having one or two substituents, $C_{3-8}$ cycloalkenyl optionally having one or two substituents, and adamanthyl. Here, aryl is preferably phenyl; heteroaryl is preferably furyl and more preferably furan-2-yl or furan-3-yl; cycloalkyl is preferably cyclohexyl; cycloalkenyl is preferably cyclohexenyl, and more preferably cyclohex-1-en-1-yl; and adamanthyl is preferably adamantan-1-yl.

Examples of the substituents are as described above, and preferable are $C_{1-6}$ (preferably $C_{1-4}$) alkyl and $C_{1-6}$ (preferably $C_{1-4}$) alkoxy.

In Formula (Ia-2), (T-D)q, $R_3$, and $R_4$ may be located at any of the ortho, meta, or para positions on the benzene ring to which $L_2$ is bound. When q is 1, (T-D)q is preferably located at the meta position or para position on the benzene ring, and $R_3$ and $R_4$ are located at other positions. When q is 0, $R_3$ and $R_4$ may be located at any position on the benzene ring.

Examples of the aromatic carboxylic acid (benzene carboxylic acid) of the present invention represented by the formula above or bioisosteres of the carboxylic acid (Ia-2) include the following compounds:

5-chloro-2-({[3-(furan-3-yl)phenoxy]acetyl}amino)benzoic acid (Example 13)
5-bromo-2-({[3-(furan-3-yl)phenoxy]acetyl}amino)benzoic acid (Example 15)
2-{[(3-tert-butylphenoxy)acetyl]amino}-5-chlorobenzoic acid (Example 16)
5-chloro-2-{[(2-cyclohexylphenoxy)acetyl]amino}benzoic acid (Example 17)
2-{[(4-tert-butylphenoxy)acetyl]amino}-5-chlorobenzoic acid (Example 18)
2-{[(biphenyl-4-yloxy)acetyl]amino}-5-chlorobenzoic acid (Example 19)
2-{[(biphenyl-3-yloxy)acetyl]amino}-5-chlorobenzoic acid (Example 20)
2-({[4-(adamantan-1-yl)phenoxy]acetyl}amino)-5-chlorobenzoic acid (Example 21)
4-({[3-(furan-3-yl)phenoxy]acetyl}amino)biphenyl-3-carboxylic acid (Example 22)
5-chloro-2-({[3-(cyclohex-1-en-1-yl)phenoxy]acetyl}amino)benzoic acid (Example 25)
5-chloro-2-{[(3-cyclohexylphenoxy)acetyl]amino}benzoic acid (Example 26)
4-({[3-(furan-3-yl)phenoxy]acetyl}amino)-3'-methylbiphenyl-3-carboxylic acid (Example 27)
4-({[3-(furan-3-yl)phenoxy]acetyl}amino)-3',5'-dimethylbiphenyl-3-carboxylic acid (Example 28)
5-chloro-2-({[4-(furan-3-yl)phenoxy]acetyl}amino)benzoic acid (Example 29)
2-({[3-(adamantan-1-yl)phenoxy]acetyl}amino)-5-chlorobenzoic acid (Example 30)
5-chloro-2-({2-[3-(furan-3-yl)phenoxy]-2-methylpropanoly}amino)benzoic acid (Example 44)
4-{[(biphenyl-3-yloxy)acetyl]amino}biphenyl-3-carboxylic acid (Example 45)
2-{[(biphenyl-4-yloxy)acetyl]amino}-5-(furan-3-yl)benzoic acid (Example 46)
2-({[4-(adamantan-1-yl)phenoxy]acetyl}amino)-5-(furan-3-yl)benzoic acid (Example 47)
5-chloro-2-({[(4'-methylbiphenyl-4-yl)oxy]acetyl}amino)benzoic acid (Example 49)
5-chloro-2-({[(3',5'-dimethylbiphenyl-4-yl)oxy]acetyl}amino)benzoic acid (Example 50)
5-chloro-2-({[3-(furan-2-yl)phenoxy]acetyl}amino)benzoic acid (Example 53)
5-chloro-2-({[4-(furan-2-yl)phenoxy]acetyl}amino)benzoic acid (Example 54)
2-({4-[4-(adamantan-1-yl)phenoxy]butanoyl}amino)-5-chlorobenzoic acid (Example 55)
2-({3-[4-(adamantan-1-yl)phenoxy]propanoly}amino)-5-chlorobenzoic acid (Example 59)
5-chloro-2-({[(2'-methoxybiphenyl-3-yl)oxy]acetyl}amino)benzoic acid (Example 61).

(Ia-3) $C_{1-6}$-Alkylene, $C_{2-6}$-alkenylene, or $C_{2-6}$-alkynylene Wherein L Optionally has a Substituent

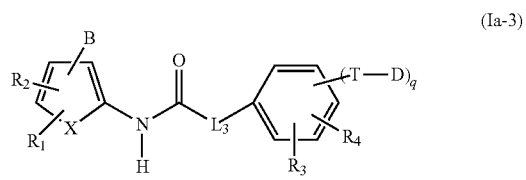

(Ia-3)

wherein $R_1$ to $R_4$, B, X, T, D, and q are as defined above. $L_3$ is substituted or unsubstituted $C_{1-6}$-alkylene, $C_{2-6}$-alkenylene, or $C_{2-6}$-alkynylene.

In the compound (Ia-3), L (represented as "$L_3$" in the above formula) is $C_{1-6}$ alkylene, $C_{2-6}$ alkenylene, or $C_{2-6}$ alkynylene.

The alkylene is preferably $C_{1-4}$ alkylene, and more preferably $C_{1-3}$ alkylene. The alkylene may be linear or branched, and some carbon atoms in the alkylene optionally form a $C_{3-8}$ cycloalkyl ring. Examples of such a cycloalkyl ring (cycloalkane) include cyclopropane, cyclobutane, cycloheptane, cyclohexane, cycloheptane, and cyclooctane. Cyclopropane is preferable.

The alkenylene is preferably $C_{2-3}$ alkenylene, and more preferably vinylene. The alkynylene is preferably $C_{2-3}$ alkynylene, and more preferably $C_2$ alkynylene. These groups optionally have one or two substituents. Such substituents are as defined above, and preferable examples thereof include unsubstituted alkylene, alkenylene, and alkynylene.

Preferable examples of the compound (Ia-3) include those represented by Formula (Ia-3) wherein X is vinylene (—CH=CH—).

In the formula, B, $R_1$, and $R_2$ may be located at any of the ortho, meta, or para positions on the benzene ring to which imino is bound. Preferable compounds include those in which B is located at the ortho position, and $R_2$ and $R_1$ are located at the meta and para position, respectively, on the benzene ring.

In the compound (Ia-3), $R_1$ and $R_2$ are as defined above, are preferably the same or different, and each represents hydrogen or halogen. More preferably, $R_2$ located at the meta position is hydrogen, and $R_1$ located at the para position is halogen. Preferable examples of halogen include chlorine, bromine, and fluorine, and more preferably chlorine.

In the formula, q, $R_3$, and $R_4$ are as defined above. When q is 1, both $R_3$ and $R_4$ are preferably hydrogen. Preferably, q is 1.

T is as defined above, and is preferably a single bond.

D is as defined above, and preferable examples thereof include aryl optionally having one or two substituents, heteroaryl optionally having one or two substituents, benzofused heteroaryl optionally having one or two substituents, $C_{3-8}$ cycloalkenyl optionally having one or two substituents, and adamanthyl optionally having one or two substituents.

The aryl is preferably phenyl. Examples of heteroaryl include 5- or 6-membered ring aryl having oxygen or nitrogen as a heteroatom. Preferable are furyl and pyridyl, and more preferable are furan-2-yl, furan-3-yl, and pyridin-3-yl. The benzo-fused heteroaryl is preferably quinolyl or isoquinolyl, and more preferably quinolin-8-yl, quinolin-3-yl, or quinolin-5-yl. The cycloalkenyl is preferably cyclohexenyl, and more preferably is cyclohex-1-en-1-yl. The adamanthyl is preferably adamantan-1-yl. Examples of the substituents are as described above, and preferable are unsubstituted aryl, heteroaryl, benzo-fused heteroaryl, cycloalkenyl, and adamanthyl.

In Formula (Ia-3), (T-D)q, $R_3$, and $R_4$ may be located at any of the ortho, meta, or para positions on the benzene ring to which $L_3$ is bound. When q is 1, (T-D)q is preferably located at the meta position or para position, and more preferably at the meta position on the benzene ring, and $R_3$ and $R_4$ are located at other positions. When q is 0, $R_3$ and $R_4$ may be located at any position on the benzene ring.

Examples of the aromatic carboxylic acid (benzene carboxylic acid) of the present invention represented by the above formula and bioisosteres thereof (Ia-3) include the following compounds:

5-chloro-2-({[3-(furan-3-yl)phenyl]acetyl}amino)benzoic acid (Example 3)
5-chloro-2-[({1-[3-(furan-3-yl)phenyl]cyclopropyl}carbonyl)amino]benzoic acid (Example 35)
5-chloro-2-({3-[3-(furan-3-yl)phenyl]propanoyl}amino)benzoic acid (Example 36)
5-chloro-2-({2-[3-(furan-3-yl)phenyl]-2-methylpropanoyl}amino)benzoic acid (Example 37)
2-[(biphenyl-4-ylacetyl)amino]-5-chlorobenzoic acid (Example 70)
2-{[(2E)-3-(biphenyl-4-yl)propa-2-enoyl]amino}-5-chlorobenzoic acid (Example 78)
2-{[(2E)-3-(biphenyl-3-yl)propa-2-enoyl]amino}-5-chlorobenzoic acid (Example 89)
5-chloro-2-({(2E)-3-[3-(cyclohex-1-en-1-yl)phenyl]propa-2-enoyl}amino)benzoic acid (Example 90)
5-chloro-2-({(2E)-3-[3-(quinolin-8-yl)phenyl]propa-2-enoyl}amino)benzoic acid (desalted product of Example 101)
5-chloro-2-({(2E)-3-[3-(pyridin-3-yl)phenyl]propa-2-enoyl}amino)benzoic acid (desalted product of Example 103)
2-({3-[4-(adamantan-1-yl)phenyl]propa-2-ynoyl}amino)-5-chlorobenzoic acid (Example 94).

(Ia-4) Compounds Wherein L is —NH—, Substituted or Unsubstituted $C_{1-6}$-alkylene-NH—, —CO—, —CONH—, Substituted or Unsubstituted $C_{1-6}$-alkylene-NHCO—, or a Group Represented by Formula (IX)

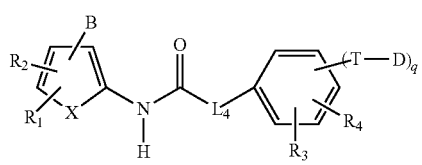

(Ia-4)

wherein $R_1$ to $R_4$, B, X, T, D, and q are as defined above. $L_4$ is —NH—, substituted or unsubstituted $C_{1-6}$-alkylene-NH, —CO—, —CONH—, substituted or unsubstituted $C_{1-6}$-alkylene-NHCO—, or a group represented by Formula (IX).

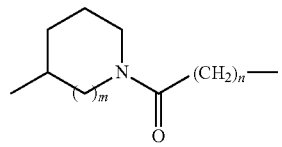

wherein, in $(CH_2)_n$, one or more carbons are optionally substituted and may form cycloalkyl, provided that m is an integer 0 or 1, and n is an integer 0 to 2.

In the compound (Ia-4), L (represented as "$L_4$" in the above formula) is —NH—, $C_{1-6}$-alkylene-NH—, —CO—, —CONH—, $C_{1-6}$-alkylene-NHCO—, or a group represented by Formula (IX).

Examples of the alkylene represented by "$C_{1-6}$-alkylene-NH—" and "$C_{1-6}$-alkylene-NHCO—" include $C_{1-6}$ alkylene, preferably $C_{1-4}$, and more preferably $C_{1-2}$ alkylene. The alkylene may be linear or branched, and some carbon atoms in the alkylene optionally form a $C_{3-8}$ cycloalkyl ring. Examples of such cycloalkyl rings (cycloalkane) include cyclopropane, cyclobutane, cycloheptane, cyclohexane, cycloheptane, and cyclooctane, preferably cyclopropane, and particularly preferably linear alkylene.

The "$C_{1-6}$-alkylene-NH—" and "$C_{1-6}$-alkylene-NHCO—" may have one or two substituents in alkylene. The substituents are as defined above, and preferably unsubstituted alkylene.

In Formula (IX), m is 0 or 1. n is an integer 0 to 2, and preferably 0 or 1. When n is an integer 1 or 2, the carbon atom in $(CH_2)_n$ may have one or two substituents. Examples of such substituents include halogen, $C_{1-6}$ alkyl, $C_{1-6}$ alkoxy, $C_{3-8}$ cycloalkyl, and the like. A preferable example of $(CH_2)_n$ is unsubstituted alkylene.

Preferable examples of the compound (Ia-4) include those represented by Formula (Ia) wherein X is vinylene (—CH=CH—). In the formula, B, $R_1$, and $R_2$ may be located at any of the ortho, meta, or para positions on the benzene ring to which imino is bound. Preferable compounds are those in which B is located at the ortho position, and $R_2$ and $R_1$ are located at the meta and para position, respectively, on the benzene ring.

In the compound (Ia-4), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the formula, q, $R_3$, and $R_4$ are as defined above, and preferably q is 1, $R_3$ and $R_4$ are the same or different, and each represents hydrogen or $C_{1-6}$ alkyl. The alkyl is preferably $C_{1-4}$, and more preferably $C_{1-2}$ alkyl. Preferable examples of $R_3$ and $R_4$ are those in which both are hydrogen or one is hydrogen and the other is alkyl.

T is as defined above, and is preferably a single bond.

D is as defined above, and is preferably aryl optionally having one or two substituents, heteroaryl optionally having one or two substituents, or substituted or unsubstituted adamanthyl.

The aryl is preferably phenyl. Examples of the substituents are as described above, and preferable are halogen, $C_{1-6}$ (preferably $C_{1-4}$) alkyl, and $C_{1-6}$ (preferably $C_{1-4}$) alkoxy. Preferable examples of aryl include unsubstituted phenyl and phenyl having halogen as a substituent. The halogen is preferably chlorine or fluorine, and more preferably fluorine.

The heteroaryl is preferably furyl, and more preferably furan-2-yl or furan-3-yl. The adamanthyl is preferably adamantan-1-yl. Examples of the substituents of the heteroaryl and adamanthyl are as described above, and preferable are unsubstituted heteroaryl and adamanthyl.

In Formula (Ia-4), (T-D)q, $R_3$, and $R_4$ may be located at any of the ortho, meta, or para positions on the benzene ring to which $L_4$ is bound. When q is 1, (T-D)q is preferably located at the meta position or para position, more preferably at the meta position on the benzene ring, and $R_3$ and $R_4$ are located at other positions. When q is 0, $R_3$ and $R_4$ may be located at any position on the benzene ring.

Examples of the aromatic carboxylic acid (benzene carboxylic acid) of the present invention represented by the above formula and bioisosteres thereof (Ia-4) include the following compounds:
2-[(biphenyl-4-ylcarbamoyl)amino]-5-chlorobenzoic acid (Example 71)
5-chloro-2-{[N-(4'-fluoro-4-methylbiphenyl-3-yl)glycyl]amino}benzoic acid (Example 72)
5-chloro-2-({[5-(furan-3-yl)-1-methyl-1H-indol-3-yl](oxo)acetyl}amino)benzoic acid (Example 14)
2-[({[4-(adamantan-1-yl)phenyl]amino}(oxo)acetyl)amino]-5-chlorobenzoic acid (desalted product of Example 106)
5-chloro-2-{[4-({[3-(furan-3-yl)phenyl]carbonyl}amino)butanoyl]amino}benzoic acid (Example 1)
5-chloro-2-[(1-{[3-(furan-3-yl)phenyl]acetyl}-L-prolyl)amino]benzoic acid (Example 9)
5-chloro-2-[(1-{[3-(furan-3-yl)phenyl]carbonyl}-L-prolyl)amino]benzoic acid (Example 10)
5-chloro-2-{[(1-{[3-(furan-3-yl)phenyl]carbonyl}piperidin-3-yl)carbonyl]amino}benzoic acid (desalted product of Example 11)
5-chloro-2-{[(1-{[3-(furan-3-yl)phenyl]acetyl}}piperidin-3-yl)carbonyl]amino}benzoic acid (Example 12)
2-({[1-(biphenyl-3-ylcarbonyl)piperidin-3-yl]carbonyl}amino)-5-chlorobenzoic acid (Example 31)
(Ia-5) Compounds Wherein L is Adamantylene

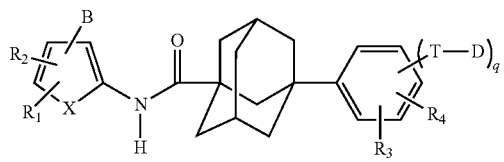

(Ia-5)

wherein $R_1$ to $R_4$, B, X, T, D and q are as defined above.

Preferable examples of the compound (Ia-5) include those represented by Formula (Ia-5) wherein X is vinylene (—CH=CH—). In the formula, B, $R_1$, and $R_2$ may be located at any of the ortho, meta, or para positions on the benzene ring to which imino is bound. Preferable compounds are those in which B is located at the ortho position, and $R_2$ and $R_1$ are located at the meta and para position, respectively, on the benzene ring.

In the compound (Ia-5), $R_1$ and $R_2$ are as defined above, and preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

q, T, D, $R_3$, and $R_4$ are as defined above, preferably q is 0, either $R_3$ or $R_4$ is hydrogen, and the other is $C_{1-6}$ alkyl. The alkyl is preferably $C_{1-4}$, and more preferably $C_{1-2}$ alkyl.

In Formula (Ia-5), (T-D)q, $R_3$ and $R_4$ may be located at any of the ortho, meta, or para positions on the benzene ring to which adamantylene is bound. When q is 1, (T-D)q is preferably located at the meta position or para position, more preferably at the meta position on the benzene ring, and $R_3$ and $R_4$ are located at other positions. When q is 0, $R_3$ and $R_4$ may be located at any position on the benzene ring, and preferably either one or the other is located at the para position.

Examples of the aromatic carboxylic acid (benzene carboxylic acid) of the present invention represented by the above formula and bioisosteres thereof (Ia-5) include the following compound:
5-chloro-2-({[3-(4-methylphenyl)adamantan-1-yl]carbonyl}amino)benzoic acid (Example 86).
(b) Compounds Wherein A is Represented by Formulae (III)-(V)

The compounds (Ib) that belong to this category include aromatic or heterocyclic carboxylic acids represented by Formulae (Ib-III) to (Ib-V) shown below and bioisosteres thereof.

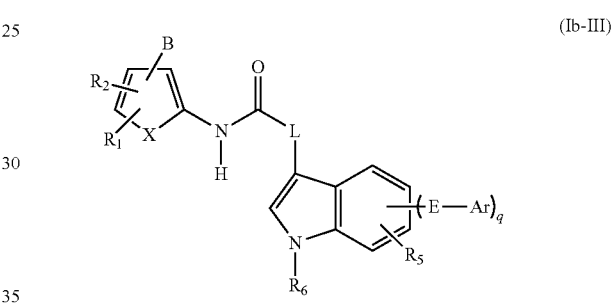

(Ib-III)

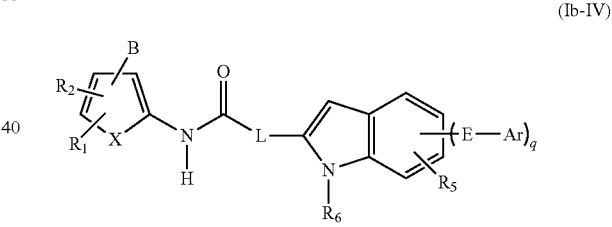

(Ib-IV)

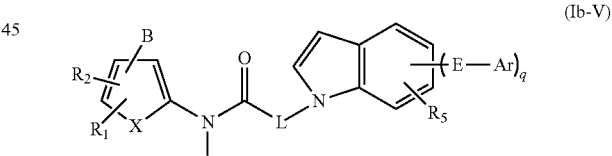

(Ib-V)

wherein $R_1$, $R_2$, $R_5$, $R_6$, B, X, L, E, Ar, and q are as defined above.

Preferable examples of the compounds (Ib-III) to (Ib-V) (which hereunder may be collectively referred to as "compound (Ib)") include the compounds wherein X in Formulae (Ib-III) to (Ib-V) (which hereunder may be collectively referred to as "Formula (Ib)") is vinylene (—CH=CH—). In the formula, B, $R_1$, and $R_2$ may be located at any of the ortho, meta, or para positions on the benzene ring to which imino is bound. Preferable compounds are those in which B is located at the ortho position, and $R_2$ and $R_1$ are located at the meta and para position, respectively, on the benzene ring.

In the compound (Ib), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the compound (Ib), q and $R_5$ are as defined above; preferably, when q is 1, $R_5$ is hydrogen, and when q is 0, $R_5$ is halogen. The halogen is preferably chlorine or bromine, and more preferably bromine.

As defined above, $R_6$ is hydrogen, $C_{1-6}$ alkyl, or $C_{1-6}$ hydroxyalkyl. The alkyl is preferably $C_{1-4}$, and more preferably $C_{1-2}$ alkyl, and the alkyl may be either linear or branched. The alkyl in hydroxyalkyl is preferably $C_{1-4}$, more preferably $C_{1-3}$ alkyl, and the alkyl may be either linear or branched.

As defined above, E is a single bond or $C_{1-6}$—O-alkylene. The alkylene in —O-alkylene is preferably $C_{1-4}$, more preferably $C_{1-3}$ alkylene, and the alkylene may be either linear or branched. E is preferably a single bond.

Ar is as defined above, and preferably aryl optionally having one or two substituents, or heteroaryl optionally having two substituents. The aryl is as defined above, and preferably phenyl optionally having one substituent. The substituents are as defined above, and preferably unsubstituted phenyl. The heteroaryl is as defined above, preferably furyl, and more preferably furan-2-yl or furan-3-yl.

In the compound (Ib), L is as defined above. Preferable examples thereof include a single bond, $C_{1-6}$ alkylene optionally having one or two substituents, and —CO—. The alkylene is preferably $C_{1-4}$, more preferably $C_{1-3}$ alkylene, and the alkylene may be either linear or branched. In the case of the compound (Ib-III), L is preferably —CO—; in the case of the compound (Ib-IV), L is preferably a single bond; and in the case of the compound (Ib-V), L is preferably $C_{1-6}$ alkylene optionally having one or two substituents.

In Formula (Ib), (E-Ar)q and $R_5$ may be located at any position of indole. Preferably, (E-Ar)q is located at the 5-position, and $R_5$ is located at any of the other positions.

Examples of the aromatic carboxylic acid (benzene carboxylic acid) of the present invention represented by the above formula and bioisosteres thereof (Ib) include the following compounds.
Compound (Ib-III)
5-chloro-2-({[5-(furan-3-yl)-1-methyl-1H-indol-3-yl](oxo) acetyl}amino)benzoic acid (Example 14)
2-({[5-(benzyloxy)-1H-indol-3-yl](oxo)acetyl}amino)-5-chlorobenzoic acid (Example 57)
Compound (Ib-IV)
2-{[(5-bromo-1-methyl-1H-indol-2-yl)carbonyl]amino}-5-chlorobenzoic acid (Example 23)
5-chloro-2-{[(1-methyl-5-phenyl-1H-indol-2-yl)carbonyl] amino}benzoic acid (Example 48)
5-chloro-2-({[1-(3-hydroxypropyl)-5-phenyl-1H-indol-2-yl]carbonyl}amino)benzoic acid (Example 60)
Compound (Ib-V)
2-{[(5-bromo-1H-indol-1-yl)acetyl]amino}-5-chlorobenzoic acid (Example 24)
5-chloro-2-{[(5-phenyl-1H-indol-1-yl)acetyl] amino}benzoic acid (Example 51)
(c) Compounds Wherein A is Represented by Formula (VI)

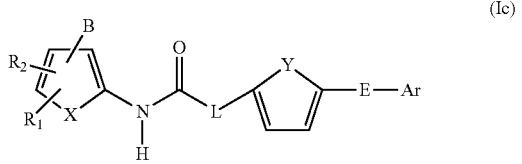

(Ic)

wherein $R_1$, $R_2$, B, X, L, Y, E, and Ar are as defined above.

Preferable examples of the compound (Ic) include those represented by Formula (Ic) wherein X is vinylene (—CH=CH—). In the formula, B, $R_1$, and $R_2$ may be located at any of the ortho, meta, or para positions on the benzene ring to which imino is bound. Preferable compounds are those in which B is located at the ortho position, and $R_2$ and $R_1$ are located at the meta and para position, respectively, on the benzene ring.

In the compound (Ic), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

As defined above, Y is sulfur or oxygen.

E is as defined above, and is preferably a single bond.

Ar is as defined above, and is preferably aryl optionally having one or two substituents, and more preferably phenyl optionally having one substituent. Examples of the substituents are as described above, and halogen is preferable. Preferable examples of halogen include chlorine, bromine, and fluorine, and more preferably fluorine.

In the compound (Ic), L is as defined above, and is preferably a single bond.

Examples of the aromatic carboxylic acid (benzene carboxylic acid) of the present invention represented by the above formula and bioisosteres thereof (Ic) include the following compounds:
5-chloro-2-({[5-(4-fluorophenyl)thiophen-2-yl] carbonyl}amino)benzoic acid (Example 104)
5-chloro-2-{[(5-phenylfuran-2-yl)carbonyl]amino}benzoic acid (Example 105)
(d) Compounds Wherein A is Represented by Formula (VII)

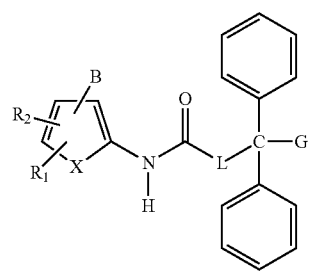

(Id)

wherein $R_1$, $R_2$, B, X, L, and G are as defined above.

Preferable examples of the compound (Id) include those represented by Formula (Id) wherein X is vinylene (—CH=CH—). In the formula, B, $R_1$, and $R_2$ may be located at any of the ortho, meta, or para positions on the benzene ring to which imino is bound. Preferable compounds are those in which B is located at the ortho position, and $R_2$ and $R_1$ are located at the meta and para position, respectively, on the benzene ring.

In the compound (Id), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the compound (Id), L is as defined above, and is preferably a single bond, $C_{1-6}$ alkylene optionally having one or two substituents (some carbon atoms in the alkylene optionally form a cycloalkyl ring), $C_{1-6}$ alkylene-O— optionally having one or two substituents (some carbon atoms in the alkylene optionally form a cycloalkyl ring), $C_{1-6}$ alkylene-NH— optionally having one or two substituents (in "alkylene-NH—", some carbon atoms in the alkylene optionally form a cycloalkyl ring), 1,4-piperazidinyl, or $C_{1-6}$ alkylene-1,4-piperazidinyl. The "alkylene" in "alkylene", "alkylene-O—", "alkylene-NH—", and "alkylene-1,4-piperazidinyl" may be $C_{1-6}$ alkylene, is preferably $C_{1-4}$, and more preferably $C_{1-2}$ alkylene. The alkylene may be either linear or branched, and some carbon atoms in the alkylene optionally form a $C_{3-6}$ cycloalkyl ring. Examples of such a cycloalkyl ring (cycloalkane) include cyclopropane, cyclobutane, cycloheptane, and cyclohexane; cyclopropane is preferable. These groups may have one or two substituents, but unsubstituted alkylene is preferable.

In the compound (Id), as defined above, G is hydrogen or $C_{1-6}$ alkyl. The alkyl is preferably $C_{1-4}$, and more preferably $C_{1-2}$ alkyl.

Examples of the aromatic carboxylic acid (benzene carboxylic acid) of the present invention represented by the above formula and bioisosteres thereof (Id) include the following compounds:

5-chloro-2-[(2,2-diphenylpropanoly)amino]benzoic acid (Example 39)

5-chloro-2-[(3,3-diphenylpropanoly)amino]benzoic acid (Example 41)

5-chloro-2-{[N-(diphenylmethyl)glycyl]amino}benzoic acid (Example 73)

5-chloro-2-({[4-(diphenylmethyl)piperazin-1-yl]carbonyl}amino) benzoate hydrochloride (Example 75)

5-chloro-2-{[(diphenylmethoxy)acetyl]amino}benzoic acid (Example 76)

5-chloro-2-({[4-(diphenylmethyl)piperazin-1-yl]acetyl}amino)benzoic acid (Example 77)

(e) Compounds Wherein A is Represented by Formula (VIII)

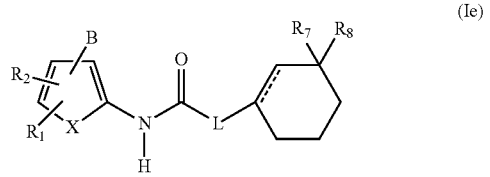

(Ie)

wherein $R_1$, $R_2$, $R_7$, $R_8$, B, X, and L are as defined above.

Preferable examples of the compound (Ie) include those represented by Formula (Ie) wherein X is vinylene (—CH═CH—). In the formula, B, $R_1$, and $R_2$ may be located at any of the ortho, meta, or para positions on the benzene ring to which imino is bound. Preferable compounds are those in which B is located at the ortho position, and $R_2$ and $R_1$ are located at the meta and para position, respectively, on the benzene ring.

In the compound (Ie), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the compound (Ie), L is as defined above, and preferably a single bond or $C_{2-6}$ alkenylene optionally having one or two substituents. The "alkenylene" is preferably $C_{2-3}$ alkenylene, and more preferably $C_2$ vinylene. The alkenylene may have one or two substituents, and a preferable example of such a substituent is halogen. The halogen is preferably chlorine or fluorine, and more preferably chlorine.

In the compound (Ie), $R_7$ and $R_8$ are as defined above. Both are hydrogen or alkylene at the same time, and bind to each other to form 3- to 8-membered ring cycloalkane. The cycloalkane is preferably 3- to 6-membered ring cycloalkane, and more preferably 6-membered ring cyclohexane.

In Formula (Ie), ═══ indicates single or double bonds.

Examples of the aromatic carboxylic acid (benzene carboxylic acid) of the present invention represented by the above formula and bioisosteres thereof (Ie) include the following compounds:

5-chloro-2-{[(2E)-3-chloro-3-cyclohexylpropa-2-enoyl]amino}benzoic acid (Example 91)

5-chloro-2-[(spiro[5.5]undec-1-en-2-yl-carbonyl)amino]benzoic acid (Example 84)

5-chloro-2-[(spiro[5.5]undec-1-en-2-yl-carbonyl)amino]benzoic acid (Example 85).

(f) Compounds Wherein A is Fluorenyl

In the compound (If), the position at which the fluorenyl binds to L is not particularly limited, and the fluorenyl may bind to L at any position. Preferably, the fluorenyl binds to L at the 1-position to form the compound represented by the formula below.

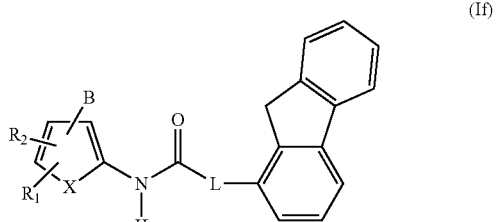

(If)

wherein $R_1$, $R_2$, B, X, and L are as defined above.

Preferable examples of the compound (If) include those represented by Formula (If) wherein X is vinylene (—CH═CH—). In the formula, B, $R_1$, and $R_2$ may be located at any of the ortho, meta, or para positions on the benzene ring to which imino is bound. Preferable compounds are those in which B is located at the ortho position, and $R_2$ and $R_1$ are located at the meta and para position, respectively, on the benzene ring.

In the compound (If), $R_1$ and $R_2$ are as defined above, and are the same or different. Preferably, each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the compound (If), L is as defined above, and preferably a single bond.

Examples of the aromatic carboxylic acid (benzene carboxylic acid) of the present invention represented by the above formula and bioisosteres thereof (If) include the following compound:

5-chloro-2-[(9H-fluoren-1-ylcarbonyl)amino]benzoic acid (Example 38).

(g) Compounds Wherein A is Substituted or Unsubstituted Quinolyl

In the compound (Ig), the position at which the quinolyl binds to L is not particularly limited, and the quinolyl may bind to L at any position. Preferably, quinolyl binds to L at the 4-position to form the compound represented by the formula below.

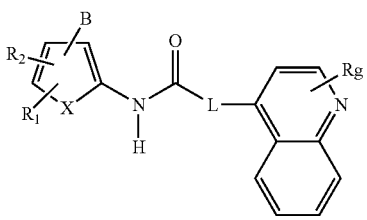

(Ig)

wherein $R_1$, $R_2$, B, X, and L are as defined above. Rc is a substituent.

Preferable examples of the compound (Ig) include those represented by Formula (Ig) wherein X is vinylene (—CH=CH—). In the formula, B, $R_1$, and $R_2$ may be located at any of the ortho, meta, or para positions on the benzene ring to which imino is bound. Preferable compounds include those in which B is located at the ortho position, and $R_2$ and $R_1$ are located at the meta and para position, respectively, on the benzene ring.

In the compound (Ig), $R_1$ and $R_2$ are as defined above, and are the same or different. Preferably, each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the compound (Ig), L is as defined above, and preferably a single bond.

In the compound (Ig), quinolyl optionally has a substituent (Rg). Examples of such substituents include halogen, $C_{1-4}$ alkyl, $C_{1-4}$ halogenated alkyl, $C_{1-4}$ alkoxy, $C_{1-4}$ halogenated alkoxy, hydroxyl, $CF_3$, $CF_3O$, $CHF_2O$, $CF_3CH_2O$, aryl (preferably phenyl), halogenated aryl, cyano, carboxy, and alkoxycarbonyl having alkoxy. The meanings of "alkyl", "alkoxy", and "aryl" are as defined above. Preferable is aryl optionally having one or two substituents, and more preferable is phenyl optionally having one substituent. Examples of the substituents of phenyl are as described above, and unsubstituted phenyl is preferable.

Examples of the benzene carboxylic acids represented by the formula above of the present invention and bioisosteres thereof (Ig) include the following compound:
5-chloro-2-{[(2-phenylquinolin-4-yl)carbonyl]amino}sodium benzoate (Example 107)

Each of the compounds (I) targeted by the present invention may be in free or salt form.

Examples of salts as used herein typically include pharmaceutically acceptable salts, e.g., a salt formed with an inorganic base or organic base, a salt formed with a basic amino acid, and other salts. Examples of inorganic bases include alkali metals such as sodium, potassium, etc.; alkaline earth metals such as calcium, magnesium, etc.; and aluminum, ammonium, etc. Examples of organic bases include primary amines such as ethanolamine, tromethamine, ethylenediamine, etc.; secondary amines such as diethylamine, diethanolamine, meglumine, dicyclohexylamine, N,N'-dibenzylethylenediamine, etc.; and tertiary amines such as trimethylamine, triethylamine, pyridine, picoline, triethanolamine, etc. Examples of basic amino acids include arginine, lysine, ornithine, histidine, etc. Further, the compound of the present invention may form a salt with an inorganic acid or organic acid. Examples of inorganic acids include hydrochloric acid, hydrobromic acid, sulfuric acid, phosphoric acid, etc. Examples of organic acids include formic acid, acetic acid, trifluoroacetic acid, maleic acid, tartaric acid, fumaric acid, citric acid, lactic acid, methanesulfonic acid, benzenesulfonic acid, toluenesulfonic acid, etc.

Further, when the carboxylic acid represented by Formula (I), a bioisostere of the carboxylic acid, or a salt thereof form a solvate (e.g., hydrate, alcohol), such a solvate is also encompassed in the present invention. Furthermore, the present invention encompasses all of the compounds (e.g., a so-called prodrug) that are converted, when metabolized in vivo, to a carboxylic acid represented by Formula (I), a bioisostere thereof, or a pharmaceutically acceptable salt.

(2) Production Method of Compound of the Present Invention

The following describes in detail the methods of producing the aromatic or heterocyclic carboxylic acids represented by Formula (I) of the present invention or bioisosteres thereof, and salts thereof (compound (I)).

Needless to say, however, the present invention, however, is not limited thereto. Further, for the production of the compound, the order of the production steps is not limited to the steps described below, and can be suitably adjusted in accordance with the practice of the industry of interest.

Furthermore, whenever a reaction functional group is found in any step, the group can be suitably protected and deprotected unless otherwise specified. Reagents in addition to those listed below can be suitably used to promote reaction progress.

(2-1) Production Method 1

As shown in the following formula, compounds (1) and (2) are condensed to produce an ester moiety (I-1) of the aromatic or heterocyclic carboxylic acid of the present invention [step (a)]. The thus-prepared ester moiety (I-1) can be subjected to hydrolysis or catalytic reduction, depending on the type of $R_{9a}$, to selectively remove only $R_{9a}$, thereby producing a compound (I-2) equivalent to the aromatic or heterocyclic carboxylic acid of the present invention [step (b)].

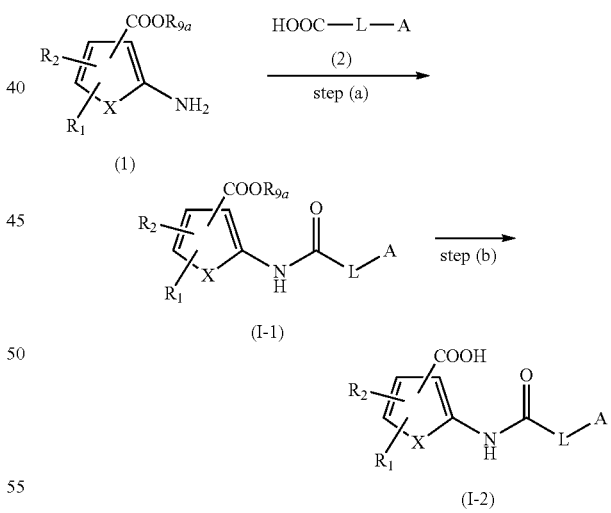

wherein $R_1$, $R_2$, X, L, and A are as defined above; and $R_{9a}$ is $C_{1-6}$ alkyl, aryl, or aralkyl.

The condensation reaction may be carried out between the compounds (1) and (2) in the presence of a known condensing agent, or by converting the compound (2) to a reactive derivative before further reacting with the compound (1).

Examples of condensing agents include known agents, such as dicyclohexylcarbodiimide (DCC), water-soluble carbodiimide (WSC) (e.g., 1-ethyl-3-(3-dimethylaminopropyl) carbodiimide hydrochloride), carbonyldiimidazole (CDI), benzotriazol-1-yloxy-tris (pyrrolidino)phosphonium hexafluorophosphate (PyBOP), and the like. Examples of additives for generating active esters include N-hydroxysuccinimide (HOSu), 1-hydroxybenzotriazole (HOBt), and the like.

Further, examples of reactive derivatives of the compound (2) include acid chlorides (e.g., chloride and bromide), active esters (e.g., p-nitrophenyl ester, pentachlorophenyl ester, esters reacted with N-hydroxysuccinimide, and esters reacted with 1-hydroxybenzotriazole), imidazolide, and mixed acid anhydrides (e.g., mixed acid anhydride formed with methoxy formic acid, ethoxy formic acid, propoxy formic acid, butoxy formic acid, isobutoxy formic acid, tert-butoxy formic acid, phenoxy formic acid, 2,2-dimethylpropionate, methanesulfonic acid, benzenesulfonic acid, and toluenesulfonic acid). Furthermore, 4-(dimethylamino)pyridine and N-methylimidazole, etc., may be used as additives for further activation. These reactive derivatives may be reacted with the compound (1) after being formed or as they are formed within a reaction system, or may be isolated from the reaction system before reacting with the compound (1).

The reaction of the compounds (1) and (2) with the reactive derivative is generally carried out in a solvent, and, if necessary, in the presence of a base. An inert organic solvent is commonly used as a solvent; however, water can sometimes be used as a solvent, or a mixture thereof can also be used. Examples of usable organic solvents include halogenated alkyls (e.g., methylene chloride and chloroform); aromatic hydrocarbons (e.g., benzene, toluene, xylene, and anisole); ethers (e.g., diethyl ether, diisopropyl ether, methyl isobutyl ether, methyl cyclopentyl ether, tetrahydrofuran (THF), and dioxane); esters (e.g., methyl acetate, ethyl acetate, isopropyl acetate, and butyl acetate); ketones (e.g., acetone, methyl ethyl ketone, and methyl isobutyl ketone); acetonitrile, N,N-dimethylformamide (DMF), N,N-dimethylacetamide (DMAc), N-methylpiperidone, dimethyl sulfoxide; etc. Examples of usable bases include inorganic bases (e.g., sodium hydrogencarbonate, potassium hydrogencarbonate, sodium carbonate, potassium carbonate, sodium hydroxide, potassium hydroxide, and lithium hydroxide); and organic bases (e.g., pyridine, triethyl amine, N,N-diisopropylethylamine, N-methylmorpholine, and N-methylpiperidine). The reaction temperature varies depending on the condensing agent used or the kind of reactive derivative of the compound (2), but typically ranges from about −30° C. to about 120° C., and preferably from about −10° C. to about 100° C. The amount of the condensing agent and base used is typically about 1 to about 5 equivalent weight, and preferably about 1 to about 3 equivalent weight, per mol of the compound (2). The amount of the compound (2), when used in the form of a reactive derivative, is about 1 to about 5 equivalent weight, and preferably about 1 to about 2 equivalent weight, per mol of the compound (1).

The thus-prepared ester moiety (I-1) can be made into the compound (I-2) of the present invention in the form of a free radical carboxylic acid by removing the ester linkage therefrom.

The conditions to perform such a removal vary depending on the kind of $R_{9a}$, but preferably used acids include hydrogen chloride, hydrogen bromide, methanesulfonic acid, benzenesulfonic acid, p-toluenesulfonic acid, trifluoroacetic acid, etc., when $R_{9a}$ is a t-butyl group. In this case, the removal reaction is typically carried out in an inactive solvent (e.g., benzene, toluene, ethyl ether, isopropyl ether, THF, ethyl acetate, dichloromethane, and chloroform) at about 0° C. to about 60° C. The amount of acid used varies depending on the kind thereof, but is typically about 1 to about 10 equivalent weight per mol of the compound (I-1). Further, when trifluoroacetic acid is used as the acid, it can also be used as a solvent.

When $R_{9a}$ is alkyl, aryl, or aralkyl, an alkali hydrolysis reaction can be employed. In this case, suitably usable alkalis include lithium hydroxide, sodium hydroxide, potassium hydroxide, barium hydroxide, etc.; and suitably usable solvents include methanol, ethanol, dioxane, THF, or mixtures thereof, etc. The amount of alkali used is typically about 1 to about 3 equivalent weight per mole of the compound (I-1), and the reaction temperature ranges from about 0° C. to about 80° C. In an alkali hydrolysis reaction, a salt is first formed from the alkali used. Thus, $R_{9a}$ can be isolated as a salt thereof, or can be isolated as a free radical carboxylic acid by neutralization using a suitable acid (e.g., acetic acid, hydrochloric acid, and sulfuric acid). Alternatively, a free radical carboxylic acid is first isolated and then converted into an alkali metal salt or alkaline earth metal salt by a known method. Further, when the compound (I) of the present invention contains a basic nitrogen functional group in molecules, $R_{9a}$ can be isolated as an acid chloride of the compound (I) by treating with an equivalent or excessive weight of an acid.

When $R_{9a}$ is aralkyl (e.g., benzyl), the compound (I-1) can be converted to a free radical carboxylic acid (I-2) by being subjected to catalytic reduction by a known method using hydrogen gas in the presence of a catalyst such as palladium carbon, palladium black, etc.

(2-2) Production Method 2

As shown in the following formula, in place of the compound (1) used in the step (a) of the production method 1, a compound (1') having a halogen group is reacted with the compound (2) to produce a compound (3) [step (a')]. The Hal (iodine or bromine) of thus-prepared amide compound (3) is replaced by a carboxyl group, as shown in the following formula, to produce a compound (I-2) equivalent to the aromatic or heterocyclic carboxylic acid of the present invention [step (c)].

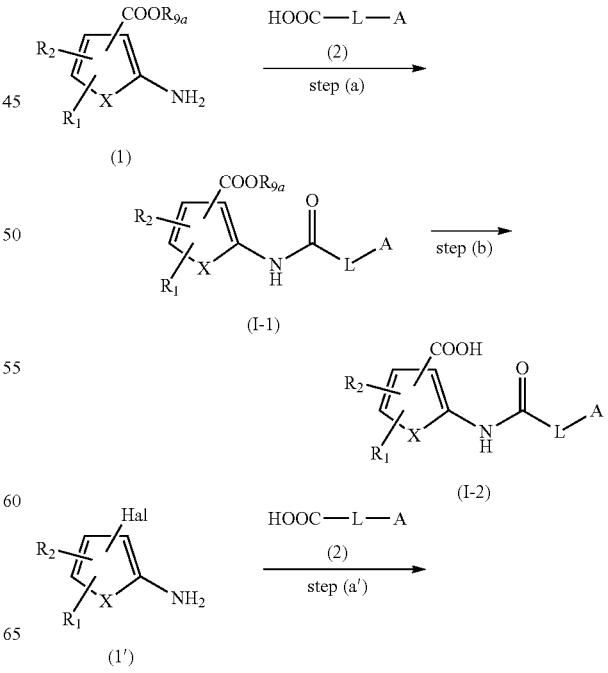

-continued

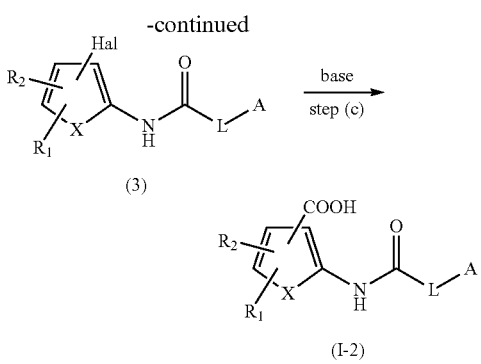

wherein $R_1$, $R_2$, X, A, and L are as defined above; and Hal is iodine or bromine.

The reaction of the step (c) is carried out by reacting the compound (3) with a strong base or preferably an organic metal base (e.g., n-butyl lithium, sec-butyl lithium, t-butyl lithium, or lithium diisopropylamide) in an inert gas (e.g., nitrogen or argon) atmosphere in an anhydrous organic solvent (or a mixed solvent) inactive in the reaction (e.g., tetrahydrofuran, diethyl ether, dipropyl ether, t-butylmethyl ether, or n-hexane) at a temperature of about –100° C. to about 0° C., and preferably about –80° C. to about –20° C. to be converted to a reactive derivative, followed by a reaction with carbon dioxide at –100° C. to 30° C., and preferably at –50° C. to 30° C. The amount of base used is typically about 1 to about 5 equivalent weight, and preferably about 2 to about 3 equivalent weight, per mole of the compound (3).

(2-3) Production Method 3

In place of the compound (1) used in the step (a) of the production method 1, a compound (1″) having a cyano group represented by the following formula is reacted with the compound (2) to easily produce a nitryl compound (4) [step (a″)]. The obtained nitrile compound (4) is then reacted with an azide (5), as shown in the following formula, to produce a compound having a 1H-tetrazol-5-yl group [step (d)].

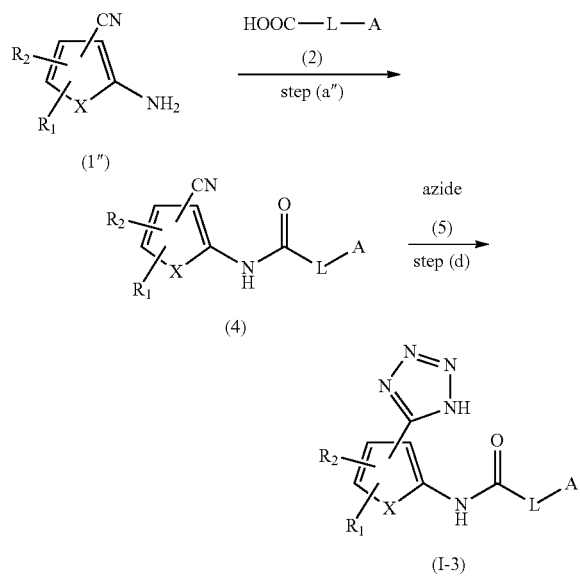

wherein $R_1$, $R_2$, X, A, and L are as defined above.

The reaction between the nitrile compound (4) and azide (5) (e.g., sodium azide and trimethylsilyl azide) is typically carried out in a solvent (e.g., chloroform, toluene, xylene, diethyl ether, THF, dioxane, ethyl acetate, methyl ethyl ketone, acetonitrile, DMF, DMAc, DMSO, ethanol, water, or a mixture thereof), preferably in the presence of a tin compound (e.g., n-tributyltinchloride and di-n-butyltinoxide) or Lewis acid (e.g., zinc bromide and copper iodide). The reaction temperature typically ranges from about 20° C. to about 120° C., and preferably from about 50° C. to about 100° C. The amount of the azide compound used is typically about 1 to about 10 equivalent weight, and preferably about 1 to about 5 equivalent weight, per mole of the compound (4). The amount of the tin compound used is typically about 0.1 to about 5 equivalent weight, and preferably about 0.1 to about 1.5 equivalent weight, per mol of the compound (4). The amount of the Lewis acid used is typically about 0.1 to about 5 equivalent weight, and preferably about 0.1 to about 1.5 equivalent weight, per mole of the compound (4).

(2-4) Production Method 4

The compound (I-2) produced by the production method 1 or 2 can be converted to an ester compound (I-1′), if necessary [step (e)].

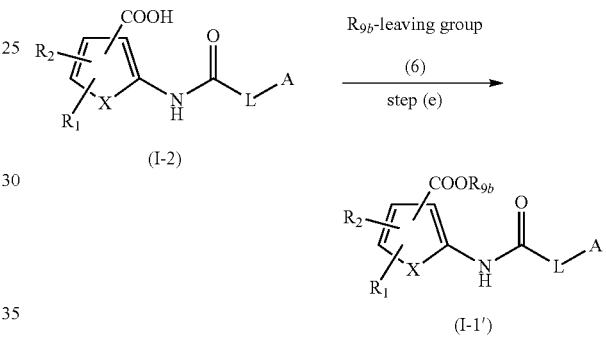

wherein $R_1$, $R_2$, X, L, and A are as defined above; and $R_{9b}$ is a group converted to hydrogen in vivo, which is selected from the group consisting of $C_{1-6}$ alkyl, —CH($R_{10}$)—O—CO—$R_{11}$, —CH($R_{10}$)—O—CO—O$R_{11}$ (wherein $R_{10}$ is hydrogen or $C_{1-6}$ alkyl, and $R_{11}$ is $C_{1-6}$ alkyl or $C_{3-6}$ cycloalkyl), and a (5-alkyl-2-oxo-1,3-dioxolen-4-yl)methyl group represented by Formula (X).

In this reaction, the compound (I-1′) is generally synthesized by reacting the aromatic or heterocyclic carboxylic acid (I-2) of the present invention or an alkali metal salt thereof with the compound (6). Examples of the leaving group in the compound (6) include halogen (e.g., chlorine, bromine, and iodine), sulfonyloxy groups (e.g., mesyloxy, besyloxy, and tosyloxy), and the like. The reaction is typically carried out in a solvent and, if necessary, in the presence of a base. The solvent employable is any of those inactive in the reaction, and examples include hydrocarbons (e.g., hexane, heptane, and cyclohexane), halogenated hydrocarbons (e.g., dichloromethane and chloroform), aromatic hydrocarbons (e.g., benzene, toluene, xylene, and anisole), ethers (e.g., ethyl ether and isopropyl ether), esters (e.g., methyl acetate, ethyl acetate, and butyl acetate), dioxane, THF, ketones (e.g., acetone, methyl ethyl ketone, and methyl isobutyl ketone), acetonitrile, pyridine, DMF, DMAc, etc. The amount of the compound (6) used is about 1 to about 2 equivalent weight, and preferably about 1 to about 1.5 equivalent weight, per mole of the compound (I-2).

Examples of bases usable in the reaction include inorganic bases, such as sodium hydrogencarbonate, potassium hydrogencarbonate, sodium carbonate, potassium carbonate, sodium hydroxide, potassium hydroxide, lithium hydroxide, and cesium hydroxide; and organic bases, such as pyridine, picoline, 4-dimethylaminopyridine, triethylamine, N-methylpiperidine, and N-methylmorpholine. The amount of such a base used is about 1 to about 3 equivalent weight, and preferably about 1 to about 2 equivalent weight, per mole of the compound (I-2).

The reaction temperature typically ranges from about −10° C. to about 100° C., and preferably from about 0° C. to about 60° C.

(2-5) Production Method 5

The nitryl compound (4) produced by the production method 3 is reacted with hydroxylamine hydrochloride (7) to produce an amide oxime compound (8) [step (f)]. The amide oxime compound (8) is then reacted with an active carbonyl compound (9) to produce a compound (I-4) having a 4,5-dihydro-5-oxo-4H-1,2,4-oxadiazol-3-yl group [step (g)].

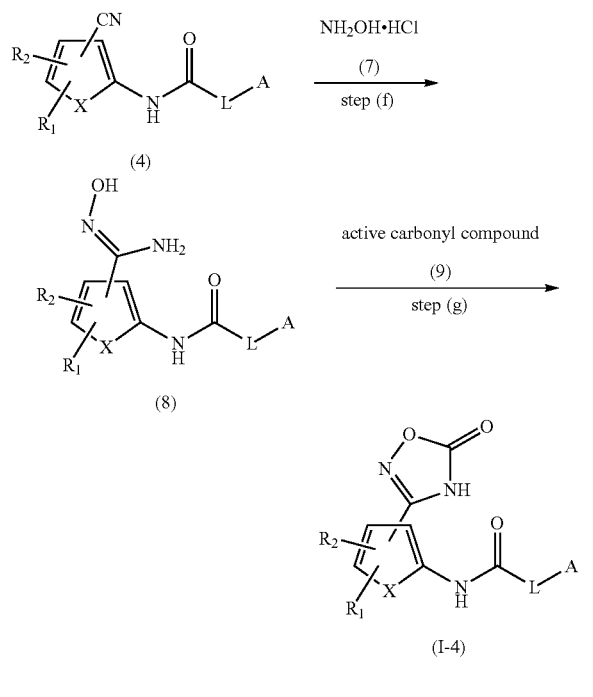

wherein $R_1$, $R_2$, A, L, and X are as defined above.

The reaction between the nitryl compound (4) and hydroxylamine hydrochloride (7) (step (f)) is typically carried out in a solvent (any solvents inactive in the reaction are usable; e.g., chloroform, toluene, xylene, diethyl ether, THF, dioxane, ethyl acetate, methyl ethyl ketone, acetonitrile, DMF, DMAc, DMSO, ethanol, water, or a mixture thereof) preferably in the presence of a base (e.g., pyridine, triethylamine, N,N-diisopropylethylamine, N-methylmorpholine, N-methylpyridine, potassium carbonate, and sodium hydroxide). The reaction temperature typically ranges from about −30° C. to about 120° C., and preferably from about 20° C. to about 100° C. The amount of hydroxylamine hydrochloride (7) and base used is typically about 1 to about 2 equivalent weight, and preferably about 1 to about 1.5 equivalent weight, per mole of the nitryl compound (4).

For the production of the compound (I-4) having a 4,5-dihydro-5-oxo-4H-1,2,4-oxadiazol-3-yl group [step (g)], the compound (8) is reacted with an active carbonyl compound, such as chlorocarbonic acid monoesters (e.g., methyl chlorocarbonate, ethyl chlorocarbonate, isopropyl chlorocarbonate, butyl chlorocarbonate, isobutyl chlorocarbonate, phenyl chlorocarbonate, and 2-ethylhexyl chlorocarbonate) in a solvent (e.g., chloroform, toluene, xylene, diethyl ether, THF, dioxane, ethyl acetate, methyl ethyl ketone, acetonitrile, DMF, DMA, DMSO, ethanol, or a mixture thereof) preferably in the presence of a base (e.g., triethylamine, N-methylmorpholine, pyridine, 1,8-diazabicyclo[5.4.0]undeca-7-ene (DBU), 1,5-diazabicyclo[4.3.0]non-5-ene (DBN), and sodium hydride), subjected to suitable aftertreatment, and cyclized with heat. Alternatively, the compound (8) is reacted with N,N'-carbonyldiimidazole (CDI) in a solvent (e.g., chloroform, toluene, xylene, diethyl ether, THF, dioxane, ethyl acetate, methyl ethyl ketone, acetonitrile, DMF, DMAc, DMSO, and ethanol) preferably in the presence of a base (e.g., triethylamine, N-methylmorpholine, pyridine, DBU, DBN, and sodium hydride). The reaction temperature of the compound (8) and chlorocarbonic acid monoester typically ranges from about −30° C. to about 100° C., and preferably from about −10° C. to about 50° C. The reaction temperature during the cyclization reaction typically ranges from about 40° C. to about 180° C., and preferably from about 80° C. to about 150° C. The temperature of the reaction between the compound (8) and CDI typically ranges from about 20° C. to about 100° C., and preferably from about 40° C. to about 100° C. The amount of chlorocarbonic acid monoester, CDI, and base is typically about 1 to about 2 equivalent weight, and preferably about 1 to about 1.5 equivalent weight, per mole of the compound (8).

(2-6) Production Method 6

The compound (8) produced by the production method 5 is reacted with 1,1'-thiocarbonyldiimidazole (TCDI) (10) in a solvent preferably in the presence of a base to form a compound (I-5) having a 4,5-dihydro-5-thioxo-4H-1,2,4-oxadiazol-3-yl group [step (h)].

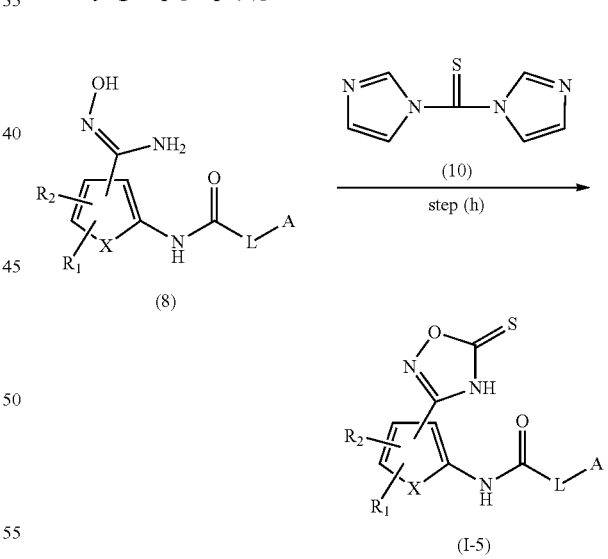

wherein $R_1$, $R_2$, A, L, and X are as defined above.

Examples of solvents include chloroform, toluene, xylene, diethyl ether, THF, dioxane, ethyl acetate, acetone, methyl ethyl ketone, acetonitrile, DMF, DMAc, DMSO, ethanol, or mixtures thereof, etc. Examples of bases include triethylamine, N-methylmorpholine, pyridine, DBU, DBN, sodium hydride, etc.

The reaction temperature typically ranges from about −30° C. to about 100° C., and preferably from about −10° C. to about 50° C.

The amount of TCDI and base used is typically about 1 to about 10 equivalent weight, and preferably about 1 to about 1.5 equivalent weight, per mole of the compound (8).

(2-7) Production Method 7

The compound (8) produced by the production method (5) is reacted with TCDI (11) in such a solvent as described in item (i) above in the absence of a base, subjected to suitable aftertreatment, and further reacted in a solvent in the presence of a boron trifluoride diethyl ether complex or silica gel to form a compound (I-6) having a 4,5-dihydro-5-oxo-4H-1,2,4-thiadiazol-3-yl group [step (i)].

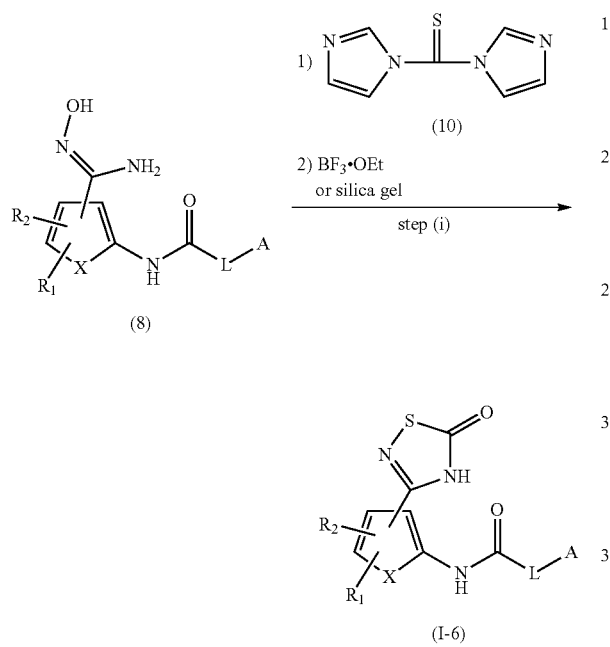

wherein $R_1$, $R_2$, A, L, and X are as defined above.

The reaction temperature typically ranges from about −30° C. to about 100° C., and preferably from about −10° C. to about 50° C. The amount of TCDI used is typically about 1 to about 3 equivalent weight, and preferably about 1 to about 1.5 equivalent weight, per mole of the compound (8). The amount of boron trifluoride diethyl ether complex used is typically about 1 to about 10 equivalent weight, and preferably about 3 to about 6 equivalent weight, per mole of the compound (8). The amount of silica gel used is typically about 1 to about 50 times, and preferably about 5 to about 20 times the weight of the compound (8). The reaction temperature typically ranges from about −30° C. to about 100° C., and preferably from about −10° C. to about 50° C.

(2-8) Production Method 8

In place of the compound (2) used in the step (a) of the production method 1, a compound (12) is condensed with the compound (1) or (1″) to produce a compound (13) [step (j)]. The compound (13) is then subjected to a coupling reaction with D-Ta-M (14) or D-Tb(15) to produce an ester moiety (I-1) or a cyano moiety (5) [step (k)].

The thus-prepared compound (I-1) or (5) can be converted to the aromatic or heterocyclic carboxylic acid of the present invention or a bioisostere thereof (I) in the same manner as in the production method 1, 3, 4, 5, or 6.

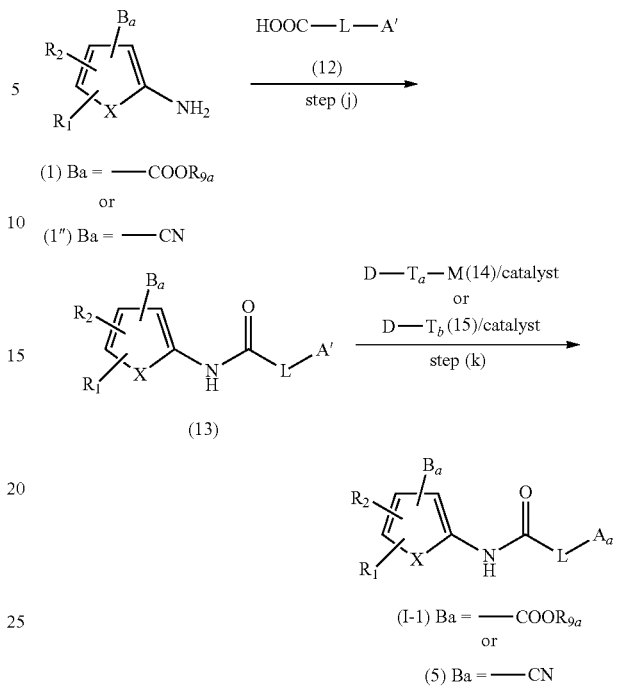

wherein $R_1$, $R_2$, D, L, $R_{9a}$, and X are as defined above; Aa is a group represented by Formula (XIV) below wherein W is replaced by D-Ta— or D-Tb—, or a group represented by Formula (XV), (XVI), or (XVII) below, wherein W is replaced by D-Ta—; Ba is ester (—$COOR_{9a}$) or cyano; A′ is a group represented by Formula (XIV), (XV), (XVI), or (XVII), wherein W is halogen or trifluoromethanesulfonyloxy; Ta is a single bond or $C_{1-3}$ alkylene; Tb is alkynylene having a terminal triple bond; and M is —$B(OR_{13})OR_{13}$ (wherein $R_{13}$ is hydrogen or alkyl; when $R_{13}$ is alkyl, $R_{13}$ may be joined to form a ring) or —ZnV (wherein Zn is zinc, and V is halogen).

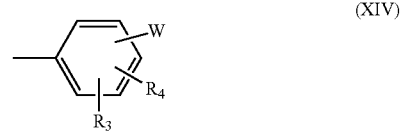

(XIV)

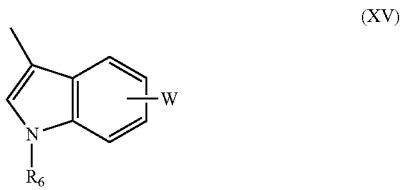

(XV)

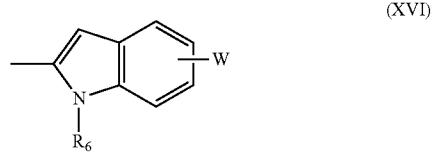

(XVI)

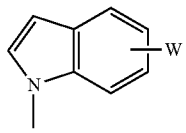

(XVII)

wherein R$_3$, R$_4$, and R$_6$ are as defined above, and W is halogen or trifluoromethanesulfonyloxy.

In the above formula, the reaction of the step (j) can be carried out under the same reaction conditions as in the step (a) of the production method 1 to produce a compound (13).

In the D-Ta-M (14) used in the reaction for producing the ester moiety (I-1) of the aromatic or heterocyclic carboxylic acid of the present invention or the compound (5) from the compound (13), M is —B(OR$_N$)OR$_N$ (wherein R$_{14}$ is hydrogen or alkyl; when R$_{14}$ is alkyl, R$_{14}$ may be joined to form a ring) or —ZnV (wherein Zn is zinc, and V is halogen).

In the step (k), the compound (13) and the compound represented by D-Ta-M (14) are reacted in the presence of a catalyst, as necessary. The reaction conditions vary depending on the kind of W, D-Ta, and M; however, when M is —B(OR$_{14}$)OR$_{14}$, that is, when a compound that is boric acid or (cyclic) boric acid ester residue is used, preferable examples of the catalyst include palladium catalysts (e.g., tetrakis(triphenylphosphine)palladium (0), bis(dibenzylideneacetone)palladium (0), and palladium acetate); and preferable examples of the substituent represented by W include a chlorine atom, bromine atom, iodine atom, and trifluoromethanesulfonyloxy group with a bromine and iodine atom, and a trifluoromethanesulfonyloxy group being particularly preferable.

The reaction is typically carried out in a solvent (e.g., DMF, 1,4-dioxane, toluene, and THF) in the presence of, if necessary, a base (e.g., sodium carbonate, potassium carbonate, and potassium phosphate). The reaction temperature is about 20° C. to about 120° C., and preferably about 30° C. to about 100° C. The amount of D-Ta-M (14) used is about 1 to about 5 equivalent weight, and preferably about 1.5 to about 2 equivalent weight, per mole of the compound (13). The amount of catalyst used is about 0.05 to about 0.5 equivalent weight, and preferably about 0.1 to about 0.2 equivalent weight, per mol of the compound (13).

Further, when a so-called zinc reagent represented by M=—ZnV (wherein Zn is zinc, and V is halogen) is used as the D-Ta-M (14), palladium catalysts (e.g., tetrakis(triphenylphosphine))palladium (0), bis(dibenzylideneacetone) palladium (0), and palladium acetate) are preferably used, in a manner similar to the above. The amount of the zinc reagent (Ar—Ta-M) used is about 1 to about 3 equivalent weight, and preferably about 1.5 to about 2 equivalent weight, per mole of the compound (13).

Moreover, in the step (k), the compound represented by D-Tb (15) and the compound (13) are subjected to a Sonogashira reaction in the presence of a catalyst. The catalyst used in the Sonogashira reaction is generally a suitable combination of a main catalyst (e.g., a palladium complex), a ligand (e.g., a phosphine compound), and a promoter (e.g., copper halide). The reaction conditions vary depending on the kind of W, D-Tb, etc.; however, examples of the palladium complex include bis(triphenylphosphine)palladium dichloride, bis(triphenylphosphine)palladium dibromide, tetrakis (triphenylphosphine)palladium, etc. Examples of the copper halide include copper iodide and copper bromide. Examples of the phosphine compound (i.e., ligand) include triphenylphosphine, tris(2-methylphenyl)phosphine, tris(3-methylphenyl)phosphine, tris(4-methylphenyl)phosphine, tris(4-methoxyphenyl)phosphine, tri-n-butylphosphine, tri-tert-butylphosphine, tricyclopentylphosphine, tri-n-hexylphosphine, tri-cyclohexyl phosphine, tri-n-octylphosphine, etc. Although the amount of the catalyst used in the Sonogashira reaction is not particularly specified, specifically, for example, the amount of bis(triphenylphosphine) palladium dichloride added is preferably 0.01 to 0.5 mol % relative to the amount of the acetylene compound (15). The amount of triphenylphosphine added is 1 to 20 equivalent weight, per mole of bis(triphenylphosphine)palladium dichloride. Moreover, the amount of copper iodide added is 1 to 10 equivalent weight, per mole of bis(triphenylphosphine) palladium dichloride. The amount of the compound (15) used in the Sonogashira reaction is generally 1 to 10 equivalent weight, per mole of the compound (13). The solvent usable in the Sonogashira reaction is, for example, an amine solvent, such as diethylamine, triethylamine, or butylamine. When the starting materials are difficult to dissolve in such an amine solvent, an aprotic polar solvent, such as N,N'-dimethylformamide (DMF), N,N'-dimethylacetamide (DMAc), or N-methylpyrrolidone (NMP), may be added. The amount of amine solvent used in the Sonogashira reaction is not particularly specified; however, the amount of amine solvent is typically 2 to 10 equivalent weight, per mole of the starting materials. The reaction temperature in the Sonogashira reaction depends on the kind of solvent used, but is room temperature to 90° C. The reaction pressure may be normal pressure, and the reaction time is not particularly limited.

(2-9) Production Method 9

The ester moiety (I-1), halogen moiety (4), or cyano moiety (5) for producing a compound represented by Formula (I-2), (I-3), (I-4), (I-5), or (I-6), wherein L is "substituted or unsubstituted C$_{1-6}$ alkylene-O— (some carbon atoms in the alkylene optionally form a cycloalkyl ring)", can be produced by the following method. The thus-prepared compound (I-1), (4), or (5) can be converted to the aromatic or heterocyclic carboxylic acid or a bioisostere thereof (I) in the same manner as in the production method 1, 3, 4, 5, or 6.

As shown in the following formula, in place of the compound (2) used in the step (a) of the production method 1, a compound (16) is reacted with the compound (1), (1'), or (1") to produce a compound (17) [step (l)]. The compound (17) is then reacted with a compound (18), thereby producing an ester moiety (I-1), halogen moiety (4), or cyano moiety (5) of the aromatic or heterocyclic carboxylic acid of the present invention [step (m)].

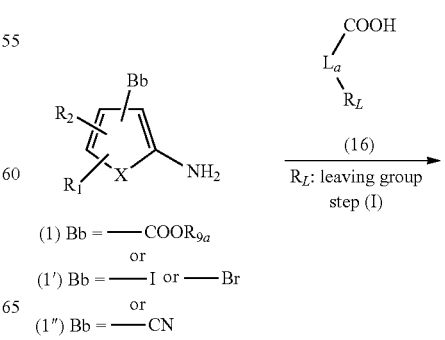

(1) Bb = —COOR$_{9a}$
or
(1') Bb = —I or —Br
or
(1") Bb = —CN

-continued

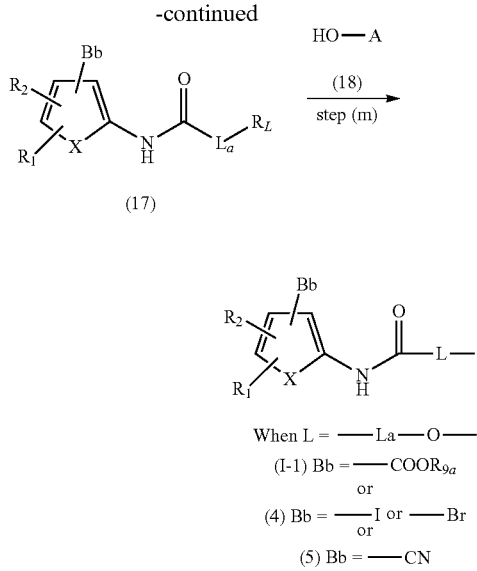

When L = —La—O—
(I-1) Bb = —COOR$_{9a}$
or
(4) Bb = —I or —Br
or
(5) Bb = —CN wherein R$_1$, R$_2$, X, R$_{9a}$, and A are as defined above; Bb is ester (—COOR$_{9a}$), halogen (iodine or bromine), or cyano; R$_L$ is a leaving group; and La is substituted or unsubstituted C$_{1-6}$ alkylene (some carbon atoms in the alkylene optionally form a cycloalkyl ring).

Examples of the leaving group used as R$_L$ include halogen (e.g., chlorine, bromine, and iodine), sulfonyloxy groups (e.g., mesyloxy, besyloxy, and tosyloxy), and the like.

In the above formula, the reaction of the step (l) can be carried out under the same reaction conditions as in the step (a) of the production method 1.

The reaction between the compounds (17) and (18) in the step (m) is typically carried out in a solvent in the presence of a base at about 0° C. to about 180° C., and preferably about 0° C. to the boiling point of the solvent.

Examples of bases include inorganic bases, such as sodium hydride, potassium hydride, potassium carbonate, sodium carbonate, and sodium hydrogencarbonate; and organic bases, such as triethylamine and diisopropylethylamine.

The solvent employable is any of those inactive in the reaction, and examples include hydrocarbons (e.g., hexane, heptane, and cyclohexane), halogenated hydrocarbons (e.g., dichloromethane, dichloroethane, and chloroform), aromatic hydrocarbons (e.g., benzene, toluene, xylene, and anisole), ethers (e.g., ethyl ether and isopropyl ether), ketones (e.g., acetone, methyl ethyl ketone, and methyl isobutyl ketone), dioxane, THF, acetonitrile, pyridine, DMF, DMAc, etc.; and mixtures of these solvents.

(2-10) Production Method 10

The ester moiety (I-1), halogen moiety (4), or cyano moiety (5) for producing a compound represented by Formula (I-2), (I-3), (I-4), (I-5), or (I-6), wherein L is represented by Formula (IX), can be produced by the following method. The thus-prepared compound (I-1), (4), or (5) can be converted to the aromatic or heterocyclic carboxylic acid or a bioisostere thereof (I) in the same manner as in the production method 1, 3, 4, 5, or 6.

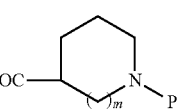

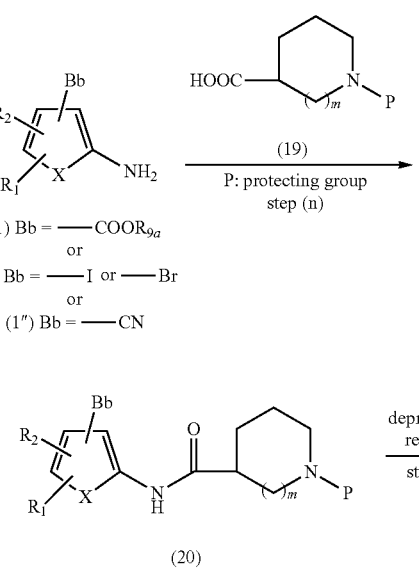

(1) Bb = —COOR$_{9a}$
or
(1') Bb = —I or —Br
or
(1") Bb = —CN

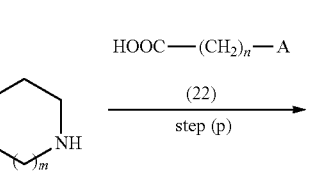

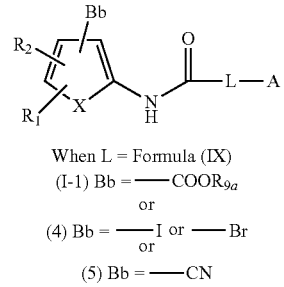

When L = Formula (IX)
(I-1) Bb = —COOR$_{9a}$
or
(4) Bb = —I or —Br
or
(5) Bb = —CN wherein R$_1$, R$_2$, R$_{9a}$, X, m, n, Bb, and A are as defined above; and P is an amino-protecting group.

The deprotection reaction of the compound (20) varies depending on the kind of protecting group used, but can be easily carried out under known deprotection conditions preferably using a deprotecting agent generally used in peptide chemistry [step (o)]. Typical examples of the amino-protecting group include benzyloxycarbonyl and t-butoxycarbonyl. The reactions of the steps (n) and (p) can be carried out under the same reaction conditions as in the step (a) of the production method 1.

(2-11) Production Method 11

The ester moiety (I-1), halogen moiety (4), or cyano moiety (5) for producing a compound represented by Formula (I-2), (I-3), (I-4), (I-5), or (I-6), wherein L is "substituted or unsubstituted alkylene—NHCO— (some carbon atoms in the alkylene optionally form a cycloalkyl ring)", can be produced by the following method. The thus-prepared compound (I-1), (4), or (5) can be converted to the aromatic or heterocyclic carboxylic acid or a bioisostere thereof (I) in the same manner as in the production method 1, 3, 4, 5, or 6.

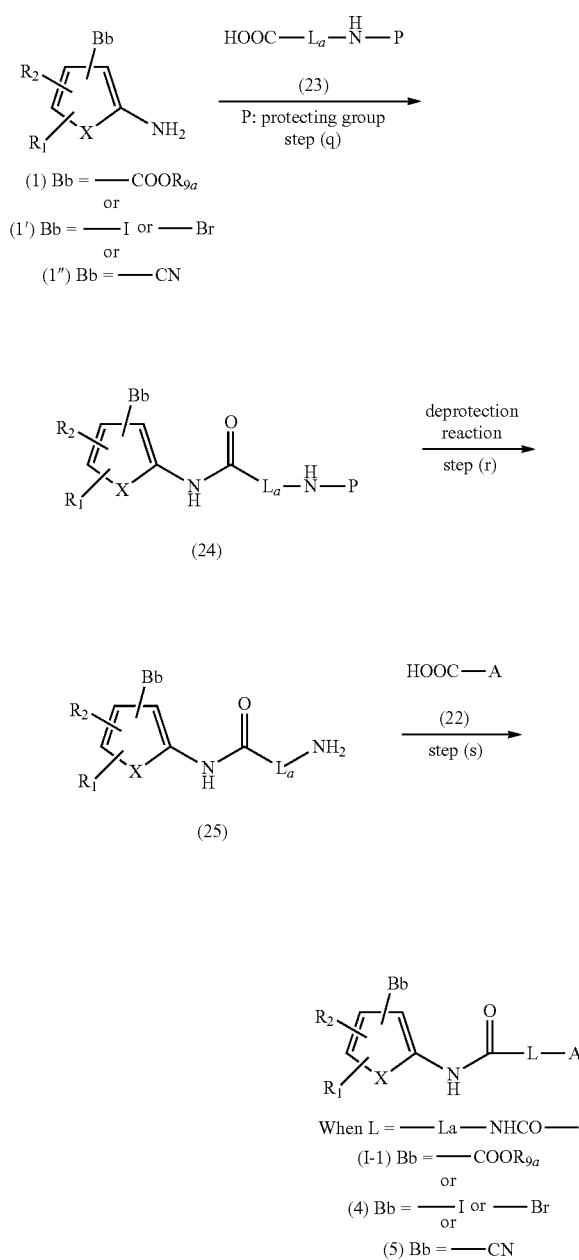

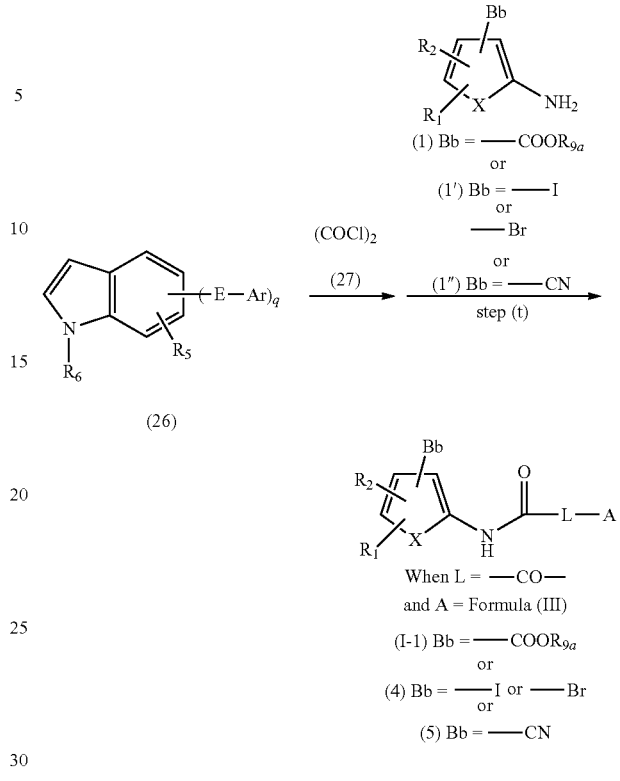

wherein $R_1$, $R_2$, $R_{9a}$, X, $L_a$, Bb, P, and A are as defined above.

In the above formula, the reactions of the steps (q) and (s) can be carried out under the same reaction conditions as in the step (a) of the production method 1. The reaction of the step (r) can be carried out under the same reaction conditions as in the step (o) of the production method 10.

(2-12) Production Method 12

The ester moiety (I-1), halogen moiety (4), or cyano moiety (5) for producing a compound represented by Formula (I-2), (I-3), (I-4), (I-5), or (I-6), wherein L is CO, and A is represented by Formula (III), can also be produced by the following method. The thus-prepared compound (I-1), (4), or (5) can be converted to the aromatic or heterocyclic carboxylic acid or a bioisostere thereof (I) in the same manner as in the production method 1, 3, 4, 5, or 6.

wherein $R_1$, $R_2$, $R_5$, $R_6$, E, Bb, Ar, $R_{9a}$, and X are as defined above.

In the reaction, a compound (26) is reacted with oxalyl chloride (27) in a solvent, and the reaction mixture is concentrated and then reacted with the compound (1), (1'), or (1") in a solvent to easily produce a compound (I-1), (4), or (5) [step (t)].

As the solvent usable in the reaction, an inert organic solvent is generally in the reaction with the oxalyl chloride (27). Examples of usable organic solvents include halogenated alkyls (e.g., methylene chloride and chloroform); aromatic hydrocarbons (e.g., benzene, toluene, xylene, and anisole); and ethers (e.g., diethyl ether, diisopropyl ether, methyl isobutyl ether, methyl cyclopentyl ether, THF, and dioxane). The reaction with the compound (1), (1'), or (1") is generally carried out in a solvent, and, if necessary, in the presence of a base. In the reaction with the compound (1), (1'), or (1"), an inert organic solvent is commonly used as a solvent. Examples of usable organic solvents include halogenated alkyls (e.g., methylene chloride and chloroform); aromatic hydrocarbons (e.g., benzene, toluene, xylene, and anisole); ethers (e.g., diethyl ether, diisopropyl ether, methyl isobutyl ether, methyl cyclopentyl ether, THF, and dioxane); esters (e.g., methyl acetate, ethyl acetate, isopropyl acetate, and butyl acetate); ketones (e.g., acetone, methyl ethyl ketone, and methyl isobutyl ketone); acetonitrile, DMF, DMAc, N-methylpiperidone, dimethyl sulfoxide, etc. Examples of usable bases include inorganic bases (e.g., sodium hydrogencarbonate, potassium hydrogencarbonate, sodium carbonate, potassium carbonate, sodium hydroxide, potassium hydroxide, and lithium hydroxide); and organic bases (e.g., pyridine, triethyl amine, N,N-diisopropylethylamine, N-methylmorpholine, and N-methylpiperidine).

(2-13) Production Method 13

A compound represented by Formula (I-2), wherein L is represented by —NH—, is produced, as shown in the following formula. More specifically, the compound (1a) is reacted with an isocyanate compound (28) to produce the compound (I-2), which is equivalent to the aromatic or heterocyclic carboxylic acid of the present invention [step (u)].

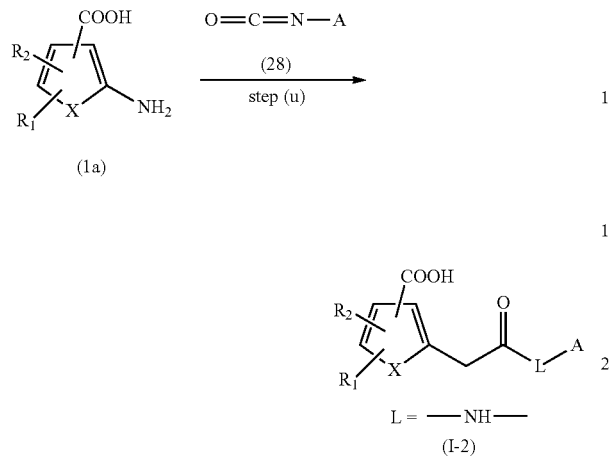

wherein $R_1$, $R_2$, X, and A are as defined above.

The reaction is typically carried out in a solvent at about −50° C. to about 100° C., and preferably about 30° C. to about 80° C. The solvent employable is any of those inactive in the reaction, and examples include hydrocarbons (e.g., hexane, heptane, and cyclohexane), halogenated hydrocarbons (e.g., dichloromethane and chloroform), aromatic hydrocarbons (e.g., benzene, toluene, xylene, and anisole), ethers (e.g., ethyl ether and isopropyl ether), esters (e.g., methyl acetate, ethyl acetate, and butyl acetate), dioxane, THF, acetonitrile, pyridine, DMF, DMAc, etc. The amount of the isocyanate compound (28) used is about 1 to about 2 equivalent weight, and preferably about 1 to about 1.5 equivalent weight, per mole of the compound (1a).

The reaction may be carried out in the presence of a base, as necessary; and, for example, pyridine, picoline, 4-dimethylaminopyridine, triethylamine, N-methylpiperidine, N-methylmorpholine, etc., can be used in an amount of about 1 to about 3 equivalent weight, and preferably about 1 to about 2 equivalent weight, per mole of the compound (1a).

(2-14) Production Method 14

The ester moiety (I-1), halogen moiety (4), or cyano moiety (5) for producing a compound represented by Formula (I-2), (I-3), (I-4), (I-5), or (I-6), wherein L is —NH— alkylene, can be produced by reacting the compound (1), (1') or (1") with p-nitrophenyl chloroformate (29) to synthesize a carbamate intermediate, followed by a reaction with a compound (30) or (31) in the same system, as shown in the following formula [step (v)]. The thus-prepared compound (I-1), (4), or (5) can be converted to the aromatic or heterocyclic carboxylic acid or a bioisostere thereof (I) in the same manner as in the production method 1, 3, 4, 5, or 6.

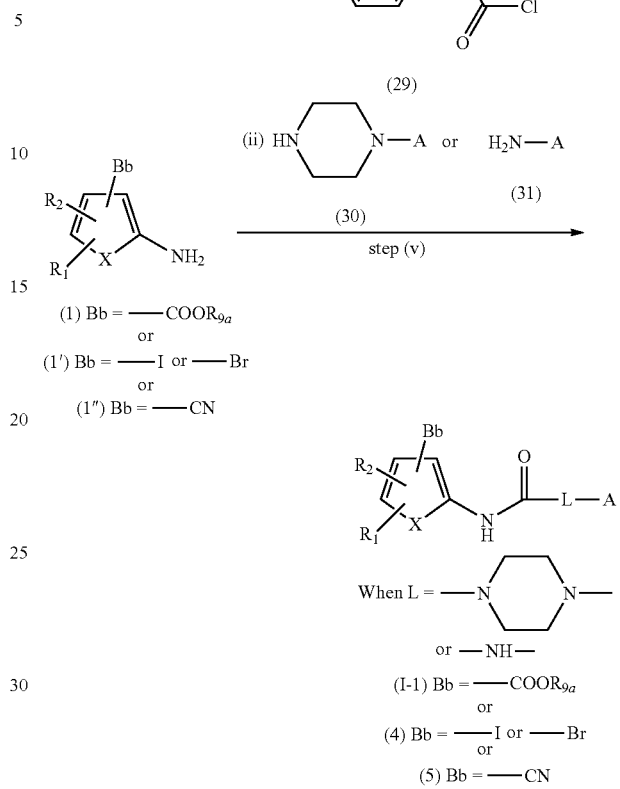

wherein $R_1$, $R_2$, $R_{9a}$, Bb, A, and X are as defined above.

In the above reaction formula, the reaction between the compound (1), (1'), or (1") and the p-nitrophenyl chloroformate (29) is typically carried out in a solvent at about −20° C. to about 50° C., and preferably about −10° C. to about 30° C., using a suitable base (e.g., pyridine, picoline, 4-dimethylaminopyridine, triethylamine, N-methylpiperidine, or N-methylmorpholine). The reaction between the generated carbamate intermediate and the compound (30) or (31) is carried out at about 0° C. to about 100° C., and preferably about 20° C. to about 50° C. The solvent employable is any of those inactive in the reaction, and examples include hydrocarbons (e.g., hexane, heptane, and cyclohexane), halogenated hydrocarbons (e.g., dichloromethane and chloroform), aromatic hydrocarbons (e.g., benzene, toluene, xylene, and anisole), ethers (e.g., ethyl ether and isopropyl ether), esters (e.g., methyl acetate, ethyl acetate, and butyl acetate), dioxane, THF, acetonitrile, pyridine, DMF, DMAc, etc. The amount of the p-nitrophenyl chloroformate (29), compound (30) or (31) used is about 1 to about 2 equivalent weight, and preferably about 1 to about 1.5 equivalent weight, per mole of the compound (1), (1'), or (1"). The amount of base used is about 1 to about 3 equivalent weight, and preferably about 1 to about 2 equivalent weight, per mole of the compound (1), (1'), or (1").

(2-15) Production Method 15

A compound represented by Formula (I-2), wherein L is alkylene —NH—, is produced, as shown in the following formula. More specifically, a compound (32) is reacted with the amino compound (31) to produce the compound (I-2), which is equivalent to the aromatic or heterocyclic carboxylic acid of the present invention [step (w)].

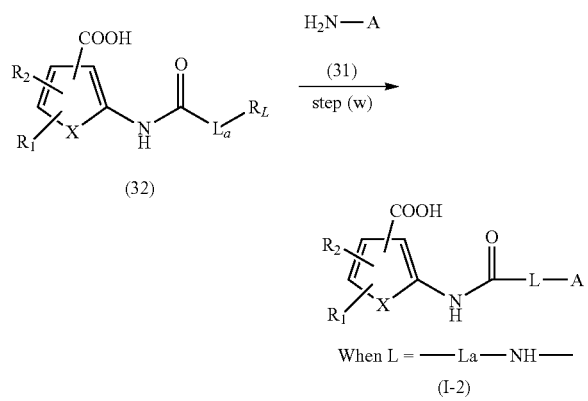

(32)

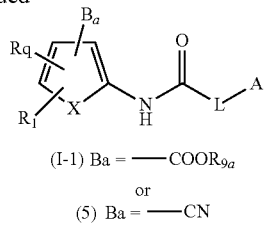

When L = ——La—NH——

(I-2)

wherein $R_1$, $R_2$, X, La, $R_L$, and A are as defined above.

The reaction between the compound (32) and the amino compound (31) in the step (w) is typically carried out in a solvent in the presence of a base at about 0° C. to about 180° C., and preferably about 0° C. to the boiling point of the solvent.

Examples of bases include inorganic bases, such as sodium hydride, potassium hydride, potassium carbonate, sodium carbonate, and sodium hydrogencarbonate; and organic bases, such as triethylamine and diisopropylethylamine.

The solvent employable is any of those inactive in the reaction, and examples include hydrocarbons (e.g., hexane, heptane, and cyclohexane), halogenated hydrocarbons (e.g., dichloromethane, dichloroethane, and chloroform), aromatic hydrocarbons (e.g., benzene, toluene, xylene, and anisole), ethers (e.g., ethyl ether and isopropyl ether), ketones (e.g., acetone, methyl ethyl ketone, and methyl isobutyl ketone), dioxane, THF, acetonitrile, pyridine, DMF, DMAc, etc.; and mixtures of these solvents.

(2-16) Production Method 16

As shown in the following formula, in place of the compound (1) used in the step (a) of the production method 1, a compound (33) represented by the following formula is reacted with the compound (2) to produce a compound (34) [step (x)]. Subsequently, in place of the compound (13) used in the step (k) of the production method 8, the compound (34) is reacted to produce a compound (I-1) or (5) into which Rq is introduced [step (y)]. The thus-prepared compound (I-1) or (5) can be converted to the aromatic or heterocyclic carboxylic acid or a bioisostere thereof (I) in the same manner as in the production method 1, 3, 4, 5, or 6.

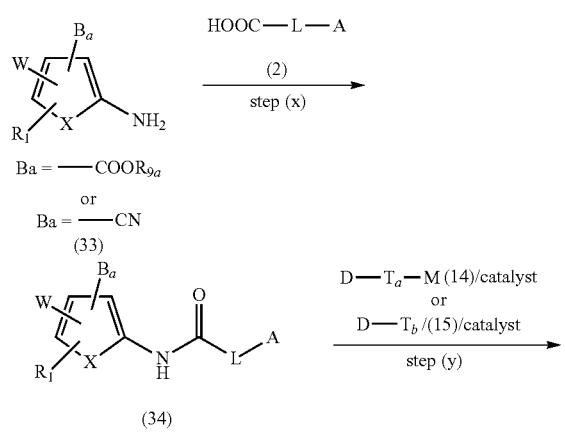

wherein $R_1$, Ba, W, X, L, A, D, Ta, Tb, M, and $R_{9a}$ are as defined above; and Rq is D-Ta— or D-Tb—.

(2-17) Production Method 17

As shown in the following formula, in place of the compound (13) used in the step (k) of the production method 8, the compound (33) is reacted to produce a starting material (1) or (1″) to be used in the production methods 1 to 5 and 7 to 16 [step (z)].

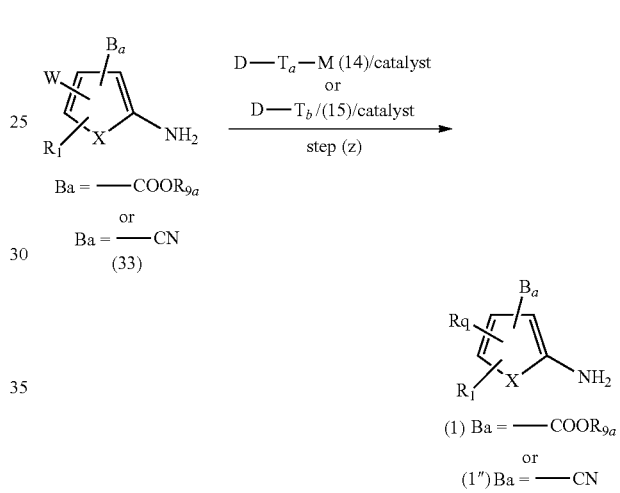

wherein $R_1$, Ba, W, X, D, Ta, Tb, M, Rq, and $R_{9a}$ are as defined above.

(2-18) Production Method 18

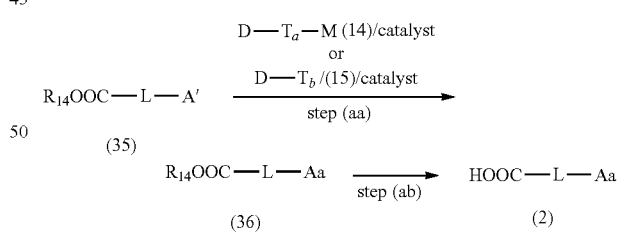

wherein A', L, D, Ta, Tb, and M are as defined above; and $R_{14}$ is alkyl, aryl, aralkyl, or hydrogen; and Aa is as defined in (2-8).

In the above formula, the compound (35) is reacted with the compound (14) or (15) under the same reaction conditions as in the step (k) of the production method 8 to produce a compound (36) [step (aa)]. The thus-prepared compound (36) is then subjected to a reaction under the same reaction conditions as in the step (b) of the production method 1 to easily produce a compound (2) [step (ab)]. When $R_{14}$ is hydrogen, the compound (36) is identical to the compound (2); thus, the compound (2) can be produced only by the step (aa). The thus-prepared compound (2) can be converted to the aromatic or heterocyclic carboxylic acid of the present invention or a bioisostere thereof (I) in the same manner as in the production method 1, 3, 4, 5, or 6.

(2-19) Production Method 19

The production intermediate (13) described above can also be produced by the following method.

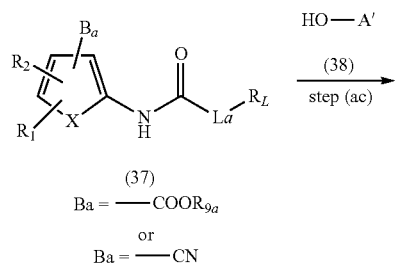

(37)
Ba = —COOR$_{9a}$
or
Ba = —CN

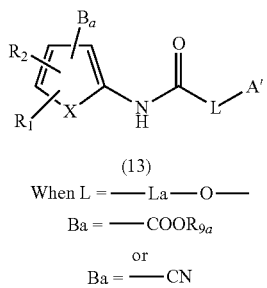

(13)
When L = —La—O—
Ba = —COOR$_{9a}$
or
Ba = —CN wherein R$_1$, R$_2$, A', Ba, La, X, R$_L$, and R$_{9a}$ are as defined above.

In the above formula, an ester moiety or cyano moiety (37) of the compound (17) produced by the step (l) of the production method 9 is reacted with a compound (38), in place of the compound (18) used in the step (m), to produce a compound (13) [step (ac)].

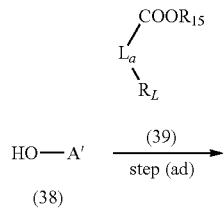

(38)

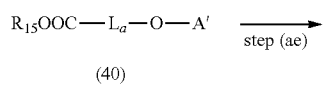

(40)

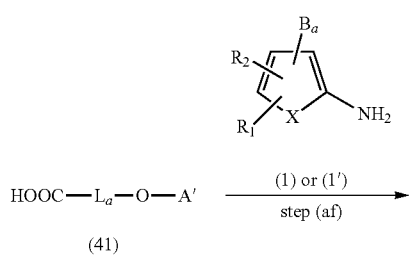

(41)

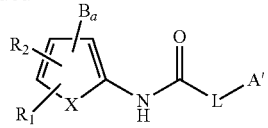

(13)
When L = —La—O—
Ba = —COOR$_{9a}$
or
Ba = —CN wherein R$_1$, R$_2$, A', Ba, La, X, R$_L$, and R$_{9a}$ are as defined above; R$_{15}$ is alkyl, aryl or aralkyl; and L is substituted or unsubstituted C$_{1-6}$ alkylene-O— (some carbon atoms in the alkylene optionally form a cycloalkyl ring).

In the above formula, the compounds (38) and (39) are reacted under the same reaction conditions as in the step (l) of the production method 9 to easily produce a compound (40) [step (ad)]. The compound (40) is then reacted under the same reaction conditions as in the step (b) of the production method 1 to easily produce a compound (41) [step (ae)]. Further, the compound (41) is reacted under the same reaction conditions as in the step (a) of the production method 1 to easily produce a compound (13) [step (af)].

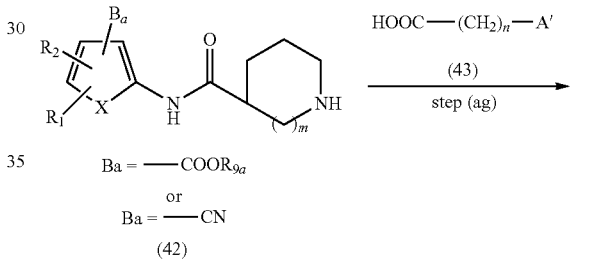

(42)

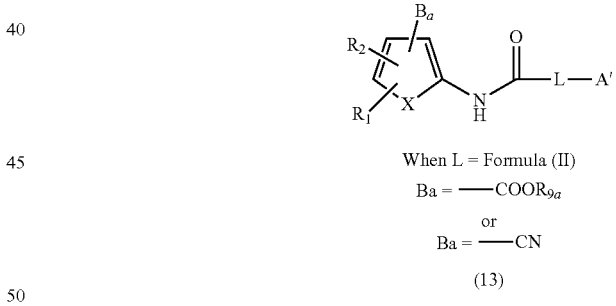

(13)

wherein R$_1$, R$_2$, Ba, X, m, n, A', and R$_{9a}$ are as defined above.

In the above formula, the compound (42), which is a compound (21) wherein Ba is —COOR$_{9a}$ or cyano, is converted to the compound (13) of the production method 8 by the reaction with a compound (43) [step (ag)]. According to the production method 8, the compound (13) is converted to the aromatic or heterocyclic carboxylic acid or a bioisostere (I) thereof.

(3) PAI-1 Inhibitor

The present invention provides an application of the compound (I) as a PAI-1 inhibitor. More specifically, the present invention provides a PAI-1 inhibitor comprising the compound (I) as an active ingredient. In other words, the PAI-1 inhibitor of the invention comprises the compound (I) having PAI-1 inhibitory activity as an active ingredient.

The PAI-1 inhibitory activity of the compound (I) can be evaluated using an in vitro assay system. For example, mentioned as such an in vitro assay system is a method for examining change in PAI-1 activity to a tissue plasminogen activator (t-PA) in the presence of the compound (I). The change in PAI-1 activity can be examined by setting, as an index, a reaction product produced by the action of t-PA on a substrate. For example, the test example described later shows an in vitro assay system for examining change in the PAI-1 activity by setting, as an index, a quantity of p-nitroaniline (reaction product) produced by the action of t-PA on a coloring substrate (S-2288). It can be judged that when the amount of reaction product is larger, the t-PA activity is higher, and accordingly the PAI-1 inhibitory activity is higher.

The evaluation of PAI-1 inhibitory activity of the compound (I) can also be carried out by examining the change in formation of a complex of PAI-1 and t-PA (PAI-1/t-PA complex) in the presence of the compound (I) using, for example, western blotting. In the invention, it can be judged that when the amount of formation of PAI-1/t-PA complex is smaller (PAI-1/t-PA complex formation inhibition), the PAI-1 inhibitory action is higher.

The action can increase plasmin-dependent degradation of fibrin and fibrinogen, thereby promoting in vivo fibrinolysis and also improving various diseases (e.g., ischemic heart diseases such as angina pectoris, myocardial infarction, and cardiac insufficiency; deep-vein thrombosis and pulmonary embolism originated therefrom; and diabetic angiopathy) caused by depression of in vivo fibrinolysis (see Non-Patent Document 11).

It has been proved that one of the causes of tissue fibrosis is PAI-1. It is also known that the development of pulmonary fibrosis can be inhibited by PAI-1 inhibitors (see Non-Patent Document 24). Therefore, the use of the compound (I) makes it possible to prevent or improve tissue fibrosis and diseases associated with tissue fibrosis (e.g., pulmonary fibrosis) based on inhibitory action on PAI-1 activity.

Additionally, it is also reported that PAI-1 inhibitors have a stimulatory effect on the degradation of Aβ, which is regarded as a cause of the development of Alzheimer's disease, as a result of being accumulated in the brain (see Non-Patent Document 27). Therefore, the compound (I) is expected to be able to promote Aβ degradation based on the PAI-1 inhibitory activity to prevent the onset of Alzheimer's disease or to improve the disease.

Furthermore, PAI-1 inhibitors are effective to prevent or alleviate various pathologies reportedly associated with PAI-1 (e.g., various thromboses, cancers, diabetes and diabetic complications, eye diseases such as glaucoma and retinopathy, polycystic ovary syndrome, radiation injuries, alopecia (calvities), hepatosplenomegaly, obesity, and arteriosclerosis) (see Non-Patent Documents 12 to 17).

The PAI-1 inhibitor of the invention comprises the compound (I) having PAI-1 inhibitory activity as an active ingredient. In the PAI-1 inhibitor of the invention, the proportion of the compound (I) may be 100%; conversely, the PAI-1 inhibitor of the invention may comprise an effective amount of the compound (I) for demonstrating PAI-1 inhibitory activity. The proportion of the compound (I) is not limited, and is usually 0.1 to 99% by weight, and preferably 1 to 80% by weight.

(4) Pharmaceutical Composition

The present invention provides a pharmaceutical composition comprising the PAI-1 inhibitor described above as an active ingredient. In other words, the pharmaceutical composition of the invention comprises the compound (I) described above as an active ingredient. The pharmaceutical composition of the invention is imparted with PAI-1 inhibitory action by including an effective amount of the compound (I). As a result, the pharmaceutical composition of the invention increases the plasmin-dependent degradation of fibrin and fibrinogen, to thereby demonstrate the actions of promoting in vivo fibrinolysis or improving depression of in vivo fibrinolysis.

Therefore, the pharmaceutical composition of the invention can be used as a fibrinolysis promoter. To be specific, the pharmaceutical composition of the invention is useful as a prophylactic and therapeutic agent for thrombotic diseases and pathologies whose development is attributed to PAI-1 activity, or diseases and pathologies whose development is attributed to depression of the fibrinolytic system. Mentioned as such diseases or pathologies are various diseases or pathologies caused by thrombus formation, such as thrombosis in arteries, thrombosis in veins, deep vein thrombosis (DVT) during surgical operations, disseminated intravascular coagulation syndrome (DIC), diabetic complications, such as angiopathy, neuropathy, retinopathy, and nephropathy, or restenosis after percutaneous transluminal coronary angioplasty (PTCA). Examples of thrombosis in arteries include thrombosis in the brain (cerebral thrombosis, cerebral embolism, and transient ischemic attack), thrombosis in the heart (angina pectoris and myocardial infarction), thrombosis in the lower extremities (lower extremity acute arterial thrombosis), and thrombosis in the upper intestinal tract (upper intestinal tract arterial thrombosis). Examples of thrombosis in veins include thrombosis in the extremities (deep-vein thrombosis) and thrombosis occurring when a blood clot travels to the lung (pulmonary embolism).

The pharmaceutical composition of the invention has an effective amount of the compound (I), and is thus imparted with a PAI-1 inhibitory action. Therefore, the pharmaceutical composition of the invention prevents or alleviates tissue or organ fibrosis. Accordingly, the pharmaceutical composition of the invention is useful as an agent for preventing or treating diseases and/or pathologies related to tissue or organ fibrosis whose development is influenced by PAI-1 activity. Examples of such diseases or pathologies include tissue fibrosis associated with pulmonary fibrosis and myocardial infarction, and organ fibrosis associated with nephropathy, etc.

Moreover, since the pharmaceutical composition of the invention has an effective amount of the compound (I), and thus is imparted with a PAI-1 inhibitory action, the pharmaceutical composition of the invention is useful as an anti-Alzheimer's drug, as described above. Therefore, the pharmaceutical composition of the invention is useful as an agent for preventing or treating Alzheimer's disease.

Furthermore, since the pharmaceutical composition of the invention has an effective amount of the compound (I), and thus is imparted with a PAI-1 inhibitory action, the pharmaceutical composition of the invention is useful as an agent for preventing or treating various pathologies mentioned above (e.g., various thromboses, cancers, diabetes and diabetic complications, eye diseases such as glaucoma and retinopathy, polycystic ovary syndrome, radiation injuries, alopecia (calvities), hepatosplenomegaly, bone-marrow regeneration, obesity, amyloidosis, and arteriosclerosis). The pharmaceutical composition of the invention generally comprises a pharmaceutically acceptable carrier or additive in addition to the compound (I) in an amount effective for exhibiting PAI-1 inhibitory action. The proportion of the compound (I) in the pharmaceutical composition of the invention is suitably determined according to the kind of target diseases and/or pathologies or manner of administrating the pharmaceutical composition, and is usually in the range of from 0.001 to 50% by weight, and particularly from 0.01 to 10% by weight, based on the total weight of the pharmaceutical composition (100% by weight).

The pharmaceutical composition of the invention can be administered orally or parenterally, such as intravenously, intramuscularly, subcutaneously, transmucosally, transdermally, intrarectally, etc. Among these, preferable are oral administration and intravenous administration, and more preferable is oral administration. The pharmaceutical composition of the invention can be provided in various forms of preparations (dosage forms) depending on the above-mentioned administration manners. Various preparations (dosage forms) are described below; however, the dosage forms employed in the invention are not limited thereto. Any dosage forms that are usually used in the field of pharmaceutical preparation can be employed.

In the case of oral administration, the dosage form of the pharmaceutical composition of the invention is suitably selected from powders, granules, capsules, pills, tablets, elixirs, suspensions, emulsions, and syrups. Such preparations can be imparted with sustained-release properties, stabilization, easy-degradation, difficult-degradation, enteric properties, easy adsorption properties, etc.

In the case of intravenous administration, intramuscular administration, or subcutaneous administration, the dosage form can be suitably selected from injections or drops (including dried products that are prepared upon use), and the like.

In the case of transmucosal administration, transdermal administration, or intrarectal administration, the dosage form can be suitably selected from masticatories, sublingual agents, buccal tablets, trochisci, ointments, patch agents, liquid agents, etc., according to the applied portion. Such preparations can be imparted with sustained-release properties, stabilization, easy-degradation, difficult-degradation, easy adsorption properties, etc.

The pharmaceutical composition of the invention can contain a pharmaceutically acceptable carrier and additive according to the dosage form (oral administration or various parenteral administrations). Examples of pharmaceutically acceptable carriers and additives include solvents, excipients, coating agents, bases, binders, lubricants, disintegrators, solubilizers, suspending agents, thickening agents, emulsifiers, stabilizers, buffers, isotonizing agents, soothing agents, preservatives, corrigents, flavors, and coloring agents. Specific examples of pharmaceutically acceptable carriers and additives are mentioned below; however, the invention is not limited thereto.

Examples of solvents include purified water, sterile purified water, water for injection, physiologic saline, peanut oil, ethanol, glycerol, etc. Examples of excipients include starches (e.g., potato starch, wheat starch, and corn starch), lactose, dextrose, saccharose, crystalline cellulose, calcium sulfate, calcium carbonate, sodium hydrogencarbonate, sodium chloride, talc, titanium oxide, trehalose, xylitol, etc.

Examples of binders include starch and starch derivatives, cellulose and cellulose derivatives (e.g., methylcellulose, ethylcellulose, hydroxypropylcellulose, and carboxymethylcellulose), natural high molecular weight compounds, such as gelatin, sodium arginine, tragacanth, gum arabic, etc., synthetic high molecular weight compounds, such as polyvinyl pyrrolidone, polyvinyl alcohol, etc., dextrin, hydroxypropyl starch, and the like.

Examples of lubricants include light anhydrous silicic acid, stearin acid and salts thereof (e.g., magnesium stearate), talc, waxes, wheat starch, macrogol, hydrogenated vegetable oil, sucrose fatty acid ester, polyethylene glycol, silicone oil, etc.

Examples of disintegrators include starch and starch derivatives, agar, gelatin powder, sodium hydrogencarbonate, calcium carbonate, cellulose and cellulose derivatives, hydroxypropyl starch, carboxymethylcellulose, salts thereof, and bridging materials thereof, low-substituted hydroxypropylcellulose, etc.

Examples of solubilizers include cyclodextrin, ethanol, propylene glycol, polyethylene glycol, etc. Examples of suspending agents include sodium carboxymethylcellulose, polyvinylpyrrolidone, gum arabic, tragacanth, sodium arginine, aluminum monostearate, citric acid, various surfactants, etc.

Examples of thickening agents include sodium carboxymethylcellulose, polyvinylpyrrolidone, methylcellulose, hydroxypropyl methylcellulose, polyvinyl alcohol, tragacanth, gum arabic, sodium arginine, etc.

Examples of emulsifiers include gum arabic, cholesterol, tragacanth, methylcellulose, lecithin, various surfactants (e.g., polyoxyl 40 stearate, sorbitan sesquioleate, polysorbate 80, and sodium lauryl sulfate), etc.

Examples of stabilizers include tocopherol, chelating agents (e.g., EDTA and thioglycolic acid), inert gases (e.g., nitrogen and carbon dioxide), reducing substances (e.g., sodium hydrogen sulfite, sodium thiosulfate, ascorbic acid, and rongalite), etc.

Examples of buffers include sodium hydrogenphosphate, sodium acetate, sodium citrate, boric acid, etc.

Examples of isotonizing agents include sodium chloride, glucose, etc. Examples of soothing agents include local anesthetics (e.g., procaine hydrochloride and lidocaine), benzyl alcohol, glucose, sorbitol, amino acid, etc.

Examples of corrigents include saccharose, saccharin, Glycyrrhiza extract, sorbitol, xylitol, glycerol, etc. Examples of flavoring agents include orange peel tincture, rose oil, etc. Examples of coloring agents include water-soluble food colors, lake pigment, etc.

Examples of preservatives include benzoic acid and salts thereof, p-hydroxybenzoate esters, chlorobutanol, invert soap, benzyl alcohol, phenol, thimerosal, dehydroacetic acid, boric acid, etc.

Examples of coating agents include saccharose, hydroxypropylcellulose (HPC), shellac, gelatin, glycerol, sorbitol, hydroxypropyl methylcellulose (HPMC), ethylcellulose, polyvinyl pyrrolidone (PVP), hydroxypropylmethylcellulose phthalate (HPMCP), cellulose acetate phthalate (CAP), methyl methacrylate-methacrylic acid copolymer and polymers described above, etc.

Examples of bases include Vaseline, liquid paraffin, carnauba wax, beef tallow, hardened oil, paraffin, yellow beeswax, vegetable oil, macrogol, macrogol fatty acid ester, stearic acid, sodium carboxymethylcellulose, bentonite, cacao butter, Witepsol, gelatin, stearyl-alcohol, hydrous lanolin, cetanol, light liquid paraffin, hydrophilic petrolatum, simple ointment, white ointment, hydrophilic ointment, macrogol ointment, hard fat, oil-in-water emulsion bases, water-in-oil emulsion bases, etc.

Known drug delivery systems (DDS) can be applied for the dosage forms given above. The term DDS preparation as used in the present specification refers to slow-release preparations, locally applied preparations (troches, buccal tablets, sublingual tablets, etc.), drug control-release preparations, enteric coated preparations and gastric soluble preparations, etc., that are all prepared in the best form considering the administration route, bioavailability, side effects, etc.

When the pharmaceutical composition of the invention is used as a prophylactic or therapeutic agent for pathologies associated with depression of the fibrinolytic system (thrombosis), the oral dose is preferably in the range of from 0.03 to 300 mg/kg of body weight, and is more preferably in the range of from 0.1 to 50 mg/kg of body weight as calculated in terms of the amount of the compound (I). In the case of intravenous administration, the administration amount can be determined in such a manner that the effective blood concentration of the compound (I) is preferably 0.2 to 50 µg/mL, and more preferably 0.5 to 20 µg/mL.

When the pharmaceutical composition of the invention is used as an agent for preventing or treating pathologies associated with tissue fibrosis, the oral dose is preferably in the range of from 0.03 to 300 mg/kg of body weight, and is more preferably in the range of from 0.1 to 50 mg/kg weight as calculated in terms of the amount of the compound (I). In the case of intravenous administration, the administration amount can be determined in such a manner that the effective blood concentration of the compound (I) is preferably 0.2 to 50 µg/mL, and more preferably 0.5 to 20 µg/mL. These dosage amounts may vary according to the age, gender, body type, etc., of a patient.

Additionally, when the pharmaceutical composition of the invention is used as an anti-Alzheimer's drug and is used to prevent or treat various pathologies, the dosage amount thereof may be determined as described above.

EXAMPLES

Hereinbelow, the present invention is described in more detail with reference to Examples and Experimental Examples. However, the present invention is not limited to such examples. All of the compounds used in Examples 1 to 107 as starting materials are known compounds. In the Examples, nuclear magnetic resonance spectra ($^1$H-NMR) were measured using a Varian Gemini 200. Chemical shift is shown as a δ value (ppm) using tetramethylsilane (TMS) as an internal standard. Each column chromatography elution was completed under observation using TLC (Thin Layer Chromatography). For TLC observation, silica gel 60F$_{254}$ produced by Merck Co. was used as the TLC plate. Silica gel 60 (70 to 230 meshes) produced by Merck Co., Inc. was used as the silica gel for each column chromatography.

Example 1

Production of 5-chloro-2-{[4-({[3-(furan-3-yl)phenyl]carbonyl}amino)butanoyl]amino}benzoic acid (1)

The target compound (1) was synthesized according to the following Steps (i) to (iv).

(i) Methyl 2-({4-[(tert-butoxycarbonyl)amino]butanoyl}amino)-5-chlorobenzoate 3.00 g (13.8 mmol) of N-tert-butoxycarbonyl-γ-aminobutyric acid, 3.38 g (17.7 mmol) of p-toluene sulfonyl chloride, and 3.64 g (44.3 mmol) of 1-methyl imidazole were stirred in an acetonitrile solvent at 0° C. for 1 hour. Subsequently, 2.74 g (14.8 mmol) of methyl 2-amino-5-chloro benzoate was added thereto, and the mixture was stirred at 50° C. for 1 hour. Thereafter, the solvent was distilled off under reduced pressure, and ethyl acetate was added. The mixture was washed with water, the organic layer was dried over anhydrous sodium sulfate, and the solvent was distilled off under reduced pressure. The obtained crude product was recrystallized using a mixed solvent of isopropyl ether (IPE) and n-hexane, thereby giving 3.18 g of methyl 2-({4-[(tert-butoxycarbonyl)amino]butanoyl}amino)-5-chlorobenzoate (yield: 58%).

$^1$H-NMR (CDCl$_3$) δ: 1.43 (9H, s), 1.85-2.01 (2H, m), 2.49 (2H, t, J=7.3 Hz), 3.22 (2H, q, J=6.5 Hz), 3.94 (3H, s), 4.72 (1H, brs), 7.48 (1H, dd, J=9.1, 2.6 Hz), 7.99 (1H, d, J=2.6 Hz), 8.69 (1H, d, J=9.1 Hz), 10.99 (1H, s).

(ii) Methyl 2-[(4-aminobutanoyl)amino]-5-chlorobenzoate hydrochloride 4N hydrogen chloride/ethyl acetate was added to an ethyl acetate solution comprising 2.16 g (5.82 mmol) of methyl 2-({4-[(tert-butoxycarbonyl)amino]butanoyl}amino)-5-chlorobenzoate at 0° C., and the mixture was stirred at room temperature for 3 hours. Thereafter, IPE was added to the reaction mixture. Crystals were collected by filtration, followed by drying, thereby giving 1.76 g of methyl 2-[(4-aminobutanoyl)amino]-5-chlorobenzoate hydrochloride (yield: 99%).

$^1$H-NMR (DMSO-d$_6$) δ: 1.81-1.98 (2H, m), 2.53 (2H, t, J=7.3 Hz), 2.85 (2H, t, J=7.5 Hz), 3.85 (3H, s), 7.67 (1H, dd, J=8.9, 2.6 Hz), 7.83 (1H, d, J=2.6 Hz), 8.09 (3H, brs), 8.13 (1H, d, J=8.9 Hz), 10.58 (1H, s).

(iii) Methyl 5-chloro-2-{[4-({[3-(furan-3-yl)phenyl]carbonyl}amino)butanoyl]amino}benzoate 1.00 g (3.3 mmol) of methyl 2-[(4-aminobutanoyl)amino]-5-chlorobenzoate hydrochloride, 0.61 g (3.3 mmol) of 3-(furan-3-yl)benzoic acid, 0.75 g (3.9 mmol) of 1-ethyl-3-(3-dimethylaminopropyl)carbodiimide hydrochloride, and 0.53 g (3.9 mmol) of 1-hydroxybenzotriazole were stirred in 10 mL of N,N-dimethylacetamide (DMAc) for 2 hours. After the completion of the reaction, ethyl acetate was added, and the mixture was diluted and washed with saturated sodium bicarbonate solution and saturated saline. After the organic layer was dried over anhydrous sodium sulfate, the solvent was distilled off under reduced pressure. The obtained crude product was recrystallized using a mixed solvent of ethyl acetate and n-hexane, thereby giving 1.22 g of methyl 5-chloro-2-{[4-({[3-(furan-3-yl)phenyl]carbonyl}amino)butanoyl]amino}benzoate (yield: 85%).

$^1$H-NMR (CDCl$_3$) δ: 2.02-2.19 (2H, m), 2.61 (2H, t, J=6.7 Hz), 3.59 (2H, q, J=5.8 Hz), 3.91 (3H, s), 6.73 (1H, dd, J=1.9, 0.9 Hz), 7.07 (1H, t, J=5.8 Hz), 7.36 (1H, t, J=7.7 Hz), 7.40 (1H, dd, J=9.1, 2.6 Hz), 7.48 (1H, t, J=1.7 Hz), 7.56 (1H, dt, J=7.8, 1.5 Hz), 7.65 (1H, dt, J=7.8, 1.5 Hz), 7.77 (1H, t, J=1.2 Hz), 7.89-7.93 (1H, m), 7.93 (1H, d, J=2.6 Hz), 8.62 (1H, d, J=9.1 Hz), 11.05 (1H, s).

(iv) 5-Chloro-2-{[4-({[3-(furan-3-yl)phenyl]carbonyl}amino)butanoyl]amino}benzoic acid 1.22 g (2.8 mmol) of methyl 5-chloro-2-{[4-({[3-(furan-3-yl)phenyl]carbonyl}amino)butanoyl]amino}benzoate was dissolved in 12 mL of tetrahydrofuran (THF). 1N aqueous sodium hydroxide was added at room temperature, and the mixture was stirred at 50° C. for 1.5 hours. After cooling the mixture, 1N hydrochloric acid was added to acidify the reaction mixture, and the solvent was distilled off under reduced pressure. Thereafter, water was added to the residue. Solids were collected by filtration, followed by washing with water, thereby giving 1.07 g of the target 5-chloro-2-{[4-({[3-(furan-3-yl)phenyl]carbonyl}amino)butanoyl]amino}benzoic acid (yield: 91%).

$^1$H-NMR (DMSO-d$_6$) δ: 1.82-2.01 (2H, m), 2.50 (2H, t, J=7.3 Hz), 3.37 (2H, td, J=6.6, 6.0 Hz), 6.97-7.02 (1H, m), 7.46 (1H, t, J=7.7 Hz), 7.62 (1H, dd, J=9.0, 2.6 Hz), 7.68-7.81 (3H, m), 7.90 (1H, d, J=2.6 Hz), 8.04 (1H, s), 8.22 (1H, s), 8.49 (1H, d, J=9.0 Hz), 8.55 (1H, J=6.0 Hz), 11.04 (1H, s).

Example 2

Production of 5-chloro-2-({[3-(furan-3-yl)phenyl]carbonyl}amino)benzoic acid (2)

The target compound (2) was synthesized according to the following Steps (i) to (ii).

(i) Methyl 5-Chloro-2-({[3-(furan-3-yl)phenyl]carbonyl}amino)benzoate 0.50 g (2.7 mmol) of 3-(furan-3-yl)benzoic acid, a catalytic amount of N,N-dimethylformamide (DMF), 0.78 g (3.7 mmol) of oxalyl chloride were stirred at 0° C. for 30 minutes in 10 mL of THF. Thereafter, the solvent was distilled off under reduced pressure. 0.49 g (2.7 mmol) of methyl 2-amino-5-chlorobenzoate and 5 mL of DMAc were added to the obtained residue at 0° C., and the mixture was stirred at room temperature for 0.5 hours. After the completion of the reaction, an aqueous sodium hydrogen carbonate solution was added. The precipitated solids were collected by filtration, followed by washing with water and IPE, thereby giving 0.63 g of methyl 5-chloro-2-({[3-(furan-3-yl)phenyl]carbonyl}amino)benzoate (yield: 67%).

$^1$H-NMR (DMSO-d$_6$) δ: 3.89 (3H, s), 7.04-7.08 (1H, m), 7.62 (1H, t, J=7.7 Hz), 7.72-7.94 (4H, m), 7.95 (1H, d, J=2.6 Hz), 8.17 (1H, s), 8.32 (1H, s), 8.49 (1H, d, J=9.0 Hz), 11.44 (1H, s).

(ii) 5-Chloro-2-({[3-(furan-3-yl)phenyl]carbonyl}amino)benzoic acid 0.61 g (1.7 mmol) of methyl 5-chloro-2-({[3-(furan-3-yl)phenyl]carbonyl}amino)benzoate was dissolved in 20 mL of THF solvent, and 4 mL of 1N aqueous sodium hydroxide was added. The mixture was stirred at 50° C. for 1.5 hours. After cooling, 1N hydrochloric acid was added to acidify the reaction mixture. Thereafter, the solvent was distilled off under reduced pressure. Subsequently, water was added to the residue, and solids were collected by filtration and washed with water. The obtained crude product was recrystallized using a mixed solvent of ethyl acetate and n-hexane, thereby giving 0.24 g of the target 5-chloro-2-({[3-(furan-3-yl)phenyl]carbonyl}amino)benzoic acid (yield: 41%).

$^1$H-NMR (DMSO-d$_6$) δ: 7.00-7.08 (1H, m), 7.61 (1H, t, J=7.7 Hz), 7.74-7.95 (3H, m), 7.75 (1H, dd, J=9.0, 2.5 Hz), 7.95 (1H, d, J=2.5 Hz), 8.16 (1H, s), 8.31 (1H, s), 8.72 (1H, d, J=9.0 Hz), 12.15 (1H, s).

Example 3

Production of 5-chloro-2-({[3-(furan-3-yl)phenyl]acetyl}amino)benzoic acid (3)

The target compound (3) was synthesized according to the following Steps (i) to (ii).

(i) Methyl 5-chloro-2-({[3-(furan-3-yl)phenyl]acetyl}amino)benzoate 0.25 g (1.2 mmol) of [3-(furan-3-yl)phenyl]acetic acid, a catalytic amount of DMF, and 0.36 g (1.7 mmol) of oxalyl chloride were stirred in 10 mL of THF at 0° C. for 1.5 hours. Thereafter, the solvent was distilled off under reduced pressure. 0.23 g (1.2 mmol) of methyl 2-amino-5-chlorobenzoate and 5 mL of DMAc were added to the residue at 0° C., and the mixture was stirred at room temperature for 1.5 hours. After the completion of the reaction, the mixture was diluted with ethyl acetate, washed with an aqueous sodium hydrogen carbonate solution and saturated saline, and dried over anhydrous sodium sulfate. The obtained crude product was separated and purified by silica gel column chromatography, thereby giving 0.3 g of methyl 5-chloro-2-({[3-(furan-3-yl)phenyl]acetyl}amino)benzoate (yield: 89%).

$^1$H-NMR (CDCl$_3$) δ: 3.78 (2H, s), 3.85 (3H, s), 6.74 (1H, dd, J=1.9, 0.8 Hz), 7.22-7.54 (6H, m), 7.78 (1H, dd, J=1.5, 0.8 Hz), 7.95 (1H, d, J=2.6 Hz), 8.69 (1H, d, J=9.1 Hz), 11.01 (1H, s).

(ii) 5-Chloro-2-({[3-(furan-3-yl)phenyl]acetyl}amino)benzoic acid 3 mL of THF and 1.2 mL of 1N aqueous sodium hydroxide were added to 0.30 g (0.81 mmol) of methyl 5-chloro-2-({[3-(furan-3-yl)phenyl]acetyl}amino)benzoate at room temperature, and the mixture was stirred at 50° C. for 2.5 hours. After cooling, 1N hydrochloric acid was added to acidify the reaction mixture. Thereafter, the solvent was distilled off under reduced pressure, and water was then added to the residue. Solids were collected by filtration, followed by drying, thereby giving 252 mg of the target 5-chloro-2-({[3-(furan-3-yl)phenyl]acetyl}amino)benzoic acid (yield: 88%).

$^1$H-NMR (DMSO-d$_6$) δ: 3.80 (2H, s), 6.97 (1H, dd, J=1.7, 0.8 Hz), 7.25 (1H, d, J=7.7 Hz), 7.37 (1H, t, J=7.7 Hz), 7.54 (1H, d, J=7.7 Hz), 7.62 (1H, s), 7.65 (1H, dd, J=9.1, 2.7 Hz), 7.75 (1H, t, J=1.7 Hz), 7.88 (1H, d, J=2.7 Hz), 8.19 (1H, dd, J=1.2, 0.8 Hz), 8.53 (1H, d, J=9.1 Hz), 11.10 (1H, s).

Example 4

Production of 2-[(biphenyl-3-ylcarbonyl)amino]-5-chlorobenzoic acid (4)

The target compound (4) was synthesized according to either one of the following two synthesized routes, i.e., the following Steps (i) and (ii), or (iii) to (iv).

(i) Methyl 2-[(biphenyl-3-ylcarbonyl)amino]-5-chlorobenzoate

Using the same method as in Example 3-(i), methyl 2-[(biphenyl-3-ylcarbonyl)amino]-5-chlorobenzoate (yield: 88%) was obtained using 3-biphenyl carboxylic acid and methyl 2-amino-5-chlorobenzoate.

$^1$H-NMR (CDCl$_3$) δ: 3.98 (3H, s), 7.34-7.73 (7H, m), 7.80 (1H, ddd, J=7.8, 1.7, 1.2 Hz), 7.98 (1H, d.dd, J=7.8, 1.7, 1.2 Hz), 8.07 (1H, d, J=2.6 Hz), 8.29 (1H, t, J=1.7 Hz), 8.95 (1H, d, J=9.1 Hz), 12.05 (1H, s).

(ii) 2-[(Biphenyl-3-ylcarbonyl)amino]-5-chlorobenzoic acid

Using the same method as in Example 3-(ii), the target 2-[(biphenyl-3-ylcarbonyl)amino]-5-chlorobenzoic acid (yield: 96%) was obtained using methyl 2-[(biphenyl-3-yl-carbonyl)amino]-5-chlorobenzoate.

$^1$H-NMR (DMSO-d$_6$) δ: 7.38-7.59 (3H, m), 7.63-7.79 (4H, m), 7.90-7.98 (2H, m), 7.99 (1H, d, J=2.6 Hz), 8.21 (1H, t, J=1.6 Hz), 8.75 (1H, d, J=9.0 Hz), 12.21 (1H, s).

(iii)

N-(4-Chloro-2-iodophenyl)biphenyl-3-carboxamide

Using the same method as in Example 3-(i), N-(4-chloro-2-iodophenyl)biphenyl-3-carboxamide (yield: 75%) was obtained using 3-biphenylcarboxylic acid and 4-chloro-2-iodoaniline.

$^1$H-NMR (CDCl$_3$) δ: 7.35-755 (4H, m), 7.55-7.69 (3H, m), 7.81 (1H, d, J=2.4 Hz), 7.82 (1H, ddd, J=7.7, 1.7, 1.3 Hz), 7.91 (1H, ddd, J=7.7, 1.7, 1.3 Hz), 8.19 (1H, t, J=1.7 Hz), 8.32 (1H, brs), 8.44 (1H, d, J=8.9 Hz).

(iv)

2-[(Biphenyl-3-ylcarbonyl)amino]-5-chlorobenzoic acid 433 mg (1.0 mmol) of N-(4-chloro-2-iodophenyl)biphenyl-3-carboxamide was dissolved in 5 mL of THF solution, and 1.6M n-butyllithium(n-BuLi)hexane solution (1.25 mL) was added dropwise under an Ar atmosphere at −78° C. The mixture was stirred for 0.5 hours. Dry ice was added thereto, and the mixture was stirred at room temperature for 2 hours. The reaction mixture was diluted with ethyl acetate, washed with 1N hydrochloric acid and saturated saline, and dried over anhydrous sodium sulfate. The resultant was separated and purified by silica gel column chromatography, thereby giving 48.2 mg of the target 2-[(biphenyl-3-ylcarbonyl)amino]-5-chlorobenzoic acid (yield: 14%).

Example 5

Production of 2-({[3-(furan-3-yl)phenyl]carbonyl}amino)-5-methyl-4-phenylthiophene-3-carboxylic acid (5)

The target compound (5) was synthesized according to the following Steps (i) to (ii).

(i) tert-Butyl 2-({[3-(Furan-3-yl)phenyl]carbonyl}amino)-5-methyl-4-phenylthiophene-3-carboxylate Using the same method as in Example 3-(i), tert-butyl 2-({[3-(furan-3-yl)phenyl]carbonyl}amino)-5-methyl-4-phenylthiophene-3-carboxylate (yield: 58%) was obtained using tert-butyl 2-amino-5-methyl-4-phenylthiophene-3-carboxylate and 3-(furan-3-yl)benzoic acid.

$^1$H-NMR (CDCl$_3$) δ: 1.15 (9H, s), 2.16 (3H, s), 6.80 (1H, dd, J=1.8, 0.9 Hz), 7.12-7.21 (2H, m), 7.28-7.43 (3H, m), 7.52 (1H, t, J=1.7 Hz), 7.55 (1H, t, J=7.8 Hz), 7.71 (1H, ddd, J=7.8, 1.6, 1.2 Hz), 7.85 (1H, dd, J=1.4, 0.9 Hz), 7.87 (1H, ddd, J=7.8, 1.6, 1.2 Hz), 8.21 (1H, t, J=1.6 Hz), 12.42 (1H, s).

(ii) 2-({[3-(Furan-3-yl)phenyl]carbonyl}amino)-5-methyl-4-phenylthiophene-3-carboxylic acid 0.5 g (1.2 mmol) of tert-butyl 2-({[3-(furan-3-yl)phenyl]carbonyl}amino)-5-methyl-4-phenylthiophene-3-carboxylate was dissolved in 2 mL of chloroform, and 5 mL of trifluoroacetic acid (TFA) was added thereto at 0° C. The mixture was stirred at room temperature for 5 hours. n-hexane was added to the reaction mixture, and solids were collected by filtration, followed by recrystallization using a mixed solvent of ethyl acetate and n-hexane, thereby giving 0.34 g of the target 2-({[3-(furan-3-yl)phenyl]carbonyl}amino)-5-methyl-4-phenylthiophene-3-carboxylic acid (yield: 70%).

$^1$H-NMR (DMSO-d$_6$) δ: 2.13 (3H, s), 7.05 (1H, dd, J=1.7, 0.8 Hz), 7.17-7.45 (5H, m), 7.65 (1H, t, J=7.7 Hz), 7.80 (1H, d, J=7.7 Hz), 7.82 (1H, t, J=1.7 Hz), 7.94 (1H, d, J=7.7 Hz), 8.16 (1H, s), 8.34 (1H, s), 12.45 (1H, s), 13.00 (1H, brs).

Example 6

Production of 2-[(biphenyl-2-ylcarbonyl)amino]-5-chlorobenzoic acid (6)

The target compound (6) was synthesized according to the following Steps (i) to (ii).

(i) Methyl 2-[(Biphenyl-2-ylcarbonyl)amino]-5-chlorobenzoate

Using the same method as in Example 3-(i), methyl 2-[(biphenyl-2-ylcarbonyl)amino]-5-chlorobenzoate (yield: 71%) was obtained using 2-biphenylcarboxylic acid and methyl 2-amino-5-chlorobenzoate.

$^1$H-NMR (CDCl$_3$) δ: 3.80 (3H, s), 7.20-7.60 (9H, m), 7.70-7.77 (1H, m), 7.88 (1H, d, J=2.6 Hz), 8.74 (1H, d, J=9.0 Hz), 10.87 (1H, s).

(ii)

2-[(Biphenyl-2-ylcarbonyl)amino]-5-chlorobenzoic acid

Using the same method as in Example 3-(ii), the target 2-[(biphenyl-2-ylcarbonyl)amino]-5-chlorobenzoic acid was obtained using methyl 2-[(biphenyl-2-ylcarbonyl)amino]-5-chlorobenzoate (yield: 86%).

$^1$H-NMR (DMSO-d$_6$) δ: 7.24-7.75 (10H, m), 7.85 (1H, d, J=2.6 Hz), 8.52 (1H, d, J=9.0 Hz), 11.21 (1H, s).

Example 7

Production of 5-chloro-2-({[4-(thiophen-2-yl)phenyl]carbonyl}amino)benzoic acid (7)

The target compound (7) was synthesized according to the following Steps (i) to (ii).

(i) Methyl 5-chloro-2-({[4-(thiophen-2-yl)phenyl]carbonyl}amino)benzoate

Using the same method as in Example 3-(i), methyl 5-chloro-2-({[4-(thiophen-2-yl)phenyl]carbonyl}amino)benzoate was obtained using 4-(thiophen-2-yl)benzoic acid and methyl 2-amino-5-chlorobenzoate (yield: 90%).

$^1$H-NMR (CDCl$_3$) δ: 3.99 (3H, s), 7.13 (1H, dd, J=5.1, 3.7 Hz), 7.37 (1H, dd, J=1.1 Hz), 7.37 (1H, dd, J=5.1, 1.1 Hz), 7.43 (1H, dd, J=3.7, 1.1 Hz), 7.56 (1H, dd, J=9.1, 2.6 Hz), 7.71-7.81 (2H, m), 8.00-8.09 (2H, m), 8.94 (1H, d, J=9.1 Hz), 12.01 (1H, s).

(ii) 5-Chloro-2-({[4-(thiophen-2-yl)phenyl]carbonyl}amino)benzoic acid

Using the same method as in Example 3-(ii), the target 5-chloro-2-({[4-(thiophen-2-yl)phenyl]carbonyl}amino)benzoic acid was obtained using methyl 5-chloro-2-({[4-(thiophen-2-yl)phenyl]carbonyl}amino)benzoate (yield: 85%).

¹H-NMR (DMSO-d₆) δ: 7.21 (1H, dd, J=5.0, 3.7 Hz), 7.65-7.73 (2H, m), 7.73 (1H, dd, J=9.0, 2.7 Hz), 7.84-7.92 (2H, m), 7.93-8.02 (3H, m), 8.73 (1H, d, J=9.0 Hz), 12.13 (1H, s).

Example 8

Production of sodium 5-chloro-2-({[3-(pyridin-4-yl)phenyl]carbonyl}amino)benzoate (8)

The target compound (8) was synthesized according to the following Steps (i) to (iii).

(i) Methyl 2-{[(3-bromophenyl)carbonyl]amino}-5-chlorobenzoate

Using the same method as in Example 3-(i), methyl 2-{[(3-bromophenyl)carbonyl]amino}-5-chlorobenzoate was obtained using 3-bromobenzoic acid and methyl 2-amino-5-chlorobenzoate (yield: 63%).

¹H-NMR (CDCl₃) δ: 3.99 (3H, s), 7.40 (1H, t, J=7.9 Hz), 7.56 (1H, dd, J=9.1, 2.6 Hz), 7.70 (1H, ddd, J=7.9, 1.8, 1.0 Hz), 7.92 (1H, ddd, J=7.9, 1.8, 1.0 Hz), 8.05 (1H, d, J=2.6 Hz), 8.18 (1H, t, J=1.8 Hz), 8.87 (1H, d, J=9.1 Hz), 11.97 (1H, s).

(ii) Methyl 5-chloro-2-({[3-(pyridin-4-yl)phenyl]carbonyl}amino)benzoate 0.67 g (5.4 mmol) of 4-pyridine boronic acid, 1.0 g (2.7 mmol) of methyl 2-{[(3-bromophenyl)carbonyl]amino}-5-chlorobenzoate, 313 mg (0.27 mmol) of tetrakis(triphenylphosphine)palladium(0), and 0.58 g (5.4 mmol) of sodium carbonate were heated under reflux in a mixed solvent of 4 mL of water, 23 mL of toluene, and 6.7 mL of methanol for 7.5 hours. After the completion of the reaction, the solvent was distilled off under reduced pressure. Ethyl acetate was added, and solids were collected by filtration. Subsequently, the organic layer was washed with saturated saline and dried over anhydrous sodium sulfate, and the solvent was then distilled off under reduced pressure. The obtained crude product was separated and purified by silica gel column chromatography, thereby giving 320 mg of methyl 5-chloro-2-({[3-(pyridin-4-yl)phenyl]carbonyl}amino)benzoate (yield: 32%).

¹H-NMR (CDCl₃) δ: 4.00 (3H, s), 7.58 (1H, dd, J=9.1, 2.6 Hz), 7.58-7.63 (2H, m), 7.66 (1H, t, J=7.8 Hz), 7.85 (1H, ddd, J=7.8, 1.7, 1.2 Hz), 8.08 (1H, ddd, J=7.8, 1.7, 1.2 Hz), 8.08 (1H, d, J=2.6 Hz), 8.34 (1H, t, J=1.7 Hz), 8.69-8.76 (2H, m), 8.94 (1H, d, J=9.1 Hz), 12.11 (1H, s).

(iii) Sodium 5-chloro-2-({[3-(pyridin-4-yl)phenyl]carbonyl}amino)benzoate 20 mL of THF and 2.6 mL of 1N aqueous sodium hydroxide were added to 0.32 g (0.87 mmol) of methyl 5-chloro-2-({[3-(pyridin-4-yl)phenyl]carbonyl}amino)benzoate at room temperature, and the mixture was stirred at 50° C. for 1 hour. After cooling, the solvent was distilled off under reduced pressure, and water was added to the residue, followed by filtration and drying, thereby giving 174 mg of the target sodium 5-chloro-2-({[3-(pyridin-4-yl)phenyl]carbonyl}amino)benzoate (yield: 53%).

¹H-NMR (DMSO-d₆) δ: 7.40 (1H, dd, J=8.8, 2.8 Hz), 7.72 (1H, t, J=7.8 Hz), 7.77-7.84 (2H, m), 8.00 (1H, d, J=2.8 Hz), 8.00-8.07 (1H, m), 8.07-8.15 (1H, m), 8.42 (1H, s), 8.66-8.75 (3H, m), 15.89 (1H, s).

Example 9

Production of 5-chloro-2-[(1-{[3-(furan-3-yl)phenyl]acetyl}-L-prolyl)amino]benzoic acid (9)

The target compound (9) was synthesized according to the following Steps (i) to (iv).

(i) tert-Butyl (2S)-2-{[4-chloro-2-(methoxycarbonyl)phenyl]carbamoyl}pyrrolidine-1-carboxylate Under ice-cooling, 1.73 mL (12.4 mmol) of triethylamine and 0.88 mL (7.23 mmol) of 2,2-dimethyl propanoyl chloride were added to a THF (10 mL) solution comprising 1.50 g (6.97 mmol) of 1-(tert-butoxycarbonyl)-L-proline, and the mixture was stirred under ice-cooling for 30 minutes. Subsequently, 269 mg (4.65 mmol) of methyl 2-amino-5-chlorobenzoate was added thereto under ice-cooling, and the mixture was heated under reflux for 19 hours. After condensation and addition of water, the mixture was extracted with ethyl acetate. The organic layer was washed with 0.1% hydrochloric acid, water, saturated sodium bicarbonate water, and saturated saline, followed by drying over magnesium sulfate. After condensation, the resultant was purified by silica gel column chromatography (n-hexane/ethyl acetate=10/1→4/1), thereby giving 1.65 g of tert-butyl (2S)-2-{[4-chloro-2-(methoxycarbonyl)phenyl]carbamoyl}pyrrolidine-1-carboxylate (yield: 93%).

¹H-NMR (CDCl₃) δ: 1.34, 1.50 (9H, s), 1.80-2.02 (2H, m), 2.18-2.42 (2H, m), 3.38-3.78 (2H, m), 3.93 (3H, s), 4.20-4.52 (1H, m), 7.49 (1H, d, J=9.0 Hz), 8.00 (1H, s), 8.76 (1H, d, J=9.0 Hz), 11.43, 11.51 (1H, s).

(ii) Methyl 5-chloro-2-(L-prolylamino)benzoate hydrochloride 4N hydrogen chloride/ethyl acetate (10 mL) was added to an ethyl acetate (10 mL) solution comprising 1.40 g (3.66 mmol) of tert-butyl (2S)-2-{[4-chloro-2-(methoxycarbonyl)phenyl]carbamoyl}pyrrolidine-1-carboxylate at 0° C., and the mixture was stirred at room temperature for 5 hours. After the reaction mixture was condensed, IPE was added to the residue, and white solids were collected by filtration, washed with IPE, and dried under reduced pressure at room temperature, thereby giving 1.15 g of methyl 5-chloro-2-(L-prolylamino)benzoate hydrochloride (yield: 98%).

¹H-NMR (CDCl₃) δ: 1.78-2.39 (5H, m), 2.46-2.70 (1H, m), 3.47-3.72 (2H, m), 3.93 (3H, s), 4.62-4.80 (1H, m), 7.41 (1H, dd, J=9.0, 2.5 Hz), 7.86 (1H, d, J=2.5 Hz), 8.53 (1H, d, J=9.0 Hz), 11.28 (1H, s).

(iii) Methyl 5-chloro-2-[(1-{[3-(furan-3-yl)phenyl]acetyl}-L-prolyl)amino]benzoate Under ice-cooling, 0.096 mL (0.690 mmol) of triethylamine and 144 mg (0.752 mmol) of 1-ethyl-3-(3-dimethylaminopropyl)carbodiimide hydrochloride were added while stirring to a DMAc (5 mL) solution comprising 127 mg (0.627 mmol) of [3-(furan-3-yl)phenyl]acetic acid, 200 mg (0.627 mmol) of methyl 5-chloro-2-(L-prolylamino)benzoate hydrochloride, and 102 mg (0.752 mmol) of 1-hydroxybenzotriazole; and the mixture was stirred overnight. After water and ethyl acetate were added to the reaction mixture and the mixture was stirred, the organic layer was separated and washed with saturated sodium bicarbonate water, 0.1% hydrochloric acid, and saturated saline, followed by drying over sodium sulfate, filtration, and condensation. The crude product was purified by silica gel chromatography (n-hexane/ethyl acetate=4/1→2/1→1/1), thereby giving 258 mg of methyl 5-chloro-2-[(1-{[3-(furan-3-yl)phenyl]acetyl}-L-prolyl)amino]benzoate (yield: 88%).

A mixture of two rotamers in the ratio ca. 3:1
$^1$H-NMR (CDCl$_3$) δ: 1.67-2.42 (4H, m), 3.53-3.99 (4H, m), 3.77 (¼×3H for one rotamer, s), 3.89 (¾×3H for another rotamer, s), 4.51-4.59 (¼×1H for one rotamer, m), 4.65-4.73 (¾×1H for another rotamer, m), 6.53 (¼×1H for one rotamer, dd, J=1.7, 0.9 Hz), 6.66 (¾×1H for another rotamer, dd, J=1.7, 0.9 Hz), 7.01-7.52 (6H, m), 7.57 (¼×1H for one rotamer, s), 7.69 (¾×1H for another rotamer, s), 7.83 (¼×1H for one rotamer, d, J=2.5 Hz), 7.96 (¾×1H for another rotamer, d, J=2.5 Hz), 8.56 (¼×1H for one rotamer, d, J=9.1 Hz), 8.71 (¾×1H for another rotamer, d, J=9.1 Hz), 11.32 (¼×1H for one rotamer, s), 11.35 (¾×1H for another rotamer, s).

(iv) 5-Chloro-2-[(1-{[3-(furan-3-yl)phenyl]acetyl}-L-prolyl)amino]benzoic acid

Using the same method as in Example 3-(ii), the target 5-chloro-2-[(1-{[3-(furan-3-yl)phenyl]acetyl}-L-prolyl)amino]benzoic acid was obtained using methyl 5-chloro-2-[(1-{[3-(furan-3-yl)phenyl]acetyl}-L-prolyl)amino]benzoate (yield: 89%).

A mixture of two rotamers in the ratio ca. 4:1
$^1$H-NMR (DMSO-d$_6$) δ: 1.69-2.37 (4H, m), 3.52-3.93 (4H, m), 4.33-4.45 (⅘×1H for one rotamer, m), 4.73-4.82 (⅕×1H for another rotamer, m), 6.73-6.76 (⅕×1H for another rotamer, m), 6.85-6.92 (⅘×1H for one rotamer, m), 6.98-7.51 (4H, m), 7.59 (⅕×1H for another rotamer, dd, J=9.0, 2.6 Hz), 7.59 (⅘×1H for one rotamer, dd, J=9.0, 2.6 Hz), 7.73 (1H, dd, J=1.6, 1.5 Hz), 7.84 (⅕×1H for another rotamer, d, J=2.6 Hz), 7.95 (⅘×1H for one rotamer, d, J=2.6 Hz), 8.11 (1H, s), 8.45 (⅕×1H for another rotamer, d, J=9.0 Hz), 8.60 (⅘×1H for one rotamer, d, J=9.0 Hz), 11.60 (⅕×1H for another rotamer, s), 11.63 (⅘×1H for one rotamer, s).

Example 10

Production of 5-chloro-2-[(1-{[3-(furan-3-yl)phenyl]carbonyl}-L-prolyl)amino]benzoic acid (10)

The target compound (10) was synthesized according to the following Steps (i) to (ii).

(i) Methyl 5-chloro-2-[(1-{[3-(furan-3-yl)phenyl]carbonyl}-L-prolyl)amino]benzoate Using the same method as in Example 9-(ii), the target methyl 5-chloro-2-[(1-{[3-(furan-3-yl)phenyl]carbonyl}-L-prolyl)amino]benzoate (yield: 91%) was obtained using the methyl 5-chloro-2-(L-prolylamino)benzoate hydrochloride obtained in Example 9-(ii) and 3-(furan-3-yl)benzoic acid.
$^1$H-NMR (CDCl$_3$) δ: 1.80-2.53 (4H, m), 3.56-4.03 (2H, m), 3.88 (3H, s), 4.88 (1H, dd, J=7.8, 6.3 Hz), 6.76 (1H, s), 7.35-7.70 (5H, m), 7.80 (1H, s), 7.93 (1H, s), 7.99 (1H, d, J=2.7 Hz), 8.80 (1H, d, J=8.9 Hz), 11.58 (1H, s).

(ii) 5-Chloro-2-[(1-{[3-(furan-3-yl)phenyl]carbonyl}-L-prolyl)amino]benzoic acid Using the same method as in Example 3-(ii), the target 5-chloro-2-[(1-{[3-(furan-3-yl)phenyl]carbonyl}-L-prolyl)amino]benzoic acid was obtained using methyl 5-chloro-2-[(1-{[3-(furan-3-yl)phenyl]carbonyl}-L-prolyl)amino]benzoate (yield: 86%).

A mixture of two rotamers in the ratio ca. 7:1
$^1$H-NMR (DMSO-d$_6$) δ: 1.82-2.45 (4H, m), 3.44-3.86 (2H, m), 4.35-4.65 (1H, m), 6.77 (⅛×1H for one rotamer, s), 7.04 (⅞×1H for another rotamer, s), 7.41-7.81 (5H, m), 7.84 (1H, s), 7.97 (1H, d, J=2.6 Hz), 8.29 (1H, s), 8.66 (1H, d, J=8.6 Hz), 11.49 (⅛×1H for one rotamer, s), 11.77 (⅞×1H for another rotamer, s).

Example 11

Production of sodium 5-chloro-2-{[(1-{[3-(furan-3-yl)phenyl]carbonyl}piperidin-3-yl)carbonyl]amino}benzoate (11)

The target compound (11) was synthesized according to the following Steps (i) to (iv).

(i) tert-Butyl 3-{[4-chloro-2-(methoxycarbonyl)phenyl]carbamoyl}piperidin-1-carboxylate Using the same method as in Example 1-(i), the target tert-butyl 3-{[4-chloro-2-(methoxycarbonyl)phenyl]carbamoyl}piperidin-1-carboxylate was obtained using 1-(tert-butoxycarbonyl)piperidin-3-carboxylic acid and methyl 2-amino-5-chlorobenzoate (yield: 88%).
$^1$H-NMR (CDCl$_3$) δ: 1.47 (9H, s), 1.52-1.85 (3H, m), 2.06-2.21 (1H, m), 2.37-2.56 (1H, m), 2.63-3.06 (2H, m), 3.95 (3H, s), 4.01-4.41 (2H, m), 7.49 (1H, dd, J=9.1, 2.6 Hz), 8.01 (1H, d, J=2.6 Hz), 8.70 (1H, d, J=9.1 Hz), 11.12 (1H, s).

(ii) Methyl 5-chloro-2-[(piperidin-3-ylcarbonyl)amino]benzoate hydrochloride

Using the same method as in Example 1-(ii), the target methyl 5-chloro-2-[(piperidin-3-ylcarbonyl)amino]benzoate hydrochloride was obtained using tert-butyl 3-{[4-chloro-2-(methoxycarbonyl)phenyl]carbamoyl}piperidin-1-carboxylate (yield: 86%).
$^1$H-NMR (DMSO-d$_6$) δ: 1.51-2.17 (4H, m), 2.77-3.53 (5H, m), 3.84 (3H, s), 7.69 (1H, dd, J=8.8, 2.6 Hz), 7.82 (1H, d, J=2.6 Hz), 7.99 (1H, d, J=8.8 Hz), 9.10 (2H, brs), 10.68 (1H, s).

(iii) Methyl 5-chloro-2-{[(1-{[3-(furan-3-yl)phenyl]carbonyl}piperidin-3-yl)carbonyl]amino}benzoate Using the same method as in Example 9-(ii), the target methyl 5-chloro-2-{[(1-{[3-(furan-3-yl)phenyl]carbonyl}piperidin-3-yl)carbonyl]amino}benzoate was quantitatively obtained using methyl 5-chloro-2-[(piperidin-3-ylcarbonyl)amino]benzoate hydrochloride and 3-(furan-3-yl)benzoic acid.
$^1$H-NMR (CDCl$_3$) δ: 1.42-2.31 (4H, m), 2.43-4.08 (4H, m), 3.94 (3H, s), 4.48-5.03 (1H, m), 6.71 (1H, s), 7.28-7.60 (5H, m), 7.54 (1H, s), 7.76 (1H, s), 8.00 (1H, s), 8.67 (1H, s), 11.16 (1H, s).

(iv) Sodium 5-chloro-2-{[(1-{[3-(furan-3-yl)phenyl]carbonyl}piperidin-3-yl)carbonyl]amino}benzoate Using the same method as in Example 8-(iii), the target sodium 5-chloro-2-{[(1-{[3-(furan-3-yl)phenyl]carbonyl}piperidin-3-yl)carbonyl]amino}benzoate was obtained using methyl 5-chloro-2-{[(1-{[3-(furan-3-yl)phenyl]carbonyl}piperidin-3-yl)carbonyl]amino}benzoate (yield: 93%).

¹H-NMR (DMSO-d₆) δ: 1.38-2.28 (4H, m), 2.80-4.80 (5H, m), 7.04 (1H, s), 7.20-7.54 (3H, m), 7.60-7.80 (3H, m), 7.93 (1H, s), 8.28 (1H, s), 8.33-8.58 (1H, m), 14.11 (1H, s).

Example 12

Production of 5-chloro-2-{[(1-{[3-(furan-3-yl)phenyl]acetyl}piperidin-3-yl)carbonyl]amino}benzoic acid (12)

The target compound (12) was synthesized according to the following Steps (i) to (ii).

(i) Methyl 5-chloro-2-{[(1-{[3-(furan-3-yl)phenyl]acetyl}piperidin-3-yl)carbonyl]amino}benzoate Using the same method as in Example 9-(ii), the target methyl 5-chloro-2-{[(1-{[3-(furan-3-yl)phenyl]carbonyl}piperidin-3-yl)carbonyl]amino}benzoate was quantitatively obtained using the methyl 5-chloro-2-[(piperidin-3-ylcarbonyl)amino]benzoate hydrochloride obtained in Example 11-(ii) and [3-(furan-3-yl)phenyl]acetic acid.

A mixture of two rotamers in the ratio ca. 1:1
¹H-NMR (CDCl₃) δ: 1.43-3.42 (7H, m), 3.79, 3.83 (2H, s), 3.94, 3.95 (3H, s), 3.70-4.20 (1H, m), 4.38-4.53, 4.74-4.89 (1H, m), 6.64, 6.71 (1H, s), 7.12-7.55 (6H, m), 7.68, 7.75 (1H, s), 9.64-8.04 (1H, m), 8.63, 8.66 (1H, d, J=9.1 Hz), 11.00, 11.09 (1H, s).

(ii) 5-Chloro-2-{[(1-{[3-(furan-3-yl)phenyl]acetyl}piperidin-3-yl)carbonyl]amino}benzoic acid Using the same method as in Example 3-(ii), the target 5-chloro-2-{[(1-{[3-(furan-3-yl)phenyl]acetyl}piperidin-3-yl)carbonyl]amino}benzoic acid was obtained using methyl 5-chloro-2-{[(1-{[3-(furan-3-yl)phenyl]acetyl}piperidin-3-yl)carbonyl]amino}benzoate (yield: 86%).

A mixture of two rotamers in the ratio ca. 1:1
¹H-NMR (DMSO-d₆) δ: 1.18-3.64 (7H, m), 3.76, 3.81 (2H, s), 3.84-4.62 (2H, m), 6.88, 6.71 (1H, d, J=1.0 Hz), 7.08-7.18 (1H, m), 7.22-7.78 (5H, m), 7.86-7.96 (1H, m), 8.11, 8.17 (1H, s), 8.40, 8.45 (1H, d, J=9.1 Hz), 11.14, 11.16 (1H, s).

Example 13

Production of 5-chloro-2-({[3-(furan-3-yl)phenoxy]acetyl}amino)benzoic acid (13)

The target compound (13) was synthesized according to the following Steps (i) to (iii).

(i) Methyl 2-{[(3-Bromophenoxy)acetyl]amino-}-5-chlorobenzoate 1.59 g (11.5 mmol) of potassium carbonate was added to a DMF (20 mL) solution comprising 1.00 g (3.82 mmol) of methyl 5-chloro-2-[(chloroacetyl)amino]benzoate and 0.66 g (3.82 mmol) of bromophenol, and the mixture was heated while stirring at 80° C. for 2 hours. The mixture was cooled to room temperature, and water and ethyl acetate were added thereto. After the mixture was extracted, the organic layer was separated, washed with saturated saline, dried over sodium sulfate, filtered, condensed, and dried under reduced pressure. IPE was added to the residue, and powders were collected by filtration, washed with IPE, and dried under reduced pressure at 50° C. for 5 hours, thereby giving 1.11 g of methyl 2-{[(3-bromophenoxy)acetyl]amino-}-5-chlorobenzoate (yield: 73%).
¹H-NMR (DMSO-d₆) δ: 3.91 (3H, s), 4.80 (2H, s), 7.07-7.18 (1H, m), 7.18-7.27 (1H, m), 7.27-7.40 (2H, m), 7.74 (1H, dd, J=9.1, 2.5 Hz), 7.96 (1H, d, J=2.5 Hz), 8.61 (1H, d, J=9.1 Hz), 11.61 (1H, s).

(ii) Methyl 5-chloro-2-({[3-(furan-3-yl)phenoxy]acetyl}amino)benzoate 210 mg (10.7 mmol) of 3-furan boronic acid, 500 mg (7.13 mmol) of methyl 2-{[(3-bromophenoxy)acetyl]amino}-5-chlorobenzoate, 144 mg (0.713 mmol) of tetrakis(triphenylphosphine)palladium(0), and 613 mg (10.7 mmol) of cesium carbonate were heated under reflux for 6 hours in THF (5 mL). After the completion of the reaction, ethyl acetate was added thereto, and the mixture was stirred for 1 hour and filtered using a silica gel pad. After the filtrate was condensed, the obtained crude product was separated and purified by silica gel column chromatography. IPE was added to the resulting solids, followed by collection by filtration, washing with IPE, and drying under reduced pressure at 50° C. for 5 hours, thereby giving 286 mg of methyl 5-chloro-2-({[3-(furan-3-yl)phenoxy]acetyl}amino)benzoate (yield: 59%).
¹H-NMR (CDCl₃) δ: 3.96 (3H, s), 4.68 (2H, s), 6.72 (1H, dd, J=1.9, 1.0 Hz), 6.97 (1H, ddd, J=8.2, 2.5, 1.0 Hz), 7.14-7.25 (2H, m), 7.35 (1H, t, J=7.9 Hz), 7.47-7.56 (2H, m), 7.73-7.78 (1H, m), 8.03 (1H, d, J=2.6 Hz), 8.80 (1H, d, J=9.0 Hz), 12.07 (1H, s).

(iii) 5-Chloro-2-({[3-(furan-3-yl)phenoxy]acetyl}amino)benzoic acid

Using the same method as in Example 3-(ii), the target 5-chloro-2-({[3-(furan-3-yl)phenoxy]acetyl}amino)benzoic acid was obtained using methyl 5-chloro-2-({[3-(furan-3-yl)phenoxy]acetyl}amino)benzoate (yield: 95%).
¹H-NMR (DMSO-d₆) δ: 4.81 (2H, s), 6.95-7.03 (2H, m), 7.24-7.41 (3H, m), 7.72 (1H, dd, J=9.0, 2.7 Hz), 7.77 (1H, dd, J=1.7, 1.6 Hz), 7.98 (1H, d, J=2.7 Hz), 8.21-8.26 (1H, m), 8.74 (1H, d, J=9.0 Hz), 12.14 (1H, s).

Example 14

Production of 5-chloro-2-({[5-(furan-3-yl)-1-methyl-1H-indol-3-yl](oxo)acetyl}amino)benzoic acid (14)

The target compound (14) was synthesized according to the following Steps (i) to (iii).

(i) 5-(Furan-3-yl)-1-methyl-1H-indole

Using the same method as in Example 13-(ii), the target 5-(furan-3-yl)-1-methyl-1H-indole was obtained using 5-bromoindole and 3-furanboronic acid (yield: 34%).
¹H-NMR (CDCl₃) δ: 3.80 (3H, s), 6.45-6.51 (1H, m), 6.72-6.78 (1H, m), 7.02-7.08 (1H, m), 7.22-7.41 (3H, m), 7.44-7.51 (1H, m), 7.68-7.77 (1H, m).

(ii) Methyl 5-chloro-2-({[5-(furan-3-yl)-1-methyl-1H-indol-3-yl](oxo) acetyl}amino)benzoate Under an Ar atmosphere, 193 mg (1.52 mmol) of oxalyl chloride was added dropwise to an ice-cooled THF (5 mL) solution comprising 150 mg (0.761 mmol) of 5-(furan-3-yl)-1-methyl-1H-indole, and the mixture was stirred at room temperature for 4 hours. THF and excess oxalyl chloride were distilled off under reduced pressure, and DMAc was added to the residue under ice-cooling, followed by dissolution. Methyl 2-amino-5-chlorobenzoate was added thereto while stirring under ice-cooling, and the mixture was stirred at room temperature overnight. Water was added to the reaction mixture, followed by stirring for 1 hour. Thereafter, the resulting solids were collected by filtration, washed with water, and dried under reduced pressure at 50° C. for 3 hours, thereby giving crude crystals. The resulting crude crystals were recrystallized from ethyl acetate, thereby giving 131 mg of methyl 5-chloro-2-({[5-(furan-3-yl)-1-methyl-1H-indol-3-yl](oxo)acetyl}amino)benzoate (yield: 34%).

$^1$H-NMR (CDCl$_3$) δ: 3.91 (3H, s), 4.03 (3H, s), 6.85 (1H, dd, J=1.9, 0.9 Hz), 7.38 (1H, dd, J=8.5, 0.4 Hz), 7.48-7.55 (2H, m), 7.58 (1H, dd, J=9.0, 2.6 Hz), 7.81-7.84 (1H, m), 8.10 (1H, d, J=2.6 Hz), 8.68-8.72 (1H, m), 8.86 (1H, d, J=9.0 Hz), 8.98 (1H, s), 12.76 (1H, s).

(iii) 5-Chloro-2-({[5-(furan-3-yl)-1-methyl-1H-indol-3-yl](oxo)acetyl}amino)benzoic acid Using the same method as in Example 3-(ii), the target 5-chloro-2-({[5-(furan-3-yl)-1-methyl-1H-indol-3-yl](oxo)acetyl}amino)benzoic acid was obtained using methyl 5-chloro-2-({[5-(furan-3-yl)-1-methyl-1H-indol-3-yl](oxo)acetyl}amino)benzoate (yield: 95%).

$^1$H-NMR (DMSO-d$_6$) δ: 3.98 (3H, s), 6.99-7.04 (1H, m), 7.66 (2H, s), 7.74-7.84 (2H, m), 8.03 (1H, d, J=2.5 Hz), 8.23 (1H, s), 8.47 (1H, s), 8.81 (1H, d, J=8.9 Hz), 9.03 (1H, s), 12.66 (1H, s).

Example 15

Production of 5-bromo-2-({[3-(furan-3-yl)phenoxy]acetyl}amino)benzoic acid (15)

The target compound (15) was synthesized according to the following Steps (i) to (iv).

(i) Ethyl [3-(furan-3-yl)phenoxy]acetate

Using the same method as in Example 13-(ii), ethyl [3-(furan-3-yl)phenoxy]acetate was obtained using ethyl (3-bromophenoxy)acetate and 3-furanboronic acid (yield: 93%).

$^1$H-NMR (CDCl$_3$) δ: 1.31 (3H, t, J=7.1 Hz), 4.29 (2H, q, J=7.1 Hz), 4.66 (2H, s), 6.68 (1H, dd, J=1.8, 0.9 Hz), 6.80 (1H, ddd, J=8.2, 2.6, 1.0 Hz), 7.07 (1H, dd, J=2.6, 1.5 Hz), 7.14 (1H, ddd, J=8.0, 1.5, 1.0 Hz), 7.30 (1H, t, J=8.0 Hz), 7.47 (1H, dd, J=1.8, 1.5 Hz), 7.72 (1H, dd, J=1.5, 0.9 Hz).

(ii) [3-(Furan-3-yl)phenoxy]acetic acid

Using the same method as in Example 3-(ii), [3-(furan-3-yl)phenoxy]acetic acid was obtained using ethyl [3-(furan-3-yl)phenoxy]acetate (yield: 95%).

$^1$H-NMR (CDCl$_3$) δ: 4.73 (2H, s), 6.68 (1H, dd, J=1.8, 0.9 Hz), 6.82 (1H, ddd, J=8.0, 2.5, 0.9 Hz), 7.08 (1H, dd, J=2.5, 1.5 Hz), 7.17 (1H, ddd, J=8.0, 1.5, 0.9 Hz), 7.32 (1H, t, J=8.0 Hz), 7.48 (1H, t, J=1.7 Hz), 7.73 (1H, dd, J=1.2, 0.9 Hz).

(iii) Methyl 5-bromo-2-({[3-(furan-3-yl)phenoxy]acetyl}amino)benzoate

Under ice-cooling, 1.53 g (7.97 mmol) of 1-ethyl-3-(3-dimethylaminopropyl)carbodiimide hydrochloride was added to a DMAc (5 mL) solution comprising 1.45 g (6.64 mmol) of [3-(furan-3-yl)phenoxy]acetic acid, 1.60 g (6.97 mmol) of methyl 2-amino-5-bromobenzoate, and 1.08 g (7.97 mmol) of 1-hydroxybenzotriazole, and the mixture was stirred at room temperature for 4 hours. Under ice-cooling, 1.63 g (19.9 mmol) of 1-methylimidazole was added, and the mixture was stirred at room temperature overnight. Water was added to the reaction mixture, and the mixture was stirred for 1 hour. The precipitates were collected by filtration and washed with water and IPE, followed by drying under reduced pressure at 50° C. for 3 hours, thereby giving 2.30 g of methyl 5-bromo-2-({[3-(furan-3-yl)phenoxy]acetyl}amino)benzoate (yield: 81%).

$^1$H-NMR (CDCl$_3$) δ: 3.97 (3H, s), 4.68 (2H, s), 6.72 (1H, dd, J=1.7, 1.0 Hz), 6.97 (1H, ddd, J=7.9, 2.6, 1.0 Hz), 7.19 (1H, ddd, J=7.9, 1.5, 1.0 Hz), 7.23 (1H, dd, J=2.6, 1.5 Hz), 7.35 (1H, t, J=7.9 Hz), 7.49 (1H, t, J=1.7 Hz), 7.67 (1H, dd, J=9.0, 2.4 Hz), 7.76 (1H, dd, J=1.4, 1.0 Hz), 8.19 (1H, d, J=2.4 Hz), 8.74 (1H, d, J=9.0 Hz), 12.08 (1H, s).

(iv) 5-Bromo-2-({[3-(furan-3-yl)phenoxy]acetyl}amino)benzoic acid

Using the same method as in Example 3-(ii), the target 5-bromo-2-({[3-(furan-3-yl)phenoxy]acetyl}amino)benzoic acid was obtained using methyl 5-bromo-2-({[3-(furan-3-yl)phenoxy]acetyl}amino)benzoate (yield: 83%).

$^1$H-NMR (DMSO-d$_6$) δ: 4.81 (2H, s), 6.94-7.04 (2H, m), 7.24-7.41 (3H, m), 7.76 (1H, t, J=1.7 Hz), 7.84 (1H, dd, J=8.9, 2.5 Hz), 8.10 (1H, d, J=2.5 Hz), 8.21-8.23 (1H, m), 8.11 (1H, d, J=8.9 Hz), 12.16 (1H, s).

Example 16

Production of 2-{[(3-tert-butylphenoxy)acetyl]amino}-5-chlorobenzoic acid (16)

The target compound (16) was synthesized according to the following Steps (i) to (ii).

(i) Methyl 2-{[(3-tert-butylphenoxy)acetyl]amino-}-5-chlorobenzoate 1.59 g (11.5 mmol) of potassium carbonate was added to a DMF (20 mL) solution comprising 1.00 g (3.82 mmol) of methyl 5-chloro-2-[(chloroacetyl)amino]benzoate and 574 mg (3.82 mmol) of 3-tert-butylphenol. The mixture was stirred at 80° C. for 7 hours, and then cooled to room temperature. Water and ethyl acetate were added thereto, and extraction was performed. Thereafter, the organic layer was separated, washed with saturated saline, dried over sodium sulfate, and filtered. After the filtrate was condensed, the obtained crude product was separated and purified by silica gel column chromatography, thereby giving 429 mg of methyl 2-{[(3-tert-butylphenoxy)acetyl]amino}-5-chlorobenzoate (yield: 30%).

$^1$H-NMR (CDCl$_3$) δ: 1.34 (9H, s), 3.96 (3H, s), 4.65 (2H, s), 6.85 (1H, ddd, J=8.0, 2.1, 0.9 Hz), 7.08 (1H, ddd, J=8.0, 2.1, 0.9 Hz), 7.20 (1H, t, J=2.1 Hz), 7.28 (1H, t, J=8.0 Hz), 7.52 (1H, dd, J=9.1, 2.6 Hz), 8.03 (1H, d, J=2.6 Hz), 8.79 (1H, d, J=9.1 Hz), 12.08 (1H, s).

(ii) 2-{[(3-tert-Butylphenoxy)acetyl]amino}-5-chlorobenzoic acid

Using the same method as in Example 3-(ii), the target 2-{[(3-tert-butylphenoxy)acetyl]amino}-5-chlorobenzoic acid was obtained using methyl 2-{[(3-tert-butylphenoxy)acetyl]amino}-5-chlorobenzoate (yield: 95%).

¹H-NMR (DMSO-d₆) δ: 1.28 (9H, s), 4.74 (2H, s), 6.91 (1H, dd, J=7.9, 1.6 Hz), 7.01-7.12 (2H, m), 7.27 (1H, t, J=7.9 Hz), 7.72 (1H, dd, J=9.1, 2.7 Hz), 7.97 (1H, d, J=2.7 Hz), 8.73 (1H, d, J=9.1 Hz), 12.10 (1H, s), 14.16 (1H, brs).

Example 17

Production of 5-chloro-2-{[(2-cyclohexylphenoxy)acetyl]amino}benzoic acid (17)

The target compound (17) was synthesized according to the following Steps (i) to (ii).

(i) Methyl 5-chloro-2-{[(2-cyclohexylphenoxy)acetyl]amino}benzoate

Using the same method as in Example 16-(i), methyl 5-chloro-2-{[(2-cyclohexylphenoxy)acetyl]amino}benzoate was obtained using methyl 5-chloro-2-[(chloroacetyl)amino]benzoate and 2-cyclohexylphenol (yield: 23%).
¹H-NMR (CDCl₃) δ: 1.20-1.67 (5H, m), 1.67-2.01 (5H, m), 3.28-3.47 (1H, m), 3.89 (3H, s), 4.66 (2H, s), 6.86 (1H, dd, J=8.0, 1.1 Hz), 7.02 (1H, td, J=7.5, 1.1 Hz), 7.16 (1H, td, J=8.0, 1.9 Hz), 7.29 (1H, dd, J=7.5, 1.9 Hz), 7.53 (1H, dd, J=9.0, 2.6 Hz), 8.03 (1H, d, J=2.6 Hz), 8.79 (1H, d, J=9.0 Hz), 11.82 (1H, s).

(ii) 5-Chloro-2-{[(2-cyclohexylphenoxy)acetyl]amino}benzoic acid

Using the same method as in Example 3-(ii), the target 5-chloro-2-{[(2-cyclohexylphenoxy)acetyl]amino}benzoic acid was obtained using methyl 5-chloro-2-{[(2-cyclohexylphenoxy)acetyl]amino}benzoate (yield: 54%).
¹H-NMR (DMSO-d₆) δ: 1.14-1.58 (5H, m), 1.58-1.89 (5H, m), 3.13-3.38 (1H, m), 4.74 (2H, s), 6.92-7.03 (2H, m), 7.16 (1H, td, J=7.8, 1.8 Hz), 7.23 (1H, dd, J=7.5, 1.8 Hz), 7.73 (1H, dd, J=8.9, 2.7 Hz), 7.97 (1H, d, J=2.7 Hz), 8.69 (1H, d, J=8.9 Hz), 11.85 (1H, s).

Example 18

Production of 2-{[(4-tert-butylphenoxy)acetyl]amino}-5-chlorobenzoic acid (18)

The target compound (18) was synthesized according to the following Steps (i) to (ii).

(i) Methyl 2-{[(4-tert-butylphenoxy)acetyl]amino}-5-chlorobenzoate

Using the same method as in Example 16-(i), methyl 2-{[(4-tert-butylphenoxy)acetyl]amino}-5-chlorobenzoate was obtained using methyl 5-chloro-2-[(chloroacetyl)amino]benzoate and 4-tert-butylphenol (yield: 20%).
¹H-NMR (CDCl₃) δ: 1.31 (9H, s), 3.96 (3H, s), 4.62 (2H, s), 7.02 (2H, dt, J=8.9, 2.4 Hz), 7.36 (2H, dt, J=8.9, 2.4 Hz), 7.52 (1H, dd, J=9.0, 2.6 Hz), 8.03 (1H, d, J=2.6 Hz), 8.79 (1H, d, J=9.0 Hz), 12.02 (1H, s).

(ii) 2-{[(4-tert-Butylphenoxy)acetyl]amino}-5-chlorobenzoic acid

Using the same method as in Example 3-(ii), the target 2-{[(4-tert-butylphenoxy)acetyl]amino}-5-chlorobenzoic acid was obtained using methyl 2-{[(4-tert-butylphenoxy)acetyl]amino}-5-chlorobenzoate (yield: 92%).

¹H-NMR (DMSO-d₆) δ: 1.26 (9H, s), 4.71 (2H, s), 7.01 (2H, dt, J=8.8, 3.1 Hz), 7.35 (2H, dt, J=8.8, 3.1 Hz), 7.72 (1H, dd, J=9.0, 2.7 Hz), 7.97 (1H, d, J=2.7 Hz), 8.74 (1H, d, J=9.0 Hz), 12.15 (1H, s), 14.23 (1H, brs).

Example 19

Production of 2-{[(biphenyl-4-yloxy)acetyl]amino}-5-chlorobenzoic acid (19)

The target compound (19) was synthesized according to the following Steps (i) to (ii).

(i) Methyl 2-{[(biphenyl-4-yloxy)acetyl]amino}-5-chlorobenzoate

Using the same method as in Example 16-(i), methyl 2-{[(biphenyl-4-yloxy)acetyl]amino}-5-chlorobenzoate was obtained using methyl 5-chloro-2-[(chloroacetyl)amino]benzoate and biphenyl-4-ol (yield: 16%).
¹H-NMR (CDCl₃) δ: 3.97 (3H, s), 4.69 (2H, s), 7.16 (2H, dt, J=8.8, 2.9 Hz), 7.28-7.63 (8H, m), 8.04 (1H, d, J=2.5 Hz), 8.80 (1H, d, J=9.0 Hz), 12.07 (1H, s).

(ii) 2-{[(Biphenyl-4-yloxy)acetyl]amino}-5-chlorobenzoic acid

Using the same method as in Example 3-(ii), the target 2-{[(biphenyl-4-yloxy)acetyl]amino}-5-chlorobenzoic acid was obtained using methyl 2-{[(biphenyl-4-yloxy)acetyl]amino}-5-chlorobenzoate (yield: 54%).
¹H-NMR (DMSO-d₆) δ: 4.80 (2H, s), 7.18 (2H, d, J=8.8 Hz), 7.28-7.37 (1H, m), 7.39-7.50 (2H, m), 7.64 (2H, d, J=7.0 Hz), 7.67 (2H, d, J=8.8 Hz), 7.73 (1H, dd, J=9.0, 2.7 Hz), 7.98 (1H, d, J=2.7 Hz), 8.75 (1H, d, J=9.0 Hz), 12.22 (1H, s).

Example 20

Production of 2-{[(biphenyl-3-yloxy)acetyl]amino}-5-chlorobenzoic acid (20)

The target compound (20) was synthesized according to the following Steps (i) to (ii).

(i) Methyl 2-{[(biphenyl-3-yloxy)acetyl]amino}-5-chlorobenzoate

Using the same method as in Example 16-(i), methyl 2-{[biphenyl-3-yloxy)acetyl]amino}-5-chlorobenzoate was obtained using methyl 5-chloro-2-[(chloroacetyl)amino]benzoate and biphenyl-3-ol (yield: 21%).
¹H-NMR (CDCl₃) δ: 3.95 (3H, s), 4.71 (2H, s), 7.06 (1H, ddd, J=8.0, 2.5, 1.1 Hz), 7.25-7.35 (3H, m), 7.35-7.51 (3H, m), 7.52 (1H, dd, J=9.1, 2.5 Hz), 7.57-7.65 (2H, m), 8.03 (1H, d, J=2.5 Hz), 8.80 (1H, d, J=9.1 Hz), 12.08 (1H, s).

(ii) 2-{[(Biphenyl-3-yloxy)acetyl]amino}-5-chlorobenzoic acid

Using the same method as in Example 3-(ii), the target 2-{[(biphenyl-3-yloxy)acetyl]amino}-5-chlorobenzoic acid was quantitatively obtained using methyl 2-{[(biphenyl-3-yloxy)acetyl]amino}-5-chlorobenzoate.
¹H-NMR (DMSO-d₆) δ: 4.85 (2H, s), 7.10 (1H, ddd, J=7.9, 2.3, 1.0 Hz), 7.28-7.54 (6H, m), 7.64-7.76 (3H, m), 7.97 (1H, d, J=2.6 Hz), 8.75 (1H, d, J=9.1 Hz), 12.17 (1H, s).

Example 21

Production of 2-({[4-(adamantan-1-yl)phenoxy]acetyl}amino)-5-chlorobenzoic acid (21)

The target compound (21) was synthesized according to the following Steps (i) to (ii).

(i) Methyl 2-({[4-(adamantan-1-yl)phenoxy]acetyl}amino)-5-chlorobenzoate

Using the same method as in Example 16-(i), methyl 2-({[4-(adamantan-1-yl)phenoxy]acetyl}amino)-5-chlorobenzoate was obtained using methyl 5-chloro-2-[(chloroacetyl)amino]benzoate and 4-(adamantan-1-yl)phenol (yield: 17%).

$^1$H-NMR (CDCl$_3$) δ: 1.72-1.81 (6H, m), 1.89 (6H, d, J=2.7 Hz), 2.04-2.15 (3H, m), 3.96 (3H, s), 4.62 (2H, s), 7.03 (2H, ddd, J=8.8, 3.1, 2.2 Hz), 7.34 (2H, ddd, J=8.8, 3.1, 2.2 Hz), 7.52 (1H, dd, J=9.0, 2.6 Hz), 8.03 (1H, d, J=2.6 Hz), 8.79 (1H, d, J=9.0 Hz), 12.01 (1H, s).

(ii) 2-({[4-(Adamantan-1-yl)phenoxy]acetyl}amino)-5-chlorobenzoic acid

Using the same method as in Example 3-(ii), the target 2-({[4-(adamantan-1-yl)phenoxy]acetyl}amino)-5-chlorobenzoic acid was obtained using methyl 2-({[4-(adamantan-1-yl)phenoxy]acetyl}amino)-5-chlorobenzoate (yield: 92%).

$^1$H-NMR (DMSO-d$_6$) δ: 1.67-1.76 (6H, m), 1.83 (6H, d, J=2.4 Hz), 1.98-2.10 (3H, m), 4.70 (2H, s), 7.01 (2H, d, J=8.8 Hz), 7.31 (2H, d, J=8.8 Hz), 7.71 (1H, dd, J=9.0, 2.6 Hz), 7.96 (1H, d, J=2.6 Hz), 8.74 (1H, d, J=9.0 Hz), 12.16 (1H, s).

Example 22

Production of 4-({[3-(furan-3-yl)phenoxy]acetyl}amino)biphenyl-3-carboxylic acid (22)

The target compound (22) was synthesized according to the following Steps (i) to (ii).

(i) Methyl 4-({[3-(furan-3-yl)phenoxy]acetyl}amino)biphenyl-3-carboxylate

Using the same method as in Example 13-(ii), methyl 4-({[3-(furan-3-yl)phenoxy]acetyl}amino)biphenyl-3-carboxylate was obtained using methyl 5-bromo-2-({[3-(furan-3-yl)phenoxy]acetyl}amino)benzoate and phenylboronic acid (yield: 91%).

$^1$H-NMR (CDCl$_3$) δ: 3.98 (3H, s), 4.71 (2H, s), 6.73 (1H, dd, J=1.7, 0.9 Hz), 6.99 (1H, ddd, J=8.1, 2.5, 0.9 Hz), 7.15-7.22 (1H, m), 7.25-7.28 (1H, m), 7.30-7.52 (5H, m), 7.56-7.64 (2H, m), 7.75-7.79 (1H, m), 7.81 (1H, dd, J=8.7, 2.3 Hz), 8.30 (1H, d, J=2.3 Hz), 8.88 (1H, d, J=8.7 Hz), 12.14 (1H, s).

(ii) 4-({[3-(Furan-3-yl)phenoxy]acetyl}amino)biphenyl-3-carboxylic acid

Using the same method as in Example 3-(ii), the target 4-({[3-(furan-3-yl)phenoxy]acetyl}amino)biphenyl-3-carboxylic acid was obtained using methyl 4-({[3-(furan-3-yl)phenoxy]acetyl}amino)biphenyl-3-carboxylate (yield: 91%).

$^1$H-NMR (DMSO-d$_6$) δ: 4.83 (2H, s), 6.97-7.05 (2H, m), 7.23-7.56 (6H, m), 7.63-7.74 (2H, m), 7.77 (1H, t, J=1.7 Hz), 7.98 (1H, dd, J=8.8, 2.3 Hz), 8.22-8.26 (1H, m), 8.28 (1H, d, J=2.3 Hz), 8.82 (1H, d, J=8.8 Hz), 12.23 (1H, s), 14.02 (1H, brs).

Example 23

Production of 2-{[(5-bromo-1-methyl-1H-indol-2-yl)carbonyl]amino}-5-chlorobenzoic acid (23)

The target compound (23) was synthesized according to the following Steps (i) to (ii).

(i) Methyl 2-{[(5-bromo-1-methyl-1H-indol-2-yl)carbonyl]amino}-5-chlorobenzoate

A catalytic amount of DMF and 560 mg (4.41 mmol) of oxalyl chloride were added to a THF (8 mL) solution comprising 800 mg (3.15 mmol) of 5-bromo-1-methyl-1H-indole-2-carboxylic acid at 0° C., and the mixture was stirred at room temperature for 40 minutes. After the solvent was distilled off under reduced pressure, 8 mL of DMAc and 585 mg (3.15 mmol) of methyl 2-amino-5-chlorobenzoate were added to the residue in this order at 0° C., and the mixture was stirred at room temperature for 1 hour. After the completion of the reaction, saturated sodium bicarbonate water was added under ice-cooling, and the mixture was stirred. The resulting solids were collected by filtration, washed with water, and dried under reduced pressure at 50° C. for 3 hours, thereby giving 1.22 g of methyl 2-{[(5-bromo-1-methyl-1H-indol-2-yl)carbonyl]amino}-5-chlorobenzoate (yield: 92%).

$^1$H-NMR (CDCl$_3$) δ: 4.00 (3H, s), 4.11 (3H, s), 7.19 (1H, d, J=0.3 Hz), 7.29 (1H, d, J=8.8 Hz), 7.43 (1H, dd, J=8.8, 1.8 Hz), 7.56 (1H, dd, J=9.1, 2.5 Hz), 7.87 (1H, d, J=1.8 Hz), 8.07 (1H, d, J=2.5 Hz), 8.83 (1H, d, J=9.1 Hz), 11.98 (1H, s).

(ii) 2-{[(5-Bromo-1-methyl-1H-indol-2-yl)carbonyl]amino}-5-chlorobenzoic acid

Using the same method as in Example 3-(ii), the target 2-{[(5-bromo-1-methyl-1H-indol-2-yl)carbonyl]amino}-5-chlorobenzoic acid was obtained using methyl 2-{[(5-bromo-1-methyl-1H-indol-2-yl)carbonyl]amino}-5-chlorobenzoate (yield: 76%).

$^1$H-NMR (DMSO-d$_6$) δ: 4.04 (3H, s), 7.18 (1H, s), 7.45 (1H, dd, J=9.0, 1.8 Hz), 7.61 (1H, d, J=9.0 Hz), 7.74 (1H, dd, J=9.0, 2.6 Hz), 7.97 (1H, d, J=1.8 Hz), 8.00 (1H, d, J=2.6 Hz), 8.65 (1H, d, J=9.0 Hz), 12.14 (1H, s).

Example 24

Production of 2-{[(5-bromo-1H-indol-1-yl)acetyl]amino}-5-chlorobenzoic acid (24)

The target compound (24) was synthesized according to the following Steps (i) to (ii).

(i) Methyl 2-{[(5-bromo-1H-indol-1-yl)acetyl]amino}-5-chlorobenzoate

Using the same method as in Example 23-(i), methyl 2-{[(5-bromo-1H-indol-1-yl)acetyl]amino}-5-chlorobenzoate was obtained using (5-bromo-1H-indol-1-yl)acetic acid and methyl 2-amino-5-chlorobenzoate (yield: 71%).

$^1$H-NMR (CDCl$_3$) δ: 3.66 (3H, s), 4.93 (2H, s), 6.63 (1H, dd, J=3.1, 0.7 Hz), 7.17 (1H, d, J=8.8 Hz), 7.19 (1H, d, J=3.1

Hz), 7.30 (1H, dd, J=8.8, 1.8 Hz), 7.47 (1H, dd, J=9.0, 2.6 Hz), 7.81 (1H, d, J=1.8 Hz), 7.88 (1H, d, J=2.6 Hz), 8.66 (1H, d, J=9.0 Hz), 10.91 (1H, s).

(ii) 2-{[(5-Bromo-1H-indol-1-yl)acetyl]amino}-5-chlorobenzoic acid

Using the same method as in Example 3-(ii), the target 2-{[(5-bromo-1H-indol-1-yl)acetyl]amino}-5-chlorobenzoic acid was obtained using methyl 2-{[(5-bromo-1H-indol-1-yl)acetyl]amino}-5-chlorobenzoate (yield: 93%).

$^1$H-NMR (DMSO-$d_6$) δ: 5.21 (2H, s), 6.53 (1H, d, J=3.1 Hz), 7.25 (1H, dd, J=8.7, 1.8 Hz), 7.45 (1H, d, J=8.7 Hz), 7.50 (1H, d, J=3.2 Hz), 7.68 (1H, dd, J=9.1, 2.6 Hz), 7.78 (1H, d, J=1.8 Hz), 7.86 (1H, d, J=2.6 Hz), 8.57 (1H, d, J=9.1 Hz), 11.21 (1H, s).

Example 25

Production of 5-chloro-2-({[3-(cyclohex-1-en-1-yl)phenoxy]acetyl}amino)benzoic acid (25)

The target compound (25) was synthesized according to the following Steps (i) to (iv).

(i) Ethyl [3-(cyclohex-1-en-1-yl)phenoxy]acetate 1.34 g (9.72 mmol) of potassium carbonate was added to a DMF (10 mL) solution comprising 564 mg (3.24 mmol) of 3-(cyclohex-1-en-1-yl)phenol and 541 mg (3.82 mmol) of ethyl bromoacetate. The mixture was heated while stirring at 80° C. for 3 hours, and then cooled to room temperature. Water and ethyl acetate were added thereto, and extraction was performed. The organic layer was then separated, washed with water 3 times, and washed with saturated saline once. The organic layer was dried over sodium sulfate, and filtered. Thereafter, the filtrate was condensed, followed by drying under reduced pressure, thereby giving 777 mg of ethyl [3-(cyclohex-1-en-1-yl)phenoxy]acetate (yield: 92%).

$^1$H-NMR (CDCl$_3$) δ: 1.30 (3H, t, J=7.1 Hz), 1.56-1.84 (4H, m), 2.13-2.26 (2H, m), 2.32-2.43 (2H, m), 4.28 (2H, q, J=7.1 Hz), 4.62 (2H, s), 6.08-6.16 (1H, m), 6.75 (1H, ddd, J=7.9, 2.6, 0.8 Hz), 6.92-6.97 (1H, m), 6.99-7.06 (1H, m), 7.22 (1H, t, J=7.9 Hz).

(ii) [3-(Cyclohex-1-en-1-yl)phenoxy]acetic acid

Using the same method as in Example 3-(ii), [3-(cyclohex-1-en-1-yl)phenoxy]acetic acid was obtained using ethyl [3-(cyclohex-1-en-1-yl)phenoxy]acetate (yield: 81%).

$^1$H-NMR (DMSO-$d_6$) δ: 1.51-1.79 (4H, m), 2.10-2.23 (2H, m), 2.28-2.39 (2H, m), 4.68 (2H, s), 6.11-6.19 (1H, m), 6.76 (1H, ddd, J=8.0, 2.5, 0.7 Hz), 6.86-6.91 (1H, m), 6.95-7.02 (1H, m), 7.22 (1H, t, J=8.0 Hz), 13.00 (1H, brs).

(iii) Methyl 5-chloro-2-({[3-(cyclohex-1-en-1-yl)phenoxy]acetyl}amino)benzoate

Using the same method as in Example 23-(i), methyl 5-chloro-2-({[3-(cyclohex-1-en-1-yl)phenoxy]acetyl}amino)benzoate was obtained using [3-(cyclohex-1-en-1-yl)phenoxy]acetic acid and methyl 2-amino-5-chlorobenzoate (yield: 98%).

$^1$H-NMR (CDCl$_3$) δ: 1.61-1.86 (4H, m), 2.15-2.28 (2H, m), 2.35-2.47 (2H, m), 3.96 (3H, s), 4.65 (2H, s), 6.13-6.21 (1H, m), 6.93 (1H, ddd, J=7.9, 2.5, 0.9 Hz), 7.04-7.13 (2H, m), 7.27 (1H, t, J=7.9 Hz), 7.52 (1H, dd, J=9.1, 2.6 Hz), 8.03 (1H, d, J=2.6 Hz), 8.79 (1H, d, J=9.1 Hz), 12.03 (1H, s).

(iv) 5-Chloro-2-({[3-(cyclohex-1-en-1-yl)phenoxy]acetyl}amino)benzoic acid

Using the same method as in Example 3-(ii), the target 5-chloro-2-({[3-(cyclohex-1-en-1-yl)phenoxy]acetyl}amino)benzoic acid was obtained using methyl 5-chloro-2-({[3-(cyclohex-1-en-1-yl)phenoxy]acetyl}amino)benzoate (yield: 96%).

$^1$H-NMR (DMSO-$d_6$) δ: 1.52-1.81 (4H, m), 2.11-2.25 (2H, m), 2.29-2.43 (2H, m), 4.76 (2H, s), 6.14-6.23 (1H, m), 6.91-6.99 (1H, m), 7.01-7.10 (2H, m), 7.28 (1H, t, J=7.9 Hz), 7.72 (1H, dd, J=9.0, 2.7 Hz), 7.97 (1H, d, J=2.7 Hz), 8.74 (1H, d, J=9.0 Hz), 12.11 (1H, s).

Example 26

Production of 5-chloro-2-{[(3-cyclohexylphenoxy)acetyl]amino}benzoic acid (26)

The target compound (26) was synthesized according to the following Steps (i) to (ii).

(i) Methyl 5-chloro-2-{[(3-cyclohexylphenoxy)acetyl]amino}benzoate

Using the same method as in Example 16-(i), methyl 5-chloro-2-{[(3-cyclohexylphenoxy)acetyl]amino}benzoate was obtained using methyl 5-chloro-2-[(chloroacetyl)amino]benzoate and 3-cyclohexylphenol (yield: 19%).

$^1$H-NMR (CDCl$_3$) δ: 1.20-1.50 (5H, m), 1.69-1.98 (5H, m), 2.43-2.59 (1H, m), 3.96 (3H, s), 4.64 (2H, s), 6.84-6.98 (3H, m), 7.26 (1H, t, J=7.8 Hz), 7.52 (1H, dd, J=9.1, 2.6 Hz), 8.03 (1H, d, J=2.6 Hz), 8.79 (1H, d, J=9.1 Hz), 12.01 (1H, s).

(ii) 5-Chloro-2-{[(3-cyclohexylphenoxy)acetyl]amino}benzoic acid

Using the same method as in Example 3-(ii), the target 5-chloro-2-{[(3-cyclohexylphenoxy)acetyl]amino}benzoic acid was obtained using methyl 5-chloro-2-{[(3-cyclohexylphenoxy)acetyl]amino}benzoate (yield: 91%).

$^1$H-NMR (DMSO-$d_6$) δ: 1.21-1.53 (5H, m), 1.65-1.86 (5H, m), 2.39-2.62 (1H, m), 4.71 (2H, s), 6.84-6.96 (3H, m), 7.24 (1H, t, J=7.8 Hz), 7.71 (1H, dd, J=9.0, 2.7 Hz), 7.97 (1H, d, J=2.7 Hz), 8.73 (1H, d, J=9.0 Hz), 12.16 (1H, s).

Example 27

Production of 4-({[3-(furan-3-yl)phenoxy]acetyl}amino)-3'-methylbiphenyl-3-carboxylic acid (27)

The target compound (27) was synthesized according to the following Steps (i) to (ii).

(i) Methyl 4-({[3-(furan-3-yl)phenoxy]acetyl}amino)-3'-methylbiphenyl-3-carboxylate Using the same method as in Example 13-(ii), methyl 4-({[3-(furan-3-yl)phenoxy]acetyl}amino)-3'-methylbiphenyl-3-carboxylate was obtained using methyl 5-bromo-2-({[3-(furan-3-yl)phenoxy]acetyl}amino)benzoate and (3-methylphenyl)boronic acid (yield: 45%).

¹H-NMR (CDCl₃) δ: 2.44 (3H, s), 3.99 (3H, s), 4.71 (2H, s), 6.73 (1H, dd, J=1.8, 0.9 Hz), 7.00 (1H, ddd, J=8.2, 2.6, 1.0 Hz), 7.14-7.44 (7H, m), 7.50 (1H, t, J=1.8 Hz), 7.76-7.78 (1H, m), 7.81 (1H, dd, J=8.8, 2.3 Hz), 8.29 (1H, d, J=2.3 Hz), 8.87 (1H, d, J=8.8 Hz), 12.13 (1H, s).

(ii) 4-({[3-(Furan-3-yl)phenoxy]acetyl}amino)-3'-methylbiphenyl-3-carboxylic acid Using the same method as in Example 3-(ii), the target 4-({[3-(furan-3-yl)phenoxy]acetyl}amino)-3'-methylbiphenyl-3-carboxylic acid was obtained using 4-({[3-(furan-3-yl)phenoxy]acetyl}amino)-3'-methylbiphenyl-3-methyl carboxylate (yield: 93%).

¹H-NMR (DMSO-d₆) δ: 2.39 (3H, s), 4.83 (2H, s), 6.96-7.06 (2H, m), 7.15-7.53 (7H, m), 7.77 (1H, t, J=1.7 Hz), 7.95 (1H, dd, J=8.8, 2.3 Hz), 8.24 (1H, dd, J=1.4, 0.8 Hz), 8.27 (1H, d, J=2.3 Hz), 8.80 (1H, d, J=8.8 Hz), 12.25 (1H, s).

Example 28

Production of 4-({[3-(furan-3-yl)phenoxy]acetyl}amino)-3',5'-dimethylbiphenyl-3-carboxylic acid (28)

The target compound (28) was synthesized according to the following Steps (i) to (ii).

(i) Methyl 4-({[3-(furan-3-yl)phenoxy]acetyl}amino)-3',5'-dimethylbiphenyl-3-carboxylate Using the same method as in Example 13-(ii), methyl 4-({[3-(furan-3-yl)phenoxy]acetyl}amino)-3',5'-dimethylbiphenyl-3-carboxylate was obtained using methyl 5-bromo-2-({[3-(furan-3-yl)phenoxy]acetyl}amino)benzoate and (3,5-dimethylphenyl)boronic acid (yield: 78%).

¹H-NMR (CDCl₃) δ: 2.39 (6H, s), 3.99 (3H, s), 4.70 (2H, s), 6.73 (1H, dd, J=1.9, 0.8 Hz), 6.95-7.03 (2H, m), 7.15-7.28 (4H, m), 7.35 (1H, t, J=7.9 Hz), 7.49 (1H, t, J=1.7 Hz), 7.74-7.83 (2H, m), 8.27 (1H, d, J=2.3 Hz), 8.85 (1H, d, J=8.8 Hz), 12.12 (1H, s).

(ii) 4-({[3-(Furan-3-yl)phenoxy]acetyl}amino)-3',5'-dimethylbiphenyl-3-carboxylic acid Using the same method as in Example 3-(ii), the target 4-({[3-(furan-3-yl)phenoxy]acetyl}amino)-3',5'-dimethylbiphenyl-3-carboxylic acid was obtained using methyl 4-({[3-(furan-3-yl)phenoxy]acetyl}amino)-3',5'-dimethylbiphenyl-3-carboxylate (yield: 90%).

¹H-NMR (DMSO-d₆) δ: 2.34 (6H, s), 4.83 (2H, s), 6.97-7.05 (3H, m), 7.25-7.42 (5H, m), 7.77 (1H, t, J=1.7 Hz), 7.94 (1H, dd, J=8.8, 2.3 Hz), 8.22-8.27 (2H, m), 8.79 (1H, d, J=8.8 Hz), 12.20 (1H, s), 14.00 (1H, brs).

Example 29

Production of 5-chloro-2-({[4-(furan-3-yl)phenoxy]acetyl}amino)benzoic acid (29)

The target compound (29) was synthesized according to the following Steps (i) to (iv).

(i) Ethyl [4-(furan-3-yl)phenoxy]acetate

Using the same method as in Example 13-(ii), ethyl [4-(furan-3-yl)phenoxy]acetate was obtained using ethyl (4-bromophenoxy)acetate and 3-furanboronic acid (yield: 85%).

¹H-NMR (CDCl₃) δ: 1.31 (3H, t, J=7.2 Hz), 4.28 (2H, q, J=7.2 Hz), 4.64 (2H, s), 6.65 (1H, dd, J=1.8, 1.0 Hz), 6.92 (2H, dt, J=8.9, 2.5 Hz), 7.41 (2H, dt, J=8.9, 2.5 Hz), 7.45 (1H, t, J=1.7 Hz), 7.66 (1H, dd, J=1.5, 1.0 Hz).

(ii) [4-(Furan-3-yl)phenoxy]acetic acid

Using the same method as in Example 3-(ii), [4-(furan-3-yl)phenoxy]acetic acid was obtained using ethyl [4-(furan-3-yl)phenoxy]acetate (yield: 93%).

¹H-NMR (DMSO-d₆) δ: 4.69 (2H, s), 6.90 (1H, dd, J=1.9, 0.7 Hz), 6.93 (2H, dt, J=8.9, 2.5 Hz), 7.52 (2H, dt, J=8.9, 2.5 Hz), 7.70 (1H, t, J=1.7 Hz), 8.07 (1H, dd, J=1.4, 0.7 Hz), 12.98 (1H, brs).

(iii) Methyl 5-chloro-2-({[4-(furan-3-yl)phenoxy]acetyl}amino)benzoate

Using the same method as in Example 23-(i), methyl 5-chloro-2-({[4-(furan-3-yl)phenoxy]acetyl}amino)benzoate was obtained using [4-(furan-3-yl)phenoxy]acetic acid and methyl 2-amino-5-chlorobenzoate (yield: 70%).

¹H-NMR (CDCl₃) δ: 3.96 (3H, s), 4.65 (2H, s), 6.66 (1H, dd, J=1.8, 0.9 Hz), 7.09 (2H, dt, J=8.8, 2.5 Hz), 7.42-7.50 (3H, m), 7.52 (1H, dd, J=9.0, 2.6 Hz), 7.68 (1H, dd, J=1.4, 0.9 Hz), 8.03 (1H, d, J=2.6 Hz), 8.79 (1H, d, J=9.0 Hz), 12.04 (1H, s).

(iv) 5-Chloro-2-({[4-(furan-3-yl)phenoxy]acetyl}amino)benzoic acid

Using the same method as in Example 3-(ii), the target 5-chloro-2-({[4-(furan-3-yl)phenoxy]acetyl}amino)benzoic acid was obtained using methyl 5-chloro-2-({[4-(furan-3-yl)phenoxy]acetyl}amino)benzoate (yield: 75%).

¹H-NMR (DMSO-d₆) δ: 4.77 (2H, s), 6.92 (1H, dd, J=1.7, 0.9 Hz), 7.10 (2H, dt, J=8.8, 2.5 Hz), 7.59 (2H, dt, J=8.8, 2.5 Hz), 7.71 (1H, dd, J=9.0, 2.6 Hz), 7.72 (1H, t, J=1.7 Hz), 7.97 (1H, d, J=2.6 Hz), 8.10 (1H, dd, J=1.4, 0.9 Hz), 8.73 (1H, d, J=9.0 Hz), 12.19 (1H, s).

Example 30

Production of 2-({[3-(adamantan-1-yl)phenoxy]acetyl}amino)-5-chlorobenzoic acid (30)

The target compound (30) was synthesized according to the following Steps (i) to (v).

(i) 3-(Adamantan-1-yl)phenol

A THF solution (20.0 mL, 10.0 mmol) comprising 1 mol/L of vinylmagnesium bromide was slowly added dropwise to a THF (45 mL) solution comprising 2.23 g (5.00 mmol) of N-methoxy-N-methyladamantan-1-carboxamide that had been cooled in a bath containing ice and salt while keeping the THF solution at −10 to 0° C. Thereafter, the mixture was stirred at 0° C. for 1 hour, and stirred at room temperature overnight. The reaction mixture was slowly added dropwise, using a Pasteur pipette, to saturated ammonium chloride water that had been cooled in a bath containing ice and salt, while keeping it at −10 to −5° C. After the completion of the dropwise addition, the mixture was heated to 0° C. Since the mixture comprises two layers, the water layer was separated, and ethyl acetate extraction was performed three times. Subsequently, the primarily separated organic layer and the combined ethyl acetate layers were combined, and the organic layer was washed with saturated ammonium chloride water 5 times, and with brine once. Drying over sodium sulfate, filtration, condensation, and drying under reduced pressure at room temperature for 3 hours were performed, thereby giving the crude product of 1-(adamantan-1-yl)prop-2-en-1-on (containing 1.56 g of impurities such as 3-[methoxy(methyl)amino]-1-(adamantan-1-yl)propan-1-on, etc.) The crude product was used in the next reaction without purification. Under an Ar atmosphere, 1.43 g of 1,8-diazabicyclo[5.4.0]undeca-7-en (DBU) was added to an ice-cooled suspension comprising 1.18 g of the crude product of 1-(adamantan-1-yl)prop-2-en-1-on, 1.60 g of 1-(2-oxopropyl)pyridinium chloride, 1.18 g of molecular sieves 4A, and ethanol (24 mL), and the mixture was stirred at room temperature for 2 days. Under ice-cooling, 1N HClaq. was added to the reaction mixture, the pH was adjusted to 1, and ethyl acetate extraction was performed. The organic layer was separated, and washed with brine three times, followed by drying over sodium sulfate, filtration, condensation, and drying under reduced pressure at room temperature for 1 hour, thereby giving the crude product (936 mg) of 3-(adamantan-1-yl)phenol. This crude product and the crude product of 3-(adamantan-1-yl)phenol (456 mg) obtained from the crude product of 400 mg of 1-(adamantan-1-yl)propa-2-en-1-on under the same conditions were combined. Then this crude product was separated and purified by silica gel column chromatography, thereby giving 222 mg of 3-(adamantan-1-yl)phenol (yield: 9.7%).

$^1$H-NMR (CDCl$_3$) δ: 1.60-1.86 (6H, m), 1.89 (6H, d, J=2.9 Hz), 1.96-2.14 (3H, m), 4.89 (1H, s), 6.65 (1H, ddd, J=7.9, 2.5, 1.0 Hz), 6.84 (1H, t, J=2.1 Hz), 6.94 (1H, ddd, J=7.9, 1.8, 1.0 Hz), 7.19 (1H, t, J=7.9 Hz).

(ii) Ethyl [3-(adamantan-1-yl)phenoxy]acetate

Using the same method as in Example 13-(i), ethyl [3-(adamantan-1-yl)phenoxy]acetate was obtained using 3-(adamantan-1-yl)phenol and ethyl bromoacetate (yield: 39%).

$^1$H-NMR (CDCl$_3$) δ: 1.30 (3H, t, J=7.2 Hz), 1.72-1.77 (6H, m), 1.87-1.92 (6H, m), 2.06-2.11 (3H, m), 4.28 (2H, q, J=7.2 Hz), 4.62 (2H, s), 6.69 (1H, ddd, J=8.0, 2.6, 1.0 Hz), 6.96-7.04 (2H, m), 7.24 (1H, t, J=8.0 Hz).

(iii) [3-(Adamantan-1-yl)phenoxy]acetic acid 5 mL of THF and 0.65 mL of 1N aqueous sodium hydroxide solution were added to 110 mg (0.35 mmol) of ethyl [3-(adamantan-1-yl)phenoxy]acetate at room temperature, and the mixture was stirred for 6 hours. 1N hydrochloric acid was added to acidify the reaction mixture, and water was added. The precipitated solids were collected by filtration, washed with water, and air-dried, thereby giving 90 mg of [3-(adamantan-1-yl)phenoxy]acetic acid (yield: 89%).

$^1$H-NMR (DMSO-d$_6$) δ: 1.70-1.75 (6H, m), 1.81-1.86 (6H, m), 2.04-2.09 (3H, m), 4.64 (2H, s), 6.65-6.72 (1H, m), 6.84-6.87 (1H, m), 6.92-6.98 (1H, m), 7.21 (1H, t, J=8.0 Hz).

(iv) Methyl 2-({[3-(adamantan-1-yl)phenoxy]acetyl}amino)-5-chlorobenzoate

Using the same method as in Example 23-(i), methyl 2-({[3-(adamantan-1-yl)phenoxy]acetyl}amino)-5-chlorobenzoate was obtained using [3-(adamantan-1-yl)phenoxy]acetic acid and methyl 2-amino-5-chlorobenzoate (yield: 57%).

$^1$H-NMR (CDCl$_3$) δ: 1.75-1.80 (6H, m), 1.90-1.95 (6H, m), 2.08-2.13 (3H, m), 3.96 (3H, s), 4.65 (2H, s), 6.83-6.90 (1H, m), 7.02-7.08 (1H, m), 7.15-7.19 (1H, m), 7.24-7.33 (1H, m), 7.52 (1H, dd, J=9.0, 2.6 Hz), 8.03 (1H, d, J=2.6 Hz), 8.79 (1H, d, J=9.0 Hz), 12.05 (1H, s).

(v) 2-({[3-(Adamantan-1-yl)phenoxy]acetyl}amino)-5-chlorobenzoic acid

Using the same method as in Example 3-(ii), the target 2-({[3-(adamantan-1-yl)phenoxy]acetyl}amino)-5-chlorobenzoic acid was obtained using methyl 2-({[3-(adamantan-1-yl)phenoxy]acetyl}amino)-5-chlorobenzoate (yield: 82%).

$^1$H-NMR (DMSO-d$_6$) δ: 1.70-1.75 (6H, m), 1.83-1.88 (6H, m), 2.04-2.09 (3H, m), 4.74 (2H, s), 6.87-7.06 (3H, m), 7.27 (1H, t, J=8.0 Hz), 7.72 (1H, dd, J=9.0, 2.6 Hz), 7.98 (1H, d, J=2.6 Hz), 8.73 (1H, d, J=9.0 Hz), 12.09 (1H, s).

Example 31

Production of 2-({[1-(biphenyl-3-ylcarbonyl)piperidin-3-yl]carbonyl}amino)-5-chlorobenzoic acid (31)

The target compound (31) was synthesized according to the following Steps (i) to (ii).

(i) Methyl 2-({[1-(biphenyl-3-ylcarbonyl)piperidin-3-yl]carbonyl}amino)-5-chlorobenzoate A catalytic amount of DMF and 114 mg (0.900 mmol) of oxalyl chloride were added at 0° C. to 2 mL of THF solution comprising 119 mg (0.600 mmol) of biphenyl-3-carboxylic acid, and the mixture was stirred at room temperature for 40 minutes. The solvent was distilled off under reduced pressure, and then 2 mL of DMAc, 200 mg (0.600 mmol) of the methyl 5-chloro-2-[(piperidin-3-ylcarbonyl)amino]benzoate hydrochloride obtained in Example 11-(ii), and 0.092 mL (0.660 mmol) of triethylamine were added in this order to the residue at 0° C., and the mixture was stirred for 3 hours. After the completion of the reaction, saturated sodium bicarbonate water was added under ice-cooling, and the mixture was stirred. The resulting solids were collected by filtration, washed with water, and dried under reduced pressure at 50° C. for 3 hours, thereby giving 270 mg of methyl 2-({[1-(biphenyl-3-ylcarbonyl)piperidin-3-yl]carbonyl}amino)-5-chlorobenzoate (yield: 94%).

$^1$H-NMR (CDCl$_3$) δ: 1.44-2.31 (4H, m), 2.43-4.14 (4H, m), 3.94 (3H, s), 4.51-5.06 (1H, m), 7.31-7.69 (10H, m), 8.00 (1H, s), 8.67 (1H, s), 11.16 (1H, s).

(ii) 2-({[1-(Biphenyl-3-ylcarbonyl)piperidin-3-yl]carbonyl}amino)-5-chlorobenzoic acid Using the same method as in Example 3-(ii), the target 2-({[1-(biphenyl-3-ylcarbonyl)piperidin-3-yl]carbonyl}amino)-5-chlorobenzoic acid was obtained using methyl 2-({[1-(biphenyl-3-ylcarbonyl)piperidin-3-yl]carbonyl}amino)-5-chlorobenzoate (yield: 91%).

$^1$H-NMR (DMSO-d$_6$) δ: 1.49-2.28 (4H, m), 2.69-4.01 (4H, m), 4.18-4.88 (1H, m), 7.43-7.92 (10H, m), 8.01 (1H, s), 8.55 (1H, s), 11.39 (1H, s).

Example 32

Production of 5-chloro-2-{[(4'-methylbiphenyl-3-yl)carbonyl]amino}benzoic acid (32)

The target compound (32) was synthesized according to the following Steps (i) to (ii).

(i) Methyl 5-chloro-2-{[(4'-methylbiphenyl-3-yl)carbonyl]amino}benzoate

Using the same method as in Example 8-(ii), methyl 5-chloro-2-{[(4'-methylbiphenyl-3-yl)carbonyl]amino}benzoate was obtained using methyl 2-{[(3-bromophenyl)carbonyl]amino}-5-chlorobenzoate obtained in Example 8-(i) and (4-methylphenyl)boronic acid (yield: 29%).

$^1$H-NMR (CDCl$_3$) δ: 2.42 (3H, s), 3.98 (3H, s), 7.30 (2H, d, J=7.9 Hz), 7.52-7.64 (4H, m), 7.79 (1H, ddd, J=7.6, 1.7, 1.2 Hz), 7.95 (1H, ddd, J=7.7, 1.7, 1.2 Hz), 8.06 (1H, d, J=2.6 Hz), 8.27 (1H, t, J=1.7 Hz), 8.95 (1H, d, J=9.1 Hz), 12.04 (1H, s).

(ii) 2-({[1-(Biphenyl-3-ylcarbonyl)piperidin-3-yl]carbonyl}amino)-5-chlorobenzoic acid Using the same method as in Example 3-(ii), the target 5-chloro-2-{[(4'-methylbiphenyl-3-yl)carbonyl]amino}benzoic acid was quantitatively obtained using methyl 5-chloro-2-{[(4'-methylbiphenyl-3-yl)carbonyl]amino}benzoate.

$^1$H-NMR (DMSO-d$_6$) δ: 2.37 (3H, s), 7.33 (2H, d, J=8.0 Hz), 7.64 (2H, d, J=8.0 Hz), 7.66 (1H, t, J=7.8 Hz), 7.75 (1H, dd, J=9.0, 2.6 Hz), 7.92 (2H, dd, J=7.8, 1.6 Hz), 8.00 (1H, d, J=2.6 Hz), 8.19 (1H, t, J=1.6 Hz), 8.74 (1H, d, J=9.0 Hz), 12.19 (1H, s), 14.23 (1H, brs).

Example 33

Production of 5-chloro-2-{[(2'-methoxybiphenyl-3-yl)carbonyl]amino}benzoic acid (33)

The target compound (33) was synthesized according to the following Steps (i) to (ii).

(i) Methyl 5-chloro-2-{[(2'-methoxybiphenyl-3-yl)carbonyl]amino}benzoate

Using the same method as in Example 23-(i), methyl 5-chloro-2-{[(2'-methoxybiphenyl-3-yl)carbonyl]amino}benzoate was obtained using 2'-methoxybiphenyl-3-carboxylic acid and methyl 2-amino-5-chlorobenzoate (yield: 91%).

$^1$H-NMR (CDCl$_3$) δ: 3.87 (3H, s), 3.97 (3H, s), 6.98-7.12 (2H, m), 7.32-7.43 (2H, m), 7.50-7.61 (2H, m), 7.74 (1H, ddd, J=7.8, 1.6, 1.3 Hz), 7.97 (1H, ddd, J=7.8, 1.6, 1.3 Hz), 8.06 (1H, d, J=2.5 Hz), 8.24 (1H, t, J=1.6 Hz), 8.95 (1H, d, J=9.1 Hz), 11.99 (1H, s).

(ii) 5-Chloro-2-{[(2'-methoxybiphenyl-3-yl)carbonyl]amino}benzoic acid

Using the same method as in Example 3-(ii), the target 5-chloro-2-{[(2'-methoxybiphenyl-3-yl)carbonyl]amino}benzoic acid was quantitatively obtained using methyl 5-chloro-2-{[(2'-methoxybiphenyl-3-yl)carbonyl]amino}benzoate.

$^1$H-NMR (DMSO-d$_6$) δ: 3.81 (3H, s), 7.03-7.21 (2H, m), 7.34-7.46 (2H, m), 7.63 (1H, t, J=7.7 Hz), 7.71-7.79 (2H, m), 7.91 (1H, dt, J=7.7, 1.7 Hz), 8.00 (1H, d, J=2.6 Hz), 8.07 (1H, t, J=1.7 Hz), 8.75 (1H, d, J=9.0 Hz), 12.18 (1H, s).

Example 34

Production of 5-chloro-2-({[4-(3,6-dihydro-2H-pyran-4-yl)phenyl]carbonyl}amino)benzoic acid (34)

The target compound (34) was synthesized according to the following Steps (i) to (iv).

(i) 4-(3,6-Dihydro-2H-pyran-4-yl)benzonitrile 2.2 g (15.1 mmol) of (4-cyanophenyl)boronic acid, 2.5 g (10.8 mmol) of 3,6-dihydro-2H-pyran-4-yltrifluoromethanesulfonate, 373 mg (0.32 mmol) of tetrakis(triphenylphosphine)palladium(0) and 1.59 g (15.1 mmol) of sodium carbonate were heated under reflux in a mixed solvent comprising 4 mL of H$_2$O, 57 mL of toluene, and 17 mL of methanol for 3 hours. After the completion of the reaction, the organic solvent was distilled off under reduced pressure, H$_2$O was added to the residue, and ethyl acetate extraction was performed. Subsequently, the organic layer was dried over anhydrous sodium sulfate, and the solvent was distilled off under reduced pressure. The obtained crude product was separated and purified by silica gel column chromatography, thereby giving 1.27 g of 4-(3,6-dihydro-2H-pyran-4-yl)benzonitrile (yield: 64%).

$^1$H-NMR (CDCl$_3$) δ: 2.46-2.57 (2H, m), 3.95 (2H, t, J=5.4 Hz), 4.35 (2H, m), 6.25-6.32 (1H, m), 7.44-7.52 (2H, m), 7.59-7.67 (2H, m).

(ii) 4-(3,6-Dihydro-2H-pyran-4-yl)benzoic acid 5 mL of n-butanol and 5 mL of 5N aqueous sodium hydroxide were added to 1.27 g (6.86 mmol) of 4-(3,6-dihydro-2H-pyran-4-yl)benzonitrile, and the mixture was heated under reflux for 4.5 hours. Thereafter, the solvent was distilled off under reduced pressure, and H$_2$O was added to the resulting residue. 5N hydrochloric acid was then added at 0° C. to acidify the mixture, and ethyl acetate extraction was performed. The organic layer was washed with a saturated saline, and dried over anhydrous sodium sulfate. The solvent was then distilled off under reduced pressure. IPE was added to the resulting residue, and solids were collected by filtration, thereby giving 0.71 g of 4-(3,6-dihydro-2H-pyran-4-yl)benzoic acid (yield: 50%).

$^1$H-NMR (DMSO-d$_6$) δ: 2.42-2.52 (2H, m), 3.83 (2H, t, J=5.4 Hz), 4.25 (1H, brs), 6.35-6.47 (1H, m), 7.47-7.64 (2H, m), 7.81-7.96 (2H, m), 12.92 (1H, brs).

(iii) Methyl 5-chloro-2-({[4-(3,6-dihydro-2H-pyran-4-yl)phenyl]carbonyl}amino)benzoate Using the same method as in Example 3-(i), methyl 5-chloro-2-({[4-(3,6-dihydro-2H-pyran-4-yl)phenyl]carbonyl}amino)benzoate was obtained using 4-(3,6-dihydro-2H-pyran-4-yl)benzoic acid and methyl 2-amino-5-chlorobenzoate (yield: 28%).

$^1$H-NMR (CDCl$_3$) δ: 2.50-2.62 (2H, m), 3.96 (2H, t, J=5.5 Hz), 3.98 (3H, s), 4.37 (2H, m), 6.25-6.31 (1H, m), 7.44-7.66 (3H, m), 7.96-8.04 (2H, m), 8.06 (1H, d, J=2.5 Hz), 8.93 (1H, d, J=9.1 Hz), 11.97 (1H, s).

(iv) 5-Chloro-2-({[4-(3,6-dihydro-2H-pyran-4-yl)phenyl]carbonyl}amino)benzoic acid Using the same method as in Example 3-(ii), the target 5-chloro-2-({[4-(3,6-dihydro-2H-pyran-4-yl)phenyl]carbonyl}amino)benzoic acid was quantitatively obtained using methyl 5-chloro-2-({[4-(3,6-dihydro-2H-pyran-4-yl)phenyl]carbonyl}amino)benzoate.
¹H-NMR (DMSO-d₆) δ: 2.45-2.55 (2H, m), 3.85 (2H, t, J=5.4 Hz), 4.27 (2H, m), 6.43-6.51 (1H, m), 7.62-7.71 (2H, m), 7.74 (1H, dd, J=9.0, 2.7 Hz), 7.88-7.97 (2H, m), 8.00 (1H, d, J=2.7 Hz), 8.73 (1H, d, J=9.0 Hz), 12.11 (1H, s).

Example 35

Production of 5-chloro-2-[({1-[3-(furan-3-yl)phenyl]cyclopropyl}carbonyl)amino]benzoic acid (35)

The target compound (35) was synthesized according to the following Steps (i) to (iii).

(i) 1-[3-(Furan-3-yl)phenyl]cyclopropane carboxylic acid

Using the same method as in Example 8-(ii), 1-[3-(furan-3-yl)phenyl]cyclopropane carboxylic acid was obtained using sodium 1-(3-bromophenyl)cyclopropane carboxylate and 3-furanboronic acid, and 1,2-dimethoxyethane as a solvent in place of toluene and methanol (yield: 73%).
¹H-NMR (DMSO-d₆) δ: 1.15-1.22 (2H, m), 1.44-1.50 (2H, m), 6.98-6.99 (1H, m), 7.19-7.63 (4H, m), 7.74 (1H, t, J=1.7 Hz), 8.21 (1H, s), 12.34 (1H, s).

(ii) Methyl 5-chloro-2-[({1-[3-(furan-3-yl)phenyl]cyclopropyl}carbonyl)amino]benzoate Using the same method as in Example 23-(i), methyl 5-chloro-2-[({1-[3-(furan-3-yl)phenyl]cyclopropyl}carbonyl)amino]benzoate was obtained using 1-[3-(furan-3-yl)phenyl]cyclopropane carboxylic acid and methyl 2-amino-5-chlorobenzoate (yield: 56%).
¹H-NMR (CDCl₃) δ: 1.20-1.26 (2H, m), 1.69-1.75 (2H, m), 3.62 (3H, s), 6.74-6.76 (1H, m), 7.38-7.53 (5H, m), 7.61-7.63 (1H, m), 7.78-7.86 (2H, m), 8.65 (1H, d, J=8.8 Hz), 10.58 (1H, s).

(iii) 5-Chloro-2-[({1-[3-(furan-3-yl)phenyl]cyclopropyl}carbonyl)amino]benzoic acid Using the same method as in Example 3-(ii), the target 5-chloro-2-[({1-[3-(furan-3-yl)phenyl]cyclopropyl}carbonyl)amino]benzoic acid was obtained using methyl 5-chloro-2-[({1-[3-(furan-3-yl)phenyl]cyclopropyl}carbonyl)amino]benzoate (yield: 71%).
¹H-NMR (DMSO-d₆) δ: 1.17-1.25 (2H, m), 1.53-1.59 (2H, m), 7.04 (1H, dd, J=1.8, 0.8 Hz), 7.34-7.47 (2H, m), 7.58-7.68 (2H, m), 7.73-7.77 (2H, m), 7.81 (1H, d, J=2.6 Hz), 8.26 (1H, dd, J=1.8, 0.8 Hz), 8.71 (1H, d, J=9.0 Hz), 11.04 (1H, s), 13.83 (1H, brs).

Example 36

Production of 5-chloro-2-({3-[3-(furan-3-yl)phenyl]propanoyl}amino)benzoic acid (36)

The target compound (36) was synthesized according to the following Steps (i) to (ii).

(i) Methyl 5-chloro-2-({3-[3-(furan-3-yl)phenyl]propanoyl}amino)benzoate

Using the same method as in Example 23-(i), methyl 5-chloro-2-({3-[3-(furan-3-yl)phenyl]propanoyl}amino)benzoate was obtained using 3-[3-(furan-3-yl)phenyl]propionic acid and methyl 2-amino-5-chlorobenzoate (yield: 59%).
¹H-NMR (CDCl₃) δ: 2.77-2.82 (2H, m), 3.05-3.14 (2H, m), 3.91 (3H, s), 6.58-6.69 (1H, m), 7.14-7.52 (6H, m), 7.71 (1H, dd, J=1.4, 1.0 Hz), 7.98 (1H, d, J=2.6 Hz), 8.72 (1H, d, J=9.0 Hz), 11.00 (1H, s).

(ii) 5-Chloro-2-({3-[3-(furan-3-yl)phenyl]propanoyl}amino)benzoic acid

Using the same method as in Example 3-(ii), the target 5-chloro-2-({3-[3-(furan-3-yl)phenyl]propanoyl}amino)benzoic acid was obtained using methyl 5-chloro-2-({3-[3-(furan-3-yl)phenyl]propanoyl}amino)benzoate (yield: 48%).
¹H-NMR (DMSO-d₆) δ: 2.73-2.81 (2H, m), 2.92-3.00 (2H, m), 6.94 (1H, dd, J=1.8, 0.8 Hz), 7.15 (1H, d, J=7.6 Hz), 7.29 (1H, t, J=7.6 Hz), 7.41-7.47 (1H, m), 7.53 (1H, s), 7.65 (1H, dd, J=9.0, 2.6 Hz), 7.74 (1H, t, J=1.8 Hz), 7.91 (1H, d, J=2.6 Hz), 8.16 (1H, dd, J=1.6, 0.8 Hz), 8.49 (1H, d, J=9.0 Hz), 11.06 (1H, s).

Example 37

Production of 5-chloro-2-({2-[3-(furan-3-yl)phenyl]-2-methylpropanoyl}amino)benzoic acid (37)

The target compound (37) was synthesized according to the following Steps (i) to (iv).

(i) Ethyl 2-[3-(furan-3-yl)phenyl]-2-methylpropionate

Using the same method as in Example 35-(i), ethyl 2-[3-(furan-3-yl)phenyl]-2-methylpropionate was obtained using ethyl 2-(3-bromophenyl)-2-methylpropionate and 3-furanboronic acid (yield: 81%).
¹H-NMR (CDCl₃) δ: 1.19 (3H, t, J=7.2 Hz), 1.60 (6H, s), 4.14 (2H, q, J=7.2 Hz), 6.70 (1H, dd, J=1.8, 0.8 Hz), 7.21-7.44 (4H, m), 7.48 (1H, t, J=1.8 Hz), 7.71-7.73 (1H, m).

(ii) 2-[3-(Furan-3-yl)phenyl]-2-methylpropionic acid

Using the same method as in Example 3-(ii), 2-[3-(furan-3-yl)phenyl]-2-methylpropionic acid was quantitatively obtained using ethyl 2-[3-(furan-3-yl)phenyl]-2-methylpropionate.
¹H-NMR (DMSO-d₆) δ: 1.51 (6H, s), 6.95-6.96 (1H, m), 7.20-7.26 (1H, m), 7.35 (1H, t, J=7.6 Hz), 7.46-7.54 (2H, m), 7.75 (1H, t, J=1.8 Hz), 8.20 (1H, s).

(iii) Methyl 5-chloro-2-({2-[3-(furan-3-yl)phenyl]-2-methylpropanoyl}amino)benzoate Using the same method as in Example 23-(i), methyl 5-chloro-2-({2-[3-(furan-3-yl)phenyl]-2-methylpropanoyl}amino)benzoate was obtained using 2-[3-(furan-3-yl)phenyl]-2-methylpropionic acid and methyl 2-amino-5-chlorobenzoate (yield: 63%).
¹H-NMR (CDCl₃) δ: 1.73 (6H, s), 3.79 (3H, s), 6.72 (1H, dd, J=1.8, 0.8 Hz), 7.34-7.49 (5H, m), 7.56-7.58 (1H, m), 7.74-7.76 (1H, m), 7.92 (1H, d, J=2.6 Hz), 8.72 (1H, d, J=9.2 Hz), 10.88 (1H, s).

(iv) 5-Chloro-2-({2-[3-(furan-3-yl)phenyl]-2-methylpropanoyl}amino)benzoic acid

Using the same method as in Example 3-(ii), the target 5-chloro-2-({2-[3-(furan-3-yl)phenyl]-2-methylpropanoyl}amino)benzoic acid was obtained using methyl 5-chloro-2-({2-[3-(furan-3-yl)phenyl]-2-methylpropanoyl}amino)benzoate (yield: 24%).

¹H-NMR (DMSO-d₆) δ: 1.68 (6H, s), 6.98 (1H, dd, J=2.0, 0.8 Hz), 7.29-7.70 (5H, m), 7.75 (1H, t, J=1.8 Hz), 7.86 (1H, d, J=2.8 Hz), 8.23 (1H, dd, J=1.6, 0.8 Hz), 8.64 (1H, d, J=9.0 Hz), 11.16 (1H, s).

Example 38

Production of 5-chloro-2-[(9H-fluoren-1-ylcarbonyl)amino]benzoic acid (38)

The target compound (38) was synthesized according to the following Steps (i) to (ii).

(i) Methyl 5-chloro-2-[(9H-fluoren-1-ylcarbonyl)amino]benzoate

Using the same method as in Example 3-(i), methyl 5-chloro-2-[(9H-fluoren-1-ylcarbonyl)amino]benzoate was obtained using 9H-fluoren-1-carboxylic acid and methyl 2-amino-5-chlorobenzoate (yield: 38%).

¹H-NMR (CDCl₃) δ: 3.97 (3H, s), 4.35 (2H, s), 7.29-7.46 (2H, m), 7.51-7.65 (3H, m), 7.77-7.87 (2H, m), 7.98 (1H, d, J=7.5 Hz), 8.07 (1H, d, J=2.6 Hz), 8.96 (1H, d, J=9.1 Hz), 11.90 (1H, s).

(ii) 5-Chloro-2-[(9H-fluoren-1-ylcarbonyl)amino]benzoic acid

Using the same method as in Example 3-(ii), the target 5-chloro-2-[(9H-fluoren-1-ylcarbonyl)amino]benzoic acid was obtained using methyl 5-chloro-2-[(9H-fluoren-1-ylcarbonyl)amino]benzoate (yield: 87%).

¹H-NMR (DMSO-d₆) δ: 4.27 (2H, s), 7.32-7.48 (2H, m), 7.55-7.69 (2H, m), 7.75 (1H, dd, J=9.0, 2.7 Hz), 7.75-7.83 (1H, m), 7.95-8.03 (1H, m), 8.00 (1H, d, J=2.7 Hz), 8.17 (1H, dd, J=7.5, 0.6 Hz), 8.75 (1H, d, J=9.0 Hz), 11.99 (1H, s), 14.17 (1H, brs).

Example 39

Production of 5-chloro-2-[(2,2-diphenylpropanoyl)amino]benzoic acid (39)

The target compound (39) was synthesized according to the following Steps (i) to (ii).

(i) Methyl 5-chloro-2-[(2,2-diphenylpropanoyl)amino]benzoate

Using the same method as in Example 23-(i), methyl 5-chloro-2-[(2,2-diphenylpropanoyl)amino]benzoate was obtained using 2,2-diphenylpropionic acid and methyl 2-amino-5-chlorobenzoate (yield: 93%).

¹H-NMR (CDCl₃) δ: 2.10 (3H, s), 3.75 (3H, s), 7.22-7.40 (10H, m), 7.50 (1H, dd, J=9.2, 2.6 Hz), 7.93 (1H, d, J=2.6 Hz), 8.83 (1H, d, J=9.2 Hz), 10.94 (1H, s).

(ii) 5-Chloro-2-[(2,2-diphenylpropanoyl)amino]benzoic acid

Using the same method as in Example 3-(ii), the target 5-chloro-2-[(2,2-diphenylpropanoyl)amino]benzoic acid was obtained using methyl 5-chloro-2-[(2,2-diphenylpropanoyl)amino]benzoate (yield: 66%).

¹H-NMR (DMSO-d₆) δ: 2.00 (3H, s), 7.23-7.40 (10H, m), 7.69 (1H, dd, J=9.0, 2.6 Hz), 7.88 (1H, d, J=2.6 Hz), 8.72 (1H, d, J=9.0 Hz), 11.24 (1H, s).

Example 40

Production of 2-({[4-(adamantan-1-yl)phenyl]carbonyl}amino)-5-chlorobenzoic acid (40)

The target compound (40) was synthesized according to the following Steps (i) to (ii).

(i) Methyl 2-({[4-(adamantan-1-yl)phenyl]carbonyl}amino)-5-chlorobenzoate

Using the same method as in Example 23-(i), methyl 2-({[4-(adamantan-1-yl)phenyl]carbonyl}amino)-5-chlorobenzoate was obtained using 4-(adamantan-1-yl)benzoic acid and methyl 2-amino-5-chlorobenzoate (yield: 45%).

¹H-NMR (CDCl₃) δ: 1.77-1.82 (6H, m), 1.91-1.96 (6H, m), 2.11-2.16 (3H, m), 3.98 (3H, s), 7.49-7.58 (3H, m), 7.98 (2H, d, J=8.6 Hz), 8.06 (1H, d, J=2.6 Hz), 8.94 (1H, d, J=9.0 Hz), 11.93 (1H, s).

(ii) 2-({[4-(Adamantan-1-yl)phenyl]carbonyl}amino)-5-chlorobenzoic acid

Using the same method as in Example 3-(ii), the target 2-({[4-(adamantan-1-yl)phenyl]carbonyl}amino)-5-chlorobenzoic acid was obtained using methyl 2-({[4-(adamantan-1-yl)phenyl]carbonyl}amino)-5-chlorobenzoate (yield: 90%).

¹H-NMR (DMSO-d₆) δ: 1.72-1.77 (6H, m), 1.88-1.93 (6H, m), 2.05-2.10 (3H, m), 7.57 (2H, d, J=8.4 Hz), 7.73 (1H, dd, J=9.0, 2.6 Hz), 7.90 (2H, d, J=8.4 Hz), 7.99 (1H, d, J=2.6 Hz), 8.74 (1H, d, J=9.0 Hz), 12.09 (1H, s).

Example 41

Production of 5-chloro-2-[(3,3-diphenylpropanoyl)amino]benzoic acid (41)

The target compound (41) was synthesized according to the following Steps (i) to (ii).

(i) Methyl 5-chloro-2-[(3,3-diphenylpropanoyl)amino]benzoate

Using the same method as in Example 23-(i), methyl 5-chloro-2-[(3,3-diphenylpropanoyl)amino]benzoate was obtained using 3,3-diphenylpropionic acid and methyl 2-amino-5-chlorobenzoate (yield: 93%).

¹H-NMR (CDCl₃) δ: 3.17 (2H, d, J=7.8 Hz), 3.92 (3H, s), 4.69 (1H, t, J=7.8 Hz), 7.16-7.30 (10H, m), 7.45 (1H, dd, J=9.0, 2.6 Hz), 7.93 (1H, d, J=2.6 Hz), 8.61 (1H, d, J=9.0 Hz), 10.97 (1H, s).

(ii) 5-Chloro-2-[(3,3-diphenylpropanoyl)amino]benzoic acid

Using the same method as in Example 3-(ii), the target 5-chloro-2-[(3,3-diphenylpropanoyl)amino]benzoic acid was obtained using methyl 5-chloro-2-[(3,3-diphenylpropanoyl)amino]benzoate (yield: 72%).

¹H-NMR (DMSO-d₆) δ: 3.23 (2H, d, J=8.0 Hz), 4.55 (1H, t, J=8.0 Hz), 7.10-7.39 (10H, m), 7.59 (1H, dd, J=9.0, 2.6 Hz), 7.88 (1H, d, J=2.6 Hz), 8.61 (1H, d, J=9.0 Hz), 11.07 (1H, s).

Example 42

Production of 5-chloro-2-{[(4-phenoxyphenyl)carbonyl]amino}benzoic acid (42)

The target compound (42) was synthesized according to the following Steps (i) to (ii).

(i) Methyl 5-chloro-2-{[(4-phenoxyphenyl)carbonyl]amino}benzoate

Using the same method as in Example 23-(i), methyl 5-chloro-2-{[(4-phenoxyphenyl)carbonyl]amino}benzoate was obtained using 4-phenoxybenzoic acid and methyl 2-amino-5-chlorobenzoate (yield: 89%).

¹H-NMR (CDCl₃) δ: 3.97 (3H, s), 7.05-7.24 (5H, m), 7.41 (1H, t, J=8.0 Hz), 7.55 (1H, dd, J=9.0, 2.6 Hz), 7.98-8.06 (3H, m), 8.92 (1H, t, J=9.0 Hz), 11.92 (1H, s).

(ii) 5-Chloro-2-{[(4-phenoxyphenyl)carbonyl]amino}benzoic acid

Using the same method as in Example 3-(ii), the target 5-chloro-2-{[(4-phenoxyphenyl)carbonyl]amino}benzoic acid was obtained using methyl 5-chloro-2-{[(4-phenoxyphenyl)carbonyl]amino}benzoate (yield: 73%).

¹H-NMR (DMSO-d₆) δ: 7.12-7.29 (5H, m), 7.43-7.51 (2H, m), 7.73 (1H, dd, J=9.0, 2.8 Hz), 7.94-8.00 (3H, m), 8.70 (1H, d, J=9.0 Hz), 12.04 (1H, s).

Example 43

Production of 2-({[3,5-bis(trifluoro-methyl)phenyl]carbonyl}amino)-5-chlorobenzoic acid (43)

The target compound (43) was synthesized according to the following Steps (i) to (ii).

(i) Methyl 2-({[3,5-bis(trifluoromethyl)phenyl]carbonyl}amino)-5-chlorobenzoate

Under ice-cooling, 660 mg (3.56 mmol) of methyl 2-amino-5-chlorobenzoate was added to a DMAc (10 mL) solution comprising 1.00 g (3.62 mmol) of 3,5-bis(trifluoromethyl)benzoyl chloride, and the mixture was stirred at room temperature for 5 hours. Water was added to the reaction mixture, and the mixture was stirred for a short time. Thereafter, the precipitates were collected by filtration, washed with water, and then air-dried, thereby giving methyl 2-({[3,5-bis(trifluoromethyl)phenyl]carbonyl}amino)-5-chlorobenzoate (yield: 99%).

¹H-NMR (CDCl₃) δ: 4.01 (3H, s), 7.60 (1H, dd, J=9.0, 2.6 Hz), 8.09-8.10 (2H, m), 8.48 (2H, s), 8.85 (1H, d, J=9.0 Hz), 12.29 (1H, s).

(ii) 2-({[3,5-Bis(trifluoromethyl)phenyl]carbonyl}amino)-5-chlorobenzoic acid

Using the same method as in Example 3-(ii), the target 2-({[3,5-bis(trifluoromethyl)phenyl]carbonyl}amino)-5-chlorobenzoic acid was obtained using methyl 2-({[3,5-bis(trifluoro-methyl)phenyl]carbonyl}amino)-5-chloro benzoate (yield: 30%).

¹H-NMR (DMSO-d₆) δ: 7.76 (1H, dd, J=9.0, 2.6 Hz), 7.98 (1H, d, J=2.6 Hz), 8.45-8.55 (4H, m), 12.24 (1H, s).

Example 44

Production of 5-chloro-2-({2-[3-(furan-3-yl)phenoxy]-2-methylpropanoyl}amino)benzoic acid (44)

The target compound (44) was synthesized according to the following Steps (i) to (iii)

(i) Ethyl 2-[3-(furan-3-yl)phenoxy]-2-methylpropionate

Using the same method as in Example 35-(i), ethyl 2-[3-(furan-3-yl)phenoxy]-2-methylpropionate was obtained using ethyl 2-(3-bromophenoxy)-2-methylpropionate and 3-furanboronic acid (yield: 97%).

¹H-NMR (CDCl₃) δ: 1.25 (3H, t, J=7.2 Hz), 1.62 (6H, s), 4.25 (2H, q, J=7.2 Hz), 6.65 (1H, dd, J=2.0, 1.0 Hz), 6.71 (1H, ddd, J=8.0, 2.6, 1.0 Hz), 7.01 (1H, dd, J=2.4, 1.6 Hz), 7.08-7.15 (1H, m), 7.23 (1H, t, J=8.0 Hz), 7.46 (1H, t, J=1.6 Hz), 7.69 (1H, dd, J=1.4, 1.0 Hz).

(ii) Methyl 5-chloro-2-({2-[3-(furan-3-yl)phenoxy]-2-methylpropanoyl}amino)benzoate 1.55 g (5.65 mmol) of ethyl 2-[3-(furan-3-yl)phenoxy]-2-methylpropate was dissolved in THF (25 mL). 10 mL of 1N aqueous sodium hydroxide solution was added thereto at room temperature, and the mixture was stirred at 50° C. for one day. The mixture was cooled to room temperature, and the solvent was distilled off under reduced pressure. Thereafter, toluene and water were added to separate the mixture. The organic layer was washed with water and dried over magnesium sulfate, followed by filtration and condensation, thereby giving a crude product of 2-[3-(furan-3-yl)phenoxy]-2-methylpropionic acid. The crude product was used in the next reaction without further purification.

A catalytic amount of DMF and 360 mg (2.84 mmol) of oxalyl chloride were added to a THF (4 mL) solution comprising 466 mg of the crude product at 0° C., and the mixture was stirred at room temperature for 30 minutes. The solvent was distilled off under reduced pressure, and 4 mL of DMAc and 315 mg (1.70 mmol) of methyl 2-amino-5-chlorobenzoate were then added in this order to the residue at 0° C. The mixture was stirred at room temperature for 5 hours. After the completion of the reaction, ethyl acetate and water were added to separate the mixture. The organic layer was washed with water two times and dried over magnesium sulfate, followed by filtration. After the filtrate was condensed, the obtained crude product was separated and purified by silica gel column chromatography, thereby giving 550 mg of methyl 5-chloro-2-({2-[3-(furan-3-yl)phenoxy]-2-methylpropanoyl}amino)benzoate (yield: 73%).

¹H-NMR (CDCl₃) δ: 1.65 (6H, s), 3.86 (3H, s), 6.67 (1H, dd, J=1.8, 0.8 Hz), 6.91 (1H, ddd, J=7.6, 2.6, 1.6 Hz), 7.16-7.32 (3H, m), 7.47 (1H, t, J=1.8 Hz), 7.53 (1H, dd, J=8.6, 2.6 Hz), 7.71 (1H, dd, J=1.6, 0.8 Hz), 8.01 (1H, d, J=2.6 Hz), 8.80 (1H, d, J=9.2 Hz), 12.05 (1H, s).

(iii) 5-Chloro-2-({2-[3-(furan-3-yl)phenoxy]-2-methylpropanoyl}amino)benzoic acid Using the same method as in Example 3-(ii), the target 5-chloro-2-({2-[3-(furan-3-yl)phenoxy]-2-methylpropanoyl}amino)benzoic acid was obtained using methyl 5-chloro-2-({2-[3-(furan-3-yl)phenoxy]-2-methylpropanoyl}amino)benzoate (yield: 24%).

¹H-NMR (DMSO-d₆) δ: 1.56 (6H, s), 6.83-6.94 (2H, m), 7.29-7.33 (3H, m), 7.69-7.75 (2H, m), 7.95 (1H, d, J=2.8 Hz), 8.19 (1H, s), 8.72 (1H, d, J=9.0 Hz), 12.26 (1H, s).

Example 45

Production of 4-{[(biphenyl-3-yloxy)acetyl]amino}biphenyl-3-carboxylic acid (45)

The target compound (45) was synthesized according to the following Steps (i) to (ii).

(i) Methyl 4-{[(biphenyl-3-yloxy)acetyl]amino}biphenyl-3-carboxylate

Using the same method as in Example 23-(i), methyl 4-{[(biphenyl-3-yloxy)acetyl]amino}biphenyl-3-carboxylate was obtained using (biphenyl-3-yloxy)acetic acid and methyl 4-aminobiphenyl-3-carboxylate (yield: 94%).
¹H-NMR (CDCl₃) δ: 3.97 (3H, s), 4.74 (2H, s), 7.06 (1H, ddd, J=8.0, 2.6, 1.2 Hz), 7.26-7.65 (13H, m), 7.81 (1H, dd, J=8.8, 2.4 Hz), 8.30 (1H, d, J=2.4 Hz), 8.88 (1H, d, J=8.8 Hz), 12.14 (1H, s).

(ii) 4-{[(Biphenyl-3-yloxy)acetyl]amino}biphenyl-3-carboxylic acid

Using the same method as in Example 3-(ii), the target 4-{[(biphenyl-3-yloxy)acetyl]amino}biphenyl-3-carboxylic acid was obtained using methyl 4-{[(biphenyl-3-yloxy)acetyl]amino}biphenyl-3-carboxylate (yield: 97%).
¹H-NMR (DMSO-d₆) δ: 4.87 (2H, s), 7.08-7.17 (1H, m), 7.31-7.53 (9H, m), 7.67-7.77 (4H, m), 7.97 (1H, dd, J=8.8, 2.2 Hz), 8.28 (1H, d, J=2.2 Hz), 8.82 (1H, d, J=8.8 Hz), 12.23 (1H, s).

Example 46

Production of 2-{[(biphenyl-4-yloxy)acetyl]amino}-5-(furan-3-yl)benzoic acid (46)

The target compound (46) was synthesized according to the following Steps (i) to (iii).

(i) Methyl 2-amino-5-(furan-3-yl)benzoate

Using the same method as in Example 34-(i), methyl 2-amino-5-(furan-3-yl)benzoate was obtained using methyl 2-amino-5-bromo benzoate and 3-furanboronic acid (yield: 88%).
¹H-NMR (CDCl₃) δ: 3.90 (3H, s), 5.74 (2H, brs), 6.65 (1H, dd, J=2.0, 1.0 Hz), 6.70 (1H, d, J=8.6 Hz), 7.41 (1H, dd, J=8.6, 2.2 Hz), 7.45 (1H, t, J=1.6 Hz), 7.64 (1H, dd, J=1.6, 1.0 Hz), 7.98 (1H, d, J=2.2 Hz).

(ii) Methyl 2-{[(biphenyl-4-yloxy)acetyl]amino}-5-(furan-3-yl)benzoate

Using the same method as in Example 23-(i), methyl 2-{[biphenyl-4-yloxy)acetyl]amino}-5-(furan-3-yl)benzoate was obtained using (biphenyl-4-yloxy)acetic acid and methyl 2-amino-5-(furan-3-yl)benzoate (yield: 96%).
¹H-NMR (CDCl₃) δ: 3.99 (3H, s), 4.70 (2H, s), 6.72 (1H, dd, J=1.8, 0.8 Hz), 7.17 (2H, d, J=9.0 Hz), 7.28-7.63 (8H, m), 7.69 (1H, dd, J=8.8, 2.4 Hz), 7.76 (1H, dd, J=1.6, 1.0 Hz), 8.17 (1H, d, J=2.4 Hz), 8.83 (1H, d, J=8.8 Hz), 12.09 (1H, s).

(iii) 2-{[(Biphenyl-4-yloxy)acetyl]amino}-5-(furan-3-yl)benzoic acid

Using the same method as in Example 3-(ii), the target 2-{[(biphenyl-4-yloxy)acetyl]amino}-5-(furan-3-yl)benzoic acid was obtained using methyl 2-{[(biphenyl-4-yloxy)acetyl]amino}-5-(furan-3-yl)benzoate (yield: 91%).
¹H-NMR (DMSO-d₆) δ: 4.80 (2H, s), 6.99 (1H, dd, J=1.8, 0.8 Hz), 7.19 (2H, d, J=8.8 Hz), 7.32-7.48 (3H, m), 7.62-7.69 (4H, m), 7.77 (1H, t, J=1.8 Hz), 7.90 (1H, dd, J=8.8, 2.2 Hz), 8.20 (1H, d, J=2.2 Hz), 8.24-8.26 (1H, m), 8.74 (1H, d, J=8.8 Hz), 12.21 (1H, s).

Example 47

Production of 2-({[4-(adamantan-1-yl)phenoxy]acetyl}amino)-5-(furan-3-yl)benzoic acid (47)

The target compound (47) was synthesized according to the following Steps (i) to (ii).

(i) Methyl 2-({[4-(adamantan-1-yl)phenoxy]acetyl}amino)-5-(furan-3-yl)benzoate

Using the same method as in Example 23-(i), methyl 2-({[4-(adamantan-1-yl)phenoxy]acetyl}amino)-5-(furan-3-yl)benzoate was obtained using [4-(adamantan-1-yl)phenoxy]acetic acid and methyl 2-amino-5-(furan-3-yl)benzoate (yield: 95%).
¹H-NMR (CDCl₃) δ: 1.73-1.78 (6H, m), 1.87-1.92 (6H, m), 2.07-2.12 (3H, m), 3.97 (3H, s), 4.64 (2H, s), 6.72 (1H, dd, J=1.8, 1.0 Hz), 7.04 (2H, d, J=9.0 Hz), 7.34 (2H, d, J=9.0 Hz), 7.49 (1H, t, J=1.8 Hz), 7.67 (1H, dd, J=8.8, 2.0 Hz), 7.75 (1H, dd, J=1.6, 1.0 Hz), 8.15 (1H, d, J=2.0 Hz), 8.81 (1H, d, J=8.8 Hz), 12.02 (1H, s).

(ii) 2-({[4-(Adamantan-1-yl)phenoxy]acetyl}amino)-5-(furan-3-yl)benzoic acid

Using the same method as in Example 3-(ii), the target 2-({[4-(adamantan-1-yl)phenoxy]acetyl}amino)-5-(furan-3-yl)benzoic acid was obtained using methyl 2-({[4-(adamantan-1-yl)phenoxy]acetyl}amino)-5-(furan-3-yl)benzoate (yield: 95%).
¹H-NMR (DMSO-d₆) δ: 1.71-1.76 (6H, m), 1.81-1.86 (6H, m), 2.02-2.07 (3H, m), 4.70 (2H, s), 6.98 (1H, dd, J=2.0, 0.8 Hz), 7.02 (2H, d, J=9.0 Hz), 7.31 (2H, d, J=9.0 Hz), 7.76 (1H, t, J=1.8 Hz), 7.88 (1H, dd, J=8.6, 2.2 Hz), 8.19 (1H, d, J=2.2 Hz), 8.23 (1H, d, J=1.4, 1.0 Hz), 8.72 (1H, d, J=8.6 Hz), 12.15 (1H, s).

Example 48

Production of 5-chloro-2-{[(1-methyl-5-phenyl-1H-indol-2-yl)carbonyl]amino}benzoic acid (48)

The target compound (48) was synthesized according to the following Steps (i) to (ii).

(i) Methyl 5-chloro-2-{[(1-methyl-5-phenyl-1H-indol-2-yl)carbonyl]amino}benzoate Using the same method as in Example 13-(ii), methyl 5-chloro-2-{[(1-methyl-5-phenyl-1H-indol-2-yl)carbonyl]amino}benzoate was obtained using methyl 2-{[(5-bromo-1- methyl-1H-indol-2-yl)carbonyl]amino}-5-chlorobenzoate obtained in Example 23-(i) and phenylboronic acid (yield: 66%).

¹H-NMR (CDCl₃) δ: 4.01 (3H, s), 4.16 (3H, s), 7.32-7.74 (9H, m), 7.94-7.96 (1H, m), 8.08 (1H, d, J=2.6 Hz), 8.86 (1H, d, J=9.0 Hz), 12.00 (1H, s).

(ii) 5-Chloro-2-{[(1-methyl-5-phenyl-1H-indol-2-yl)carbonyl]amino}benzoic acid

Using the same method as in Example 3-(ii), the target 5-chloro-2-{[(1-methyl-5-phenyl-1H-indol-2-yl)carbonyl]amino}benzoic acid was obtained using methyl 5-chloro-2-{[(1-methyl-5-phenyl-1H-indol-2-yl)carbonyl]amino}benzoate (yield: 59%).

¹H-NMR (DMSO-d₆) δ: 4.09 (3H, s), 7.27 (1H,$), 7.35 (1H, d, J=7.2 Hz), 7.43-7.51 (2H, m), 7.68-7.78 (5H, m), 8.00-8.02 (2H, m), 8.69 (1H, d, J=9.0 Hz), 12.15 (1H, s).

Example 49

Production of 5-chloro-2-({[(4'-methylbiphenyl-4-yl)oxy]acetyl}amino)benzoic acid (49)

The target compound (49) was synthesized according to the following Steps (i) to (ii).

(i) Methyl 5-chloro-2-({[(4'-methylbiphenyl-4-yl)oxy]acetyl}amino)benzoate

Using the same method as in Example 23-(i), methyl 5-chloro-2-({[(4'-methylbiphenyl-4-yl)oxy]acetyl}amino)benzoate was obtained using [(4'-methylbiphenyl-4-yl)oxy]acetic acid and methyl 2-amino-5-chlorobenzoate (yield: 95%).

¹H-NMR (CDCl₃) δ: 2.39 (3H, s), 3.97 (3H, s), 4.68 (2H, s), 7.13 (2H, d, J=8.6 Hz), 7.21-7.26 (2H, m), 7.43-7.58 (5H, m), 8.03 (1H, d, J=2.6 Hz), 8.79 (1H, d, J=9.0 Hz), 12.06 (1H, s).

(ii) 5-Chloro-2-({[(4'-methylbiphenyl-4-yl)oxy]acetyl}amino)benzoic acid

Using the same method as in Example 3-(ii), the target 5-chloro-2-({[(4'-methylbiphenyl-4-yl)oxy]acetyl}amino)benzoic acid was obtained using methyl 5-chloro-2-({[(4'-methylbiphenyl-4-yl)oxy]acetyl}amino)benzoate (yield: 87%).

¹H-NMR (DMSO-d₆) δ: 2.33 (3H, s), 4.79 (2H, s), 7.16 (2H, d, J=8.6 Hz), 7.24 (2H, d, J=8.0 Hz), 7.52 (2H, d, J=8.0 Hz), 7.63 (2H, d, J=8.6 Hz), 7.72 (1H, dd, J=9.0, 2.6 Hz), 7.97 (1H, d, J=2.6 Hz), 8.75 (1H, d, J=9.0 Hz), 12.18 (1H, s), 14.50 (1H, brs).

Example 50

Production of 5-chloro-2-({[(3',5'-dimethylbiphenyl-4-yl)oxy]acetyl}amino)benzoic acid (50)

The target compound (50) was synthesized according to the following Steps (i) to (iv).

(i) Ethyl[(3',5'-dimethylbiphenyl-4-yl)oxy]acetate

Using the same method as in Example 13-(ii), ethyl [(3',5'-dimethylbiphenyl-4-yl)oxy]acetate was quantitatively obtained using ethyl 4-bromophenoxy acetate and 3,5-dimethylphenylboronic acid.

¹H-NMR (CDCl₃) δ: 1.31 (3H, t, J=7.2 Hz), 2.37 (6H, s), 4.29 (2H, q, J=7.2 Hz), 4.65 (2H, s), 6.92-7.00 (3H, m), 7.14-7.18 (2H, m), 7.50 (2H, d, J=9.0 Hz).

(ii) [(3',5'-Dimethylbiphenyl-4-yl)oxy]acetic acid

Using the same method as in Example 3-(ii), [(3',5'-dimethylbiphenyl-4-yl)oxy]acetic acid was obtained using ethyl [(3',5'-dimethylbiphenyl-4-yl)oxy]acetate (yield: 93%).

¹H-NMR (DMSO-d₆) δ: 2.31 (6H, s), 4.71 (2H, s), 6.94-7.00 (3H, m), 7.20 (2H, s), 7.55 (2H, d, J=8.8 Hz).

(iii) Methyl 5-chloro-2-({[(3',5'-dimethylbiphenyl-4-yl)oxy]acetyl}amino)benzoate Using the same method as in Example 23-(i), methyl 5-chloro-2-({[(3',5'-dimethylbiphenyl-4-yl)oxy]acetyl}amino)benzoate was obtained using [(3',5'-dimethylbiphenyl-4-yl)oxy]acetic acid and methyl 2-amino-5-chlorobenzoate (yield: 85%).

¹H-NMR (CDCl₃) δ: 2.38 (6H, s), 3.97 (3H, s), 4.67 (2H, s), 6.98 (1H, s), 7.10-7.18 (4H, m), 7.44-7.59 (3H, m), 8.03 (1H, d, J=2.6 Hz), 8.80 (1H, d, J=8.8 Hz), 12.05 (1H, s).

(iv) 5-Chloro-2-({[(3',5'-dimethylbiphenyl-4-yl)oxy]acetyl}amino)benzoic acid

Using the same method as in Example 3-(ii), the target 5-chloro-2-({[(3',5'-dimethylbiphenyl-4-yl)oxy]acetyl}amino)benzoic acid was obtained using methyl 5-chloro-2-({[(3',5'-dimethylbiphenyl-4-yl)oxy]acetyl}amino)benzoate (yield: 89%).

¹H-NMR (DMSO-d₆) δ: 2.32 (6H, s), 4.79 (2H, s), 6.95 (1H, s), 7.15 (2H, d, J=8.8 Hz), 7.22 (2H, s), 7.62 (2H, d, J=8.8 Hz), 7.72 (1H, dd, J=9.0, 2.6 Hz), 7.97 (1H, d, J=2.6 Hz), 8.75 (1H, d, J=9.0 Hz), 12.18 (1H, s), 14.20 (1H, brs).

Example 51

Production of 5-chloro-2-{[(5-phenyl-1H-indol-1-yl)acetyl]amino}benzoic acid (51)

The target compound (51) was synthesized according to the following Steps (i) to (ii).

(i) Methyl 5-chloro-2-{[(5-phenyl-1H-indol-1-yl)acetyl]amino}benzoate

Using the same method as in Example 34-(i), methyl 5-chloro-2-{[(5-phenyl-1H-indol-1-yl)acetyl]amino}benzoate was obtained using methyl 2-{[(5-bromo-1H-indol-1-yl)acetyl]amino}-5-chlorobenzoate obtained in Example 24-(i) and phenylboronic acid (yield: 64%).

¹H-NMR (CDCl₃) δ: 3.60 (3H, s), 4.98 (2H, s), 6.74 (1H, dd, J=3.2, 0.8 Hz), 7.23 (1H, d, J=3.0 Hz), 7.31-7.52 (6H, m), 7.61-7.67 (2H, m), 7.87-7.91 (2H, m), 8.68 (1H, d, J=9.0 Hz), 10.90 (1H, s).

(ii) 5-Chloro-2-{[(5-phenyl-1H-indol-1-yl)acetyl]amino}benzoic acid

Using the same method as in Example 3-(ii), the target 5-chloro-2-{[(5-phenyl-1H-indol-1-yl)acetyl]amino}benzoic acid was obtained using methyl 5-chloro-2-{[(5-phenyl-1H-indol-1-yl)acetyl]amino}benzoate (yield: 82%).

¹H-NMR (DMSO-d₆) δ: 5.22 (2H, s), 6.60 (1H, d, J=3.2 Hz), 7.26-7.35 (1H, m), 7.40-7.56 (5H, m), 7.64-7.72 (3H, m), 7.84-7.87 (2H, m), 8.59 (1H, d, J=9.2 Hz), 11.28 (1H, s).

Example 52

Production of 2-({[4-(adamantan-1-ylmethoxy)phenyl]carbonyl}amino)-5-chlorobenzoic acid (52)

The target compound (52) was synthesized according to the following Steps (i) to (ii).

(i) Methyl 2-({[4-(adamantan-1-ylmethoxy)phenyl]carbonyl}amino)-5-chlorobenzoate Using the same method as in Example 23-(i), methyl 2-({[4-(adamantan-1-ylmethoxy)phenyl]carbonyl}amino)-5-chlorobenzoate was obtained using 4-(adamantan-1-ylmethoxy)benzoic acid and methyl 2-amino-5-chlorobenzoate (yield: 90%).

¹H-NMR (CDCl₃) δ: 1.66-1.76 (12H, m), 2.01-2.06 (3H, m), 3.57 (2H, s), 3.98 (3H, s), 7.00 (2H, d, J=8.8 Hz), 7.54 (1H, dd, J=9.0, 2.6 Hz), 7.98 (2H, d, J=8.8 Hz), 8.05 (1H, d, J=2.6 Hz), 8.92 (2H, d, J=9.0 Hz), 11.87 (1H, s).

(ii) 2-({[4-(Adamantan-1-ylmethoxy)phenyl]carbonyl}amino)-5-chlorobenzoic acid

Using the same method as in Example 3-(ii), the target 2-({[4-(adamantan-1-ylmethoxy)phenyl]carbonyl}amino)-5-chlorobenzoic acid was obtained using methyl 2-({[4-(adamantan-1-ylmethoxy)phenyl]carbonyl}amino)-5-chlorobenzoate (yield: 75%).

¹H-NMR (DMSO-d₆) δ: 1.61-1.76 (12H, m), 1.97-2.02 (3H, m), 3.64 (2H, s), 7.12 (2H, d, J=8.8 Hz), 7.73 (1H, dd, J=9.0, 2.6 Hz), 7.90 (2H, d, J=8.8 Hz), 7.99 (1H, d, J=2.6 Hz), 8.73 (1H, d, J=9.0 Hz), 12.03 (1H, s).

Example 53

Production of 5-chloro-2-({[3-(furan-2-yl)phenoxy]acetyl}amino)benzoic acid (53)

The target compound (53) was synthesized according to the following Steps (i) to (iv).

(i) Ethyl [3-(furan-2-yl)phenoxy]acetate

Using the same method as in Example 13-(i), ethyl [3-(furan-2-yl)phenoxy]acetate was quantitatively obtained using 3-(furan-2-yl)phenol and ethyl bromoacetate.

¹H-NMR (CDCl₃) δ: 1.31 (3H, t, J=7.2 Hz), 4.29 (2H, q, J=7.2 Hz), 4.67 (2H, s), 6.47 (1H, dd, J=3.2, 1.8 Hz), 6.65 (1H, dd, J=3.6, 0.8 Hz), 6.78-6.89 (1H, m), 7.23-7.32 (3H, m), 7.46 (1H, dd, J=1.8, 0.6 Hz).

(ii) [3-(Furan-2-yl)phenoxy]acetic acid 10 mL of ethanol and 4.0 mL of 1N aqueous sodium hydroxide solution were added to 615 mg (2.50 mmol) of ethyl [3-(furan-2-yl)phenoxy]acetate, and the mixture was stirred at room temperature for 4 hours. 1N hydrochloric acid was added to acidify the reaction mixture, and water was added thereto. The precipitated solids were collected by filtration, washed with water, and air-dried, thereby giving 448 mg of [3-(furan-2-yl)phenoxy]acetic acid (yield: 82%).

¹H-NMR (DMSO-d₆) δ: 4.74 (2H, s), 6.60 (1H, dd, J=3.4, 1.6 Hz), 6.81-6.88 (1H, m), 6.99 (1H, dd, J=3.4, 0.6 Hz), 7.22-7.24 (1H, m), 7.30-7.34 (2H, m), 7.75 (1H, dd, J=1.8, 0.6 Hz), 13.05 (1H, brs).

(iii) Methyl 5-chloro-2-({[3-(furan-2-yl)phenoxy]acetyl}amino)benzoate

Using the same method as in Example 23-(i), methyl 5-chloro-2-({[3-(furan-2-yl)phenoxy]acetyl}amino)benzoate was obtained using [3-(furan-2-yl)phenoxy]acetic acid and methyl 2-amino-5-chlorobenzoate (yield: 62%).

¹H-NMR (CDCl₃) δ: 3.97 (3H, s), 4.69 (2H, s), 6.49 (1H, dd, J=3.2, 1.8 Hz), 6.67-6.70 (1H, m), 6.96-7.04 (1H, m), 7.34-7.40 (3H, m), 7.47-7.55 (2H, m), 8.03 (1H, d, J=2.6 Hz), 8.79 (1H, d, J=8.8 Hz), 12.06 (1H, s).

(iv) 5-Chloro-2-({[3-(furan-2-yl)phenoxy]acetyl}amino)benzoic acid

Using the same method as in Example 3-(ii), the target 5-chloro-2-({[3-(furan-2-yl)phenoxy]acetyl}amino)benzoic acid was obtained using methyl 5-chloro-2-({[3-(furan-2-yl)phenoxy]acetyl}amino)benzoate (yield: 88%).

¹H-NMR (DMSO-d₆) δ: 4.82 (2H, s), 6.62 (1H, dd, J=3.4, 1.8 Hz), 6.99-7.05 (2H, m), 7.35-7.45 (3H, m), 7.72 (1H, dd, J=9.0, 2.6 Hz), 7.77-7.79 (1H, m), 7.97 (1H, d, J=2.6 Hz), 8.74 (1H, d, J=9.0 Hz), 12.15 (1H, s).

Example 54

Production of 5-chloro-2-({[4-(furan-2-yl)phenoxy]acetyl}amino)benzoic acid (54)

The target compound (54) was synthesized according to the following Steps (i) to (iv).

(i) Ethyl [4-(furan-2-yl)phenoxy]acetate

Using the same method as in Example 13-(i), ethyl [4-(furan-2-yl)phenoxy]acetate was quantitatively obtained using 4-(furan-2-yl)phenol and ethyl bromoacetate.

¹H-NMR (CDCl₃) δ: 1.30 (3H, t, J=7.2 Hz), 4.28 (2H, q, J=7.2 Hz), 4.64 (2H, s), 6.44 (1H, dd, J=3.4, 1.8 Hz), 6.53 (1H, dd, J=3.4, 0.8 Hz), 6.93 (2H, d, J=9.0 Hz), 7.43 (1H, dd, J=1.8, 0.8 Hz), 7.60 (2H, d, J=9.0 Hz).

(ii) [4-(Furan-2-yl)phenoxy]acetic acid

Using the same method as in Example 30-(iii), [4-(furan-2-yl)phenoxy]acetic acid was obtained using ethyl [4-(furan-2-yl)phenoxy]acetate (yield: 87%).

¹H-NMR (DMSO-d₆) δ: 4.71 (2H, s), 6.55 (1H, dd, J=3.4, 1.8 Hz), 6.79 (1H, dd, J=3.4, 0.8 Hz), 6.97 (2H, d, J=9.0 Hz), 7.62 (2H, d, J=9.0 Hz), 7.69 (1H, dd, J=1.8, 0.8 Hz).

(iii) Methyl 5-chloro-2-({[4-(furan-2-yl)phenoxy]acetyl}amino)benzoate

Using the same method as in Example 23-(i), methyl 5-chloro-2-({[4-(furan-2-yl)phenoxy]acetyl}amino)benzoate was obtained using [4-(furan-2-yl)phenoxy]acetic acid and methyl 2-amino-5-chlorobenzoate (yield: 33%).

¹H-NMR (DMSO-d₆) δ: 3.97 (3H, s), 4.67 (2H, s), 6.46 (1H, dd, J=3.4, 1.8 Hz), 6.56 (1H, dd, J=3.4, 0.8 Hz), 7.10 (1H, d, J=9.0 Hz), 7.44 (1H, dd, J=1.8, 0.8 Hz), 7.52 (1H, dd,

J=9.0, 2.6 Hz), 7.66 (1H, d, J=9.0 Hz), 8.03 (1H, d, J=2.6 Hz), 8.79 (1H, d, J=9.0 Hz), 12.05 (1H, s).

(iv) 5-Chloro-2-({[4-(furan-2-yl)phenoxy]acetyl}amino)benzoic acid

Using the same method as in Example 3-(ii), the target 5-chloro-2-({[4-(furan-2-yl)phenoxy]acetyl}amino)benzoic acid was obtained using methyl 5-chloro-2-({[4-(furan-2-yl)phenoxy]acetyl}amino)benzoate (yield: 94%).

$^1$H-NMR (DMSO-d$_6$) δ: 4.79 (2H, s), 6.57 (1H, dd, J=3.4, 1.8 Hz), 6.83 (1H, d, J=3.4 Hz), 7.14 (2H, d, J=8.8 Hz), 7.66-7.75 (4H, m), 7.97 (1H, d, J=2.6 Hz), 8.74 (1H, d, J=8.8 Hz), 12.16 (1H, s).

Example 55

Production of 2-({4-[4-(adamantan-1-yl)phenoxy]butanoyl}amino)-5-chlorobenzoic acid (55)

The target compound (55) was synthesized according to the following Steps (i) to (ii).

(i) Methyl 2-({4-[4-(Adamantan-1-yl)phenoxy]butanoyl}amino)-5-chlorobenzoate Using the same method as in Example 23-(i), methyl 2-({4-[4-(adamantan-1-yl)phenoxy]butanoyl}amino)-5-chlorobenzoate was obtained using 4-[4-(adamantan-1-yl)phenoxy]butyric acid and methyl 2-amino-5-chlorobenzoate (yield: 80%).

$^1$H-NMR (CDCl$_3$) δ: 1.73-1.78 (6H, m), 1.84-1.89 (6H, m), 2.05-2.10 (3H, m), 2.14-2.28 (2H, m), 2.66 (2H, t, J=7.2 Hz), 3.91 (3H, s), 4.04 (2H, t, J=6.0 Hz), 6.84 (2H, d, J=8.8 Hz), 7.25 (2H, d, J=8.8 Hz), 7.49 (1H, dd, J=9.0, 2.6 Hz), 7.99 (1H, d, J=2.6 Hz), 8.72 (1H, d, J=9.0 Hz), 11.03 (1H, s).

(ii) 2-({4-[4-(Adamantan-1-yl)phenoxy]butanoyl}amino)-5-chlorobenzoic acid

Using the same method as in Example 3-(ii), the target 2-({4-[4-(adamantan-1-yl)phenoxy]butanoyl}amino)-5-chlorobenzoic acid was obtained using methyl 2-({4-[4-(adamantan-1-yl)phenoxy]butanoyl}amino)-5-chlorobenzoate (yield: 92%).

$^1$H-NMR (DMSO-d$_6$) δ: 1.69-1.74 (6H, m), 1.79-1.84 (6H, m), 2.00-2.05 (5H, m), 2.56 (2H, t, J=7.4 Hz), 3.99 (2H, t, J=6.4 Hz), 6.84 (2H, d, J=8.8 Hz), 7.22 (2H, d, J=8.8 Hz), 7.66 (1H, dd, J=9.0, 2.6 Hz), 7.90 (1H, d, J=2.6 Hz), 8.48 (1H, d, J=9.0 Hz), 11.06 (1H, s), 13.95 (1H, brs).

Example 56

Production of 2-({[4-(adamantan-1-ylcarbonyl)phenyl]carbonyl}amino)-5-chlorobenzoic acid (56)

The target compound (56) was synthesized according to the following Steps (i) to (iii).

(i) 4-(Adamantan-1-ylcarbonyl)benzoic acid 64.6 mL of acetic acid, 3.4 mL of water, 333 mg (1.34 mmol) of cobalt acetate tetrahydrate, 33 mg (0.134 mmol) of manganese acetate tetrahydrate and 138 mg (1.34 mmol) of sodium bromide were added to 3.4 g (13.4 mmol) of (4-methylphenyl) (adamantan-1-yl)methanone, and the mixture was stirred at room temperature for a short time. While blowing air into the mixture, the mixture was stirred in an oil bath at 100 to 110° C. for one day. The reaction mixture was cooled to room temperature, and water was added thereto. The precipitated solids were collected by filtration, washed with water, and air-dried, thereby giving 2.99 mg of 4-(adamantan-1-ylcarbonyl)benzoic acid (yield: 78%).

$^1$H-NMR (CDCl$_3$) δ: 1.67-1.72 (6H, m), 1.87-1.92 (6H, m), 1.99-2.04 (3H, m), 7.60 (2H, d, J=8.6 Hz), 7.99 (2H, d, J=8.6 Hz), 13.18 (1H, s).

(ii) Methyl 2-({[4-(adamantan-1-ylcarbonyl)phenyl]carbonyl}amino)-5-chlorobenzoate Using the same method as in Example 23-(i), methyl 2-({[4-(adamantan-1-ylcarbonyl)phenyl]carbonyl}amino)-5-chlorobenzoate was obtained using 4-(adamantan-1-ylcarbonyl)benzoic acid and methyl 2-amino-5-chlorobenzoate (yield: 44%).

$^1$H-NMR (DMSO-d$_6$) δ: 1.72-1.77 (6H, m), 1.98-2.03 (6H, m), 2.07-2.12 (3H, m), 3.99 (3H, s), 7.54-7.67 (3H, m), 8.03-8.09 (3H, m), 8.93 (1H, d, J=9.2 Hz), 12.04 (1H, s).

(iii) 2-({[4-(Adamantan-1-ylcarbonyl)phenyl]carbonyl}amino)-5-chlorobenzoic acid Using the same method as in Example 3-(ii), the target 2-({[4-(adamantan-1-ylcarbonyl)phenyl]carbonyl}amino)-5-chlorobenzoic acid was obtained using methyl 2-({[4-(adamantan-1-ylcarbonyl)phenyl]carbonyl}amino)-5-chlorobenzoate (yield: 88%).

$^1$H-NMR (DMSO-d$_6$) δ: 1.69-1.74 (6H, m), 1.90-1.95 (6H, m), 2.00-2.05 (3H, m), 7.69-7.79 (3H, m), 7.97-8.10 (3H, m), 8.69 (1H, d, J=9.0 Hz), 12.12 (1H, s).

Example 57

Production of 2-({[5-(benzyloxy)-1H-indol-3-yl](oxo)acetyl}amino)-5-chlorobenzoic acid (57)

The target compound (57) was synthesized according to the following Steps (i) to (ii).

(i) Methyl 2-({[5-(benzyloxy)-1H-indol-3-yl](oxo)acetyl}amino)-5-chlorobenzoate Using the same method as in Example 14-(ii), methyl 2-({[5-(benzyloxy)-1H-indol-3-yl](oxo)acetyl}amino)-5-chlorobenzoate was obtained using 5-(benzyloxy)-1H-indole and methyl 2-amino-5-chlorobenzoate (yield: 87%).

$^1$H-NMR (DMSO-d$_6$) δ: 3.94 (3H, s), 5.18 (2H, s), 7.01 (1H, dd, J=8.8, 2.6 Hz), 7.33-7.56 (6H, m), 7.81 (1H, dd, J=8.8, 2.6 Hz), 7.92 (1H, d, J=2.6 Hz), 8.01 (1H, d, J=2.6 Hz), 8.74 (1H, d, J=9.2 Hz), 8.93 (1H, d, J=3.8 Hz), 12.30-12.40 (2H, m).

(ii) 2-({[5-(Benzyloxy)-1H-indol-3-yl](oxo)acetyl}amino)-5-chlorobenzoic acid Using the same method as in Example 3-(ii), the target 2-({[5-(benzyloxy)-1H-indol-3-yl](oxo)acetyl}amino)-5-chlorobenzoic acid was obtained using methyl 2-({[5-(benzyloxy)-1H-indol-3-yl](oxo)acetyl}amino)-5-chlorobenzoate (yield: 41%).

$^1$H-NMR (DMSO-d$_6$) δ: 5.18 (2H, s), 7.01 (1H, dd, J=8.8, 2.4 Hz), 7.33-7.56 (6H, m), 7.79 (1H, dd, J=9.0, 2.6 Hz), 7.91

(1H, d, J=2.4 Hz), 8.02 (1H, d, J=2.6 Hz), 8.80 (1H, d, J=9.2 Hz), 8.93 (1H, d, J=3.4 Hz), 12.34 (1H, d, J=3.0 Hz), 12.57 (1H, s), 14.15 (1H, brs).

Example 58

Production of 5-chloro-2-({[3-(naphthalen-1-yl)phenyl]carbonyl}amino)benzoic acid (58)

The target compound (58) was synthesized according to the following Steps (i) to (ii).

(i) Methyl 5-chloro-2-({[3-(naphthalen-1-yl)phenyl]carbonyl}amino)benzoate

Using the same method as in Example 8-(ii), methyl 5-chloro-2-({[3-(naphthalen-1-yl)phenyl]carbonyl}amino)benzoate was obtained using 2-{[(3-bromophenyl)carbonyl]amino}-5-chloro benzoic acid methyl ester obtained in Example 8-(i) and (naphthalen-1-yl)boronic acid (yield: 79%).

$^1$H-NMR (CDCl$_3$) δ: 3.95 (3H, s), 7.42-7.76 (7H, m), 7.88-7.97 (3H, m), 8.04-8.10 (2H, m), 8.17-8.20 (1H, m), 8.94 (1H, d, J=8.8 Hz), 12.05 (1H, s).

(ii) 5-Chloro-2-({[3-(naphthalen-1-yl)phenyl]carbonyl}amino)benzoic acid

Using the same method as in Example 3-(ii), the target 5-chloro-2-({[3-(naphthalen-1-yl)phenyl]carbonyl}amino)benzoic acid was obtained using methyl 5-chloro-2-({[3-(naphthalen-1-yl)phenyl]carbonyl}amino)benzoate (yield: 95%).

$^1$H-NMR (DMSO-d$_6$) δ: 7.50-7.84 (8H, m), 7.98 (1H, d, J=2.8 Hz), 8.00-8.10 (4H, m), 8.74 (1H, d, J=9.2 Hz), 12.21 (1H, s), 14.20 (1H, brs).

Example 59

Production of 2-({3-[4-(adamantan-1-yl)phenoxy]propanoyl}amino)-5-chlorobenzoic acid (59)

The target compound (59) was synthesized according to the following Steps (i) to (ii).

(i) t-Butyl 2-({3-[4-(adamantan-1-yl)phenoxy]propanoyl}amino)-5-chlorobenzoate

Using the same method as in Example 23-(i), t-butyl 2-({3-[4-(adamantan-1-yl)phenoxy]propanoyl}amino)-5-chlorobenzoate was obtained using 3-[4-(adamantan-1-yl)phenoxy]propionic acid and t-butyl 2-amino-5-chlorobenzoate (yield: 75%).

$^1$H-NMR (CDCl$_3$) δ: 1.59 (9H, s), 1.72-1.77 (6H, m), 1.84-1.89 (6H, m), 2.04-2.09 (3H, m), 2.91 (2H, t, J=6.2 Hz), 4.34 (2H, t, J=6.2 Hz), 6.90 (2H, d, J=8.8 Hz), 7.23-7.29 (2H, m), 7.45 (1H, dd, J=9.2, 2.6 Hz), 7.91 (1H, d, J=2.6 Hz), 8.71 (1H, d, J=9.2 Hz), 11.35 (1H, s).

(ii) 2-({3-[4-(Adamantan-1-yl)phenoxy]propanoyl}amino)-5-chlorobenzoic acid

Using the same method as in Example 5-(ii), the target 2-({3-[4-(adamantan-1-yl)phenoxy]propanoyl}amino)-5-chlorobenzoic acid was obtained using t-butyl 2-({3-[4-(adamantan-1-yl)phenoxy]propanoyl}amino)-5-chlorobenzoate (yield: 56%).

$^1$H-NMR (DMSO-d$_6$) δ: 1.68-1.73 (6H, m), 1.78-1.83 (6H, m), 1.99-2.05 (3H, m), 2.85 (2H, t, J=5.8 Hz), 4.24 (2H, t, J=5.8 Hz), 6.87 (2H, d, J=8.8 Hz), 7.24 (2H, d, J=8.8 Hz), 7.67 (1H, dd, J=8.8, 2.8 Hz), 7.92 (1H, d, J=2.6 Hz), 8.50 (1H, d, J=9.2 Hz), 11.17 (1H, s), 14.00 (1H, brs).

Example 60

Production of 5-chloro-2-({[1-(3-hydroxypropyl)-5-phenyl-1H-indol-2-yl]carbonyl}amino)benzoic acid (60)

The target compound (60) was synthesized according to the following Steps (i) to (iv).

(i) Ethyl 5-phenyl-1-[3-(trityloxy)propyl]-1H-indole-2-carboxylate Under an Ar atmosphere, 91 mg (2.28 mmol) of 60% sodium hydride was added to a DMF (6 mL) solution comprising 385 mg (1.45 mmol) of ethyl 5-phenyl-1H-indole-2-carboxylate and 560 mg (1.47 mmol) of 3-bromopropyltrityl ether under ice-cooling, and the mixture was stirred at 60° C. for 7 hours. The mixture was cooled to room temperature, water was added thereto, and quenching was performed. Ethyl acetate and saturated saline were added, and the mixture was separated. The organic layer was washed with saturated saline and then dried over magnesium sulfate, followed by filtration and condensation, thereby giving a crude product. The obtained crude product was separated and purified by silica gel column chromatography, thereby giving 250 mg of ethyl 5-phenyl-1-[3-(trityloxy)propyl]-1H-indole-2-carboxylate (yield: 30%).

$^1$H-NMR (CDCl$_3$) δ: 1.39 (3H, t, J=7.0 Hz), 2.06-2.18 (2H, m), 3.14 (2H, t, J=5.8 Hz), 4.34 (2H, q, J=7.0 Hz), 4.72 (2H, t, J=7.4 Hz), 7.21-7.51 (21H, m), 7.61-7.67 (2H, m), 7.83-7.85 (1H, m).

(ii) 5-Phenyl-1-[3-(trityloxy)propyl]-1H-indole-2-carboxylic acid

Using the same method as in Example 3-(ii), 5-phenyl-1-[3-(trityloxy)propyl]-1H-indole-2-carboxylic acid was obtained using ethyl 5-phenyl-1-[3-(trityloxy)propyl]-1H-indole-2-carboxylate (yield: 98%).

$^1$H-NMR (DMSO-d$_6$) δ: 1.98-2.09 (2H, m), 2.95-3.05 (2H, m), 4.66-4.75 (2H, m), 7.21-7.70 (23H, m), 7.92 (1H, s), 13.00 (1H, brs).

(iii) t-Butyl 5-chloro-2-[({1-[3-(trityloxy)propyl]-5-phenyl-1H-indol-2-yl]carbonyl)amino}benzoate Using the same method as in Example 23-(i), t-butyl 5-chloro-2-[({1-[3-(trityloxy)propyl]-5-phenyl-1H-indol-2-yl]carbonyl)amino}benzoate was obtained using 5-phenyl-1-[3-(trityloxy)propyl]-1H-indole-2-carboxylic acid and t-butyl 2-amino-5-chlorobenzoate (yield: 71%).

$^1$H-NMR (CDCl$_3$) δ: 1.66 (9H, s), 2.15-2.25 (2H, m), 3.18 (2H, t, J=5.8 Hz), 4.75-4.83 (2H, m), 7.15-7.55 (22H, m), 7.63-7.70 (2H, m), 7.93-7.98 (2H, m), 8.80 (1H, d, J=9.0 Hz), 12.10 (1H, s).

(iv) 5-Chloro-2-({[1-(3-hydroxypropyl)-5-phenyl-1H-indol-2-yl]carbonyl}amino)benzoic acid Using the same method as in Example 5-(ii), the target 5-chloro-2-({[1-(3-hydroxypropyl)-5-phenyl-1H-indol-2-yl]carbonyl}amino)benzoic acid was obtained using t-butyl 5-chloro-2-[({1-[3-(trityloxy)propyl]-5-phenyl-1H-indol-2-yl]carbonyl)amino}benzoate (yield: 71%).

¹H-NMR (DMSO-d₆) δ: 2.22-2.30 (2H, m), 4.39 (2H, t, J=6.0 Hz), 4.72-4.80 (2H, m), 7.31-7.38 (2H, m), 7.48 (2H, t, J=7.6 Hz), 7.68-7.80 (5H, m), 8.00-8.04 (2H, m), 8.68 (1H, d, J=9.0 Hz), 12.23 (1H, s).

Example 61

Production of 5-chloro-2-({[(2'-methoxybiphenyl-3-yl)oxy]acetyl}amino)benzoic acid (61)

The target compound (61) was synthesized according to the following Steps (i) to (iii).

(i) [(2'-Methoxybiphenyl-3-yl)oxy]acetic acid

Under an Ar atmosphere, 12 mL of toluene, 3 mL of methanol, and 3 mL of 2M aqueous sodium carbonate solution were added to 500 mg (1.93 mmol) of ethyl (3-bromophenoxy) acetate and 352 mg (2.32 mmol) of (2-methoxyphenyl)boronic acid, and the mixture was degassed. Further, 112 mg (0.097 mmol) of tetrakis(triphenylphosphine)palladium(0) was added thereto, and the mixture was heated under stirring at 80° C. for 6 hours. After the mixture was cooled to room temperature, ethyl acetate and water were added thereto to separate the mixture. The water layer was separated, and filtration was performed. Thereafter, acidification was performed with 1N hydrochloric acid, and extraction with ethyl acetate was performed. The organic layer was washed with saturated saline and dried over anhydride magnesium sulfate, followed by filtration and condensation, thereby giving 290 mg of [(2'-methoxybiphenyl-3-yl)oxy]acetic acid (yield: 58%).

¹H-NMR (DMSO-d₆) δ: 3.76 (3H, s), 4.70 (2H, s), 6.86 (2H, ddd, J=8.2, 2.4, 1.0 Hz), 6.97-7.13 (4H, m), 7.26-7.40 (3H, m), 13.00 (1H, brs).

(ii) Methyl 5-chloro-2-({[(2'-methoxybiphenyl-3-yl)oxy]acetyl}amino)benzoate

Using the same method as in Example 23-(i), methyl 5-chloro-2-({[(2'-methoxybiphenyl-3-yl)oxy]acetyl}amino)benzoate was obtained using [(2'-methoxybiphenyl-3-yl)oxy]acetic acid and methyl 2-amino-5-chlorobenzoate (yield: 65%).

¹H-NMR (CDCl₃) δ: 3.81 (3H, s), 3.94 (3H, s), 4.68 (2H, s), 6.99 (1H, dd, J=4.8, 1.2 Hz), 7.01-7.05 (1H, m), 7.08 (1H, dd, J=2.6, 1.0 Hz), 7.21 (1H, dt, J=7.8, 1.2 Hz), 7.26-7.43 (4H, m), 7.52 (1H, dd, J=9.0, 2.6 Hz), 8.03 (1H, d, J=2.6 Hz), 8.80 (1H, d, J=9.0 Hz), 12.04 (1H, s).

(iii) 5-Chloro-2-({[(2'-methoxybiphenyl-3-yl)oxy]acetyl}amino)benzoic acid

Using the same method as in Example 3-(ii), the target 5-chloro-2-({[(2'-methoxybiphenyl-3-yl)oxy]acetyl}amino)benzoic acid was obtained using methyl 5-chloro-2-({[(2'-methoxybiphenyl-3-yl)oxy]acetyl}amino)benzoate (yield: 91%).

¹H-NMR (DMSO-d₆) δ: 3.75 (3H, s), 4.79 (2H, s), 6.99-7.19 (5H, m), 7.28-7.42 (3H, m), 7.73 (1H, dd, J=8.8, 2.6 Hz), 7.97 (1H, d, J=2.6 Hz), 8.75 (1H, d, J=8.8 Hz), 12.19 (1H, s), 14.19 (1H, brs).

Example 62

Production of 2-({[3-(adamantan-1-yl)phenyl]carbonyl}amino)-5-chlorobenzoic acid (62)

The target compound (62) was synthesized according to the following Steps (i) to (ii).

(i) Methyl 2-({[3-(adamantan-1-yl)phenyl]carbonyl}amino)-5-chlorobenzoate

Using the same method as in Example 23-(i), methyl 2-({[3-(adamantan-1-yl)phenyl]carbonyl}amino)-5-chlorobenzoate was obtained using 3-(adamantan-1-yl)benzoic acid and methyl 2-amino-5-chlorobenzoate (yield: 97%).

¹H-NMR (CDCl₃) δ: 1.77-2.82 (6H, m), 1.96-2.01 (6H, m), 2.10-2.15 (3H, m), 3.98 (3H, s), 7.42-7.61 (3H, m), 7.78-7.84 (1H, m), 8.05-8.10 (42H, m), 8.94 (1H, d, J=9.2 Hz), 11.96 (1H, s).

(ii) 2-({[3-(Adamantan-1-yl)phenyl]carbonyl}amino)-5-chlorobenzoic acid

Using the same method as in Example 3-(ii), the target 2-({[3-(adamantan-1-yl)phenyl]carbonyl}amino)-5-chlorobenzoic acid was obtained using methyl 2-({[3-(adamantan-1-yl)phenyl]carbonyl}amino)-5-chlorobenzoate (yield: 82%).

¹H-NMR (DMSO-d₆) δ: 1.52-2.19 (15H, m), 7.52 (1H, t, J=7.7 Hz), 7.66 (1H, d, J=7.7 Hz), 7.74 (1H, dd, J=8.9, 2.7 Hz), 7.77 (1H, d, J=7.7 Hz), 7.94 (1H, s), 8.00 (1H, d, J=2.7 Hz), 8.76 (1H, d, J=8.9 Hz), 12.13 (1H, s).

Example 63

Production of sodium 5-chloro-2-({[3-(quinolin-3-yl)phenyl]carbonyl}amino)benzoate (63)

The target compound (63) was synthesized according to the following Steps (i) to (iii).

(i) Methyl 5-chloro-2-{[(3-iodophenyl)carbonyl]amino}benzoate

Using the same method as in Example 23-(i), methyl 5-chloro-2-{[(3-iodophenyl)carbonyl]amino}benzoate was obtained using 3-iodobenzoic acid and methyl 2-amino-5-chlorobenzoate (yield: 80%).

¹H-NMR (CDCl₃) δ: 3.99 (3H, s), 7.26 (1H, t, J=7.9 Hz), 7.56 (1H, dd, J=9.2, 2.7 Hz), 7.86-7.99 (2H, m), 8.05 (1H, d, J=2.7 Hz), 8.38 (1H, t, J=1.7 Hz), 8.87 (1H, d, J=9.2 Hz), 11.95 (1H, s).

(ii) Methyl 5-chloro-2-({[3-(quinolin-3-yl)phenyl]carbonyl}amino)benzoate

Under an Ar atmosphere, 9 mL of toluene, 2.5 mL of methanol, 2.5 mL of 2M aqueous sodium carbonate solution were added to 500 mg (1.20 mmol) of 5-chloro-2-{[(3-iodophenyl)carbonyl]amino}benzoic acid methyl ester and 330 mg (1.91 mmol) of quinolin-3-ylboronic acid, and the mixture was degassed. Further, 100 mg (0.087 mmol) of tetrakis(triphenylphosphine)palladium(0) was added, and the mixture was heated under stirring at 90° C. for 6 hours. After the mixture was cooled to room temperature, water was added thereto, followed by collection by filtration, water-washing, and drying. Thereafter, the resultant was dissolved in chloroform, followed by filtration. The filtrate was condensed, thereby giving 340 mg of methyl 5-chloro-2-({[3-(quinolin-3-yl)phenyl]carbonyl}amino)benzoate (yield: 67%).

$^1$H-NMR (CDCl$_3$) δ: 4.00 (3H, s), 7.56-7.82 (4H, m), 7.90-7.98 (2H, m), 8.05-8.13 (2H, m), 8.17 (1H, d, J=8.6 Hz), 8.42-8.47 (2H, m), 8.97 (2H, d, J=8.6 Hz), 9.27 (2H, d, J=2.6 Hz), 12.16 (1H, s).

(iii) Sodium 5-chloro-2-({[3-(quinolin-3-yl)phenyl]carbonyl}amino)benzoate 10 mL of THF and 1.3 mL of 1N aqueous sodium hydroxide solution were added to 340 mg (0.816 mmol) of methyl 5-chloro-2-({[3-(quinolin-3-yl)phenyl]carbonyl}amino)benzoate, and the mixture was stirred at room temperature for 1 day. The mixture was further stirred at 50° C. for 1 hour. THF was distilled off under reduced pressure, and water was added. Water-washing was then conducted, thereby giving 360 mg of the target sodium 5-chloro-2-({[3-(quinolin-3-yl)phenyl]carbonyl}amino)benzoate (yield: 77%).

$^1$H-NMR (DMSO-d$_6$) δ: 7.40 (1H, dd, J=8.8, 3.0 Hz), 7.64-7.87 (3H, m), 8.93 (1H, d, J=2.8 Hz), 8.08-8.16 (4H, m), 8.48-8.52 (1H, m), 8.73 (1H, d, J=8.8 Hz), 8.77 (1H, d, J=2.4 Hz), 9.34 (1H, d, J=2.0 Hz), 15.94 (1H, s).

Example 64

Production of sodium 5-chloro-2-({[3-(isoquinolin-4-yl)phenyl]carbonyl}amino)benzoate (64)

The target compound (64) was synthesized according to the following Steps (i) to (ii).

(i) Methyl 5-chloro-2-({[3-(isoquinolin-4-yl)phenyl]carbonyl}amino)benzoate

Under an Ar atmosphere, 10 mL of toluene, 2.5 mL of methanol, and 2.5 mL of 2M aqueous sodium carbonate solution were added to 500 mg (1.36 mmol) of methyl 2-{[(3-bromophenyl)carbonyl]amino}-5-chlorobenzoate obtained in Example 8-(i) and 352 mg (2.03 mmol) of isoquinolin-4-ylboronic acid, and the mixture was degassed. Further, 100 mg (0.087 mmol) of tetrakis(triphenylphosphine)palladium (0) was added, and the mixture was heated under stirring at 90° C. for 7 hours. The mixture was cooled to room temperature, and then water and ethyl acetate were added, followed by collection by filtration, water-washing, and drying. Thereafter, the resultant was dissolved in chloroform and filtered. The filtrate was condensed, thereby giving 360 mg of methyl 5-chloro-2-({[3-(isoquinolin-4-yl)phenyl]carbonyl}amino)benzoate (yield: 63%).

$^1$H-NMR (CDCl$_3$) δ: 3.96 (3H, s), 7.58 (1H, dd, J=9.0, 2.8 Hz), 7.64-7.78 (4H, m), 7.92-7.97 (1H, m), 8.05-8.16 (3H, m), 8.20-8.22 (1H, m), 8.56 (1H, s), 8.94 (1H, d, J=9.2 Hz), 9.31 (1H, s), 12.10 (1H, s).

(ii) Sodium 5-chloro-2-({[3-(isoquinolin-4-yl)phenyl]carbonyl}amino)benzoate 20 mL of THF and 1.6 mL of 1N aqueous sodium hydroxide solution were added to 360 mg (0.86 mmol) of methyl 5-chloro-2-({[3-(isoquinolin-4-yl)phenyl]carbonyl}amino)benzoate, and the mixture was stirred at room temperature for one day. THF was distilled off under reduced pressure and water-washing was performed by adding water, thereby giving 360 mg of the target sodium 5-chloro-2-({[3-(isoquinolin-4-yl)phenyl]carbonyl}amino)benzoate (yield: 98%).

$^1$H-NMR (DMSO-d$_6$) δ: 7.39 (1H, dd, J=8.8, 2.6 Hz), 7.74-7.88 (5H, m), 7.98 (1H, d, J=2.8 Hz), 8.14-8.19 (2H, m), 8.25-8.30 (1H, m), 8.53 (1H, s), 8.72 (1H, d, J=9.0 Hz), 9.41 (1H, s), 15.82 (1H, s).

Example 65

Production of sodium 5-chloro-2-({[3-(quinolin-6-yl)phenyl]carbonyl}amino)benzoate (65)

The target compound (65) was synthesized according to the following Steps (i) to (ii).

(i) Methyl 5-chloro-2-({[3-(quinolin-6-yl)phenyl]carbonyl}amino)benzoate

Using the same method as in Example 64-(i), methyl 5-chloro-2-({[3-(quinolin-6-yl)phenyl]carbonyl}amino)benzoate was obtained using methyl 2-{[(3-bromophenyl)carbonyl]amino}-5-chlorobenzoate obtained in Example 8-(i) and 6-(4,4,5,5,-tetramethyl-1,3,2-dioxaborolan-2-yl)quinoline (yield: 67%).

$^1$H-NMR (CDCl$_3$) δ: 4.00 (3H, s), 7.47 (1H, dd, J=8.4, 4.4 Hz), 7.59 (1H, dd, J=9.0, 2.6 Hz), 7.67 (1H, t, J=7.6 Hz), 7.91-7.98 (1H, m), 8.01-8.14 (4H, m), 8.20-8.29 (2H, m), 8.44 (1H, t, J=1.8 Hz), 8.94-8.99 (2H, m), 12.12 (1H, s).

(ii) Sodium 5-chloro-2-({[3-(quinolin-6-yl)phenyl]carbonyl}amino)benzoate

Using the same method as in Example 64-(ii), the target sodium 5-chloro-2-({[3-(quinolin-6-yl)phenyl]carbonyl}amino)benzoate was obtained using methyl 5-chloro-2-({[3-(quinolin-6-yl)phenyl]carbonyl}amino)benzoate (yield: 98%).

$^1$H-NMR (DMSO-d$_6$) δ: 7.43 (1H, dd, J=8.8, 2.8 Hz), 7.61 (1H, dd, J=8.4, 4.4 Hz), 7.72 (1H, t, J=7.6 Hz), 8.03 (1H, d, J=3.0 Hz), 8.08 (2H, dd, J=7.6, 1.8 Hz), 8.18-8.21 (2H, m), 8.39-8.54 (3H, m), 8.75 (1H, d, J=8.8 Hz), 8.95 (1H, dd, J=4.4, 1.8 Hz), 15.76 (1H, s).

Example 66

Production of sodium 5-chloro-2-({[3-(isoquinolin-5-yl)phenyl]carbonyl}amino)benzoate (66)

The target compound (66) was synthesized according to the following Steps (i) to (ii).

(i) Methyl 5-chloro-2-({[3-(isoquinolin-5-yl)phenyl]carbonyl}amino)benzoate

Using the same method as in Example 64-(i), methyl 5-chloro-2-({[3-(isoquinolin-5-yl)phenyl]carbonyl}amino)benzoate was obtained using methyl 2-{[(3-bromophenyl)carbonyl]amino}-5-chlorobenzoate obtained in Example 8-(i) and isoquinolin-5-yl boronic acid (yield: 75%).

$^1$H-NMR (CDCl$_3$) δ: 3.97 (3H, s), 7.58 (1H, dd, J=9.2, 2.6 Hz), 7.68-7.81 (5H, m), 8.02-8.19 (4H, m), 8.54 (1H, d, J=6.2 Hz), 8.94 (1H, d, J=9.2 Hz), 9.34-9.36 (1H, m), 12.10 (1H, s).

(ii) Sodium 5-chloro-2-({[3-(isoquinolin-5-yl)phenyl]carbonyl}amino)benzoate

Using the same method as in Example 64-(ii), the target sodium 5-chloro-2-({[3-(isoquinolin-5-yl)phenyl]

carbonyl}amino)benzoate was obtained using methyl 5-chloro-2-({[3-(isoquinolin-5-yl)phenyl]carbonyl}amino)benzoate (yield: 74%).

¹H-NMR (DMSO-d₆) δ: 7.38 (1H, dd, J=9.0, 2.8 Hz), 7.66-7.86 (5H, m), 7.97 (1H, d, J=2.8 Hz), 8.12-8.24 (3H, m), 8.52 (1H, d, J=5.8 Hz), 8.71 (1H, d, J=9.0 Hz), 9.42-9.45 (1H, m), 15.85 (1H, s).

Example 67

Production of sodium 5-chloro-2-({[4-(quinolin-8-yl)phenyl]carbonyl}amino)benzoate (67)

The target compound (67) was synthesized according to the following Steps (i) to (iii).

(i) Methyl 5-chloro-2-{[(4-iodophenyl)carbonyl]amino}benzoate

Using the same method as in Example 23-(i), methyl 5-chloro-2-{[(4-iodophenyl)carbonyl]amino}benzoate was obtained using 4-iodobenzoic acid and methyl 2-amino-5-chlorobenzoate (yield: 94%).

¹H-NMR (CDCl₃) δ: 3.98 (3H, s), 7.56 (1H, dd, J=9.2, 2.6 Hz), 7.74 (1H, dt, J=8.6, 2.0 Hz), 7.88 (1H, dt, J=8.6, 2.0 Hz), 8.05 (1H, d, J=2.6 Hz), 8.88 (1H, d, J=9.2 Hz), 11.97 (1H, s).

(ii) Methyl 5-chloro-2-({[4-(quinolin-8-yl)phenyl]carbonyl}amino)benzoate

Using the same method as in Example 64-(i), methyl 5-chloro-2-({[4-(quinolin-8-yl)phenyl]carbonyl}amino)benzoate was obtained using 5-chloro-2-{[(4-iodophenyl)carbonyl]amino}-benzoic acid methyl ester and quinolin-8-ylboronic acid (yield: 81%).

¹H-NMR (CDCl₃) δ: 3.99 (3H, s), 7.46 (1H, dd, J=8.2, 4.2 Hz), 7.55-7.68 (2H, m), 7.78 (1H, dd, J=7.2, 1.6 Hz), 7.85-7.91 (3H, m), 8.08 (1H, d, J=2.6 Hz), 8.17 (2H, d, J=8.6 Hz), 8.24 (1H, dd, J=8.4, 1.8 Hz), 8.95-9.02 (2H, m), 12.04 (1H, s).

(iii) Sodium 5-chloro-2-({[4-(quinolin-8-yl)phenyl]carbonyl}amino)benzoate

Using the same method as in Example 64-(ii), the target sodium 5-chloro-2-({[4-(quinolin-8-yl)phenyl]carbonyl}amino)benzoate was obtained using methyl 5-chloro-2-({[4-(quinolin-8-yl)phenyl]carbonyl}amino)benzoate (yield: 77%).

¹H-NMR (DMSO-d₆) δ: 7.44 (1H, dd, J=8.8, 2.6 Hz), 7.61 (1H, dd, J=8.2, 4.2 Hz), 7.73 (1H, t, J=7.6 Hz), 7.81-7.89 (3H, m), 8.02-8.15 (4H, m), 8.48 (1H, dd, J=8.2, 1.8 Hz), 8.77 (1H, d, J=8.8 Hz), 8.95 (1H, dd, J=4.2, 1.8 Hz), 15.39 (1H, s).

Example 68

Production of sodium 5-chloro-2-({[3-(quinolin-8-yl)phenyl]carbonyl}amino)benzoate (68)

The target compound (68) was synthesized according to either one of the following two synthesized routes, i.e., the following Steps (i) to (iv) or (v) and (iv).

(i) Methyl 3-(quinolin-8-yl)benzoate 1.04 g (5.77 mmol) of m-(methoxycarbonyl)phenyl boronic acid, 1.00 g (3.67 mmol) of quinolin-8-yl trifluoromethanesulfonate, 125 mg (0.11 mmol) of tetrakis(triphenylphosphine)palladium(0), and 611 mg (5.77 mmol) of sodium carbonate were heated under reflux in a mixed solvent comprising 4 mL of H₂O, 23 mL of toluene, and 6.7 mL of methanol for 20 hours. After the completion of the reaction, the organic solvent was distilled off under reduced pressure, H₂O was added to the residue, and ethyl acetate extraction was performed. Subsequently, the organic layer was washed with saturated saline and dried over anhydrous sodium sulfate. The solvent was distilled off under reduced pressure. The obtained crude product was separated and purified by silica gel column chromatography, thereby giving 820 mg of methyl 3-(quinolin-8-yl)benzoate (yield: 86%).

¹H-NMR (CDCl₃) δ: 3.93 (3H, s), 7.44 (1H, dd, J=8.3, 4.2 Hz), 7.58 (1H, td, J=7.7, 0.3 Hz), 7.62 (1H, dd, J=8.0, 7.2 Hz), 7.76 (1H, dd, J=7.2, 1.6 Hz), 7.87 (1H, dd, J=8.0, 1.6 Hz), 7.94 (1H, ddd, J=7.7, 1.7, 1.3 Hz), 8.10 (1H, ddd, J=7.7, 1.7, 1.3 Hz), 8.23 (1H, dd, J=8.3, 1.8 Hz), 8.37 (1H, td, J=1.7, 0.3 Hz), 8.96 (1H, dd, J=4.2, 1.8 Hz).

(ii) 3-(Quinolin-8-yl)benzoic acid 820 mg (3.11 mmol) of methyl 3-(quinolin-8-yl)benzoate was dissolved in 8.2 mL of THF, and a 1N aqueous sodium hydroxide solution (4.7 mL) was added thereto at room temperature. The mixture was stirred at 60° C. for 1.5 hours. Thereafter, the organic solvent was distilled off under reduced pressure, H₂O was added to the resulting residue, and then dissolution was conducted. Thereafter, 1N hydrochloric acid was added to the resultant at 0° C., and the pH was adjusted to 4. The precipitated solids were collected by filtration and dried, thereby giving 711 mg of 3-(quinolin-8-yl)benzoic acid (yield: 92%).

¹H-NMR (DMSO-d₆) δ: 7.55 (3H, m), 7.83 (1H, dd, J=7.1, 1.7 Hz), 7.9 (1H, dt, J=7.7, 1.5 Hz), 8.00 (1H, dt, J=7.7, 1.5 Hz), 8.06 (1H, dd, J=8.0, 1.6 Hz), 8.23 (1H, t, J=1.5 Hz), 8.47 (1H, dd, J=8.3, 1.8 Hz), 8.93 (1H, dd, J=4.2, 1.8 Hz), 13.04 (1H, s).

(iii) Methyl 5-chloro-2-({[3-(quinolin-8-yl)phenyl]carbonyl}amino)benzoate 0.70 g (2.8 mmol) of 3-(quinolin-8-yl)benzoic acid, a catalytic amount of DMF, and 0.57 g (4.49 mmol) of oxalyl chloride were stirred in 14 mL of THF at room temperature for 2.5 hours. Thereafter, the solvent was distilled off under reduced pressure. 0.52 g (2.81 mmol) of methyl 2-amino-5-chloro benzoate and 28 mL of DMAc were added to the residue at 0° C., and the mixture was stirred at room temperature for 19 hours. The reaction mixture was cooled, and then the mixture was alkalified by adding a 0.2 N aqueous sodium hydroxide solution. Thereafter, solids were collected by filtration, followed by drying, thereby quantitatively giving methyl 5-chloro-2-({[3-(quinolin-8-yl)phenyl]carbonyl}amino)benzoate.

(iv) Sodium 5-chloro-2-({[3-(quinolin-8-yl)phenyl]carbonyl}amino)benzoate

Using the same method as in Example 64-(ii), the target sodium 5-chloro-2-({[3-(quinolin-8-yl)phenyl]carbonyl}amino)benzoate was obtained using methyl 5-chloro-2-({[3-(quinolin-8-yl)phenyl]carbonyl}amino)benzoate (yield: 76%).

¹H-NMR (DMSO-d₆) δ: 7.39 (1H, dd, J=8.8, 2.8 Hz), 7.60 (1H, dd, J=8.3, 4.1 Hz), 7.65 (1H, t, J=7.7 Hz), 7.74 (1H, dd, J=7.9, 7.3 Hz), 7.82-7.92 (2H, m), 7.98 (1H, d, J=2.8 Hz), 8.02-8.11 (2H, m), 8.27 (1H, t, J=1.5 Hz), 8.48 (1H, dd, J=8.3, 1.7 Hz), 8.73 (1H, d, J=8.8 Hz), 8.93 (1H, dd, J=4.1, 1.7 Hz), 15.63 (1H, s).

(v) Methyl 5-chloro-2-({[3-(quinolin-8-yl)phenyl]carbonyl}amino)benzoate

Using the same method as in Example 64-(i), methyl 5-chloro-2-({[3-(quinolin-8-yl)phenyl]carbonyl}amino)benzoate was obtained using methyl 5-chloro-2-{[(3-iodophenyl)carbonyl]amino}benzoate obtained in Example 63-(i) and quinolin-8-ylboronic acid (yield: 70%).

$^1$H-NMR (CDCl$_3$) δ: 3.96 (3H, s), 7.45 (1H, dd, J=8.4, 4.0 Hz), 7.56 (1H, dd, J=9.0, 2.6 Hz), 7.64-7.70 (2H, m), 7.82 (1H, dd, J=7.2, 1.8 Hz), 7.88 (1H, dd, J=8.0, 1.6 Hz), 7.95 (1H, dt, J=8.4, 1.4 Hz), 8.02-8.08 (2H, m), 8.24 (1H, dd, J=8.2, 1.8 Hz), 8.40 (1H, t, J=1.8 Hz), 8.93-9.01 (2H, m), 12.02 (1H, s).

Example 69

Production of 5-chloro-2-{[(4-cyclohexylphenyl)carbonyl]amino}benzoic acid (69)

The target compound (69) was synthesized according to the following Steps (i) to (ii).

(i) Methyl 5-chloro-2-{[(4-cyclohexylphenyl)carbonyl]amino}benzoate

Using the same method as in Example 3-(i), methyl 5-chloro-2-{[(4-cyclohexylphenyl)carbonyl]amino}benzoate was obtained using 4-cyclohexylbenzoic acid and methyl 2-amino-5-chlorobenzoate (yield: 97%).

$^1$H-NMR (CDCl$_3$) δ: 1.14-1.58 (5H, m), 1.68-2.00 (5H, m), 2.46-2.69 (1H, m), 3.98 (3H, s), 7.31-7.40 (2H, m), 7.55 (1H, dd, J=9.1, 2.6 Hz) 7.90-8.00 (2H, m), 8.05 (1H, d, J=2.6 Hz), 8.93 (1H, d, J=9.1 Hz), 11.91 (1H, s).

(ii) 5-Chloro-2-{[(4-cyclohexylphenyl)carbonyl]amino}benzoic acid

Using the same method as in Example 3-(ii), the target 5-chloro-2-{[(4-cyclohexylphenyl)carbonyl]amino}benzoic acid was obtained using methyl 5-chloro-2-{[(4-cyclohexylphenyl)carbonyl]amino}benzoate (yield: 79%).

$^1$H-NMR (DMSO-d$_6$) δ: 1.09-1.55 (5H, m), 1.60-1.94 (5H, m), 2.51-2.68 (1H, m), 7.35-7.47 (2H, m), 7.71 (1H, dd, J=9.0, 2.7 Hz), 7.80-7.91 (2H, m), 7.99 (1H, d, J=2.7 Hz), 8.75 (1H, d, J=9.0 Hz), 12.10 (1H, s).

Example 70

Production of 2-[(biphenyl-4-ylacetyl)amino]-5-chlorobenzoic acid (70)

The target compound (70) was synthesized according to the following Steps (i) to (ii).

(i) Methyl 2-[(biphenyl-4-ylacetyl)amino]-5-chlorobenzoate

Using the same method as in Example 3-(i), methyl 2-[(biphenyl-4-ylacetyl)amino]-5-chlorobenzoate was obtained using biphenyl-4-ylacetic acid and methyl 2-amino-5-chlorobenzoate (yield: 83%).

$^1$H-NMR (CDCl$_3$) δ: 3.80 (2H, s), 3.86 (3H, s), 7.28-7.52 (6H, m), 7.54-7.65 (4H, m), 7.96 (1H, d, J=2.6 Hz), 8.72 (1H, d, J=9.1 Hz), 11.03 (1H, s).

(ii) 2-[(Biphenyl-4-ylacetyl)amino]-5-chlorobenzoic acid

Using the same method as in Example 3-(ii), the target 2-[(biphenyl-4-ylacetyl)amino]-5-chlorobenzoic acid was obtained using methyl 2-[(biphenyl-4-ylacetyl)amino]-5-chlorobenzoate (yield: 62%).

$^1$H-NMR (DMSO-d$_6$) δ: 3.83 (2H, s), 7.31-7.53 (5H, m), 7.61-7.72 (5H, m), 7.90 (1H, d, J=2.6 Hz), 8.53 (1H, d, J=9.0 Hz), 11.13 (1H, s).

Example 71

Production of 2-[(biphenyl-4-ylcarbamoyl)amino]-5-chlorobenzoic acid (71)

The target compound (71) was synthesized according to the following steps.

1.0 g (5.83 mmol) of 2-amino-5-chlorobenzoic acid and 1.19 g (6.10 mmol) of 4-biphenyl isocyanic acid were stirred in 10 mL of THF at room temperature for 9 days. Thereafter, the solvent was distilled off under reduced pressure. Ethyl acetate was added to the resulting residue, and solids were collected by filtration, thereby giving 1.81 g of the target 2-[(biphenyl-4-ylcarbamoyl)amino]-5-chlorobenzoic acid (yield: 85%).

$^1$H-NMR (DMSO-d$_6$) δ: 7.27-7.75 (10H, m), 7.93 (1H, d, J=2.7 Hz), 8.47 (1H, d, J=9.2 Hz), 10.04 (1H, s), 10.46 (1H, s).

Example 72

Production of 5-chloro-2-{[N-(4'-fluoro-4-methylbiphenyl-3-yl)glycyl]amino}benzoic acid (72)

The target compound (72) was synthesized according to the following Steps (i) to (ii).

(i) 5-Chloro-2-[(chloroacetyl)amino]benzoic acid 3.0 g (17.5 mmol) of 2-amino-5-chlorobenzoic acid and 3.95 g (35.0 mmol) of chloroacetyl chloride were heated under reflux in 60 mL of toluene for 1 hour. Thereafter, the solvent was distilled off under reduced pressure, and H$_2$O was added to the resulting residue. Solids were collected by filtration to give 4.15 g of 5-chloro-2-[(chloroacetyl)amino]benzoic acid (yield: 96%).

$^1$H-NMR (DMSO-d$_6$) δ: 4.48 (2H, s), 7.70 (1H, dd, J=9.0, 2.6 Hz), 7.96 (1H, d, J=2.6 Hz), 8.55 (1H, d, J=9.0 Hz), 11.77 (1H, s), 14.08 (1H, brs).

(ii) 5-Chloro-2-{[N-(4'-fluoro-4-methylbiphenyl-3-yl)glycyl]amino}benzoic acid 1.0 g (4.0 mmol) of 5-chloro-2-[(chloroacetyl)amino]benzoic acid, 1.78 g (8.9 mmol) of 4'-fluoro-4-methylbiphenyl-3-amine, and 60 mg (0.4 mmol) of sodium iodide were stirred in 3 mL of DMF at 90° C. for 5.5 hours. Thereafter, the reaction mixture was diluted with ethyl acetate and washed with 1N hydrochloric acid. The organic layer was dried over anhydrous sodium sulfate and the solvent was distilled off under reduced pressure. The obtained crude product was separated and purified by silica gel column chromatography. The separated fractions containing a target compound were combined and condensed. Ethyl acetate was added to the residue, and solids were collected by filtration. The resulting solids were recrystallized using ethyl acetate/n-hexane, thereby giving 334 mg of the target 5-chloro-2-{[N-(4'-fluoro-4-methylbiphenyl-3-yl)glycyl]amino}benzoic acid (yield: 20%).

$^1$H-NMR (DMSO-$d_6$) δ: 2.29 (3H, s), 4.04 (2H, s), 6.04 (1H, brs), 6.59 (1H, d, J=1.5 Hz), 6.84 (1H, dd, J=7.8, 1.5 Hz), 7.11 (1H, d, J=7.8 Hz), 7.15-7.29 (2H, m), 7.50-7.62 (2H, m), 7.67 (1H, dd, J=9.0, 2.7 Hz), 7.88 (1H, d, J=2.7 Hz), 8.77 (1H, d, J=9.0 Hz), 11.96 (1H, s), 13.89 (1H, brs).

Example 73

Production of 5-chloro-2-{[N-(diphenylmethyl)glycyl]amino}benzoic acid (73)

The target compound (73) was synthesized according to the following steps.

1.0 g (4.0 mmol) of 5-chloro-2-[(chloroacetyl)amino]benzoic acid obtained in Example 72-(i), 2.94 g (16.0 mmol) of benzhydrylamine, and 60 mg (0.4 mmol) of sodium iodide were stirred in 3 mL of DMF solution at 80° C. for 1 hour. Thereafter, the mixture was diluted with ethyl acetate, and washed with 1N hydrochloric acid. The organic layer was dried over anhydrous sodium sulfate, and then the solvent was distilled off under reduced pressure. Ethyl acetate was added to the condensed residue, and solids were collected by filtration, followed by drying, thereby giving 744 mg of the target 5-chloro-2-{[N-(diphenylmethyl)glycyl]amino}benzoic acid (yield: 49%).

$^1$H-NMR (DMSO-$d_6$) δ: 3.86 (2H, s), 5.64 (1H, s), 7.30-7.50 (6H, m), 7.64-7.78 (5H, m), 7.90 (1H, d, J=2.6 Hz), 8.20 (1H, J=8.9 Hz), 10.55 (1H, brs), 11.05 (1H, s).

Example 74

Production of 2-{[(4-cyclohexylphenyl)carbonyl]amino}-5-methyl-4-phenylthiophene-3-carboxylic acid (74)

The target compound (74) was synthesized according to the following Steps (i) to (ii).

(i) tert-Butyl 2-{[(4-cyclohexylphenyl)carbonyl]amino}-5-methyl-4-phenylthiophene-3-carboxylate Using the same method as in Example 3-(i), tert-butyl 2-{[(4-cyclohexylphenyl)carbonyl]amino}-5-methyl-4-phenylthiophene-3-carboxylate was obtained using 4-cyclohexylbenzoic acid and tert-butyl 2-amino-5-methyl-4-phenylthiophene-3-carboxylate (yield: 85%).

$^1$H-NMR (CDCl$_3$) δ: 1.14 (9H, s), 1.20-1.58 (5H, m), 1.70-1.98 (5H, m), 2.15 (3H, s), 2.49-2.69 (1H, m), 7.10-7.21 (2H, m), 7.43-7.44 (5H, m), 7.92-8.00 (2H, m), 12.28 (1H, s).

(ii) 2-{[(4-Cyclohexylphenyl)carbonyl]amino}-5-methyl-4-phenylthiophene-3-carboxylic acid Using the same method as in Example 5-(ii), the target 2-{[(4-cyclohexylphenyl)carbonyl]amino}-5-methyl-4-phenylthiophene-3-carboxylic acid was obtained using tert-butyl 2-{[(4-cyclohexylphenyl)carbonyl]amino}-5-methyl-4-phenylthiophene-3-carboxylate (yield: 78%).

$^1$H-NMR (DMSO-$d_6$) δ: 1.10-1.58 (5H, m), 1.62-1.92 (5H, m), 2.11 (3H, s), 2.52-2.70 (1H, m), 7.15-7.51 (7H, m), 7.80-7.90 (2H, m), 12.39 (1H, s), 12.92 (1H, brs).

Example 75

Production of 5-chloro-2-({[4-(diphenylmethyl)piperazin-1-yl]carbonyl}amino)benzoic acid hydrochloride (75)

The target compound (75) was synthesized according to the following Steps (i) to (ii).

(i) Methyl 5-chloro-2-({[4-(diphenylmethyl)piperazine-1-yl]carbonyl}amino)benzoate 0.77 g (5.9 mmol) of N,N-diisopropylethylamine and 1.19 g (5.9 mmol) of p-nitrophenyl chloroformate were added to a mixed solution of THF/chloroform (30 mL/60 mL) comprising 1.0 g (5.4 mmol) of methyl 2-amino-5-chlorobenzoate at 0° C. The mixture was stirred at room temperature for 1.5 hours. Thereafter, 1.36 g (5.4 mmol) of 1-benzhydrylpiperazine was added at room temperature, and the mixture was stirred for 16 hours. Ethyl acetate was added to the reaction mixture, and the mixture was washed with saturated saline. The organic layer was dried over anhydrous sodium sulfate and filtered through silica gel. The resulting organic layer was condensed under reduced pressure, and the residue was recrystallized with ethyl acetate/n-hexane, thereby giving 1.81 g of methyl 5-chloro-2-({[4-(diphenylmethyl)piperazine-1-yl]carbonyl}amino)benzoate (yield: 73%).

$^1$H-NMR (DMSO-$d_6$) δ: 2.22-2.47 (4H, m), 3.41-3.55 (4H, m), 3.82 (3H, s), 4.35 (1H, s), 7.14-7.37 (6H, m), 7.39-7.49 (4H, m), 7.60 (1H, dd, J=9.1, 2.7 Hz), 7.84 (1H, d, J=2.7 Hz), 8.31 (1H, d, J=9.1 Hz), 10.23 (1H, s).

(ii) 5-Chloro-2-({[4-(diphenylmethyl)piperazine-1-yl]carbonyl}amino)benzoic acid hydrochloride Using the same method as in Example 3-(ii), the target 5-chloro-2-({[4-(diphenylmethyl)piperazine-1-yl]carbonyl}amino)benzoic acid hydrochloride was obtained using methyl 5-chloro-2-({[4-(diphenylmethyl)piperazine-1-yl]carbonyl}amino)benzoate (yield: 95%).

$^1$H-NMR (DMSO-$d_6$) δ: 2.87-4.24 (9H, m), 5.58 (1H, brs), 7.31-7.53 (6H, m), 7.63 (1H, dd, J=9.1, 2.7 Hz), 7.73-8.01 (4H, m), 7.89 (1H, d, J=2.7 Hz), 8.32 (1H, d, J=9.1 Hz), 10.81 (1H, s), 12.51 (1H, brs).

Example 76

Production of 5-chloro-2-{[(diphenylmethoxy)acetyl]amino}benzoic acid (76)

The target compound (76) was synthesized according to the following Steps (i) to (ii).

(i) Methyl 5-chloro-2-{[(diphenylmethoxy)acetyl]amino}benzoate

Using the same method as in Example 3-(i), methyl 5-chloro-2-{[(diphenylmethoxy)acetyl]amino}benzoate was obtained using (diphenylmethoxy)acetic acid and methyl 2-amino-5-chlorobenzoate (yield: 61%).

$^1$H-NMR (CDCl$_3$) δ: 3.90 (3H, s), 4.13 (2H, s), 5.51 (1H, s), 7.21-7.58 (11H, m), 8.02 (1H, d, J=2.6 Hz), 8.76 (1H, d, J=9.1 Hz), 11.89 (1H, s).

(ii) 5-Chloro-2-{[(diphenylmethoxy)acetyl]amino}benzoic acid

Using the same method as in Example 3-(ii), the target 5-chloro-2-{[(diphenylmethoxy)acetyl]amino}benzoic acid was obtained using methyl 5-chloro-2-{[(diphenylmethoxy)acetyl]amino}benzoate (yield: 76%).

$^1$H-NMR (DMSO-d$_6$) δ: 4.10 (2H, s), 5.69 (1H, s), 7.21-7.41 (6H, m), 7.50-7.59 (4H, m), 7.69 (1H, dd, J=9.1, 2.7 Hz), 7.99 (1H, d, J=2.7 Hz), 8.68 (1H, d, J=9.1 Hz), 12.03 (1H, s).

Example 77

Production of 5-chloro-2-({[4-(diphenylmethyl)piperazin-1-yl]acetyl}amino)benzoic acid (77)

The target compound (77) was synthesized according to the following steps.

1.0 g (4.0 mmol) of 5-chloro-2-[(chloroacetyl)amino]benzoic acid obtained in Example 72-(i), 1.0 g (4.0 mmol) of 1-benzhydrylpiperazine, 1.1 g (8.8 mmol) of N,N-diisopropylethylamine, and 60 mg (0.4 mmol) of sodium iodide were stirred in 5 mL of DMF solution at 80° C. for 3 hours. Thereafter, the solvent was distilled off under reduced pressure, H$_2$O was added to the residue, and solids were collected by filtration and dried. The obtained crude product was separated and purified by silica gel column chromatography, and the resultant was then recrystallized using ethyl acetate/n-hexane, thereby giving 198 mg of the target 5-chloro-2-({[4-(diphenylmethyl)piperazine-1-yl]acetyl}amino)benzoic acid (yield: 11%).

$^1$H-NMR (DMSO-d$_6$) δ: 2.27-2.74 (8H, m), 3.19 (2H, s), 4.22 (1H, s), 7.12-7.49 (10H, m), 7.64 (1H, dd, J=9.1, 2.7 Hz), 7.93 (1H, d, J=2.7 Hz), 8.72 (1H, d, J=9.1 Hz), 12.09 (1H, s), 13.90 (1H, brs).

Example 78

Production of 2-{[(2E)-3-(biphenyl-4-yl)prop-2-enoyl]amino}-5-chlorobenzoic acid (78)

The target compound (78) was synthesized according to the following Steps (i) to (ii).

(i) Methyl 2-{[(2E)-3-(biphenyl-4-yl)prop-2-enoyl]amino}-5-chlorobenzoate

Using the same method as in Example 3-(i), methyl 2-{[(2E)-3-(biphenyl-4-yl)prop-2-enoyl]amino}-5-chlorobenzoate was obtained using (2E)-3-(biphenyl-4-yl)prop-2-enoic acid and methyl 2-amino-5-chlorobenzoate (yield: 83%).

$^1$H-NMR (CDCl$_3$) δ: 3.90 (3H, s), 6.99 (1H, d, J=15.7 Hz), 7.34-7.57 (3H, m), 7.61-7.89 (8H, m), 7.90 (1H, d, J=2.5 Hz), 8.40 (1H, d, J=9.0 Hz), 10.79 (1H, s).

(ii) 2-{[(2E)-3-(Biphenyl-4-yl)prop-2-enoyl]amino}-5-chlorobenzoic acid

Using the same method as in Example 3-(ii), the target 2-{[(2E)-3-(biphenyl-4-yl)prop-2-enoyl]amino}-5-chlorobenzoic acid was obtained using methyl 2-{[(2E)-3-(biphenyl-4-yl)prop-2-enoyl]amino}-5-chlorobenzoate (yield: 36%).

$^1$H-NMR (DMSO-d$_6$) δ: 6.95 (1H, d, J=15.7 Hz), 7.34-7.56 (3H, m), 7.62-7.88 (8H, m), 7.96 (1H, d, J=2.6 Hz), 8.65 (1H, d, J=9.0 Hz), 11.37 (1H, s).

Example 79

Production of 5-chloro-2-({[3-(cyclohex-1-en-1-yl)phenyl]carbonyl}amino)benzoic acid (79)

The target compound (79) was synthesized according to the following Steps (i) to (iv).

(i) 3-(Cyclohex-1-en-1-yl)benzonitrile

Using the same method as in Example 32-(i), 3-(cyclohex-1-en-1-yl)benzonitrile was obtained using 1-cyclohexenyl trifluoromethanesulfonate and (3-cyanophenyl)boronic acid (yield: 88%).

$^1$H-NMR (CDCl$_3$) δ: 1.57-1.87 (4H, m), 2.15-2.29 (2H, m), 2.31-2.45 (2H, m), 6.14-6.22 (1H, m), 7.39 (1H, td, J=7.7, 0.6 Hz), 7.49 (1H, dt, J=7.7, 1.5 Hz), 7.60 (1H, dt, J=7.7, 1.5 Hz), 7.60-7.66 (1H m).

(ii) 3-(Cyclohex-1-en-1-yl)benzoic acid

Using the same method as in Example 32-(ii), 3-(cyclohex-1-en-1-yl)benzoic acid was quantitatively obtained using 3-(cyclohex-1-en-1-yl)benzonitrile.

$^1$H-NMR (CDCl$_3$) δ: 1.60-1.90 (4H, m), 2.17-2.31 (2H, m), 2.38-2.52 (2H, m), 6.18-6.26 (1H, m), 7.41 (1H, t, J=7.8 Hz), 7.63 (1H, dt, J=7.8, 1.6 Hz), 7.96 (1H, dt, J=7.8, 1.6 Hz), 8.13 (1M, t, J=1.6 Hz).

(iii) Methyl 5-chloro-2-({[3-(cyclohex-1-en-1-yl)phenyl]carbonyl}amino)benzoate

Using the same method as in Example 3-(i), methyl 5-chloro-2-({[3-(cyclohex-1-en-1-yl)phenyl]carbonyl}amino)benzoate was obtained using 3-(cyclohex-1-en-1-yl)benzoic acid and methyl 2-amino-5-chlorobenzoate (yield: 83%).

$^1$H-NMR (CDCl$_3$) δ: 1.56-1.90 (4H, m), 2.18-2.32 (2H, m), 2.41-2.54 (2H, m), 3.98 (3H, s), 6.22-6.30 (1H, m), 7.45 (1H, t, J=7.8 Hz), 7.55 (1H, dd, J=9.1, 2.6 Hz), 7.58 (1H, dt, J=7.8, 1.5 Hz), 7.84 (1H, dt, J=7.8, 1.5 Hz), 8.03-8.09 (2H, m), 8.93 (1H, d, J=9.1 Hz), 11.95 (1H, s).

(iv) 5-Chloro-2-({[3-(cyclohex-1-en-1-yl)phenyl]carbonyl}amino)benzoic acid

Using the same method as in Example 3-(ii), the target 5-chloro-2-({[3-(cyclohex-1-en-1-yl)phenyl]carbonyl}amino)benzoic acid was obtained using methyl 5-chloro-2-({[3-(cyclohex-1-en-1-yl)phenyl]carbonyl}amino)benzoate (yield: 90%).

$^1$H-NMR (DMSO-d$_6$) δ: 1.54-1.85 (4H, m), 2.14-2.29 (2H, m), 2.36-2.50 (2H, m), 6.25-6.34 (1H, m), 7.52 (1H, t, J=7.7 Hz), 7.68 (1H, d, J=7.7 Hz), 7.73 (1H, dd, J=9.1, 2.7 Hz), 7.81 (1H, d, J=7.7 Hz), 7.95 (1H, s), 7.99 (1H, d, J=2.7 Hz), 8.74 (1H, d, J=9.1 Hz), 12.13 (1H, s), 14.26 (1H, brs).

Example 80

Production of 5-chloro-2-{[(3-cyclohexylphenyl)carbonyl]amino}benzoic acid (80)

The target compound (80) was synthesized according to the following Steps (i) to (iii).

(i) 3-Cyclohexylbenzoic acid 28 mg of 10% Pd—C was added to an ethanol (10 mL) solution comprising 289 mg (1.4 mmol) of 3-(cyclohex-1-en- 1-yl)benzoic acid (10 mL) obtained in Example 79-(ii), and the mixture was stirred for 41 hours under a hydrogen atmosphere at room temperature. The reaction mixture was filtered using filter paper, and the filtrate was condensed, thereby quantitatively giving 3-cyclohexylbenzoic acid.

$^1$H-NMR (CDCl$_3$) δ: 1.14-1.60 (5H, m), 1.68-2.01 (5H, m), 2.48-2.68 (1H, m), 7.39 (1H, t, J=7.6 Hz), 7.47 (1H, d, J=7.6 Hz), 7.90-8.00 (2H, m).

(ii) Methyl 5-chloro-2-{[(3-cyclohexylphenyl)carbonyl]amino}benzoate

Using the same method as in Example 3-(i), methyl 5-chloro-2-{[(3-cyclohexylphenyl)carbonyl]amino}benzoate was obtained using 3-cyclohexylbenzoic acid and methyl 2-amino-5-chlorobenzoate (yield: 80%).

$^1$H-NMR (CDCl$_3$) δ: 1.18-2.01 (10H, m), 2.51-2.72 (1H, m), 3.98 (3H, s), 7.37-7.49 (2H, m), 7.56 (1H, dd, J=9.1, 2.6 Hz), 7.79-7.86 (1H, m), 7.88-7.93 (1H, m), 8.06 (1H, d, J=2.6 Hz), 8.93 (1H, d, J=9.1 Hz), 11.93 (1H, s).

(iii) 5-Chloro-2-{[(3-cyclohexylphenyl)carbonyl]amino}benzoic acid

Using the same method as in Example 3-(ii), the target 5-chloro-2-{[(3-cyclohexylphenyl)carbonyl]amino}benzoic acid was obtained using methyl 5-chloro-2-{[(3-cyclohexylphenyl)carbonyl]amino}benzoate (yield: 97%).

$^1$H-NMR (DMSO-d$_6$) δ: 1.08-1.59 (5H, m), 1.63-1.98 (5H, m), 2.51-2.72 (1H, m), 7.44-7.55 (2H, m), 7.74 (1H, dd, J=9.0, 2.6 Hz), 7.74-7.84 (2H, m), 7.99 (1H, d, J=2.6 Hz), 8.75 (1H, d, J=9.0 Hz), 12.12 (1H, s), 14.26 (1H, brs).

Example 81

Production of 5-(cyclohex-1-en-1-yl)-2-{[(4-cyclohexylphenyl)carbonyl]amino}benzoic acid (81)

The target compound (81) was synthesized according to the following Steps (i) to (iii).

(i) Methyl 5-bromo-2-{[(4-cyclohexylphenyl)carbonyl]amino}benzoate

Using the same method as in Example 3-(i), methyl 5-bromo-2-{[(4-cyclohexylphenyl)carbonyl]amino}benzoate was obtained using 4-cyclohexylbenzoic acid and methyl 2-amino-5-bromobenzoate (yield: 92%).

$^1$H-NMR (CDCl$_3$) δ: 1.08-1.58 (5H, m), 1.69-2.01 (5H, m), 2.42-2.72 (1H, m), 3.97 (3H, s), 7.30-7.40 (2H, m), 7.68 (1H, dd, J=9.1, 2.5 Hz), 7.90-7.99 (2H, m), 8.20 (1H, d, J=2.5 Hz), 8.87 (1H, d, J=9.1 Hz), 11.91 (1H, s).

(ii) Methyl 5-(cyclohex-1-en-1-yl)-2-{[(4-cyclohexylphenyl)carbonyl]amino}benzoate Using the same method as in Example 13-(ii), methyl 5-(cyclohex-1-en-1-yl)-2-{[(4-cyclohexylphenyl)carbonyl]amino}benzoate was obtained using methyl 5-bromo-2-{[(4-cyclohexylphenyl)carbonyl]amino}benzoate and 1-cyclohexen-1-yl-boronic acid pinacol ester (yield: 65%).

$^1$H-NMR (CDCl$_3$) δ: 1.15-1.99 (14H, m), 2.15-2.30 (2H, m), 2.35-2.48 (2H, m), 2.48-2.67 (1H, m), 3.97 (3H, s), 6.11-6.20 (1H, m), 7.30-7.40 (1H, m), 7.63 (1H, dd, J=8.9, 2.3 Hz), 7.91-8.01 (2H, m), 8.08 (1H, d, J=2.3 Hz), 8.86 (1H, d, J=8.9 Hz), 11.93 (1H, s).

(iii) 5-(Cyclohex-1-en-1-yl)-2-{[(4-cyclohexylphenyl)carbonyl]amino}benzoic acid Using the same method as in Example 3-(ii), the target 5-(cyclohex-1-en-1-yl)-2-{[(4-cyclohexylphenyl)carbonyl]amino}benzoic acid was obtained using methyl 5-(cyclohex-1-en-1-yl)-2-{[(4-cyclohexylphenyl)carbonyl]amino}benzoate (yield: 96%).

$^1$H-NMR (DMSO-d$_6$) δ: 1.06-1.94 (14H, m), 2.11-2.27 (2H, m), 2.30-2.44 (2H, m), 2.52-2.70 (1H, m), 6.16-6.26 (1H, m), 7.37-7.48 (2H, m), 7.73 (1H, d, J=8.8, 2.3 Hz), 7.82-7.92 (2H, m), 8.04 (1H, d, J=2.3 Hz), 8.68 (1H, d, J=8.8 Hz), 12.11 (1H, s), 13.84 (1H, brs).

Example 82

Production of 5-cyclohexyl-2-{[(4-cyclohexylphenyl)carbonyl]amino}benzoic acid (82)

The target compound (82) was synthesized according to the following steps.

22 mg of 10% Pd—C was added to an ethanol (11 mL)/DMF (1 mL) solution comprising 216 mg (0.54 mmol) of 5-(cyclohex-1-en-1-yl)-2-{[(4-cyclohexylphenyl)carbonyl]amino}benzoic acid obtained in Example 81, and the mixture was stirred under hydrogen atmosphere at room temperature for 72 hours. The reaction mixture was filtered using filter paper, and the filtrate was condensed, thereby giving 195 mg of the target 5-cyclohexyl-2-{[(4-cyclohexylphenyl)carbonyl]amino}benzoic acid (yield: 90%).

$^1$H-NMR (DMSO-d$_6$) δ: 1.09-1.98 (20H, m), 2.52-2.68 (2H, m), 7.37-7.47 (2H, m), 7.52 (1H, dd, J=8.7, 2.1 Hz), 7.80-7.93 (3H, m), 8.63 (1H, d, J=8.7 Hz), 12.13 (1H, s), 13.77 (1H, brs).

Example 83

Production of 5-chloro-2-({[4-(pyrrolidin-1-yl)phenyl]carbonyl}amino)benzoic acid hydrochloride (83)

The target compound (83) was synthesized according to the following Steps (i) to (ii).

(i) Methyl 5-chloro-2-({[4-(pyrrolidin-1-yl)phenyl]carbonyl}amino)benzoate

Using the same method as in Example 3-(i), methyl 5-chloro-2-({[4-(pyrrolidin-1-yl)phenyl]carbonyl}amino)benzoate was obtained using 4-(pyrrolidin-1-yl)benzoic acid and methyl 2-amino-5-chlorobenzoate (yield: 43%).

$^1$H-NMR (CDCl$_3$) δ: 1.97-2.12 (4H, m), 3.30-3.43 (4H, m), 3.97 (3H, s), 6.55-6.65 (2H, m), 7.51 (1H, dd, J=9.2, 2.6 Hz), 7.88-7.98 (2H, m), 8.02 (1H, d, J=2.6 Hz), 8.95 (1H, d, J=9.2 Hz), 11.77 (1H, s).

(ii) 5-Chloro-2-({[4-(pyrrolidin-1-yl)phenyl]carbonyl}amino)benzoic acid hydrochloride Using the same method as in Example 3-(ii), the target 5-chloro-2-({[4-(pyrrolidin-1-yl)phenyl]carbonyl}amino)benzoic acid hydrochloride was obtained using methyl 5-chloro-2-({[4-(pyrrolidin-1-yl)phenyl]carbonyl}amino)benzoate (yield: 82%).

$^1$H-NMR (DMSO-d$_6$) δ: 1.82-2.12 (4H, m), 3.14-3.46 (4H, m), 6.56-6.70 (2H, m), 7.68 (1H, dd, J=9.1, 2.7 Hz), 7.71-7.83 (2H, m), 7.97 (1H, d, J=2.7 Hz), 8.79 (1H, d, J=9.1 Hz), 11.94 (1H, s), 14.07 (1H, brs).

Example 84

Production of 5-chloro-2-[(spiro[5.5]undec-1-en-2-ylcarbonyl)amino]benzoic acid (84)

The target compound (84) was synthesized according to the following Steps (i) to (ii).

(i) Methyl 5-chloro-2-[(spiro[5.5]undec-1-en-2-ylcarbonyl)amino]benzoate

Using the same method as in Example 3-(i), methyl 5-chloro-2-[(spiro[5.5]undec-1-en-2-ylcarbonyl)amino]benzoate was obtained using spiro[5.5]undec-1-en-2-carboxylic acid and methyl 2-amino-5-chlorobenzoate (yield: 72%).

$^1$H-NMR (CDCl$_3$) δ: 1.23-1.83 (14H, m), 2.33-2.44 (2H, m), 3.95 (3H, s), 6.80 (1H, s), 7.49 (1H, dd, J=9.1, 2.6 Hz), 8.01 (1H, d, J=2.6 Hz), 8.83 (1H, d, J=9.1 Hz), 11.34 (1H, s).

(ii) 5-Chloro-2-[(spiro[5.5]undec-1-en-2-ylcarbonyl)amino]benzoic acid

Using the same method as in Example 3-(ii), the target 5-chloro-2-[(spiro[5.5]undec-1-en-2-ylcarbonyl)amino]benzoic acid was obtained using methyl 5-chloro-2-[(spiro[5.5]undec-1-en-2-ylcarbonyl)amino]benzoate (yield: 59%).

$^1$H-NMR (DMSO-d$_6$) δ: 1.25-1.87 (14H, m), 2.19-2.34 (2H, m), 6.70 (1H, s), 7.67 (1H, dd, J=9.0, 2.7 Hz), 7.95 (1H, d, J=2.7 Hz), 8.68 (1H, d, J=2.7 Hz), 11.66 (1H, s), 14.15 (1H, brs).

Example 85

Production of 5-chloro-2-[(spiro[5.5]undec-2-ylcarbonyl)amino]benzoic acid (85)

The target compound (85) was synthesized according to the following Steps (i) to (ii).

(i) Methyl 5-chloro-2-[(spiro[5.5]undec-2-ylcarbonyl)amino]benzoate

Using the same method as in Example 3-(i), methyl 5-chloro-2-[(spiro[5.5]undec-2-ylcarbonyl)amino]benzoate was obtained using spiro[5.5]undecane-2-carboxylic acid and methyl 2-amino-5-chlorobenzoate (yield: 84%).

$^1$H-NMR (CDCl$_3$) δ: 0.83-1.79 (16H, m), 1.86-2.06 (2H, m), 2.36-2.58 (1H, m), 3.95 (3H, s), 7.48 (1H, dd, J=9.1, 2.7 Hz), 8.00 (1H, d, J=2.7 Hz), 8.74 (1H, d, J=9.1 Hz), 11.01 (1H, s).

(ii) 5-Chloro-2-[(spiro[5.5]undec-2-ylcarbonyl)amino]benzoic acid

Using the same method as in Example 3-(ii), the target 5-chloro-2-[(spiro[5.5]undec-2-ylcarbonyl)amino]benzoic acid was obtained using methyl 5-chloro-2-[(spiro[5.5]undec-2-ylcarbonyl)amino]benzoate (yield: 59%).

$^1$H-NMR (DMSO-d$_6$) δ: 0.80-1.69 (16H, m), 1.77-2.02 (2H, m), 2.35-2.51 (1H, m), 7.64 (1H, dd, J=9.0, 2.7 Hz), 7.91 (1H, d, J=2.7 Hz), 8.53 (1H, d, J=9.0 Hz), 11.14 (1H, s), 14.00 (1H, brs).

Example 86

Production of 5-chloro-2-({[3-(4-methylphenyl)adamantan-1-yl]carbonyl}amino)benzoic acid (86)

The target compound (86) was synthesized according to the following Steps (i) to (ii).

(i) Methyl 5-chloro-2-({[3-(4-methylphenyl)adamantan-1-yl]carbonyl}amino)benzoate Using the same method as in Example 3-(i), methyl 5-chloro-2-({[3-(4-methylphenyl)adamantan-1-yl]carbonyl}amino)benzoate was obtained using 3-(4-methylphenyl)adamantan-1-carboxylic acid and methyl 2-amino-5-chlorobenzoate (yield: 87%).

$^1$H-NMR (CDCl$_3$) δ: 1.75-2.39 (14H, m), 2.32 (3H, s), 3.95 (3H, s), 7.10-7.19 (2H, m), 7.26-7.34 (2H, m), 7.49 (1H, dd, J=9.1, 2.6 Hz), 8.01 (1H, d, J=2.6 Hz), 8.80 (1H, d, J=9.1 Hz), 11.25 (1H, s).

(ii) 5-Chloro-2-({[3-(4-methylphenyl)adamantan-1-yl]carbonyl}amino)benzoic acid Using the same method as in Example 3-(ii), the target 5-chloro-2-({[3-(4-methylphenyl)adamantan-1-yl]carbonyl}amino)benzoic acid was obtained using methyl 5-chloro-2-({[3-(4-methylphenyl)adamantan-1-yl]carbonyl}amino)benzoate (yield: 49%).

$^1$H (DMSO-d$_6$) δ: 1.56-2.32 (14H, m), 2.26 (3H, s), 7.06-7.16 (2H, m), 7.22-7.32 (2H, m), 7.66 (1H, dd, J=9.0, 2.7 Hz), 7.94 (1H, d, J=2.7 Hz), 8.66 (1H, d, J=9.0 Hz), 11.46 (1H, s), 14.12 (1H, brs).

Example 87

Production of 5-chloro-2-({[3-(cyclohexylethynyl)phenyl]carbonyl}amino)benzoic acid (87)

The target compound (87) was synthesized according to the following Steps (i) to (ii).

(i) Methyl 5-chloro-2-({[3-(cyclohexylethynyl)phenyl]carbonyl}amino)benzoate 0.5 g (1.2 mmol) of methyl 5-chloro-2-{[(3-iodophenyl)carbonyl]amino}benzoate obtained in Example 63-(i), 146 mg (1.4 mmol) of triethylamine, 11.5 mg (0.06 mmol) of copper iodide, 25 mg (0.036 mmol) of bis(triphenylphosphine)palladium(II) dichloride (PdCl$_2$(PPh$_3$)$_2$), and 208 mg (1.92 mmol) of cyclohexylacetylene were stirred in DMF (10 mL) at room temperature for 21 hours. The reaction mixture was diluted with ethyl acetate, and washed with H$_2$O, diluted hydrochloric acid, aqueous saturated sodium hydrogen carbonate solution, and saturated saline in this order. Thereafter, the organic layer was dried over anhydrous sodium sulfate, and the solvent was distilled off under reduced pressure. The obtained crude product was separated and purified by silica gel column chromatography, thereby giving 169 mg of methyl 5-chloro-2-({[3-(cyclohexylethynyl)phenyl]carbonyl}amino)benzoate (yield: 36%).

$^1$H-NMR (CDCl$_3$) δ: 1.22-1.99 (10H, m), 2.54-2.70 (1H, m), 3.99 (3H, s), 7.43 (1H, t, J=7.8 Hz), 7.56 (1H, dd, J=9.1, 2.6 Hz), 7.58 (1H, dt, J=7.7, 1.4 Hz), 7.88 (1H, dt, J=7.7, 1.4 Hz), 8.04-8.09 (1H, m), 8.06 (1H, d, J=2.6 Hz), 8.91 (1H, d, J=9.1 Hz), 11.92 (1H, s).

(ii) 5-Chloro-2-({[3-(cyclohexylethynyl)phenyl]carbonyl}amino)benzoic acid

Using the same method as in Example 3-(ii), the target 5-chloro-2-({[3-(cyclohexylethynyl)phenyl]carbonyl}amino)benzoic acid was obtained using methyl 5-chloro-2-({[3-(cyclohexylethynyl)phenyl]carbonyl}amino)benzoate (yield: 90%).

$^1$H-NMR (DMSO-$d_6$) δ: 1.20-1.95 (10H, m), 2.58-2.76 (1H, m), 7.56 (1H, t, J=7.9 Hz), 7.64 (1H, dt, J=7.6, 1.5 Hz), 7.74 (1H, dd, J=8.9, 2.7 Hz), 7.85-7.93 (2H, m), 7.99 (1H, d, J=2.7 Hz), 8.65 (1H, d, J=8.9 Hz), 12.03 (1H, s), 14.15 (1H, brs).

Example 88

Production of 5-chloro-2-({[4-(cyclohexylethynyl)phenyl]carbonyl}amino)benzoic acid (88)

The target compound (88) was synthesized according to the following Steps (i) to (iii).

(i) Methyl 5-chloro-2-{[(4-iodophenyl)carbonyl]amino}benzoate

Using the same method as in Example 3-(i), methyl 5-chloro-2-{[(4-iodophenyl)carbonyl]amino}benzoate was obtained using 4-iodobenzoic acid and methyl 2-amino-5-chlorobenzoate (yield: 94%).

$^1$H-NMR (CDCl$_3$) δ: 3.98 (3H, s), 7.55 (1H, dd, J=9.1, 2.6 Hz), 7.70-7.78 (2H, m), 7.84-7.92 (2H, m), 8.05 (1H, d, J=2.6 Hz), 8.88 (1H, d, J=9.1 Hz), 11.97 (1H, s).

(ii) Methyl 5-chloro-2-({[4-(cyclohexylethynyl)phenyl]carbonyl}amino)benzoate Using the same method as in Example 87-(i), methyl 5-chloro-2-({[4-(cyclohexylethynyl)phenyl]carbonyl}amino)benzoate was quantitatively obtained using methyl 5-chloro-2-{[(4-iodophenyl)carbonyl]amino}benzoate and cyclohexylacetylene.

$^1$H-NMR (CDCl$_3$) δ: 1.17-2.00 (10H, s), 2.54-2.70 (1H, m), 3.98 (3H, s), 7.48-7.57 (2H, m), 7.55 (1H, dd, J=9.1, 2.6 Hz), 7.90-7.99 (2H, m), 8.05 (1H, d, J=2.6 Hz), 8.91 (1H, d, J=9.1 Hz), 11.95 (1H, s).

(iii) 5-Chloro-2-({[4-(cyclohexylethynyl)phenyl]carbonyl}amino)benzoic acid Using the same method as in Example 3-(ii), the target 5-chloro-2-({[4-(cyclohexylethynyl)phenyl]carbonyl}amino)benzoic acid was obtained using methyl 5-chloro-2-({[4-(cyclohexylethynyl)phenyl]carbonyl}amino)benzoate (yield: 80%).

$^1$H-NMR (DMSO-$d_6$) δ: 1.12-1.96 (10H, m), 2.58-2.78 (1H, m), 7.52-7.62 (2H, m), 7.73 (1H, dd, J=9.0, 2.7 Hz), 7.85-7.95 (2H, m), 7.98 (1H, d, J=2.7 Hz), 8.69 (1H, d, J=9.0 Hz), 12.09 (1H, s), 14.13 (1H, brs).

Example 89

Production of 2-{[(2E)-3-(biphenyl-3-yl)prop-2-enoyl]amino}-5-chlorobenzoic acid (89)

The target compound (89) was synthesized according to the following Steps (i) to (iii).

(i) Methyl 2-{[(2E)-3-(3-bromophenyl)prop-2-enoyl]amino}-5-chlorobenzoate

Using the same method as in Example 3-(i), methyl 2-{[(2E)-3-(3-bromophenyl)prop-2-enoyl]amino}-5-chlorobenzoate was obtained using (2E)-3-(3-bromophenyl)prop-2-enoic acid and methyl 2-amino-5-chlorobenzoate (yield: 85%).

$^1$H-NMR (CDCl$_3$) δ: 3.98 (3H, s), 6.58 (1H, J=15.6 Hz), 7.27 (1H, t, J=7.8 Hz), 7.44-7.55 (2H, m), 7.53 (1H, d, J=9.1, 2.5 Hz), 7.67 (1H, dd, J=15.6 Hz), 7.73 (1H, t, J=1.7 Hz), 8.03 (1H, d, J=2.5 Hz), 8.85 (1H, d, J=9.1 Hz), 11.31 (1H, s).

(ii) Methyl 2-{[(2E)-3-(biphenyl-3-yl)prop-2-enoyl]amino}-5-chlorobenzoate

Using the same method as in Example 32-(i), methyl 2-{[(2E)-3-(biphenyl-3-yl)prop-2-enoyl]amino}-5-chlorobenzoate was obtained using methyl 2-{[(2E)-3-(3-bromophenyl)prop-2-enoyl]amino}-5-chlorobenzoate and phenylboronic acid (yield: 85%).

$^1$H-NMR (CDCl$_3$) δ: 3.97 (3H, s), 6.66 (1H, J=15.7 Hz), 7.29-7.67 (9H m), 7.79 (1H, s), 7.82 (1H, d, J=15.7 Hz), 8.03 (1H, d, J=2.5 Hz), 8.89 (1H, d, J=9.1 Hz), 11.30 (1H, s).

(iii) 2-{[(2E)-3-(Biphenyl-3-yl)prop-2-enoyl]amino}-5-chlorobenzoic acid

Using the same method as in Example 3-(ii), the target 2-{[(2E)-3-(biphenyl-3-yl)prop-2-enoyl]amino}-5-chloro benzoic acid was obtained using methyl 2-{[(2E)-3-(biphenyl-3-yl)prop-2-enoyl]amino}-5-chlorobenzoate (yield: 53%).

$^1$H-NMR (DMSO-$d_6$) δ: 7.06 (1H, d, J=15.7 Hz), 7.35-7.59 (4H, m), 7.66-7.81 (6H, m), 7.96 (1H, d, J=2.6 Hz), 8.05 (1H, s), 8.64 (1H, d, J=9.0 Hz), 11.27 (1H, s).

Example 90

Production of 5-chloro-2-({(2E)-3-[3-(cyclohex-1-en-1-yl)phenyl]prop-2-enoyl}amino)benzoic acid (90)

The target compound (90) was synthesized according to the following Steps (i) to (ii).

(i) Methyl 5-chloro-2-({(2E)-3-[3-(cyclohex-1-en-1-yl)phenyl]prop-2-enoyl}amino)benzoate Using the same method as in Example 13-(ii), methyl 5-chloro-2-({(2E)-3-[3-(cyclohex-1-en-1-yl)phenyl]prop-2-enoyl}amino)benzoate was obtained using methyl 2-{[(2E)-3-(3-bromophenyl)prop-2-enoyl]amino}-5-chlorobenzoate obtained in Example 89-(i) and 2-(cyclohex-1-en-1-yl)-4,4,5,5-tetramethyl-1,3,2-dioxaborolane (yield: 60%).

$^1$H-NMR (CDCl$_3$) δ: 1.59-1.90 (4H, m), 2.16-2.31 (2H, m), 2.36-2.51 (2H, m), 3.98 (3H, s), 6.12-6.20 (1H, s), 6.60 (1H, d, J=15.6 Hz), 7.28-7.48 (3H, m), 7.53 (1H, dd, J=9.1, 2.6 Hz), 7.58 (1H, s), 7.77 (1H, d, J=15.6 Hz), 8.03 (1H, d, J=2.6 Hz), 8.88 (1H, d, J=9.1 Hz), 11.26 (1H, s).

(ii) 5-Chloro-2-({(2E)-3-[3-(cyclohex-1-en-1-yl)phenyl]prop-2-enoyl}amino)benzoic acid Using the same method as in Example 3-(ii), the target 5-chloro-2-({(2E)-3-[3-(cyclohex-1-en-1-yl)phenyl]prop-2-enoyl}amino)benzoic acid was obtained using methyl 5-chloro-2-({(2E)-3-[3-(cyclohex-1-en-1-yl)phenyl]prop-2-enoyl}amino)benzoate (yield: 73%).

$^1$H-NMR (DMSO-d$_6$) δ: 1.50-1.85 (4H, m), 2.12-2.28 (2H, m), 2.35-2.49 (2H, m), 6.20-6.30 (1H, m), 6.96 (1H, d, J=15.7 Hz), 7.37 (1H, t, J=7.5 Hz), 7.45 (1H, d, J=7.5 Hz), 7.59 (1H, d, J=7.5 Hz), 7.64 (1H, d, J=15.7 Hz), 7.70 (1H, dd, J=9.0, 2.6 Hz), 7.74 (1H, s), 7.95 (1H, d, J=2.6 Hz), 8.61 (1H, d, J=9.0 Hz), 11.23 (1H, s).

Example 91

Production of 5-chloro-2-{[(2E)-3-chloro-3-cyclohexylprop-2-enoyl]amino}benzoic acid (91)

The target compound (91) was synthesized according to the following Steps (i) to (ii).

(i) Methyl 5-chloro-2-{[(2E)-3-chloro-3-cyclohexylprop-2-enoyl]amino}benzoate and methyl 5-chloro-2-{[(2Z)-3-chloro-3-cyclohexylprop-2-enoyl]amino}benzoate Using the same method as in Example 3-(i), the mixture of methyl 5-chloro-2-{[(2E)-3-chloro-3-cyclohexylprop-2-enoyl]amino}benzoate and methyl 5-chloro-2-{[(2Z)-3-chloro-3-cyclohexylprop-2-enoyl]amino}benzoate was obtained using 3-cyclohexylprop-2-ynoic acid and methyl 2-amino-5-chlorobenzoate. The mixture was separated and purified using silica gel chromatography, thereby giving methyl 5-chloro-2-{[(2E)-3-chloro-3-cyclohexylprop-2-enoyl]amino}benzoate (yield: 26%) and methyl 5-chloro-2-{[(2Z)-3-chloro-3-cyclohexylprop-2-enoyl]amino}benzoate (yield: 36%).

Methyl 5-chloro-2-{[(2E)-3-chloro-3-cyclohexylprop-2-enoyl]amino}benzoate $^1$H-NMR (CDCl$_3$) δ: 1.03-1.86 (10H, m), 3.94 (3H, s), 3.94-4.12 (1H, m), 6.11 (1H, s), 7.49 (1H, dd, J=9.1, 2.6 Hz), 8.01 (1H, d, J=2.6 Hz), 8.73 (1H, d, J=9.1 Hz), 11.03 (1H, s).

Methyl 5-chloro-2-{[(2Z)-3-chloro-3-cyclohexylprop-2-enoyl]amino}benzoate $^1$H-NMR (CDCl$_3$) δ: 1.09-1.55 (5H, m), 1.63-2.02 (5H, m), 2.23-2.40 (1H, m), 3.94 (3H, s), 6.11 (1H, d, J=0.5 Hz), 7.50 (1H, dd, J=9.1, 2.5 Hz), 8.00 (1H, d, J=2.5 Hz), 8.79 (1H, d, J=9.1 Hz), 11.16 (1H, s).

(ii) 5-Chloro-2-{[(2E)-3-chloro-3-cyclohexylprop-2-enoyl]amino}benzoic acid

Using the same method as in Example 3-(ii), the target 5-chloro-2-{[(2E)-3-chloro-3-cyclohexylprop-2-enoyl]amino}benzoic acid was obtained using methyl 5-chloro-2-{[(2E)-3-chloro-3-cyclohexylprop-2-enoyl]amino}benzoate (yield: 49%).

$^1$H-NMR (DMSO-d$_6$) δ: 0.97-1.85 (10H, m), 3.84-4.03 (1H, m), 6.32 (1H, s), 7.65 (1H, dd, J=9.0, 2.7 Hz), 7.90 (1H, d, J=2.7 Hz), 8.38 (1H, d, J=9.0 Hz), 10.99 (1H, s).

Example 92

Production of 5-(cyclohexylethynyl)-2-{[(4-cyclohexylphenyl)carbonyl]amino}benzoic acid (92)

The target compound (92) was synthesized according to the following Steps (i) to (ii).

(i) Methyl 5-(cyclohexylethynyl)-2-{[(4-cyclohexylphenyl)carbonyl]amino}benzoate Using the same method as in Example 87-(i), methyl 5-(cyclohexylethynyl)-2-{[(4-cyclohexylphenyl)carbonyl]amino}benzoate was obtained using methyl 5-bromo-2-{[(4-cyclohexylphenyl)carbonyl]amino}benzoate and cyclohexylacetylene (yield: 54%).

$^1$H-NMR (CDCl$_3$) δ: 1.10-2.00 (20H, m), 2.45-2.68 (2H, m), 3.96 (3H, s), 7.30-7.40 (2H, m), 7.60 (1H, dd, J=8.8, 2.1 Hz), 7.90-8.00 (2H, m), 8.12 (1H, d, J=2.1 Hz), 8.88 (1H, d, J=8.8 Hz), 11.99 (1H, s).

(ii) 5-(Cyclohexylethynyl)-2-{[(4-cyclohexylphenyl)carbonyl]amino}benzoic acid

Using the same method as in Example 3-(ii), the target 5-(cyclohexylethynyl)-2-{[(4-cyclohexylphenyl)carbonyl]amino}benzoic acid was obtained using methyl 5-(cyclohexylethynyl)-2-{[(4-cyclohexylphenyl)carbonyl]amino}benzoate (yield: 69%).

$^1$H-NMR (DMSO-d$_6$) δ: 1.09-2.02 (20H, m), 2.51-2.74 (2H, m), 7.38-7.49 (2H, m), 7.64 (1H, dd, J=8.7, 2.1 Hz), 7.81-7.92 (2H, m), 7.99 (1H, d, J=2.1 Hz), 8.71 (1H, d, J=8.7 Hz), 12.18 (1H, s), 13.99 (1H, brs).

Example 93

Production of 5-(2-cyclohexylethyl)-2-{[(4-cyclohexylphenyl)carbonyl]amino}benzoic acid (93)

The target compound (93) was synthesized according to the following steps.

55 mg (0.13 mmol) of 5-(cyclohexylethynyl)-2-{[(4-cyclohexylphenyl)carbonyl]amino}benzoic acid obtained in Example 92 and 55 mg of Pd—C were stirred in ethanol (4 mL) at room temperature for 5 days. Thereafter, the mixture was filtered, and the filtrate was condensed, thereby giving 45 mg of the target 5-(2-cyclohexylethyl)-2-{[(4-cyclohexylphenyl)carbonyl]amino}benzoic acid (yield: 81%).

$^1$H-NMR (DMSO-d$_6$) δ: 0.75-1.92 (23H, m), 2.51-2.69 (3H, m), 7.35-7.48 (3H, m), 7.82-7.93 (3H, m), 8.61 (1H, d, J=8.5 Hz), 12.73 (1H, s).

Example 94

Production of 2-({3-[4-(adamantan-1-yl)phenyl]prop-2-ynoyl}amino)-5-chlorobenzoic acid (94)

The target compound (94) was synthesized according to the following Steps (i) to (ii).

(i) 3-[4-(Adamantan-1-yl)phenyl]prop-2-ynoic acid

Using the same method as in Example 4-(iii), 3-[4-(adamantan-1-yl)phenyl]prop-2-ynoic acid was obtained using 1-(4-ethynylphenyl)adamantane (yield: 83%).

$^1$H-NMR (DMSO-d$_6$) δ: 1.56-2.19 (15H, m), 7.44-7.50 (2H, m), 7.53-7.62 (2H, m), 13.73 (1H, brs).

(ii) 2-({3-[4-(Adamantan-1-yl)phenyl]prop-2-ynoyl}amino)-5-chlorobenzoic acid

Using the same method as in Example 3-(i), the mixture of methyl 2-({3-[4-(adamantan-1-yl)phenyl]prop-2-ynoyl}amino)-5-chlorobenzoate and methyl 2-({3-[4-(adamantan-1-yl)phenyl]-3-chloroprop-2-enoyl}amino)-5-chlorobenzoate was obtained using 3-[4-(adamantan-1-yl)phenyl]prop-2-yonic acid and methyl 2-amino-5-chlorobenzoate. Thereafter, using the same method as in Example 3-(ii), the target 2-({3-[4-(adamantan-1-yl)phenyl]prop-2-ynoyl}amino)-5-chlorobenzoic acid was obtained using the above mixture (yield: 35%).

$^1$H-NMR (DMSO-d$_6$) δ: 1.60-2.17 (15H, m), 7.43-7.53 (2H, m), 7.55-7.65 (2H, m), 7.71 (1H, d, J=8.9, 2.7 Hz), 8.34 (1H, d, J=8.9 Hz), 11.58 (1H, s).

Example 95

Production of 2-{[(4-cyclohexylphenyl)carbonyl]amino}-5-ethynylbenzoic acid (95)

The target compound (95) was synthesized according to the following Steps (i) to (iv).

(i) Methyl 2-{[(4-cyclohexylphenyl)carbonyl]amino}-5-iodobenzoate

Using the same method as in Example 3-(i), methyl 2-{[(4-cyclohexylphenyl)carbonyl]amino}-5-iodobenzoate was obtained using 4-cyclohexylbenzoic acid and methyl 2-amino-5-iodobenzoate (yield: 66%).

$^1$H-NMR (CDCl$_3$) δ: 1.16-1.57 (5H, m), 1.67-2.01 (5H, m), 2.47-2.68 (1H, m), 3.97 (3H, s), 7.31-7.40 (2H, m), 7.86 (1H, dd, J=9.0, 2.2 Hz), 7.90-7.99 (2H, m), 8.38 (1H, d, J=2.2 Hz), 8.74 (1H, d, J=9.0 Hz), 11.91 (1H, s).

(ii) Methyl 2-{[(4-cyclohexylphenyl)carbonyl]amino}-5-[(trimethylsilyl)ethynyl]benzoate Using the same method as in Example 87-(i), methyl 2-{[(4-cyclohexylphenyl)carbonyl]amino}-5-[(trimethylsilyl)ethynyl]benzoate was quantitatively obtained using 2-{[(4-cyclohexylphenyl)carbonyl]amino}-5-methyl iodobenzoate and ethynyltrimethylsilane.

$^1$H-NMR (CDCl$_3$) δ: 0.26 (9H, s), 1.16-1.58 (5H, m), 1.69-2.00 (5H, m), 2.47-2.70 (1H, m), 3.97 (3H, s), 7.31-7.40 (2H, m), 7.67 (1H, dd, J=8.8, 2.0 Hz), 7.91-8.00 (2H, m), 8.20 (1H, d, J=2.0 Hz), 8.91 (1H, d, J=8.8 Hz), 12.04 (1H, s).

(iii) Methyl 2-{[(4-cyclohexylphenyl)carbonyl]amino}-5-ethynylbenzoate 351 mg (1.1 mmol) of tetrabutyl ammonium fluoride trihydrate was added to a THF (9 mL) solution comprising 322 mg (0.74 mmol) of methyl 2-{[(4-cyclohexylphenyl)carbonyl]amino}-5-[(trimethylsilyl)ethynyl]benzoate at 0° C., and the mixture was stirred for 1.5 hours. Thereafter, the reaction mixture was diluted with ethyl acetate, and washed with saturated saline. The organic layer was dried over anhydrous sodium sulfate, and the solvent was distilled off under reduced pressure. The obtained crude product was separated and purified by silica gel column chromatography, thereby giving 208 mg of methyl 2-{[(4-cyclohexylphenyl)carbonyl]amino}-5-ethynylbenzoate (yield: 78%).

$^1$H-NMR (CDCl$_3$) δ: 1.14-1.55 (5H, m), 1.68-2.00 (5H, m), 2.47-2.70 (1H, m), 3.08 (1H, s), 3.98 (3H, s), 7.32-7.41 (2H, m), 7.70 (1H, dd, J=8.8, 2.1 Hz), 7.92-8.01 (2H, m), 8.23 (1H, d, J=2.1 Hz), 8.93 (1H, d, J=8.8 Hz), 12.05 (1H, s).

(iv) 2-{[(4-Cyclohexylphenyl)carbonyl]amino}-5-ethynylbenzoic acid

Using the same method as in Example 3-(ii), the target 2-{[(4-cyclohexylphenyl)carbonyl]amino}-5-ethynyl benzoic acid was obtained using methyl 2-{[(4-cyclohexylphenyl)carbonyl]amino}-5-ethynylbenzoate (yield: 85%).

$^1$H-NMR (DMSO-d$_6$) δ: 1.08-1.16 (5H, m), 1.61-1.95 (5H, m), 2.50-2.70 (1H, m), 4.25 (1H, s), 7.83-7.50 (2H, m), 7.76 (1H, dd, J=8.7, 2.1 Hz), 7.81-7.92 (2H, m), 8.09 (1H, d, J=2.1 Hz), 8.74 (1H, d, J=8.7 Hz), 12.22 (1H, s), 14.03 (1H, brs).

Example 96

Production of 2-({[4-(adamantan-1-ylmethyl)phenyl]carbonyl}amino)-5-chlorobenzoic acid (96)

The target compound (96) was synthesized according to the following Steps (i) to (ii).

(i) Methyl 2-({[4-(adamantan-1-ylmethyl)phenyl]carbonyl}amino)-5-chlorobenzoate and methyl 2-{[(4-{adamantan-1-yl[(trifluoroacetyl)oxy]methyl}phenyl)carbonyl]amino}-5-chlorobenzoate 4 mL of TFA was added at room temperature to 350 mg (0.77 mmol) of methyl 2-({[4-(adamantan-1-ylcarbonyl)phenyl]carbonyl}amino)-5-chlorobenzoate obtained in Example 56-(ii). 360 mg (3.1 mmol) of triethyl silane was added thereto, and the mixture was stirred for 17 hours. The reaction mixture was diluted with ethyl acetate, and washed with an aqueous saturated sodium hydrogen carbonate solution and saturated saline. The organic layer was dried over anhydrous sodium sulfate, and the solvent was distilled off under reduced pressure. The obtained crude product was separated and purified by silica gel chromatography, thereby giving 70 mg of methyl 2-({[4-(adamantan-1-ylmethyl)phenyl]carbonyl}amino)-5-chlorobenzoate (yield: 21%) and 262 mg of methyl 2-{[(4-{adamantan-1-yl[(trifluoro-acetyl)oxy]methyl}phenyl)carbonyl]amino}-5-chlorobenzoate (yield: 62%).

Methyl 2-({[4-(adamantan-1-ylmethyl)phenyl]carbonyl}amino)-5-chlorobenzoate $^1$H-NMR (CDCl$_3$) δ: 1.38-1.75 (12H, m), 1.94 (3H, brs), 2.45 (2H, s), 3.99 (3H, s), 7.19-7.29 (2H, m), 7.55 (1H, dd, J=9.1, 2.6 Hz), 7.89-7.98 (2H, m), 8.06 (1H, d, J=2.6 Hz), 8.94 (1H, d, J=9.1), 11.93 (1H, s).

Methyl 2-{[(4-{adamantan-1-yl[(trifluoro-acetyl)oxy]methyl}phenyl)carbonyl]amino}-5-chlorobenzoate $^1$H-NMR (CDCl$_3$) δ: 1.44-1.80 (12H, m), 2.01 (3H, brs), 3.99 (3H, s), 5.52 (1H, s), 7.36-7.44 (2H, m), 7.56 (1H, dd, J=9.1, 2.6 Hz), 7.98-7.06 (2H, m), 8.06 (1H, d, J=2.6 Hz), 8.92 (1H, d, J=9.1 Hz), 11.99 (1H, s).

(ii) 2-({[4-(Adamantan-1-ylmethyl)phenyl]carbonyl}amino)-5-chlorobenzoic acid

Using the same method as in Example 3-(ii), the target 2-({[4-(adamantan-1-ylmethyl)phenyl]carbonyl}amino)-5-chlorobenzoic acid was obtained using methyl 2-({[4-(adamantan-1-ylmethyl)phenyl]carbonyl}amino)-5-chlorobenzoate (yield: 83%).

$^1$H-NMR (DMSO-d$_6$) δ: 1.30-1.79 (12H, m), 1.91 (3H, brs), 2.45 (2H, s), 7.24-7.35 (2H, m), 7.74 (1H, dd, J=9.0, 2.7 Hz), 7.80-7.91 (2H, m), 8.00 (1H, d, J=2.6 Hz), 8.73 (1H, d, J=9.0 Hz), 12.08 (1H, s).

Example 97

Production of 2-[({4-[adamantan-1-yl(hydroxy)methyl]phenyl}carbonyl)amino]-5-chlorobenzoic acid (97)

The target compound (97) was synthesized according to the following steps.

Using the same method as in Example 3-(ii), the target 2-[({4-[adamantan-1-yl(hydroxy)methyl]phenyl}carbonyl) amino]-5-chlorobenzoic acid was obtained using methyl 2-{[(4-{adamantan-1-yl[(trifluoroacetyl)oxy] methyl}phenyl)carbonyl]amino}-5-chlorobenzoate obtained in Example 96-(i) (yield: 95%).

$^1$H-NMR (DMSO-$d_6$) δ: 1.21-2.05 (15H, m), 4.14 (1H, s), 5.27 (1H, brs), 7.38-7.48 (2H, m), 7.74 (1H, dd, J=9.0, 2.7 Hz), 7.83-7.93 (2H, m), 8.00 (1H, d, J=2.7 Hz), 8.74 (1H, d, J=9.0 Hz), 12.08 (1H, s), 13.97 (1H, brs).

Example 98

Production of 5-chloro-2-({[4-(1-methylcyclohexyl) phenyl]carbonyl}amino)benzoic acid (98)

The target compound (98) was synthesized according to the following Steps (i) to (ii).

(i) Methyl 5-chloro-2-({[4-(1-methylcyclohexyl) phenyl]carbonyl}amino)benzoate Using the same method as in Example 3-(i), methyl 5-chloro-2-({[4-(1-methylcyclohexyl)phenyl] carbonyl}amino)benzoate was obtained using 4-(1-methylcyclohexyl)benzoic acid and methyl 2-amino-5-chlorobenzoate (yield: 76%).

$^1$H-NMR (CDCl$_3$) δ: 1.21 (3H, s), 1.28-1.71 (8H, m), 1.96-2.15 (2H, m), 3.98 (3H, s), 7.49-7.58 (2H, m), 7.55 (1H, dd, J=9.1, 2.6 Hz), 7.94-8.02 (2H, m), 8.06 (1H, d, J=2.6 Hz), 8.95 (1H, d, J=9.1), 11.94 (1H, s).

(ii) 5-Chloro-2-({[4-(1-methylcyclohexyl)phenyl] carbonyl}amino)benzoic acid Using the same method as in Example 3-(ii), the target 5-chloro-2-({[4-(1-methylcyclohexyl)phenyl] carbonyl}amino)benzoic acid was obtained using methyl 5-chloro-2-({[4-(1-methylcyclohexyl)phenyl] carbonyl}amino)benzoate (yield: 70%).

$^1$H-NMR (DMSO-$d_6$) δ: 1.17 (3H, s), 1.23-1.68 (8H, m), 1.93-2.13 (2H, m), 7.54-7.65 (2H, m), 7.74 (1H, dd, J=9.0, 2.7 Hz), 7.85-7.96 (2H, m), 8.00 (1H, d, J=2.7 Hz), 8.74 (1H, d, J=9.0 Hz), 12.08 (1H, s), 14.19 (1H, brs).

Example 99

Production of sodium 5-chloro-2-({[3-(quinolin-2-ylmethoxy)phenyl]carbonyl}amino)benzoate (99)

The target compound (99) was synthesized according to the following Steps (i) to (ii).

(i) Methyl 5-chloro-2-({[3-(quinolin-2-ylmethoxy) phenyl]carbonyl}amino)benzoate Using the same method as in Example 3-(i), methyl 5-chloro-2-({[3-(quinolin-2-ylmethoxy)phenyl] carbonyl}amino)benzoate was obtained using 3-(quinolin-2-ylmethoxy)benzoic acid and methyl 2-amino-5-chlorobenzoate (yield: 61%).

$^1$H-NMR (CDCl$_3$) δ: 3.96 (3H, s), 5.76 (2H, s), 7.28 (1H, dd, J=8.0, 2.6 Hz), 7.47 (1H, t, J=8.0 Hz), 7.55 (1H, dd, J=9.1, 2.6 Hz), 7.60-7.76 (3H, m), 7.85-8.01 (3H, m), 8.05 (1H, d, J=2.6 Hz), 8.47-8.57 (2H, m), 8.90 (1H, d, J=9.1 Hz), 11.96 (1H, s).

(ii) Sodium 5-chloro-2-({[3-(quinolin-2-ylmethoxy) phenyl]carbonyl}amino)benzoate Using the same method as in Example 8-(iii), the target sodium 5-chloro-2-({[3-(quinolin-2-ylmethoxy)phenyl] carbonyl}amino)benzoate was obtained using methyl 5-chloro-2-({[3-(quinolin-2-ylmethoxy)phenyl] carbonyl}amino)benzoate (yield: 83%).

$^1$H-NMR (DMSO-$d_6$): δ 5.46 (2H, s), 7.30 (1H, dd, J=8.2, 2.4 Hz), 7.38 (1H, dd, J=8.8, 2.8 Hz), 7.48 (1H, t, J=7.9 Hz), 7.58-7.86 (5H, m), 7.97-8.10 (3H, m), 8.45 (1H, d, J=8.5 Hz), 8.69 (1H, d, J=8.8 Hz) 15.59 (1H, s).

Example 100

Production of sodium 5-chloro-2-({[4-(quinolin-2-ylmethoxy)phenyl]carbonyl}amino)benzoate (100)

The target compound (100) was synthesized according to the following Steps (i) to (ii).

(i) Methyl 5-chloro-2-({[4-(quinolin-2-ylmethoxy) phenyl]carbonyl}amino)benzoate Using the same method as in Example 3-(i), methyl 5-chloro-2-({[4-(quinolin-2-ylmethoxy)phenyl] carbonyl}amino)benzoate was obtained using 4-(quinolin-2-ylmethoxy)benzoic acid and methyl 2-amino-5-chlorobenzoate (yield: 34%).

$^1$H-NMR (CDCl$_3$) δ: 3.97 (3H, s), 5.46 (2H, s), 7.09-7.18 (2H, m), 7.51-7.62 (1H, m), 7.53 (1H, dd, J=9.1, 2.6 Hz), 7.66 (1H, d, J=8.5 Hz), 7.71-7.81 (1H, m), 7.84 (1H, dd, J=8.2, 1.1 Hz), 7.95-8.03 (2H, m), 8.04 (1H, d, J=2.6 Hz), 8.10 (1H, d, J=8.4 Hz), 8.21 (1H, d, J=8.5 Hz), 8.91 (1H, d, J=9.1 Hz), 11.88 (1H, s).

(ii) Sodium 5-chloro-2-({[4-(quinolin-2-ylmethoxy) phenyl]carbonyl}amino)benzoate Using the same method as in Example 8-(iii), the target sodium 5-chloro-2-({[4-(quinolin-2-ylmethoxy)phenyl] carbonyl}amino)benzoate was obtained using methyl 5-chloro-2-({[4-(quinolin-2-ylmethoxy)phenyl] carbonyl}amino)benzoate (yield: 93%).

$^1$H-NMR (DMSO-$d_6$) δ: 5.48 (2H, s), 7.17-7.28 (2H, m), 7.38 (1H, dd, J=8.9, 2.8 Hz), 7.59-7.69 (1H, m), 7.72 (1H, d, J=8.5 Hz), 7.76-7.86 (1H, m), 7.95-8.10 (5H, m), 8.45 (1H, d, J=8.5 Hz), 8.70 (1H, d, J=8.9 Hz), 15.32 (1H, s).

Example 101

Production of sodium 5-chloro-2-({(2E)-3-[3-(quinolin-8-yl)phenyl]prop-2-enoyl}amino)benzoate (101)

The target compound (101) was synthesized according to the following Steps (i) to (ii).

(i) Methyl 5-chloro-2-({(2E)-3-[3-(quinolin-8-yl) phenyl]prop-2-enoyl}amino)benzoate Using the same method as in Example 32-(i), methyl 5-chloro-2-({(2E)-3-[3-(quinolin-8-yl)phenyl]propa-2-enoyl}amino)benzoate was obtained using methyl 2-{[(2E)-3-(3-bromophenyl)prop-2-enoyl]amino}-5-chlorobenzoate obtained in Example 89-(i) and 8-quinolinylboronic acid (yield: 48%).

$^1$H-NMR (CDCl$_3$) δ: 3.95 (3H, s), 6.65 (1H, d, J=15.6 Hz), 7.41-7.94 (10H, m), 8.02 (1H, d, J=2.5 Hz), 8.25 (1H, dd, J=8.3, 1.8 Hz), 8.88 (1H, d, J=9.1 Hz), 8.97 (1H, dd, J=4.2, 1.8 Hz), 11.27 (1H, s).

(ii) Sodium 5-chloro-2-({(2E)-3-[3-(quinolin-8-yl) phenyl]prop-2-enoyl}amino)benzoate Using the same method as in Example 8-(iii), the target sodium 5-chloro-2-({(2E)-3-[3-(quinolin-8-yl)phenyl]prop-2-enoyl}amino)benzoate was obtained using methyl 5-chloro-2-({(2E)-3-[3-(quinolin-8-yl)phenyl]prop-2-enoyl}amino)benzoate (yield: 31%).

$^1$H-NMR (DMSO-d$_6$) δ: 6.72 (1H, d, J=15.8 Hz), 7.35 (1H, dd, J=8.8, 2.8 Hz), 7.47-7.80 (6H, m), 7.86 (1H, dd, J=7.1, 1.5 Hz), 7.93 (1H, s), 7.95 (1H, d, J=2.8 Hz), 8.05 (1H, dd, J=8.1, 1.4 Hz), 8.47 (1H, dd, J=8.3, 1.7 Hz), 8.63 (1H, d, J=8.8 Hz), 8.94 (1H, dd, J=4.1, 1.8 Hz), 14.81 (1H, s).

Example 102

Production of N-[4-chloro-2-(1H-tetrazol-5-yl)phenyl]-3-(quinolin-8-yl)benzamide (102)

The target compound (102) was synthesized according to the following Steps (i) to (iii).

(i) 3-Bromo-N-(4-chloro-2-cyanophenyl)benzamide

Using the same method as in Example 3-(i), 3-bromo-N-(4-chloro-2-cyanophenyl)benzamide was obtained using 2-amino-5-chlorobenzonitrile and 3-bromobenzoic acid (yield: 71%).

$^1$H-NMR (CDCl$_3$) δ: 7.41 (1H, t, J=7.9 Hz), 7.58-7.68 (2H, m), 7.75 (1H, ddd, J=7.9, 1.8, 0.9 Hz), 7.80 (1H, ddd, J=7.9, 1.8, 0.9 Hz), 8.09 (1H, t, J=1.8 Hz), 8.30 (1H, brs), 8.49-8.57 (1H, m).

(ii) N-(4-Chloro-2-cyanophenyl)-3-(quinolin-8-yl) benzamide

Using the same method as in Example 32-(i), N-(4-chloro-2-cyanophenyl)-3-(quinolin-8-yl)benzamide was obtained using 3-bromo-N-(4-chloro-2-cyanophenyl)benzamide and 8-quinolineboronic acid (yield: 30%).

$^1$H-NMR (CDCl$_3$) δ: 7.46 (1H, dd, J=8.3, 4.2 Hz), 7.56-7.72 (4H, m), 7.79 (1H, dd, J=7.2, 1.6 Hz), 7.89 (1H, dd, J=8.1, 1.5 Hz), 7.92-8.00 (2H, m), 8.24 (1H, dd, J=8.3, 1.8 Hz), 8.33 (1H, t, J=1.6 Hz), 8.51 (1H, brs), 8.60-8.68 (1H, m), 8.99 (1H, dd, J=4.2, 1.8 Hz).

(iii) N-[4-Chloro-2-(1H-tetrazol-5-yl)phenyl]-3-(quinolin-8-yl)benzamide 240 mg (2.08 mmol) of trimethylsilyl azide and 25.9 mg (0.10 mmol) of dibutyl tin oxide were added to a toluene (50 mL) solution comprising 400 mg (1.04 mmol) of N-(4-chloro-2-cyanophenyl)-3-(quinolin-8-yl)benzamide, and the mixture was stirred at 100° C. for 66 hours. The reaction mixture was condensed, and ethyl acetate was added thereto. Solids were collected by filtration. The obtained solids were recrystallized using DMF/IPE. The resulting solids were suspended in H$_2$O, and stirred at 80° C. for 6 hours. Thereafter, diluted hydrochloric acid was added, and solids were collected by filtration and dried, thereby giving 242 mg of the target N-[4-chloro-2-(1H-tetrazol-5-yl)phenyl]-3-(quinolin-8-yl)benzamide (yield: 54%).

$^1$H-NMR (DMSO-d$_6$) δ: 7.62 (1H, d, J=8.3, 4.2 Hz), 7.67-7.81 (3H, m), 7.89-8.02 (2H, m), 8.04-8.14 (3H, m), 8.35 (1H, s), 8.50 (1H, dd, J=8.3, 1.8 Hz), 8.61 (1H, d, J=9.0 Hz), 8.95 (1H, dd, J=4.2, 1.8 Hz), 11.65 (1H, s).

Example 103

Production of sodium 5-chloro-2-({(2E)-3-[3-(pyridin-3-yl)phenyl]prop-2-enoyl}amino)benzoate (103)

The target compound (103) was synthesized according to the following Steps (i) to (ii).

(i) Methyl 5-chloro-2-({(2E)-3-[3-(pyridin-3-yl)phenyl]prop-2-enoyl}amino)benzoate Using the same method as in Example 32-(i), methyl 5-chloro-2-({(2E)-3-[3-(pyridin-3-yl)phenyl]prop-2-enoyl}amino)benzoate was obtained using methyl 2-{[(2E)-3-(3-bromophenyl)prop-2-enoyl]amino}-5-chlorobenzoate obtained in Example 89-(i) and 3-pyridinboronic acid (yield: 50%).

$^1$H-NMR (CDCl$_3$) δ: 3.98 (3H, s), 6.67 (1H, d, J=15.6 Hz), 7.42 (1H, dd, J=7.9. 4.8, 0.7 Hz), 7.47-7.69 (4H, m), 7.77 (1H, t, J=1.6 Hz), 7.82 (1H, d, J=15.6 Hz), 7.92 (1H, ddd, J=7.9, 2.4, 1.7 Hz), 8.03 (1H, d, J=2.5 Hz), 8.65 (1H, dd, J=4.8, 1.7 Hz), 8.88 (1H, d, J=9.1 Hz), 8.88 (1H, dd, J=2.4, 0.7 Hz), 11.33 (1H, s).

(ii) Sodium 5-chloro-2-({(2E)-3-[3-(pyridin-3-yl) phenyl]prop-2-enoyl}amino)benzoate Using the same method as in Example 8-(iii), the target sodium 5-chloro-2-({(2E)-3-[3-(pyridin-3-yl)phenyl]prop-2-enoyl}amino)benzoate was obtained using methyl 5-chloro-2-({(2E)-3-[3-(pyridin-3-yl)phenyl]prop-2-enoyl}amino)benzoate (yield: 85%).

$^1$H-NMR (DMSO-d$_6$) δ: 6.86 (1H, d, J=15.7 Hz), 7.37 (1H, dd, J=8.8, 2.8 Hz), 7.47-7.62 (2H, m), 7.67 (1H, d, J=15.7 Hz), 7.72-7.82 (2H, m), 7.98 (1H, d, J=2.8 Hz), 8.09 (1H, s), 8.19 (1H, ddd, J=8.0, 2.2, 1.7 Hz), 8.61 (1H, dd, J=4.6, 1.7 Hz), 8.68 (1H, d, J=8.8 Hz), 9.00 (1H, d, J=2.2 Hz), 14.72 (1H, s).

Example 104

Production of 5-chloro-2-({[5-(4-fluorophenyl) thiophen-2-yl]carbonyl}amino)benzoic acid (104)

The target compound (104) was synthesized according to the following steps.

Using the same method as in Example 3-(i), methyl 5-chloro-2-({[5-(4-fluorophenyl)thiophen-2-yl] carbonyl}amino)benzoate was obtained using 5-(4-fluorophenyl)thiophen-2-carboxylic acid and methyl 2-amino-5-chlorobenzoate. Thereafter, using the same method as in Example 3-(ii), the target 5-chloro-2-({[5-(4-fluorophenyl)thiophen-2-yl]carbonyl}amino)benzoic acid was obtained (yield: 47%).

$^1$H-NMR (DMSO-d$_6$) δ: 7.23-7.40 (2H, m), 7.53-7.92 (5H, m), 7.98 (1H, d, J=2.7 Hz), 8.56 (1H, d, J=9.0 Hz), 12.06 (1H, s).

Example 105

Production of 5-chloro-2-{[(5-phenylfuran-2-yl)carbonyl]amino}benzoic acid (105)

The target compound (105) was synthesized according to the following steps.

Using the same method as in Example 3-(i), methyl 5-chloro-2-{[(5-phenylfuran-2-yl)carbonyl]amino}benzoate was obtained using 5-phenylfuran-2-carboxylic acid and methyl 2-amino-5-chlorobenzoate. Thereafter, using the same method as in Example 3-(ii), the target 5-chloro-2-{[(5-phenylfuran-2-yl)carbonyl]amino}benzoic acid was obtained (yield: 77%).

$^1$H-NMR (DMSO-d$_6$) δ: 7.26 (1H, d, J=3.7 Hz), 7.36-7.58 (3H, m), 7.42 (1H, d, J=3.7 Hz), 7.73 (1H, dd, J=9.0, 2.7 Hz), 7.89-7.99 (2H, m), 8.01 (1H, d, J=2.7 Hz), 8.77 (1H, d, J=9.0 Hz), 12.47 (1H, s), 14.33 (1H, brs).

Example 106

Production of sodium 2-[({[4-(adamantan-1-yl)phenyl]amino}(oxo)acetyl)amino]-5-chlorobenzoate (106)

The target compound (106) was synthesized according to the following Steps (i) to (vi).

(i) tert-Butyl[4-(Adamantan-1-yl)phenyl]carbamate 1.18 g (4.29 mmol) of diphenylphosphoryl azide and 434 mg (4.29 mmol) of triethylamine were added to 30 mL of a tert-butanol suspension comprising 1.0 g (3.9 mmol) of 4-(adamantan-1-yl)benzoic acid at 0° C. The mixture was stirred at 80° C. for 4.5 hours, and 40 mL of THF was added. The mixture was stirred for an additional 2 hours. Thereafter, the solvent was distilled off under reduced pressure. Ethyl acetate was added to the residue, and the resultant was washed with an aqueous saturated sodium hydrogen carbonate solution and saturated saline in this order. The resultant was dried over anhydrous sodium sulfate, and the solvent was distilled off under reduced pressure. The obtained crude product was separated and purified by silica gel column chromatography, thereby giving 679 mg of tert-butyl [4-(adamantan-1-yl)phenyl]carbamate (yield: 53%).

$^1$H-NMR (CDCl$_3$) δ: 1.51 (9H, s), 1.71-1.81 (6H, m), 1.84-1.92 (6H, m), 2.02-2.14 (3H, m), 6.40 (1H, brs), 7.26-7.31 (4H, m).

(ii) 4-(Adamantan-1-yl)aniline 4 mL of ethyl acetate was added to 678 mg (2.07 mmol) of tert-butyl [4-(adamantan-1-yl)phenyl]carbamate, and then 4 mL of 4N hydrogen chloride/ethyl acetate was added at 0° C. The mixture was stirred at room temperature for 10 hours. The solvent was distilled off under reduced pressure, and ethyl acetate was added to the residue. The resultant was washed with an aqueous sodium hydrogen carbonate solution and saturated saline in this order, and dried over anhydrous sodium sulfate. The solvent was distilled off under reduced pressure, thereby quantitatively giving 4-(adamantan-1-yl)aniline.

$^1$H-NMR (CDCl$_3$) δ: 1.60-2.17 (15H, m), 3.46 (2H, brs), 6.61-6.71 (2H, m), 7.11-7.21 (2H, m).

(iii) Ethyl {[4-(adamantan-1-yl)phenyl]amino}(oxo)acetate 5 mL of THF was added to 400 mg (1.76 mmol) of 4-(adamantan-1-yl)aniline, after which 292 mg (2.11 mmol) of potassium carbonate was added. 291 mg (1.94 mmol) of ethyl chloroglyoxylate was added at 0° C., and the mixture was stirred at room temperature for 2 hours. Thereafter, the mixture was filtered using silica gel, and the filtrate was condensed. The obtained crude product was then separated and purified by silica gel column chromatography, thereby quantitatively giving ethyl {[4-(adamantan-1-yl)phenyl]amino}(oxo)acetate.

$^1$H-NMR (CDCl$_3$) δ: 1.43 (3H, t, J=7.2 Hz), 1.64-2.18 (15H, m), 4.42 (2H, q, J=7.2 Hz), 7.32-7.41 (2H, m), 7.53-7.62 (2H, m), 8.85 (1H, s).

(iv) {[4-(Adamantan-1-yl)phenyl]amino}(oxo)acetic acid

THF (18 mL) and ethanol (6 mL) were added to 600 mg (1.83 mmol) of ethyl {[4-(adamantan-1-yl)phenyl]amino}(oxo)acetate. Thereafter, 2.7 mL of 1N aqueous sodium hydroxide solution was added, and the mixture was heated at 70° C. for 2 hours. Next, 1N hydrochloric acid was added to acidify the mixture, and the organic solvent was distilled off under reduced pressure. The resulting solids were filtered and washed with H$_2$O and n-hexane, followed by drying, thereby giving 492 mg of {[4-(adamantan-1-yl)phenyl]amino}(oxo)acetic acid (yield: 90%).

$^1$H-NMR (DNSO-d$_6$) δ: 1.52-2.13 (15H, m), 7.27-7.38 (2H, m), 7.62-7.72 (2H, m), 10.65 (1H, s).

(v) Methyl 2-[({[4-(adamantan-1-yl)phenyl]amino}(oxo)acetyl)amino]-5-chlorobenzoate Using the same method as in Example 3-(i), methyl 2-[({[4-(adamantan-1-yl)phenyl]amino}(oxo)acetyl)amino]-5-chlorobenzoate was obtained using {[4-(adamantan-1-yl)phenyl]amino}(oxo)acetic acid and methyl 2-amino-5-chlorobenzoate (yield: 84%).

$^1$H-NMR (DMSO-d$_6$) δ: 1.55-2.16 (15H, m), 3.93 (3H, s), 7.29-7.41 (2H, m), 7.73-7.83 (2H, m), 7.83 (1H, dd, J=9.0, 2.6 Hz), 8.01 (1H, d, J=2.6 Hz), 8.65 (1H, d, J=9.0 Hz), 10.92 (1H, s), 12.39 (1H, s).

(vi) Sodium 2-[({[4-(adamantan-1-yl)phenyl]amino}(oxo)acetyl)amino]-5-chlorobenzoate Using the same method as in Example 8-(iii), the target sodium 2-[({[4-(adamantan-1-yl)phenyl]amino}(oxo)acetyl)amino]-5-chlorobenzoate was obtained using methyl 2-[({[4-(adamantan-1-yl)phenyl]amino}(oxo)acetyl)amino]-5-chlorobenzoate (yield: 68%).

$^1$H-NMR (DMSO-d$_6$) δ: 1.62-2.14 (15H, m), 7.29-7.39 (2H, m), 7.43 (1H, dd, J=8.8, 2.8 Hz), 7.73-7.84 (2H, m), 7.99 (1H, d, J=2.8 Hz), 8.60 (1H, d, =8.8 Hz), 10.65 (1H, s), 15.39 (1H, s).

Example 107

Production of sodium 5-chloro-2-{[(2-phenylquinolin-4-yl)carbonyl]amino}benzoate (107)

The target compound (107) was synthesized according to the following Steps (i) to (ii).

(i) Methyl 5-chloro-2-{[(2-phenylquinolin-4-yl)carbonyl]amino}benzoate

Using the same method as in Example 3-(i), methyl 5-chloro-2-{[(2-phenylquinolin-4-yl)carbonyl]amino}benzoate was obtained using 2-phenylquinoline-4-carboxylic acid and methyl 2-amino-5-chlorobenzoate (yield: 44%).

$^1$H-NMR (CDCl$_3$) δ: 3.90 (3H, s), 7.42-7.68 (5H, m), 7.80 (1H, ddd, J=8.3, 6.9, 1.4 Hz), 8.09 (1H, d, J=2.6 Hz), 8.16 (1H, s), 8.18-8.29 (3H, m), 8.40 (1H, dd, J=8.4, 0.9 Hz), 8.99 (1H, d, J=9.1 Hz), 11.85 (1H, s).

(ii) Sodium 5-chloro-2-{[(2-phenylquinolin-4-yl)carbonyl]amino}benzoate

Using the same method as in Example 8-(iii), the target sodium 5-chloro-2-{[(2-phenylquinolin-4-yl)carbonyl]amino}benzoate was obtained using methyl 5-chloro-2-{[(2-phenylquinolin-4-yl)carbonyl]amino}benzoate (yield: 89%).

$^1$H-NMR (DMSO-d$_6$) δ: 7.50 (1H, dd, J=8.8, 2.8 Hz), 7.58-7.66 (3H, m), 7.68 (1H, ddd, J=8.2, 7.0, 1.2 Hz), 7.87 (1H, ddd, J=8.2, 6.8, 1.3 Hz), 8.03 (1H, d, J=2.8 Hz), 8.19 (1H, d, J=8.2 Hz), 8.29-8.46 (3H, m), 8.39 (1H, s), 8.77 (1H, d, J=8.8 Hz), 15.67 (1H, s).

Test Example 1

Measurement of PAI-1 Inhibitory Activity

Each of compounds (1) to (7) and (9) to (14) prepared in Examples 1 to 14, and the known compounds (1) and (2) (see Table 1) was evaluated for inhibitory activity against human PAI-1 (manufactured by Molecular Innovations, Inc. (USA); the same applies hereinafter).

Specifically, human-derived PAI-1 was added to a 0.1% Tween 80-containing 100 mM Tris-HCl (pH 8) solution containing each of the above compounds in a given concentration (0.29 mM or 0.12 mM), and the mixture was incubated at 37° C. for 15 minutes. Subsequently, human-derived tissue plasminogen activator (t-PA) (manufactured by American Diagnostica, Inc. (USA); the same applies hereinafter) adjusted to 0.35 pmol/μL, was added thereto, and the mixture was further incubated at 37° C. for 15 minutes. Then, 1.25 mM of S-2288 synthetic substrate (manufactured by Chromogenix, (Italy); the same applies hereinafter), which was a chromogenic substrate, was added. The final mixture contained 100 mM Tris-HCl (pH 8), 30 mM NaCl, 1% DMSO, 0.1% Tween 80, 67 nM PAI-1, 9.8 nM t-PA, 1 mM S-2288 synthetic substrate, and the compound (50 μM or 20 μM).

Free radical p-nitroaniline removed from the chromogenic substrate (S-2288) by t-PA action was measured using a spectrophotometer at an absorbance of 405 nm at 5-minute intervals for 30 minutes. A systems that did not contain each of compounds (1) to (7) and (9) to (14) was similarly evaluated, and the PAI-1 activity of the system after 30 minutes was taken as 100% to evaluate the PAI-1 activity of a system in which test compound was added. The results are shown in Table 1.

TABLE 1

| Examples | Compounds | Formula M.W. | PAI-1 activity % 50 μM | PAI-1 activity % 20 μM |
|---|---|---|---|---|
| 1 | 5-chloro-2-{[4-({[3-(furan-3-yl)phenyl]carbonyl}amino)butanoyl]amino}benzoic acid | C22H19ClN2O5 426.85 | 48.9 | 95.5 |
| 2 | 5-chloro-2-({[3-(furan-3-yl)phenyl]carbonyl}amino)benzoic acid | C18H12ClNO4 341.75 | 8.7 | 49.0 |
| 3 | 5-chloro-2-({[3-(furan-3-yl)phenyl]acetyl}amino)benzoic acid | C19H14ClNO4 355.77 | 19.6 | 63.7 |
| 4 | 2-[(biphenyl-3-ylcarbonyl)amino]-5-chlorobenzoic acid | C20H14ClNO3 351.78 | 7.6 | 47.7 |
| 5 | 2-({[3-(furan-3-yl)phenyl]carbonyl}amino)-5-methyl-4-phenylthiophene-3-carboxylic acid | C23H17NO4S 403.45 | 6.1 | 14.7 |
| 6 | 2-[(biphenyl-2-ylcarbonyl)amino]-5-chlorobenzoic acid | C20H14ClNO3 351.78 | 22.2 | 51.4 |
| 7 | 5-chloro-2-({[4-(thiophen-2-yl)phenyl]carbonyl}amino)benzoic acid | C18H12ClNO3S 357.81 | 7.4 | 54.2 |
| 9 | 5-chloro-2-[(1-{[3-(furan-3-yl)phenyl]acetyl}-L-prolyl)amino]benzoic acid | C24H21ClN2O5 452.89 | 53.2 | 98.1 |
| 10 | 5-chloro-2-[(1-{[3-(furan-3-yl)phenyl]carbonyl}-L-prolyl)amino]benzoic acid | C23H19ClN2O5 438.86 | 38.3 | 73.0 |
| 11 | sodium 5-chloro-2-{[(1-{[3-(furan-3-yl)phenyl]carbonyl}piperidin-3-yl)carbonyl]amino}benzoate | C24H20ClN2NaO5 474.87 | 26.1 | 68.2 |
| 12 | 5-chloro-2-{[(1-{[3-(furan-3-yl)phenyl]acetyl}piperidin-3-yl)carbonyl]amino}benzoic acid | C25H23ClN2O5 466.91 | 15.7 | 57.7 |
| 13 | 5-chloro-2-({[3-(furan-3-yl)phenoxy]acetyl}amino)benzoic acid | C19H14ClNO5 371.77 | 8.2 | 39.9 |
| 14 | 5-chloro-2-({[5-(furan-3-yl)-1-methyl-1H-indol-3-yl](oxo)acetyl}amino)benzoic acid | C22H15ClN2O5 422.82 | 12.9 | 22.1 |
| Known compound (1) | 2-{[(4-tert-butylphenyl) carbonyl] amino}-5-chlorobenzoic acid | C18H18ClNO3 331.79 | 11.0 | 44.0 |
| Known compound (2) | 2-[(biphenyl-4-ylcarbonyl) amino]-5-chlorobenzoic acid | C20H14ClNO3 351.78 | 8.0 | 41.8 |

Test Example 2

Measurement of PAI-1 Inhibitory Activity

Each of compounds (2), (4), (5), (7), (8), (13), (14), and (15) to (107) prepared in Examples 2, 4, 5, 7, 8, and 13 to 107, the known compounds (1) to (6), and hydrochloride salt of the known compound (7) (see Table 1) was used as a test compound and evaluated for inhibitory activity against human PAI-1 (manufactured by Molecular Innovations, Inc. (USA); the same applies hereinafter).

Specifically, human PAI-1 was added to a 0.1% PEG-6000- and 0.2 mM CHAPS-containing 50 mM tris-HCL (pH 8) solution containing each of the above compounds in a given concentration (62.5 µM or 15.6 µM), and the mixture was incubated at 37° C. for 15 minutes. Subsequently, human-derived tissue plasminogen activator (t-PA) (manufactured by American Diagnostica, Inc. (USA); the same applies hereinafter) adjusted to 0.05 pmol/µL was added thereto, and the mixture was further incubated at 37° C. for 60 minutes. Then, 0.25 mM of Spectrozyme t-PA synthetic substrate (manufactured by American Diagnostica, Inc. (USA); the same applies hereinafter), which is a chromogenic substrate, was added. The final mixture contained 50 mM Tris-HCl (pH 8), 150 mM NaCl, 1% DMSO, 0.1% PEG-6000, 0.2 mM CHAPS, 5 nMPAI-1, 2 nM t-PA, 0.2 mM Spectrozyme t-PA synthetic substrate, and the compound (10 µM or 2.5 µM).

Free radical p-nitroaniline removed from the chromogenic substrate (Spectrozyme t-PA) by t-PA action was measured using a spectrophotometer at an absorbance of 405 nm at 20-minute intervals, for 120 minutes. A system that did not contain the test compounds was similarly evaluated, and the PAI-1 activity of the system after 120 minutes was taken as 100% to evaluate the PAI-1 activity of a system to which a test compound was added. The results are shown in Tables 2-1 to 2-8.

[Tables 2-1 to 2-8]

TABLE 2-1

| Examples | Compounds | Formula M.W. | PAI-1 activity % 10 µM | PAI-1 activity % 2.5 µM |
|---|---|---|---|---|
| 2 | 5-chloro-2-({[3-(furan-3-yl)phenyl]carbonyl}amino)benzoic acid | C18H12ClNO4 341.75 | 12.7 | 100.6 |
| 4 | 2-[(biphenyl-3-ylcarbonyl)amino]-5-chlorobenzoic acid | C20H14ClNO3 351.78 | 0.6 | 62.1 |
| 5 | 2-({[3-(furan-3-yl)phenyl]carbonyl}amino)-5-methyl-4-phenylthiophene-3-carboxylic acid | C23H17NO4S 403.45 | 0.3 | 46.4 |
| 7 | 5-chloro-2-({[4-(thiophen-2-yl)phenyl]carbonyl}amino)benzoic acid | C18H12ClNO3S 357.81 | 0.4 | 99.8 |
| 8 | sodium 5-chloro-2-({[3-(pyridin-4-yl)phenyl]carbonyl}amino)benzoate | C19H12ClN2NaO3 374.75 | 28.5 | 100.3 |
| 13 | 5-chloro-2-({[3-(furan-3-yl)phenoxy]acetyl}amino)benzoic acid | C19H14ClNO5 371.77 | 4.9 | 92.7 |
| 14 | 5-chloro-2-({[5-(furan-3-yl)-1-methyl-1H-indol-3-yl](oxo)acetyl}amino)benzoic acid | C22H15ClN2O5 422.82 | 4.3 | 87.4 |
| 15 | 5-bromo-2-({[3-(furan-3-yl)phenoxy]acetyl}amino)benzoic acid | C19H14BrNO5 416.22 | 3.0 | 87.3 |
| 16 | 2-{[(3-tert-butylphenoxy)acetyl]amino}-5-chlorobenzoic acid | C19H20ClNO4 361.82 | 21.9 | 77.4 |
| 17 | 5-chloro-2-{[(2-cyclohexylphenoxy)acetyl]amino}benzoic acid | C21H22ClNO4 387.86 | 0.8 | 52.8 |
| 18 | 2-{[(4-tert-butylphenoxy)acetyl]amino}-5-chlorobenzoic acid | C19H20ClNO4 361.82 | 16.1 | 81.4 |
| 19 | 2-{[(biphenyl-4-yloxy)acetyl]amino}-5-chlorobenzoic acid | C21H16ClNO4 381.81 | 2.5 | 72.4 |
| 20 | 2-{[(biphenyl-3-yloxy)acetyl]amino}-5-chlorobenzoic acid | C21H16ClNO4 381.81 | 1.9 | 55.7 |
| 21 | 2-({[4-(adamantan-1-yl)phenoxy]acetyl}amino)-5-chlorobenzoic acid | C25H26ClNO4 439.93 | 0.3 | 10.0 |
| 22 | 4-({[3-(furan-3-yl)phenoxy]acetyl}amino)biphenyl-3-carboxylic acid | C25H19NO5 413.42 | 0.4 | 29.9 |

TABLE 2-2

| Examples | Compounds | Formula M.W. | PAI-1 activity % 10 µM | PAI-1 activity % 2.5 µM |
|---|---|---|---|---|
| 23 | 2-{[(5-bromo-1-methyl-1H-indol-2-yl)carbonyl]amino}-5-chlorobenzoic acid | C17H12BrClN2O3 407.65 | 1.8 | 97.3 |
| 24 | 2-{[(5-bromo-1H-indol-1-yl)acetyl]amino}-5-chlorobenzoic acid | C17H12BrClN2O3 407.65 | 19.1 | 101.5 |
| 25 | 5-chloro-2-({[3-(cyclohex-1-en-1-yl)phenoxy]acetyl}amino)benzoic acid | C21H20ClNO4 385.84 | 0.0 | 85.8 |
| 26 | 5-chloro-2-{[(3-cyclohexylphenoxy)acetyl]amino}benzoic acid | C21H22ClNO4 387.86 | 0.6 | 98.0 |

TABLE 2-2-continued

|  |  |  | PAI-1 activity % | |
|---|---|---|---|---|
| Examples | Compounds | Formula M.W. | 10 μM | 2.5 μM |
| 27 | 4-({[3-(furan-3-yl)phenoxy]acetyl}amino)-3'-methylbiphenyl-3-carboxylic acid | C26H21NO5 427.45 | 0.7 | 69.1 |
| 28 | 4-({[3-(furan-3-yl)phenoxy]acetyl}amino)-3',5'-dimethylbiphenyl-3-carboxylic acid | C27H23NO5 441.48 | 0.5 | 33.6 |
| 29 | 5-chloro-2-({[4-(furan-3-yl)phenoxy]acetyl}amino)benzoic acid | C19H14ClNO5 371.77 | 24.3 | 93.2 |
| 30 | 2-({[3-(adamantan-1-yl)phenoxy]acetyl}amino)-5-chlorobenzoic acid | C25H26ClNO4 439.93 | 1.3 | 19.3 |
| 31 | 2-({[1-(biphenyl-3-ylcarbonyl)piperidin-3-yl]carbonyl}amino)-5-chlorobenzoic acid | C26H23ClN2O4 462.92 | 20.2 | 88.0 |
| 32 | 5-chloro-2-{[(4'-methylbiphenyl-3-yl)carbonyl]amino}benzoic acid | C21H16ClNO3 365.81 | 1.7 | 94.4 |
| 33 | 5-chloro-2-{[(2'-methoxybiphenyl-3-yl)carbonyl]amino}benzoic acid | C21H16ClNO4 381.81 | 21.6 | 92.8 |
| 34 | 5-chloro-2-({[4-(3,6-dihydro-2H-pyran-4-yl)phenyl]carbonyl}amino)benzoic acid | C19H16ClNO4 357.79 | 45.1 | 97.1 |
| 35 | 5-chloro-2-[({1-[3-(furan-3-yl)phenyl]cyclopropyl}carbonyl)amino]benzoic acid | C21H16ClNO4 381.81 | 15.6 | 98.8 |
| 36 | 5-chloro-2-({3-[3-(furan-3-yl)phenyl]propanoyl}amino)benzoic acid | C20H16ClNO4 369.80 | 3.7 | 95.7 |
| 37 | 5-chloro-2-({2-[3-(furan-3-yl)phenyl]-2-methylpropanoyl}amino)benzoic acid | C21H18ClNO4 383.82 | 5.9 | 53.1 |

TABLE 2-3

|  |  |  | PAI-1 activity % | |
|---|---|---|---|---|
| Examples | Compounds | Formula M.W. | 10 μM | 2.5 μM |
| 38 | 5-chloro-2-[(9H-fluoren-1-ylcarbonyl)amino]benzoic acid | C21H14ClNO3 363.79 | 2.5 | 94.8 |
| 39 | 5-chloro-2-[(2,2-diphenylpropanoyl)amino]benzoic acid | C22H18ClNO3 379.84 | 22.1 | 88.6 |
| 40 | 2-({[4-(adamantan-1-yl)phenyl]carbonyl}amino)-5-chlorobenzoic acid | C24H24ClNO3 409.91 | 1.7 | 19.3 |
| 41 | 5-chloro-2-[(3,3-diphenylpropanoyl)amino]benzoic acid | C22H18ClNO3 379.84 | 12.9 | 72.4 |
| 42 | 5-chloro-2-{[(4-phenoxyphenyl)carbonyl]amino}benzoic acid | C20H14ClNO4 367.78 | 3.8 | 98.6 |
| 43 | 2-({[3,5-bis(trifluoro-methyl)phenyl]carbonyl}amino)-5-chlorobenzoic acid | C16H8ClF6NO3 411.68 | 14.1 | 98.4 |
| 44 | 5-chloro-2-({2-[3-(furan-3-yl)phenoxy]-2-methylpropanoyl}amino)benzoic acid | C21H18ClNO5 399.82 | 20.4 | 97.8 |
| 45 | 4-{[(biphenyl-3-yloxy)acetyl]amino}biphenyl-3-carboxylic acid | C27H21NO4 423.46 | 0.9 | 76.9 |
| 46 | 2-{[(biphenyl-4-yloxy)acetyl]amino}-5-(furan-3-yl)benzoic acid | C25H19NO5 413.42 | 0.4 | 69.9 |
| 47 | 2-({[4-(adamantan-1-yl)phenoxy]acetyl}amino)-5-(furan-3-yl)benzoic acid | C29H29NO5 471.54 | 0.6 | 9.7 |
| 48 | 5-chloro-2-{[(1-methyl-5-phenyl-1H-indol-2-yl)carbonyl]amino}benzoic acid | C23H17ClN2O3 404.85 | 1.7 | 2.5 |
| 49 | 5-chloro-2-({[(4'-methylbiphenyl-4-yl)oxy]acetyl}amino)benzoic acid | C22H18ClNO4 395.84 | 1.1 | 82.1 |
| 50 | 5-chloro-2-({[(3',5'-dimethylbiphenyl-4-yl)oxy]acetyl}amino)benzoic acid | C23H20ClNO4 409.86 | 0.1 | 58.9 |
| 51 | 5-chloro-2-{[(5-phenyl-1H-indol-1-yl)acetyl]amino}benzoic acid | C23H17ClN2O3 404.85 | 1.7 | 37.8 |
| 52 | 2-({[4-(adamantan-1-ylmethoxy)phenyl]carbonyl}amino)-5-chlorobenzoic acid | C25H26ClNO4 439.93 | 5.1 | 7.2 |

TABLE 2-4

| Examples | Compounds | Formula M.W. | PAI-1 activity % 10 μM | PAI-1 activity % 2.5 μM |
|---|---|---|---|---|
| 53 | 5-chloro-2-({[3-(furan-2-yl)phenoxy]acetyl}amino)benzoic acid | C19H14ClNO5 371.77 | 21.6 | 95.3 |
| 54 | 5-chloro-2-({[4-(furan-2-yl)phenoxy]acetyl}amino)benzoic acid | C19H14ClNO5 371.77 | 15.5 | 94.4 |
| 55 | 2-({4-[4-(adamantan-1-yl)phenoxy]butanoyl}amino)-5-chlorobenzoic acid | C27H30ClNO4 467.98 | 1.1 | 29.8 |
| 56 | 2-({[4-(adamantan-1-ylcarbonyl)phenyl]carbonyl}amino)-5-chlorobenzoic acid | C25H24ClNO4 437.92 | 0.7 | 75.8 |
| 57 | 2-({[5-(benzyloxy)-1H-indol-3-yl](oxo)acetyl}amino)-5-chlorobenzoic acid | C24H17ClN2O5 448.85 | 0.2 | 38.6 |
| 58 | 5-chloro-2-({[3-(naphthalen-1-yl)phenyl]carbonyl}amino)benzoic acid | C24H16ClNO3 401.84 | 0.0 | 0.0 |
| 59 | 2-({3-[4-(adamantan-1-yl)phenoxy]propanoyl}amino)-5-chlorobenzoic acid | C26H28ClNO4 453.96 | 1.4 | 56.3 |
| 60 | 5-chloro-2-({[1-(3-hydroxypropyl)-5-phenyl-1H-indol-2-yl]carbonyl}amino)benzoic acid | C25H21ClN2O4 448.90 | 0.9 | 25.0 |
| 61 | 5-chloro-2-({[(2'-methoxybiphenyl-3-yl)oxy]acetyl}amino)benzoic acid | C22H18ClNO5 411.84 | 38.9 | 92.4 |
| 62 | 2-({[3-(adamantan-1-yl)phenyl]carbonyl}amino)-5-chlorobenzoic acid | C24H24ClNO3 409.91 | 0.6 | 29.1 |
| 63 | sodium 5-chloro-2-({[3-(quinolin-3-yl)phenyl]carbonyl}amino)benzoate | C23H14ClN2NaO3 424.81 | 0.3 | 21.3 |
| 64 | sodium 5-chloro-2-({[3-(isoquinolin-4-yl)phenyl]carbonyl}amino)benzoate | C23H14ClN2NaO3 424.81 | 0.7 | 74.3 |
| 65 | sodium 5-chloro-2-({[3-(quinolin-6-yl)phenyl]carbonyl}amino)benzoate | C23H14ClN2NaO3 424.81 | 0.4 | 71.7 |
| 66 | sodium 5-chloro-2-({[3-(isoquinolin-5-yl)phenyl]carbonyl}amino)benzoate | C23H14ClN2NaO3 424.81 | 0.1 | 22.6 |
| 67 | sodium 5-chloro-2-({[4-(quinolin-8-yl)phenyl]carbonyl}amino)benzoate | C23H14ClN2NaO3 424.81 | 0.6 | 90.4 |

TABLE 2-5

| Examples | Compounds | Formula M.W. | PAI-1 activity % 10 μM | PAI-1 activity % 2.5 μM |
|---|---|---|---|---|
| 68 | sodium 5-chloro-2-({[3-(quinolin-8-yl)phenyl]carbonyl}amino)benzoate | C23H14ClN2NaO3 424.81 | 2.1 | 2.4 |
| 69 | 5-chloro-2-{[(4-cyclohexylphenyl)carbonyl]amino}benzoic acid | C20H20ClNO3 357.83 | 0.6 | 44.7 |
| 70 | 2-[(biphenyl-4-ylacetyl)amino]-5-chlorobenzoic acid | C21H16ClNO3 365.81 | 4.4 | 94.6 |
| 71 | 2-[(biphenyl-4-ylcarbamoyl)amino]-5-chlorobenzoic acid | C20H15ClN2O3 366.80 | 2.1 | 39.6 |
| 72 | 5-chloro-2-{[N-(4'-fluoro-4-methylbiphenyl-3-yl)glycyl]amino}benzoic acid | C22H18ClFN2O3 412.84 | 3.6 | 31.1 |
| 73 | 5-chloro-2-{[N-(diphenylmethyl)glycyl]amino}benzoic acid | C22H19ClN2O3 394.85 | 31.2 | 82.2 |
| 74 | 2-{[(4-cyclohexylphenyl)carbonyl]amino}-5-methyl-4-phenylthiophene-3-carboxylic acid | C25H25NO3S 419.54 | 0.2 | 8.6 |
| 75 | 5-chloro-2-({[4-(diphenylmethyl)piperazin-1-yl]carbonyl}amino)benzoic acid hydrochloride | C25H25Cl2N3O3 486.39 | 4.7 | 86.4 |
| 76 | 5-chloro-2-{[(diphenylmethoxy)acetyl]amino}benzoic acid | C22H18ClNO4 395.84 | 30.6 | 92.9 |
| 77 | 5-chloro-2-({[4-(diphenylmethyl)piperazin-1-yl]acetyl}amino)benzoic acid | C26H26ClN3O3 463.96 | 19.3 | 89.6 |
| 78 | 2-{[(2E)-3-(bipheny-4-yl)prop-2-enoyl]amino}-5-chlorobenzoic acid | C22H16ClNO3 377.82 | 0.3 | 25.3 |
| 79 | 5-chloro-2-({[3-(cyclohex-1-en-1-yl)phenyl]carbonyl}amino)benzoic acid | C20H18ClNO3 355.81 | 1.6 | 44.5 |
| 80 | 5-chloro-2-{[(3-cyclohexylphenyl)carbonyl]amino}benzoic acid | C20H20ClNO3 357.83 | 0.0 | 45.5 |
| 81 | 5-(cyclohex-1-en-1-yl)-2-{[(4-cyclohexylphenyl)carbonyl]amino}benzoic acid | C26H29NO3 403.51 | 0.0 | 1.0 |
| 82 | 5-cyclohexyl-2-{[(4-cyclohexylphenyl)carbonyl]amino}benzoic acid | C26H31NO3 405.53 | 1.4 | 1.7 |

TABLE 2-6

| Examples | Compounds | Formula M.W. | PAI-1 activity % 10 µM | PAI-1 activity % 2.5 µM |
|---|---|---|---|---|
| 83 | 5-chloro-2-({[4-(pyrrolidin-1-yl)phenyl]carbonyl}amino)benzoic acid hydrochloride | C18H18Cl2N2O3 381.25 | 26.6 | 99.1 |
| 84 | 5-chloro-2-[(spiro[5.5]undec-1-en-2-ylcarbonyl)amino]benzoic acid | C19H22ClNO3 347.84 | 5.5 | 97.0 |
| 85 | 5-chloro-2-[(spiro[5.5]undec-2-ylcarbonyl)amino]benzoic acid | C19H24ClNO3 349.85 | 11.0 | 97.5 |
| 86 | 5-chloro-2-({[3-(4-methylphenyl)adamantan-1-yl]carbonyl}amino)benzoic acid | C25H26ClNO3 423.93 | 1.4 | 63.5 |
| 87 | 5-chloro-2-({[3-(cyclohexylethynyl)phenyl]carbonyl}amino)benzoic acid | C22H20ClNO3 381.85 | 1.2 | 20.5 |
| 88 | 5-chloro-2-({[4-(cyclohexylethynyl)phenyl]carbonyl}amino)benzoic acid | C22H20ClNO3 381.85 | 0.8 | 35.5 |
| 89 | 2-{[(2E)-3-(biphenyl-3-yl)prop-2-enoyl]amino}-5-chlorobenzoic acid | C22H16ClNO3 377.82 | 0.1 | 60.7 |
| 90 | 5-chloro-2-({(2E)-3-[3-(cyclohex-1-en-1-yl)phenyl]prop-2-enoyl}amino)benzoic acid | C22H20ClNO3 381.85 | 0.1 | 65.3 |
| 91 | 5-chloro-2-{[(2E)-3-chloro-3-cyclohexylprop-2-enoyl]amino}benzoic acid | C16H17Cl2NO3 342.22 | 16.7 | 96.9 |
| 92 | 5-(cyclohexylethynyl)-2-{[(4-cyclohexylphenyl)carbonyl]amino}benzoic acid | C28H31NO3 429.55 | 0.4 | 0.0 |
| 93 | 5-(2-cyclohexylethyl)-2-{[(4-cyclohexylphenyl)carbonyl]amino}benzoic acid | C28H35NO3 433.58 | 0.0 | 0.0 |
| 94 | 2-({3-[4-(adamantan-1-yl)phenyl]prop-2-ynoyl}amino)-5-chlorobenzoic acid | C26H24ClNO3 433.93 | 7.4 | 3.5 |
| 95 | 2-{[(4-cyclohexylphenyl)carbonyl]amino}-5-ethynylbenzoic acid | C22H21NO3 347.41 | 0.3 | 80.5 |
| 96 | 2-({[4-(adamantan-1-ylmethyl)phenyl]carbonyl}amino)-5-chlorobenzoic acid | C25H26ClNO3 423.93 | 5.0 | 23.9 |
| 97 | 2-[({4-[adamantan-1-yl(hydroxy)methyl]phenyl}carbonyl)amino]-5-chlorobenzoic acid | C25H26ClNO4 439.93 | 0.7 | 89.9 |

TABLE 2-7

| Examples | Compounds | Formula M.W. | PAI-1 activity % 10 µM | PAI-1 activity % 2.5 µM |
|---|---|---|---|---|
| 98 | 5-chloro-2-({[4-(1-methylcyclohexyl)phenyl]carbonyl}amino)benzoic acid | C21H22ClNO3 371.86 | 0.1 | 41.5 |
| 99 | sodium 5-chloro-2-({[3-(quinolin-2-ylmethoxy)phenyl]carbonyl}amino)benzoate | C24H16ClN2NaO4 454.84 | 0.3 | 87.8 |
| 100 | sodium 5-chloro-2-({[4-(quinolin-2-ylmethoxy)phenyl]carbonyl}amino)benzoate | C24H16ClN2NaO4 454.84 | 0.7 | 92.1 |
| 101 | sodium 5-chloro-2-({(2E)-3-[3-(quinolin-8-yl)phenyl]prop-2-enoyl}amino)benzoate | C25H16ClN2NaO3 450.85 | 0.2 | 24.7 |
| 102 | N-[4-chloro-2-(1H-tetrazol-5-yl)phenyl]-3-(quinolin-8-yl)benzamide | C23H15ClN6O 426.86 | 1.5 | 91.3 |
| 103 | sodium 5-chloro-2-({(2E)-3-[3-(pyridin-3-yl)phenyl]prop-2-enoyl}amino)benzoate | C21H14ClN2NaO3 400.79 | 34.2 | 92.3 |
| 104 | 5-chloro-2-({[5-(4-fluorophenyl)thiophen-2-yl]carbonyl}amino)benzoic acid | C18H11ClFNO3S 375.80 | 0.9 | 84.8 |
| 105 | 5-chloro-2-{[(5-phenylfuran-2-yl)carbonyl]amino}benzoic acid | C18H12ClNO4 341.75 | 23.5 | 89.9 |
| 106 | sodium 2-[({[4-(adamantan-1-yl)phenyl]amino}(oxo)acetyl)amino]-5-chlorobenzoate | C25H24ClN2NaO4 474.91 | 26.3 | 88.4 |
| 107 | sodium 5-chloro-2-{[(2-phenylquinolin4-yl)carbonyl]amino}benzoate | C23H14ClN2NaO3 424.81 | 6.7 | 100.0 |

TABLE 2-8

| Examples | Compounds | Formula M.W. | PAI-1 activity % | |
| --- | --- | --- | --- | --- |
| Known compound (1) | 2-{[(4-tert-butylphenyl) carbonyl] amino}-5-chlorobenzoic acid | C18H18ClNO3 331.79 | 12.7 | 100.5 |
| Known compound (2) | 2-[(biphenyl-4-ylcarbonyl) amino]-5-chlorobenzoic acid | C20H14ClNO3 351.78 | 0.2 | 70.7 |
| Known compound (3) | 5-chloro-2-{[(4-cyclohexylphenoxy)acetyl]amino} benzoic acid | C21H22ClNO4 387.86 | 0.3 | 36.3 |
| Known compound (4) | 5-chloro-2-{[(4-(phenylcarbonyl)phenyl]carbonyl}amino} benzoic acid | C21H14ClNO4 379.79 | 8.1 | 79.6 |
| Known compound (5) | 5-chloro-2-[(5,6,7,8-tetrahydronaphthalene-2-ylcarbonyl)amino] benzoic acid | C18H16ClNO3 329.78 | 18.8 | 98.5 |
| Known compound (6) | 5-chloro-2-[(diphenylacetyl)amino] benzoic acid | C21H16ClNO3 365.81 | 37.4 | 85.0 |
| Salt of Known compound (7) | 5-chloro-2-({[4-(1H-pyrrol-1-yl)phenyl]carbonyl}amino)benzoic acid hydrochloride | C18H14Cl2N2O3 377.22 | 3.7 | 100.1 |

Test Example 3

The Antithrombotic Effect Confirmation Test in a Rat Model of Ferric Chloride-Induced Thrombosis The antithrombotic effect of each of compounds (4), (13), (68), and (79) prepared in Examples 4, 13, 68, and 79 (hereinafter referred to as a test compound) was confirmed using a rat model of ferric chloride-induced thrombosis.

Male 9-week-old SD rats (Japan SLC) were used, and divided into a vehicle group and a test compound group (each having n=10). Two hours before the operation for performing a test, in the test compound group, a 0.5% aqueous sodium carboxymethylcellulose (CMC) solution obtained by suspending a test compound in a mortar was added so that the test compound was orally administered in an amount of 0.3 mg/kg or 1 mg/kg. In the vehicle group, a 0.5% CMC aqueous solution that contained no test compound was orally administered. Two hours after oral administration, the rats in each group were anesthetized using 50 mg/kg i.p., and the following operations were performed on a heat pad that had been kept at 38° C.

An incision was made on the cervical skin, and the left carotid artery was exposed in such a manner that the cervical skeletal muscle was not injured. The adhesion tissue was carefully peeled off. Silk thread was placed over the carotid artery, and filter paper was put on the backside of the carotid artery to prevent effusion and facilitate experiment operations. A semicircular tube 5 mm in length (SP 110, inside diameter: 1.5 mm, produced by Natsume Seisakusho Co., Ltd.) was placed on the filter paper, and the blood vessel was placed in the tube. The carotid artery blood flow was measured using a cuff-type Doppler blood flow meter (inside diameter: 1 mm) placed at the periphery side, and recorded on a recorder (Graphtec WR3320) via an amplifier (Nihon Kohden, RMP-6004M). After the carotid artery blood flow was confirmed, filter paper (Whatman, No. 1, 2.5 mm×4.2 mm), to which 2 µL of physiological saline comprising 35% (w/w) ferric chloride was added dropwise, was wrapped around the origin of the carotid artery (the filter paper was positioned so that the length in the blood vessel circumferential direction was 4.2 mm). Five minutes later, the filter paper was removed from the blood vessel, and the blood vessel was thoroughly washed in 0.5 mL of physiological saline filled into a syringe. Observation was then continued until a blood clot was formed and the carotid artery was occluded (maximum 30 minutes). The blood flow was considered to be occluded when the average blood flow indicated zero on the chart.

The results are shown in FIG. 1. Observation reveals that, in the test compound group, the initial occlusion time was significantly prolonged, as shown in FIG. 1, compared to the vehicle group; and confirms that the compounds of the present invention (compounds (4), (13), (68), and (79)) had an excellent antithrombotic effect.

Reference Test Example

2-[3-(3'-Carboxy-4'-phenylthiophen-2'-ylcarbamoyl)-pentanoylamino]-4-phenylthiophen-3-carboxylic acid (hereinafter referred to as "compound a"), and 2-[3-(3'-carboxy-4'-thienylthiophen-2'-ylcarbamoyl)-pentanoylamino]-4-thienylthiophen-3-carboxylic acid (hereinafter referred to as "compound b") were each evaluated for (1) PAI-1 inhibitory activity, (2) fibrinolytic action, and (3) effects on bleomycin-induced pulmonary fibrosis.

(1) Measurement of PAI-1 Inhibitory Activity

Compounds a and b (test compounds) were evaluated for inhibitory action on human PAI-1 (produced by Molecular Innovations, Inc. (USA); the same applies hereinafter).

Specifically, human-derived PAI-1 was added to a 0.1% Tween 80-containing 100 mM Tris-HCl (pH 8) solution containing each of the test compounds at a given concentration (0.12, 0.20, and 0.29 mM), and the mixture was incubated at 37° C. for 15 minutes. Subsequently, human-derived tissue plasminogen activator (t-PA) (produced by American Diagnostica, Inc. (USA); the same applies hereinafter) adjusted to 0.35 pmol/µL was added thereto, and the mixture was incubated at 37° C. for 15 minutes. Then, 1.25 mM of 5-2288 synthetic substrate (manufactured by Chromogenix (Italy); the same applies hereinafter), which is a chromogenic substrate, was added thereto. The final mixture contained 100 mM Tris-HCl (pH 8), 30 mM NaCl, 1% DMSO, 0.1% Tween 80, 67 nM PAI-1, 9.8 nM t-PA, 1 mM S-2288, and test compound a or b (20, 35, or 50 µM).

Free radical P-nitroaniline removed from the chromogenic substrate (S-2288) by t-PA action was measured using a spectrophotometer at an absorbance of 405 nm at 5-minute intervals for 30 minutes. A system that did not contain the test compounds was similarly evaluated, and the PAI-1 activity of the system (control systems) after 30 minutes was taken as 100% to evaluate the PAI-1 activity of a systems to which a test compound was added.

Comparative tests were carried out in the same manner using, in place of the above test compounds, a compound (tiplaxtinin) of the formula below that is used as an antithrombotic drug in US clinical trials (concentration: 20, 35, and 50 µM).

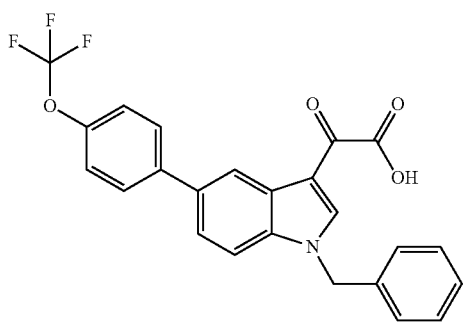 [SMILES: O=C(O)C(=O)c1cn(Cc2ccccc2)c2ccc(-c3ccc(OC(F)(F)F)cc3)cc12]

Figure 2:
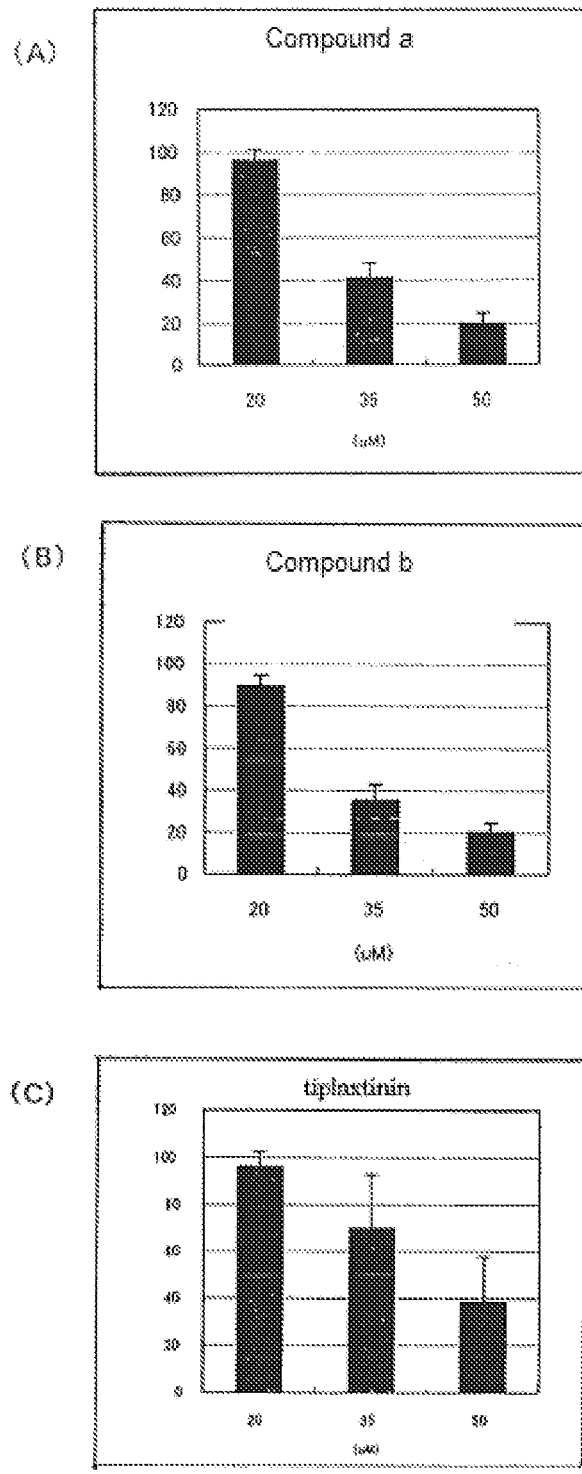
FIG. 2 is a graph showing PAI-1 inhibitory activities of (A) N,N'-bis[3,3'-carboxy-4,4'-phenyl-2,2'-thienyl]hexanedicarboxyamide (compound a), (B) N,N'-bis[3,3'-carboxy-4,4'-(2,2'-thienyl)-2,2'-thienyl]hexanedicarboxyamide (compound b), and (C) tiplaxtinin. The longitudinal axis indicates PAI-1 activity (%) (see Reference Test Example (1)).

The results are shown in FIGS. 2 (A) to (C). FIGS. 2 (A), (B), and (C) show PAI-1 activity (%) when compound a (concentrations: 20, 35, and 50 µM), compound b (concentrations: 20, 35, and 50 µM), and tiplaxtinin (comparative compound) (concentrations: 20, 35, and 50 µM) were added, respectively. The results reveal that compounds a and b had higher PAI-1 activity inhibitory action at concentrations of 35 µM and 50 µM than tiplaxtinin (comparative compound) (PAI-1 inhibitory activity).

(2) Evaluation of Fibrinolytic Action

The fibrinolytic action of Compounds a and b were evaluated in accordance with the document (Matsuo, O. et al., Haemostasis, 16, 43-50 (1986)).

Specifically, an aqueous solution (containing 25 mM barbital-sodium, 50 mM NaCl, and 25 mM $CaCl_2$) containing a concentration of 1.5 mg/mL of fibrinogen (produced by Organon Teknica) was added, on a 9 cm-plate, to thrombin dissolved in 0.2 mL of physiological saline (10NIH U/mL: produced by Mochida Pharmaceutical Co., Ltd.), and the mixture was allowed to stand at room temperature for 2 hours. Using this mixture, fibrinolysis assay was conducted.

Namely, a mixture of PAI-1, t-PA, and a test compound was added dropwise to the plate and incubated at room temperature for 18 hours. Then, fibrinolysis due to plasminogen activation was measured from the lysis area on the plate.

The results demonstrate that compounds a and b inhibit the suppression of fibrinolysis caused by PAI-1.

(3) Evaluation of Effects on Bleomycin-Induced Pulmonary Fibrosis

In order to evaluate the in vivo antifibrotic action of compound b having PAI-1 inhibitory activity, the following experiments were carried out using an animal (mouse) model with pulmonary fibrosis artificially induced by bleomycin.

A C57BL/6 mouse (male, body weight: 19 to 21 g) was intraperitoneally anesthetized with pentobarbital, and an incision was made on the cervical organ. Ten mice were used as controls. Bleomycin (produced by Nippon Kayaku Co., Ltd.) (1.5 U/kg) lysed in physiological saline was endotracheally administered to each of the control mice (n=10) twice a day for 14 days. On the other hand, the test mice were subjected to forcible oral administration of compound b (200 mg/kg), suspended in a 0.5% carboxymethyl cellulose aqueous solution, twice a day for 14 days, in addition to the above endotracheal administration. Then, the lung tissues taken from these control mice and test mice were analyzed, and further assayed for hydroxyproline level. The hydroxyproline level in the lung tissues was measured as the hydrolysate level of the lung tissues, according to the method of Kivirikko et al. (Anal. Biochem. 19, 249-255 (1967)). The level (severity) of pulmonary fibrosis was scored from 0 to 8, based on the method of Ashcort et al. (J. Clin. Pathol. 41, 467-470 (1988)).

Further, the control mice and the test mice were assayed for plasma PAI-1 activity (ng/mL).

Figure 3:
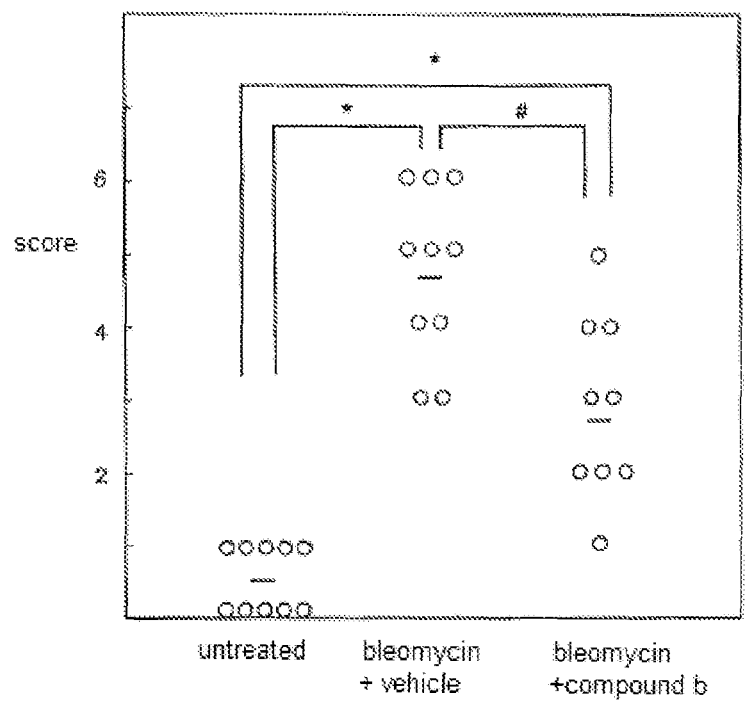
Figure 3:
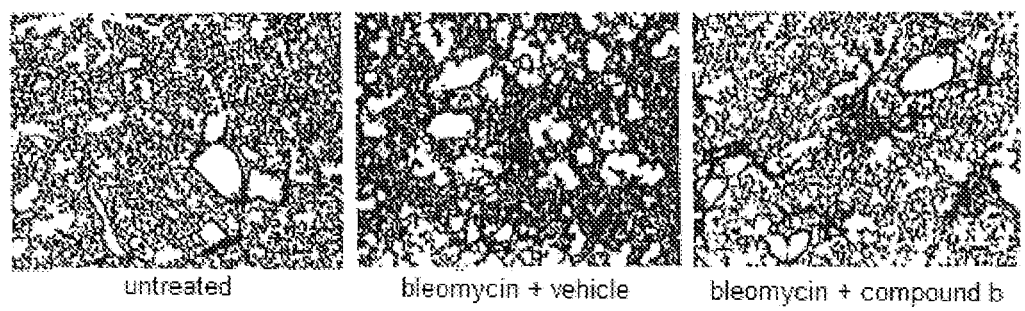

FIG. 3 shows the results of the lung tissue analysis (a: fibrosis scores, b: tissue stained images), and the following table shows the hydroxyproline level (n=10, mean±SE) in the lung tissues and plasma PAI-1 activity (n=10, mean±SE).

TABLE 3

| Treatment | Hydroxyproline level in the lung tissues (µg/lung) | Plasma PAI-1 activity (ng/mL) |
|---|---|---|
| Control (untreated) | 140.2 ± 4.8 | 0.8 ± 0.1 |
| Bleomycin (0.5% CMC) | 232.9 ± 8.5[a] | 1.7 ± 0.2[a] |
| Bleomycin + compound b (0.5% CMC) (200 mg/kg, p.o., twice/day) | 204.2 ± 9.5[b] | 1.2 ± 0.1[b] |

[a]$P < 0.001$ vs control by Mann Whitney U test
[b]$P < 0.05$ vs control by Mann Whitney U test The results reveal that the administration of compound b significantly reduced the hydroxyproline level in the lung tissues, which had been dramatically increased by the administration of bleomycin. Further, the results demonstrate that the administration of bleomycin remarkably increased plasma PAI-1 activity, and that such increases in plasma PAI-1 activity were significantly reduced by the administration of compound b.

As is clear from FIG. 3, pulmonary fibrosis induced by the administered bleomycin (fibrosis score: 4.7±0.17, Control group: 0.5±0.17, P<0.001) was significantly ameliorated by the administration of compound b (fibrosis score: 2.9±0.42, P<0.01). These results agree with the results of the above PAI-1 activity.

The results suggest that compound b and other compounds having PAI-1 inhibitory action have an effect of preventing the process of pulmonary fibrosis, in addition to an effect of promoting fibrinolytic system. It has already been reported by Eitzman et al. that a strong relationship is observed between PAI-1 expression and the accumulation of collagen in the lung tissues of mice in which the PAI-1 gene is overexpressed or deficient (J. Clin. Invest. 97, 232-237 (1996)). The above results, showing that pulmonary fibrosis is alleviated by compound b having a strong PAI-1 inhibitory activity, suggest that PAI-1 is not a simply an indicator of pulmonary fibrosis, but the primary factor thereof. Fibril formation occurs in many tissues and organs such as the heart, blood vessels, liver, kidneys, etc., in addition to lungs. For this reason, this finding is critical.

Additionally, PAI-1 is also known to be involved in radiation injuries, and in the development and metastasis of cancer. More specifically, some studies on humans or animals have reported increased expression of PAI-1 in radiation injuries and growth and metastasis of cancer, in addition to thrombosis, fibrosis, and atherosclerosis (Thromb. Haemost. 2005 April; 93 (4), pp. 631-640).

Another finding related to PAI-1 is that in myocardial infarction, for example, cardiomyocytes and mast cells are involved in the expression of PAI-1, playing a critical role in interstitial and perivascular fibrosis (Am. J. Pathol. 2004 February; 164 (2): 449-456). It is also suggested that in atherosclerosis and vascular restenosis, intravascular fibrin deposition is involved in intimal hyperplasia, and that PAI-1 plays a key role in fibrin homeostasis (Trends Cardiovasc. Med. 2004 July; 14 (5); 196-202). In liver fibrosis in cirrhotic liver, PAI-1 increased together with u-PA, u-PAR, and t-PA increased in fibrotic liver is suggested to be associated with the inhibition of matrix degradation in cirrhotic liver. This implies that PAI-1 has an important role in the development of liver fibrosis in cirrhotic liver (J. Hepatol. 1999. October; 31 (4): 703-711). Furthermore, it is known that PAI-1 is related to expansion of the mesangium in diabetic nephropathy (J. Lab. Clin. Med. 2004 August; 144 (2): 69-77), and that PAI-1 is involved in the development and metastasis of breast cancer (Oncogene. 2003 Jul. 10; 22 (28): 4389-4397). Regarding radiation injuries, it is reported that in radiation therapy for abdominal and pelvic cancers, radiation-induced PAI-1 plays a critical role in intestinal damage (Am. J. Pathol. 2008 March; 172 (3): 691-701). From such numerous findings relating to PAI-1, PAI-1 is considered to be deeply associated with the development of many diseases in various organs, as explained in the Prior Art section. (Non-Patent Literature 4 to 20)

Moreover, regarding Alzheimer's disease, whose onset is said to be triggered by the accumulation of amyloid-β peptide (Aβ) in the brain, it has recently been reported that the degradation of Aβ is promoted by inhibiting PAI-1 (Jacobsen J S et al., Proc. Natl. Acad. Sci. USA, 105 (25), 8754-8759, 2008), suggesting the possibility that PAI-1 inhibitors are useful as therapeutic agents for Alzheimer's disease.

In light of the above, compound (I) of the present invention is expected to prevent or treat various diseases whose onset is associated with PAI-1 (e.g., various thromboses; cancers; diabetes; diabetic complications such as macroangiopathy and microangiopathy; tissue fibrosis such as pulmonary fibrosis, hepatic fibrosis, and renal fibrosis; diabetic nephropathy and chronic kidney disease (CKD); various renal diseases such as nephrotic syndrome, postrenal renal damage, and pyelonephritis; eye diseases such as glaucoma, diabetic retinopathy, and oxygen-induced retinopathy; polycystic ovary syndrome; radiation injury; alopecia (baldness); liver splenomegaly; bone marrow regeneration; obesity; amyloidosis; tissue fibrosis; Alzheimer's disease; and arteriosclerosis) and Alzheimer's disease, on the basis of the PAI-1 inhibitory action.

The invention claimed is:

1. A compound represented by Formula (I) or a salt thereof:

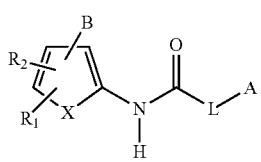

(I)

wherein $R_1$ represents halogen, $R_2$ represents hydrogen, halogen, $C_{1-6}$-alkyl, $C_{3-8}$-cycloalkyl, $C_{3-8}$-cycloalkyl-$C_{1-6}$-alkyl, $C_{3-8}$-cycloalkenyl, $C_{2-6}$-alkynyl, $C_{3-8}$-cycloalkyl-$C_{2-6}$-alkynyl, substituted or unsubstituted aryl, or substituted or unsubstituted heteroaryl;

X represents —CH=CH—;

A represents a group represented by the following Formula (II):

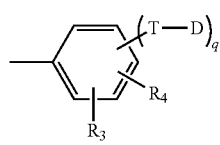

(II)

wherein $R_3$ and $R_4$ are the same or different, and each represents hydrogen, substituted or unsubstituted $C_{1-6}$-alkyl, or $CF_3$;

T represents a single bond;

D represents substituted or unsubstituted aryl, heteroaryl except pyrazolyl, or benzo-condensed heteroaryl; substituted or unsubstituted $C_{4-8}$-cycloalkyl;

substituted or unsubstituted $C_{3-8}$-cycloalkenyl or heterocycloalkenyl; or adamantyl;

q is 1;

L represents a single bond;

B is located at ortho position on the benzene ring to which imino is bound, and is $COOR_9$ wherein $R_9$ represents hydrogen; or a group converted to hydrogen in vivo, which is selected from the group consisting of $C_{1-6}$-alkyl, aryl, aralkyl, —CH($R_{10}$)—O—CO—$R_{11}$, —CH($R_{10}$)—O—CO—$OR_{11}$, and a (5-alkyl-2-oxo-1,3-dioxolen-4-yl)methyl group represented by the following formula:

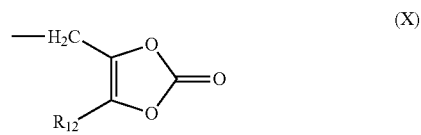

(X)

wherein $R_{10}$ is hydrogen or $C_{1-6}$-alkyl, $R_{11}$ is $C_{1-6}$-alkyl or $C_{3-8}$-cycloalkyl, and $R_{12}$ is $C_{1-6}$ alkyl; or a heterocyclic group represented by any of the following Formulae (XI)-(XIII):

(XI)

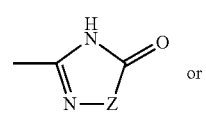

(XII)

or

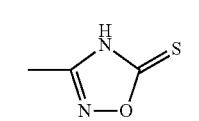

(XIII)

wherein Z represents oxygen or sulfur, provided that the following compounds and salts thereof are excluded:

2-[(biphenyl-4-ylcarbonyl)amino]-5-chlorobenzoic acid, and 5-chloro-2-({[4-(1H-pyrrol-1-yl)phenyl]carbonyl}amino)benzoic acid.

2. A pharmaceutical composition comprising an effective amount of the compound or a salt thereof according to claim 1, or a solvate thereof; and a pharmacologically acceptable carrier or additive.

3. A method for producing a compound represented by Formula (I-2), comprising steps (a) and (b) below:

(a) a step of condensing a compound (1) and a compound (2), which are represented by the following formulae, to form an ester compound (I-1); and (b) a step of removing $R_{9a}$ in the compound (I-1) formed in step (a) above to form a carboxylic acid (I-2):

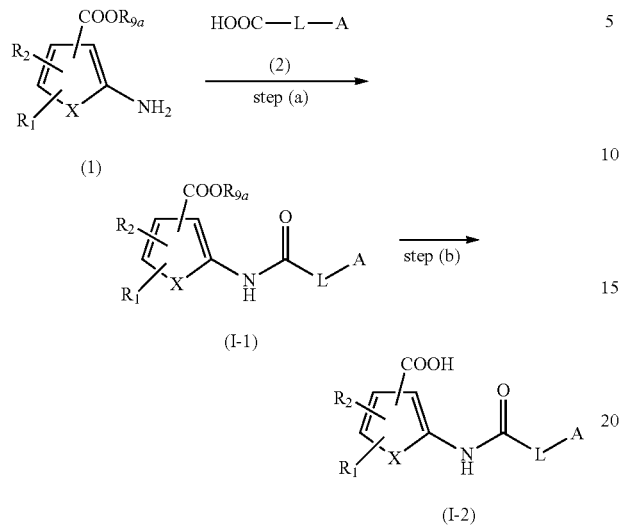

wherein $R_1$, $R_2$, X, L, and A are as defined claim 1; and $R_{9a}$ represents alkyl, aryl, or aralkyl.

4. A method for producing a compound represented by Formula (I-3), comprising steps (a") and (d) below:
  (a") a step of condensing a compound (1") and a compound (2), which are represented by the following formulae, to form a nitrile compound (4); and
  (d) a step of reacting the nitrile compound (4) formed in step (a") above with an azide (5) to form a tetrazole compound (I-3):

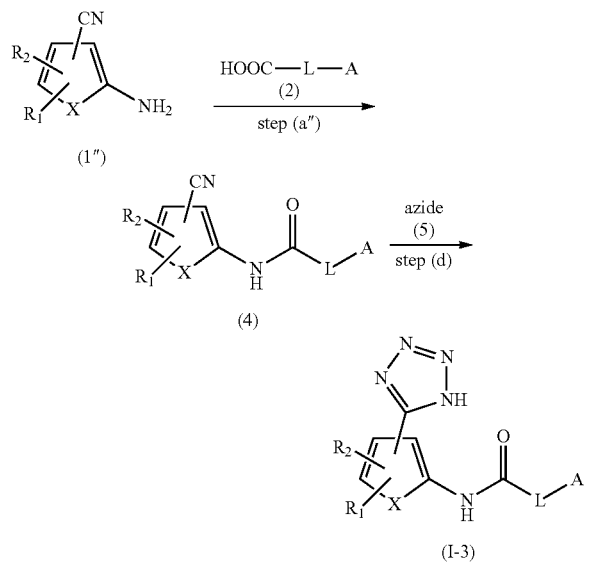

wherein $R_1$, $R_2$, X, A, and L are as defined claim 1.

5. A method for producing a compound represented by Formula (I-1) or a compound (5), comprising steps (j) and (k) below:
  (j) a step of condensing a compound (1) and a compound (12), which are represented by the following formulae, to form a compound (13); and (k) a step of reacting the compound (13) formed in step (j) above with a compound (14) to form a compound (I-1):

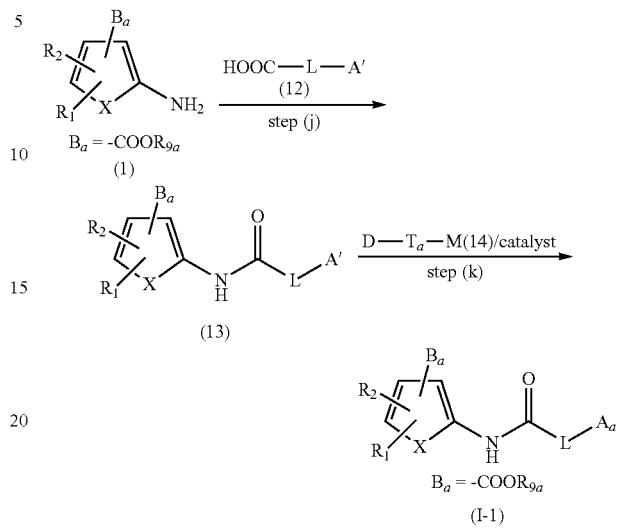

wherein $R_1$, $R_2$, D, L, $R_{9a}$, and X are as defined claims 1 and 3, provided that Aa represents a group in which W in a group represented by Formula (XIV) below is replaced by D-Ta—;
Ba represents ester (—$COOR_{9a}$);
A' represents a group represented by Formula (XIV) below having halogen or trifluoromethanesulfonyloxy represented by W;
Ta represents a single bond;
M represents —$B(OR_{13})OR_{13}$ ($R_{13}$ represents hydrogen or alkyl: in the case of alkyl, $R_{13}$ substituents may bind to each other to form a ring);
or —ZnV (Zn represents zinc, and V represents halogen):

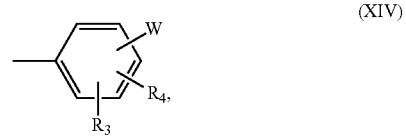

wherein $R_3$ and $R_4$ are the same or different, and each represents hydrogen, substituted or unsubstituted $C_{1-6}$-alkyl, or $CF_3$; and W represents halogen or trifluoromethanesulfonyloxy.

6. The compound or a salt thereof according to claim 1, wherein the compound represented by Formula (I) above is a compound wherein $R_1$ is halogen except bromine when D is unsubstituted aryl.

7. The compound or a salt thereof according to claim 1, wherein the compound represented by Formula (I) above is a compound wherein D represents substituted or unsubstituted heteroaryl, aryl or $C_{4-8}$-cycloalkyl.

8. The compound or a salt thereof according to claim 6, wherein the compound represented by Formula (I) above is a compound wherein D represents substituted or unsubstituted heteroaryl, aryl or $C_{4-8}$-cycloalkyl.

9. The compound or a salt thereof according to claim 1, wherein the compound represented by Formula (I) above is a compound wherein B is COOH, or a heterocyclic group represented by the following Formula (XI):

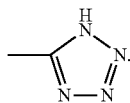

(XI)

10. The compound or a salt thereof according to claim 6, wherein the compound represented by Formula (I) above is a compound wherein B is COOH, or a heterocyclic group represented by the following Formula (XI):

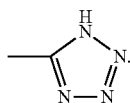

(XI)

11. The compound or a salt thereof according to claim 1, wherein the compound represented by Formula (I) above is a compound selected from the following compounds:
- 5-chloro-2-({[3-(furan-3-yl)phenyl]carbonyl}amino)benzoic acid,
- 5-chloro-2-({[4-(thiophen-2-yl)phenyl]carbonyl}amino)benzoic acid,
- 5-chloro-2-({[3-(pyridin-4-yl)phenyl]carbonyl}amino)benzoic acid,
- 5-chloro-2-{[(4'-methylbiphenyl-3-yl)carbonyl]amino}benzoic acid,
- 5-chloro-2-{[(2'-methoxybiphenyl-3-yl)carbonyl]amino}benzoic acid,
- 5-chloro-2-({[4-(3,6-dihydro-2H-pyran-4-yl)phenyl]carbonyl}amino)benzoic acid,
- 2-({[4-(adamantan-1-yl)phenyl]carbonyl}amino)-5-chlorobenzoic acid,
- 5-chloro-2-({[3-(naphthalen-1-yl)phenyl]carbonyl}amino)benzoic acid,
- 2-({[3-(adamantan-1-yl)phenyl]carbonyl}amino)-5-chlorobenzoic acid,
- 5-chloro-2-({[3-(quinolin-3-yl)phenyl]carbonyl}amino)benzoic acid,
- 5-chloro-2-({[3-(isoquinolin-4-yl)phenyl]carbonyl}amino)benzoic acid,
- 5-chloro-2-({[3-(quinolin-6-yl)phenyl]carbonyl}amino)benzoic acid,
- 5-chloro-2-({[3-(isoquinolin-5-yl)phenyl]carbonyl}amino)benzoic acid,
- 5-chloro-2-({[4-(quinolin-8-yl)phenyl]carbonyl}amino)benzoic acid,
- 5-chloro-2-({[3-(quinolin-8-yl)phenyl]carbonyl}amino)benzoic acid,
- 5-chloro-2-{[(4-cyclohexylphenyl)carbonyl]amino}benzoic acid,
- 5-chloro-2-({[3-(cyclohex-1-en-1-yl)phenyl]carbonyl}amino)benzoic acid,
- 5-chloro-2-{[(3-cyclohexylphenyl)carbonyl]amino}benzoic acid,
- 5-chloro-2-({[4-(1-methylcyclohexyl)phenyl]carbonyl}amino) benzoic acid, and
- N-[4-chloro-2-(1H-tetrazol-5-yl)phenyl]-3-(quinolin-8-yl)benzamide.

12. The pharmaceutical composition according to claim 2, wherein the compound is a compound selected from the following compounds:
- 5-chloro-2-({[3-(furan-3-yl)phenyl]carbonyl}amino)benzoic acid,
- 2-[(biphenyl-3-ylcarbonyl)amino]-5-chlorobenzoic acid,
- 2-[(biphenyl-2-ylcarbonyl)amino]-5-chlorobenzoic acid,
- 5-chloro-2-({[4-(thiophen-2-yl)phenyl]carbonyl}amino) benzoic acid,
- 5-chloro-2-({[3-(pyridin-4-yl)phenyl]carbonyl}amino) benzoic acid,
- 5-chloro-2-{[(4'-methylbiphenyl-3-yl)carbonyl]amino}benzoic acid,
- 5-chloro-2-{[(2'-methoxybiphenyl-3-yl)carbonyl]amino}benzoic acid,
- 5-chloro-2-({[4-(3,6-dihydro-2H-pyran-4-yl)phenyl]carbonyl}amino)benzoic acid,
- 2-({[4-(adamantan-1-yl)phenyl]carbonyl}amino)-5-chlorobenzoic acid,
- 5-chloro-2-({[3-(naphthalen-1-yl)phenyl]carbonyl}amino)benzoic acid,
- 2-({[3-(adamantan-1-yl)phenyl]carbonyl}amino)-5-chlorobenzoic acid,
- 5-chloro-2-({[3-(quinolin-3-yl)phenyl]carbonyl}amino) benzoic acid,
- 5-chloro-2-({[3-(isoquinolin-4-yl)phenyl]carbonyl}amino)benzoic acid,
- 5-chloro-2-({[3-(quinolin-6-yl)phenyl]carbonyl}amino) benzoic acid,
- 5-chloro-2-({[3-(isoquinolin-5-yl)phenyl]carbonyl}amino)benzoic acid,
- 5-chloro-2-({[4-(quinolin-8-yl)phenyl]carbonyl}amino) benzoic acid,
- 5-chloro-2-({[3-(quinolin-8-yl)phenyl]carbonyl}amino) benzoic acid,
- 5-chloro-2-{[(4-cyclohexylphenyl)carbonyl]amino}benzoic acid,
- 5-chloro-2-({[3-(cyclohex-1-en-1-yl)phenyl]carbonyl}amino) benzoic acid,
- 5-chloro-2-{[(3-cyclohexylphenyl)carbonyl]amino}benzoic acid,
- 5-chloro-2-({[4-(1-methylcyclohexyl)phenyl]carbonyl}amino) benzoic acid, and
- N-[4-chloro-2-(1H-tetrazol-5-yl)phenyl]-3-(quinolin-8-yl)benzamide.

13. The pharmaceutical composition according to claim 12, the composition comprising the compound in the range of from 0.001% to 50% by weight.

14. The pharmaceutical composition according to claim 12, the composition being orally administered.

* * * * *